(12) United States Patent
Moscou et al.

(10) Patent No.: US 11,739,343 B2
(45) Date of Patent: Aug. 29, 2023

(54) WHEAT STRIPE RUST RESISTANCE GENES AND METHODS OF USE

(71) Applicant: The Sainsbury Laboratory, Norwich (GB)

(72) Inventors: Matthew James Moscou, Norwich (GB); Andrew Marc Dawson, London (GB)

(73) Assignee: The Sainsbury Laboratory, Norwich (GB)

( * ) Notice: Subject to any disclaimer, the term of this patent is extended or adjusted under 35 U.S.C. 154(b) by 433 days.

(21) Appl. No.: 15/773,026

(22) PCT Filed: Nov. 2, 2016

(86) PCT No.: PCT/US2016/060101
§ 371 (c)(1),
(2) Date: May 2, 2018

(87) PCT Pub. No.: WO2017/079286
PCT Pub. Date: May 11, 2017

(65) Prior Publication Data
US 2018/0320195 A1     Nov. 8, 2018

Related U.S. Application Data

(60) Provisional application No. 62/250,136, filed on Nov. 3, 2015.

(51) Int. Cl.
C12N 15/82       (2006.01)
C07K 14/415      (2006.01)

(52) U.S. Cl.
CPC ........ *C12N 15/8282* (2013.01); *C07K 14/415* (2013.01)

(58) Field of Classification Search
CPC ................................................ C12N 15/8282
See application file for complete search history.

(56) References Cited

FOREIGN PATENT DOCUMENTS

| | | |
|---|---|---|
| CN | 104531409 A | 4/2015 |
| WO | 2014/194371 A1 | 12/2014 |

OTHER PUBLICATIONS

Nover et al, Theor. Appl. Genet. (1969) 39:150-155.*
Dawson et al, Theor. Appl. Genet (2016) 129:831-843.*
UniProt Accession No. M8C858, integrated into UniProt on May 29, 2013.*
Friedberg I., Automated Protein Function Prediction—the Genomic Challenge, Brief. Bioinformatics (2006) 7:225-242.*
International Search Report and Written Opinion dated Feb. 3, 2017 in PCT/US2016/060101.
K Kumar et al, "Virulence of Puccinia striiformis on wheat and barley in central Alberta," Canadian Journal of Plant Pathology,vol. 34, No. 4, pp. 551-561, Sep. 3, 2012 (Sep. 3, 2012).
S. Seah et al, "Resistance Gene Analogs within an Introgressed Chromosomal Segment Derived from Triticum ventricosum That Confers Resistance to Nematode and Rust Pathogens in Wheat", Molecular Plant-Microbe Interactions,vol. 13, No. 3, pp. 334-341, Mar. 1, 2000 (Mar. 1, 2000).
Database UniProt accession No. M7YKD4, May 29, 2013 (May 29, 2013).
Dawson Andrew M et al, "Isolation and fine mapping of Rps6: an intermediate host resistance gene in barley to wheat stripe rust," Theorethical and Applied Genentics, vol. 129, No. 4, p. 831-843, Jan. 11, 2016 (Jan. 11, 2016).
Database EMBL accession No. EMS47732.1, May 29, 2013.
Lv et al., "Functional Analysis of Pid3-A4, an Ortholog of Rice Blast Resistance Gene Pid3 Revealed by Allele Mining in Common Wild Rice", Phytopathology, The American Phytopathological Society, vol. 103, No. 6, pp. 594-599, Jan. 24, 2013.
Zhou et al., "Identification of Novel Alleles of the Rice Blast-Resistance Gene Pi9 through Sequence-Based Allele Mining", Rice, vol. 13, Article No. 80 (15 pgs.), 2020.
Bhullar et al., Wheat Gene Bank Accessions as a Source of new Alleles of the Powdery Mildew Resistance Gene Pm3: a Large Scale Allele Mining Project, BMC Plant Biology, vol. 10, Article No. 88 (13 pgs.), 2010.
Wang et al., "Allele mining in Solanum: conserved homologues of Rpi-blb1 are identifed in Solanum stoloniferum", Theor Appl Genet, vol. 116, pp. 933-943 Feb. 15, 2008.
Huang et al. "Molecular Evolution of the Pi-ta Gene Resistant to Rice Blast in Wild Rice (*Oryza rufipogon*)", Genetics, Genetics Society of America, vol. 179, Issue 3, pp. 1527-1538, Jul. 2008.

* cited by examiner

*Primary Examiner* — Mykola V. Kovalenko
(74) *Attorney, Agent, or Firm* — Williams Mullen; David M. Saravitz

(57) ABSTRACT

Compositions and methods for enhancing the resistance of wheat and barley plants to wheat stripe rust caused by *Puccinia striiformis* f. sp. *tritici* are provided. The compositions comprise nucleic acid molecules encoding resistance (R) gene products and variants thereof and plants, seeds, and plant cells comprising such nucleic acid molecules. The methods for enhancing the resistance of wheat and barley plants to wheat stripe rust comprise introducing a nucleic acid molecule encoding an R gene product into a wheat or barley plant cell. Additionally provided are methods for using the wheat and barley plants in agriculture to limit wheat stripe rust.

6 Claims, 8 Drawing Sheets

Specification includes a Sequence Listing.

WHEAT STRIPE RUST RESISTANCE GENES AND METHODS OF USE

CROSS-REFERENCE TO RELATED APPLICATIONS

This application is the U.S. National Stage of International Application PCT/US2016/060101, filed Nov. 2, 2016, which designates the U.S and was published by the International Bureau in English on May 11, 2017, and which claims the benefit of U.S. Provisional Patent Application No. 62/250,136, filed Nov. 3, 2015, all of which are hereby incorporated herein in their entirety by reference.

REFERENCE TO A SEQUENCE LISTING SUBMITTED AS A TEXT FILE

The official copy of the sequence listing is submitted electronically via EFS-Web as an ASCII formatted sequence listing with a file named 070294-0106SEQLST.TXT, created on Nov. 1, 2016, and having a size of 440 kilobytes, and is filed concurrently with the specification. The sequence listing contained in this ASCII formatted document is part of the specification and is herein incorporated by reference in its entirety.

FIELD OF THE INVENTION

The present invention relates to the fields of gene isolation and plant improvement, particularly to enhancing the resistance of plants to plant disease through the use of disease resistance genes.

BACKGROUND OF THE INVENTION

Plant diseases cause significant yield losses in world-wide wheat production. Among the most damaging diseases of wheat are the rusts. Wheat stripe rust (also known as wheat yellow rust) caused by *Puccinia striiformis* f. sp. *tritici* is currently the most damaging disease of wheat on the global scale (RustTracker.org, available on the worldwide web at rusttracker.cimmyt.org/?page_id=9; accessed Oct. 5, 2015). While wheat plants comprising resistance (R) genes against *Puccinia striiformis* f. sp. *tritici* have proven effective in limiting the agronomic losses caused by wheat stripe rust, new races of *Puccinia striiformis* f. sp. *tritici* have appeared recently for which the R genes are not effective. While pesticides can be used to control wheat stripe rust, pesticides are expensive and at odds with the sustainable intensification of agriculture, and in developing countries, pesticides are simply unaffordable for subsistence farmers.

The sustainable intensification of agriculture will require increased use of genetic solutions instead of chemical solutions (e.g. pesticides) to protect crops against pathogens and pests (Jones et al. (2014) *Philos. T Roy. Soc.* B 369: 20130087). Wild relatives of domesticated crops, such as wheat, contain an immense diversity of useful R genes that are a valuable resource for sustainable disease control in wheat production. However, traditional methods for introducing R genes typically involve long breeding timelines to break linkage to deleterious alleles of other genes. R genes can be overcome within a few seasons when deployed one at a time (McDonald and Linde (2002) *Annu. Rev. Phytopathol.* 40:349-379). In addition to wild relatives of wheat, other grain species that are hosts for wheat pathogens have the potential to be sources of R genes for use in sustainable disease control in wheat production. Molecular cloning makes it possible to simultaneously introduce multiple R genes (Dangl et al. (2013) *Science* 341:746-751), which should delay resistance-breaking pathogen race evolution and thus, provide more durable resistance (McDonald and Linde (2002) *Annu. Rev. Phytopathol.* 40:349-379).

BRIEF SUMMARY OF THE INVENTION

The present invention provides nucleic acid molecules for resistance (R) genes that are capable of conferring upon a plant resistance to at least one race of a pathogen that causes plant disease, particularly resistance to at least one race of a pathogen in the genus Puccinia that causes a rust disease. In one embodiment, the present invention provides nucleic acid molecules comprising the R gene, Rps6, and variants thereof including, for example, orthologs and non-naturally occurring variants. In certain embodiments, the present invention provides nucleic acid molecules comprising Rps6 that are capable of conferring upon a plant, particularly a wheat or barley plant, resistance to *Puccinia striiformis* f. sp. *tritici* (Pst) that causes wheat stripe rust.

The present invention further provides plants, plant cells, and seeds comprising in their genomes one or more polynucleotide constructs of the invention. The polynucleotide constructs comprise a nucleotide sequence encoding a resistance (R) protein of the present invention. Such R proteins are encoded by the R genes of the present invention. In a preferred embodiment, the plants and seeds are transgenic grain plants and seeds, particularly wheat and barley plants and seeds, that have been transformed with one or more polynucleotide constructs of the invention. Preferably, such grain plants comprise enhanced resistance to Pst, when compared to the resistance of a control grain plant that does not comprise the polynucleotide construct.

The present invention provides methods for producing a plant with enhanced resistance to a plant disease, particularly a rust disease, more particularly wheat stripe rust. Such methods comprise introducing into at least one plant cell a polynucleotide construct comprising a nucleotide sequence of an R gene of the present invention. In some embodiments, the polynucleotide construct or part thereof is stably incorporated into the genome of the plant cell, and in other embodiments, the polynucleotide construct is not stably incorporated into the genome of the plant cell. The methods for producing a plant with enhanced resistance to a plant disease can optionally further comprise regenerating the plant cell into a plant that comprises in its genome the polynucleotide construct. Preferably, such a plant comprises enhanced resistance to the plant disease, relative to the resistance of a control plant to the plant disease. In certain embodiments, the plant is a wheat or barley that comprises enhanced resistance to wheat stripe rust caused by Pst, relative to the resistance of a control wheat or barley plant to Pst.

The present invention further provides methods for producing a barley plant with enhanced resistance to wheat stripe rust. Such methods comprise modifying in a barley plant or at least one cell thereof a non-functional allele of the resistance gene Rps6 so as to make a functional allele, whereby the resistance of the barley plant to wheat stripe rust is enhanced. In the methods of the present invention, modifying the non-functional allele comprises introducing at least one genetic modification into the non-functional allele. Such genetic modifications include, for example, one or more insertions, deletions, and/or substitutions of at least one base pair in the non-functional allele, whereby a functional allele is produced. The present invention additional provides non-transgenic and transgenic barley plants and seeds produced by such methods.

Methods of using the plants of the present invention in agricultural crop production to limit wheat stripe rust are also provided. The methods comprise planting a seed, particularly a wheat or barley seed, produced by a plant of the present invention, wherein the wheat or barley seed comprises at least one R gene nucleotide sequence of the present invention, particularly an Rps6 nucleotide sequence. The methods further comprise growing the plant under conditions favorable for the growth and development of the plant, and optionally harvesting at least one seed from the plant.

Additionally provided are non-transgenic and transgenic plants, plant parts, seeds, plant cells, other host cells, expression cassettes, and vectors comprising one or more of the nucleic acid molecules of the present invention.

SEQUENCE LISTING

Figure 1:
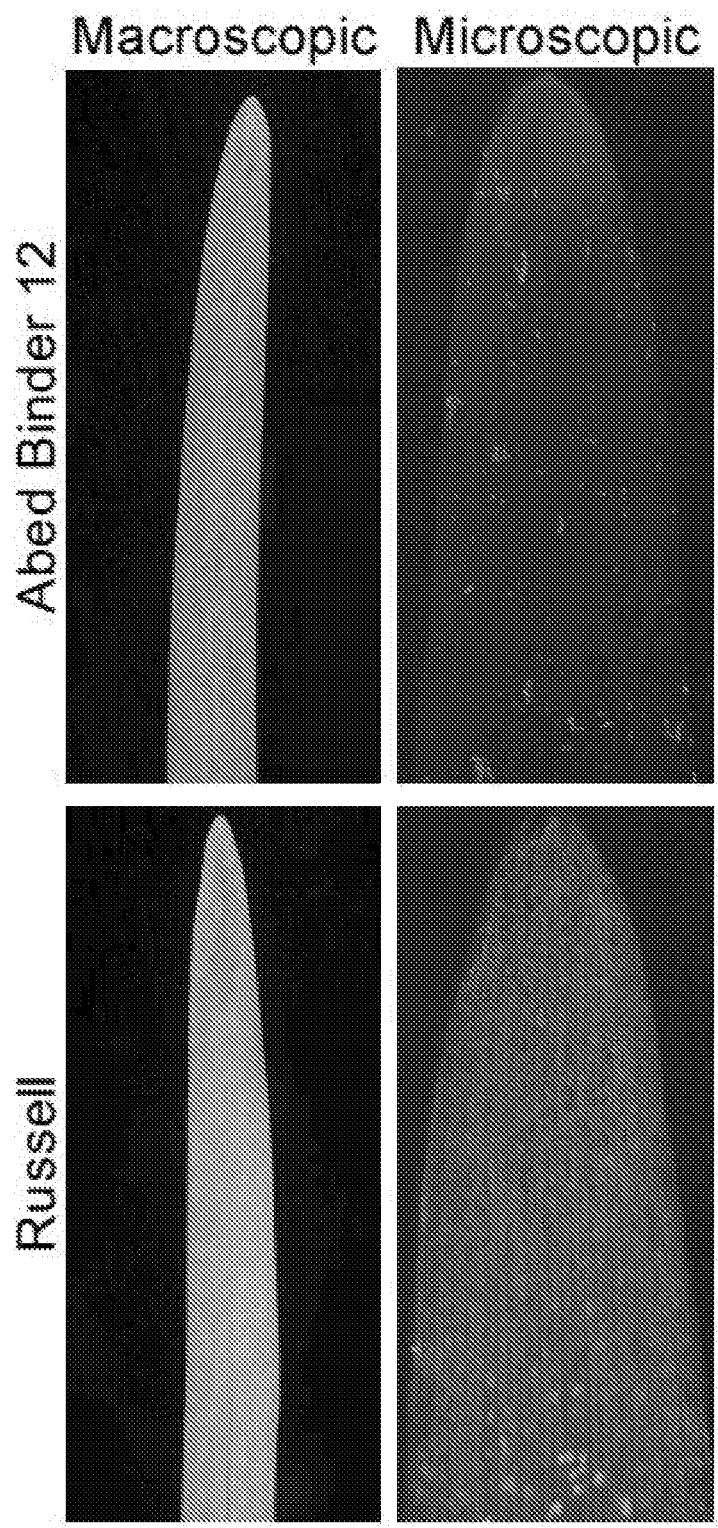
FIG. 1. Macroscopic and microscopic phenotypes of barley cultivars Abed Binder 12 and Russell inoculated with Pst.
Figure 2:
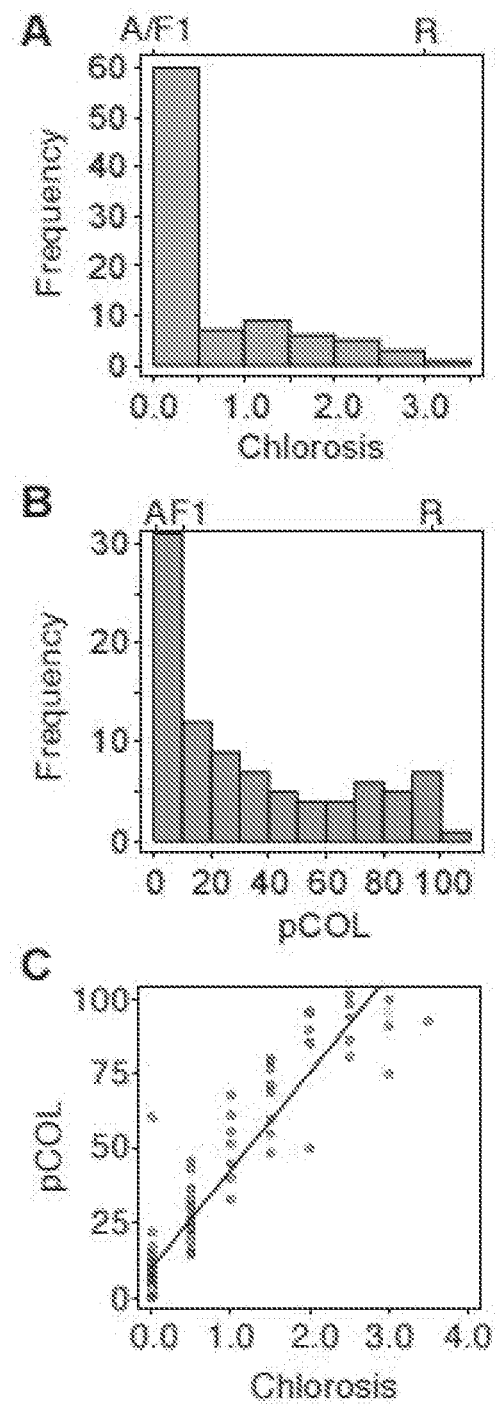
FIG. 2. Histograms and two-way plot of chlorosis and colonization on the Abed Binder 12×Russell $F_2$ population inoculated with Pst isolate 08/501. Histograms showing the segregation of chlorosis (A) and pCOL (B) in the $F_2$ population. Parental and $F_1$ phenotypes shown above plots (A: Abed Binder 12, R: Russell). (C) Two-way plot showing correlation of chlorosis and pCOL phenotypes. The phenotypes of Abed Binder 12 and Russell are shown as the triangle and square, respectively.
Figure 3:
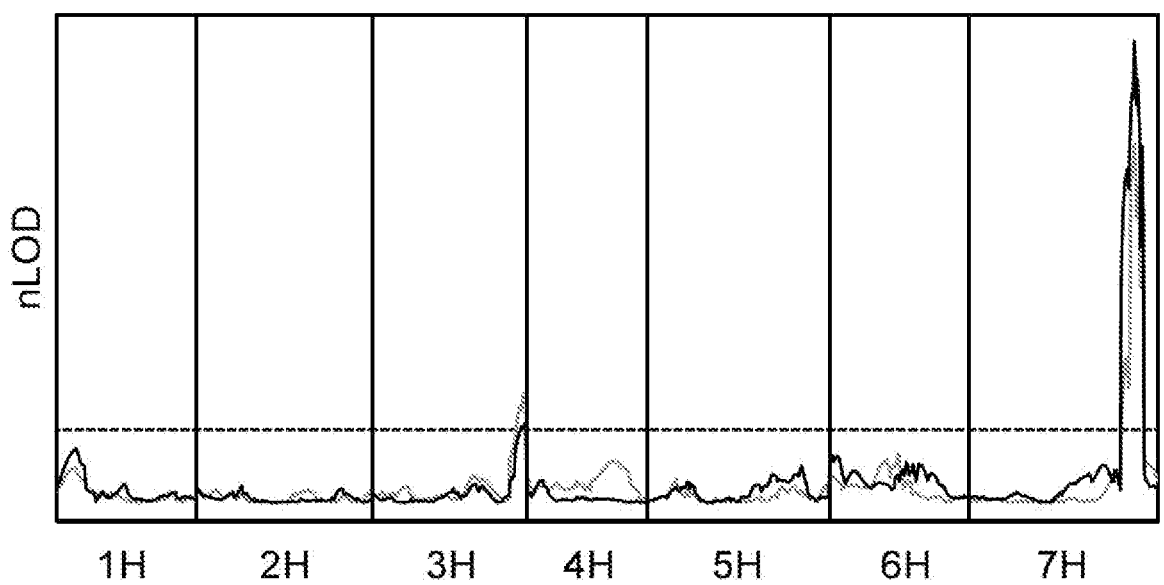
FIG. 3. Composite interval mapping of chlorosis and pCOL phenotypes in the Abed Binder 12×Russell $F_2$ population inoculated with Pst. LOD curves were normalized (nLOD) for chlorosis (grey) and pCOL (black) based on individual experiment-wide thresholds (dashed line) based on 1,000 permutations. A step size of 2 cM was used, with the x-axis spanning the length of the AxR-Pst $F_2$ population genetic map.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the nucleotide sequence of the R gene, Rps6, from *Hordeum vulgare* 'Abed Binder 12'.

SEQ ID NO: 2 sets forth the nucleotide sequence of the coding region of the cDNA of Rps6 from *H. vulgare* 'Abed Binder 12'. If desired, a stop codon (e.g. TAA, TAG, or TGA) can be operably linked to the 3' end of nucleic acid molecule comprising SEQ ID NO: 2.

SEQ ID NO: 3 sets forth the amino acid sequence of the R protein encoded by Rps6 from *H. vulgare* 'Abed Binder 12'.

SEQ ID NO: 4 set forth the nucleotide sequence of the bacterial artificial chromosome (BAC), BAC_4931-1-11E. This BAC is a nucleic acid molecule comprising nucleotide sequences that correspond to the region of the genome of *H. vulgare* 'Abed Binder 12' in which Rps6 is located.

SEQ ID NO: 5 sets forth the nucleotide sequence of the coding region of the cDNA of Rps6 from *H. vulgare* 'Hindmarsh'. If desired, a stop codon (e.g. TAA, TAG, or TGA) can be operably linked to the 3' end of nucleic acid molecule comprising SEQ ID NO: 2.

SEQ ID NO: 6 sets forth the amino acid sequence of the R protein encoded by Rps6 from *H. vulgare* 'Hindmarsh'.

SEQ ID NO: 7 sets forth the nucleotide sequence of the coding region of the cDNA of Rps6 from *H. vulgare* 'WBDC008'. If desired, a stop codon (e.g. TAA, TAG, or TGA) can be operably linked to the 3' end of nucleic acid molecule comprising SEQ ID NO: 2.

SEQ ID NO: 8 sets forth the amino acid sequence of the R protein encoded by Rps6 from *H. vulgare* 'WBDC008'.

SEQ ID NO: 9 sets forth the nucleotide sequence of the coding region of the cDNA of Rps6 from *H. vulgare* 'WBDC085'. If desired, a stop codon (e.g. TAA, TAG, or TGA) can be operably linked to the 3' end of nucleic acid molecule comprising SEQ ID NO: 2.

SEQ ID NO: 10 sets forth the amino acid sequence of the R protein encoded by Rps6 from *H. vulgare* 'WBDC085'.

SEQ ID NO: 11 sets forth the nucleotide sequence of the coding region of the cDNA of Rps6 from *H. vulgare* 'WBDC109'. If desired, a stop codon (e.g. TAA, TAG, or TGA) can be operably linked to the 3' end of nucleic acid molecule comprising SEQ ID NO: 2.

SEQ ID NO: 12 sets forth the amino acid sequence of the R protein encoded by Rps6 from *H. vulgare* 'WBDC109'.

SEQ ID NO: 13 sets forth the nucleotide sequence of the coding region of the cDNA of Rps6 from *H. vulgare* 'WBDC110'. If desired, a stop codon (e.g. TAA, TAG, or TGA) can be operably linked to the 3' end of nucleic acid molecule comprising SEQ ID NO: 2.

SEQ ID NO: 14 sets forth the amino acid sequence of the R protein encoded by Rps6 from *H. vulgare* 'WBDC110'.

Figure 8:
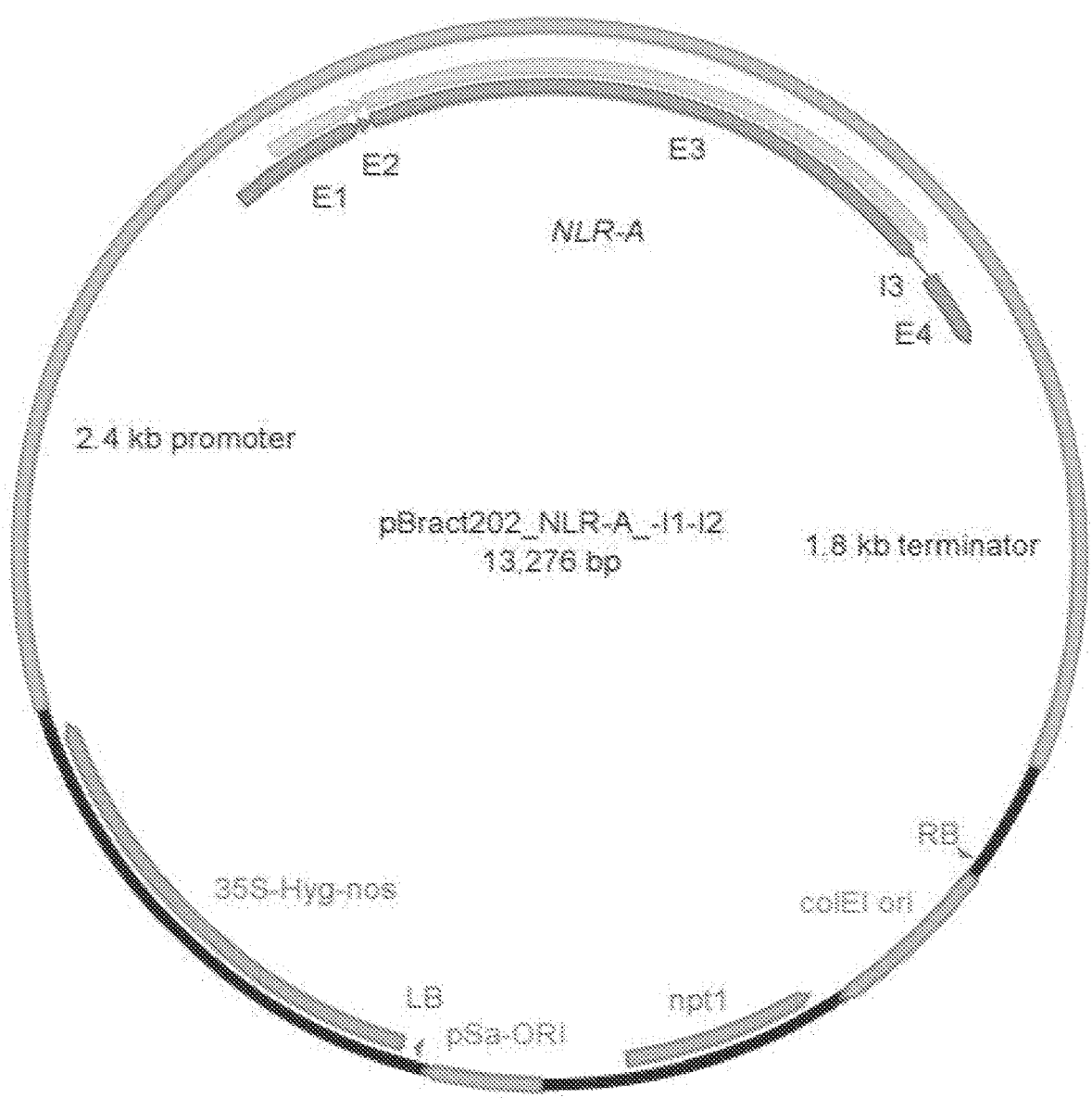
FIG. 8. NLR-A construct development for *Agrobacterium tumefaciens*-based transformation. T-DNA design flanked by the left (LB) and right (RB) border sequences includes a hygromycin resistance gene driven by a 35S promoter and nos terminator followed by 2.4 kb promoter, exons 1, 2, and 3, intron 3, exon 4, and 1.8 kb terminator of NLR-A. Other features include two replication origin sites (pSa-ORI and colEI-ori) and kanamycin resistance (npt1). An embodiment of the construct shown in FIG. 8 comprises the nucleotide sequence set forth in SEQ ID NO: 15.

SEQ ID NO: 15 is the nucleotide sequence of the IHP_0205_NLR-A_construct described in Example 2 and illustrated in FIG. 8.

SEQ ID NO: 16 is the nucleotide sequence of the portion of the IHP_0205_NLR-A_T-DNA construct that is expected to be transferred to a plant during transformation with *Agrobacterium tumefaciens* comprising the IHP_0205_NLR-A_construct.

SEQ ID NO: 17 is the nucleotide sequence of the portion of the IHP_0205_NLR-A construct that comprises sequences of NLR-A.

SEQ ID NOS: 18-33 are the PCR primers that are referred to in Table 4.

SEQ ID NO: 34 is the nucleotide sequence of the IHP_0300_NLR-A_native construct described in Example 2.

SEQ ID NO: 35 is the nucleotide sequence of pBract202_TSL_pMla6_NLR-A_CDS_gDNA_tMla6 construct described in Example 2.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention relates to plant resistance (R) genes, particularly R genes that confer upon plant resistance to a plant disease caused by a plant pathogen. The present invention further relates to the mapping and isolation of an R gene that is capable of conferring upon a barley plant resistance to multiple races of wheat stripe rust caused by *Puccinia striiformis* f. sp. *tritici* (Pst). As disclosed hereinbelow, a Pst resistance gene from barley (*Hordeum vulgare*) designated as Rps6, was fine mapped to a 0.1 cM region of the barley genome. By anchoring the Rps6 locus to the barley physical map, this region was placed on a single fingerprinted contig spanning a physical region of 267 kb. After sequencing this region, several candidate genes encoding nucleotide-binding, leucine-rich repeat proteins (NLRB) were identified. From among these candidate NLR genes, NLR-A was determined to correspond to be Rps6.

The present invention provides nucleic acid molecules comprising the nucleotide sequences of R genes, particularly the nucleotide sequence of Rps6 and naturally occurring (e.g. orthologs and allelic variants) and synthetic or artificial (i.e. non-naturally occurring) variants thereof. Such nucleotide sequences of R genes, which are also referred to herein as R gene nucleotide sequences, encode R proteins. R gene nucleotide sequences of the invention include, but not limited to, wild-type R genes comprising a native promoter and the 3' adjacent region comprising the coding region, cDNA sequences, and nucleotide sequences comprising only the coding region. Examples of such R gene nucleotide sequences include the nucleotide sequences set forth in SEQ ID NOS: 1, 2, 5, 7, 9, 11, and 13 and variants thereof. In embodiments in which the native R gene promoter is not used to drive the expression of the nucleotide sequence encoding the R protein, a heterologous promoter can be operably linked to a nucleotide sequence encoding an R protein of the invention to drive the expression of nucleotide sequence encoding an R protein in a plant.

Preferably, the R proteins of the invention are functional R proteins that are capable of conferring on a plant comprising the R protein enhanced resistance to a plant disease caused by a plant pathogen. More preferably, the R proteins of the invention are functional R proteins that are capable of conferring on a barley and/or wheat plant comprising the R protein enhanced resistance to wheat stripe rust caused by at least one race of *Puccinia striiformis* f. sp. *tritici*. In some embodiments, of the present invention, the R proteins of the present invention comprise broad-spectrum resistance to multiple (i.e. two or more) races of *Puccinia striiformis* f. sp. *tritici*.

Functional R proteins of the present invention are encoded by functional alleles of the present invention. As used herein unless stated otherwise or apparent from the context of usage, a "non-functional allele of an R protein" of the present invention is an allele that is not capable of conferring resistance to at least one race of a particular plant pathogen to a plant that comprises the allele in a heterozygous or homozygous state.

Similarly, functional RPS6 proteins of the present invention are encoded by functional Rps6 alleles of the present invention. As used herein unless stated otherwise or apparent from the context of usage, a "non-functional allele of Rps6" of the present invention is an allele that is not capable of conferring resistance to a plant pathogen, particularly at least one race of Pst, to a barley plant that comprises the allele in a heterozygous or homozygous state. It is recognized that such a "non-functional allele" may encode a protein that comprises a biological activity or other function in a barley plant but nevertheless is non-functional with respect to resistance to Pst or other pathogen in the barley plant.

The present invention further provides transgenic plants comprising a polynucleotide construct which comprises an R gene nucleotide sequence of the invention, particularly an Rps6 nucleotide sequence. In some embodiments, the polynucleotide construct is stably incorporated into the genome of the plant, and in other embodiments, the plant is transformed by a transient transformation method and the polynucleotide construct is not stably incorporated into the genome of the plant. Methods for both the stable and transient transformation of plants are disclosed elsewhere herein or otherwise known in the art. In a preferred embodiment of the invention, the transgenic plants are grass plants, particularly grain plants, more particularly wheat or barley plants. Such transgenic comprise enhanced resistance to at least one plant disease, particularly a rust disease, more particularly wheat stripe rust caused by at least one, but preferably multiple, races of *Puccinia striiformis* f. sp. *tritici*.

In certain embodiments, a transgenic plant of the invention comprises a polynucleotide construct comprising a nucleotide sequence encoding an R protein and a heterologous promoter that is operably linked for expression of the nucleotide sequence encoding an R protein. The choice of heterologous promoter can depend on a number of factors such as, for example, the desired timing, localization, and pattern of expression as well as responsiveness to particular biotic or abiotic stimulus. Promoters of interest include, but are not limited to, pathogen-inducible, constitutive, tissue-preferred, wound-inducible, and chemical-regulated promoters.

The present invention further provides methods for producing a plant with enhanced resistance to at least one plant disease. The methods comprise introducing a polynucleotide construct of the invention into at least one plant cell. In certain embodiments, the polynucleotide construct is stably incorporated into the genome of the plant cell. If desired, the methods can further comprise regenerating the plant cell into a transgenic or transformed plant comprising in its genome the polynucleotide construct. Preferably, such a regenerated plant is a wheat or barley plant comprising enhanced resistance to plant disease caused by a plant pathogen. In certain embodiments, the regenerated plant is a wheat or barley plant comprising enhanced resistance to more than one plant disease caused by more than one plant pathogen. In certain other embodiments, the regenerated plant is a wheat or barley plant comprising enhanced resistance to plant disease caused by one, two, three, four, five or more, or even all races, of a particular plant pathogen. In a preferred embodiment of the invention, the regenerated plant is a wheat or barley plant comprising enhanced resistance to wheat stripe rust caused by at least one race of *Puccinia striiformis* f. sp. *tritici*, relative to the resistance of a control wheat or barley plant to wheat stripe rust caused by the at least one race of *Puccinia striiformis* f. sp. *tritici*. In another preferred embodiment of the invention, the regenerated plant is a wheat or barley plant comprising enhanced resistance to wheat stripe rust caused by multiple races, or even all known races, of *Puccinia striiformis* f. sp. *tritici*, relative to the resistance of a control wheat or barley plant to wheat stripe rust caused by the same group of races of *Puccinia striiformis* f. sp. *tritici*.

In yet another preferred embodiment of the invention, the regenerated plant is a wheat or barley plant comprising enhanced resistance to two, three, four, five or more different rust diseases caused by two, three, four, five or more different *Puccinia* spp., relative to the resistance of a control wheat or barley plant to the two, three, four, five or more different rust diseases caused by the two, three, four, five or more different *Puccinia* spp. The two or more *Puccinia* spp. can include, but is not required to include, *Puccinia striiformis* f. sp. *tritici*. The regenerated wheat or barley plant of this embodiment can comprise resistance against rust disease caused by one, two, three, four, five, or more races or even all known races, of each *Puccinia* spp.

The wheat and barley plants disclosed herein find use in methods for limiting wheat stripe rust in agricultural crop production, particularly in regions where wheat stripe rust is prevalent. The methods of the invention comprise planting a wheat seed or a barley seed produced by a wheat plant or a barley plant of the present invention, wherein the wheat seed or the barley seed comprises at least one R gene nucleotide sequence of the present invention, particularly an Rps6 nucleotide sequence. The methods further comprise growing the wheat or barley plant that originates from the seed under conditions favorable for the growth and development of the wheat or barley plant therefrom, and optionally harvesting at least one seed from the wheat or barley plant.

The present invention additionally provides methods for identifying a barley plant that displays newly conferred or enhanced resistance to wheat stripe rust. The methods find use in breeding barley plants for resistance to wheat stripe rust. Such resistant barley plants find use in the agricultural production of barley seeds. The methods comprise detecting in a barley plant the presence of at least one R gene, particularly Rps6 or functional variant thereof. In some embodiments of the invention, detecting the presence of the R gene comprises detecting the entire R gene in genomic DNA isolated from the barley plant. In preferred embodiments, however, detecting the presence of an R gene comprises detecting the presence of at least one marker within the R gene. In other embodiments of the invention, detecting the presence of an R gene comprises detecting the presence of the R protein encoded by the R gene using, for example, immunological detection methods involving antibodies specific to the R protein.

In the methods for identifying a barley plant that displays newly conferred or enhanced resistance to wheat stripe rust, detecting the presence of the R gene in barley can involve one or more to the following molecular biology techniques that are disclosed elsewhere herein or otherwise known in the art including, but not limited to, isolating genomic DNA and/or RNA from the barley plant, amplifying nucleic acid molecules comprising the R gene and/or marker therein by PCR amplification, sequencing nucleic acid molecules comprising the R gene and/or marker, identifying the R gene, the marker, or a transcript of the R gene by nucleic acid hybridization, and conducting an immunological assay for the detection of the R protein encoded by the R gene. It is recognized that oligonucleotide probes and PCR primers can be designed to identity the R genes of the present invention and that such probes and PCR primers can be utilized in methods disclosed elsewhere herein or otherwise known in the art to rapidly identify in a population of barley plants one or more barley plants comprising the presence of an R gene of the present invention.

Depending on the desired outcome, the polynucleotide constructs of the invention can be stably incorporated into the genome of the plant cell or not stably incorporated into genome of the plant cell. If, for example, the desired outcome is to produce a stably transformed plant with enhanced resistance to wheat stripe rust caused by at least one race of *Puccinia striiformis f* sp. *tritici*, then the polynucleotide construct can be, for example, fused into a plant transformation vector suitable for the stable incorporation of the polynucleotide construct into the genome of the plant cell. Typically, the stably transformed plant cell will be regenerated into a transformed plant that comprises in its genome the polynucleotide construct. Such a stably transformed plant is capable of transmitting the polynucleotide construct to progeny plants in subsequent generations via sexual and/or asexual reproduction. Plant transformation vectors, methods for stably transforming plants with an introduced polynucleotide construct and methods for plant regeneration from transformed plant cells and tissues are generally known in the art for both monocotyledonous and dicotyledonous plants or described elsewhere herein.

The present invention provides nucleic acid molecules comprising R genes. Preferably, such R genes are capable of conferring upon a host plant enhanced resistance to at least one race of at least one plant pathogen that causes a plant disease on the host plant. In certain preferred embodiments of the invention, such R genes are capable of conferring upon a wheat or barley plant enhanced resistance to at least one race of the pathogen that causes wheat stripe rust, *Puccinia striiformis* f. sp. *tritici*. Thus, such R genes find use in limiting wheat stripe rust caused by *Puccinia striiformis* f. sp. *tritici* in agricultural production. The R genes of the present invention include, but are not limited to, the R genes whose nucleotide sequences are disclosed herein but also include orthologs and other variants that are capable of conferring to a wheat or barley plant resistance to wheat stripe rust caused by at least one race, but preferably multiple races, of *Puccinia striiformis* f. sp. *tritici*. Methods are known in the art or otherwise disclosed herein for determining the resistance of a plant to a plant disease caused by a plant pathogen such as, for example, stripe rust caused by *Puccinia striiformis* f. sp. *tritici*.

The methods of the present invention find use in producing plants with enhanced resistance to a plant disease caused by a plant pathogen. Typically, the methods of the present invention will enhance or increase the resistance of the subject plant to one race of a plant pathogen or to each of two or more races of the plant pathogen by at least 25%, 50%, 75%, 100%, 150%, 200%, 250%, 500% or more when compared to the resistance of a control to same race or races of the plant pathogen. Unless stated otherwise or apparent from the context of a use, a control plant for the present invention is a plant that does not comprise the polynucleotide construct of the present invention. Preferably, the control plant is essentially identical (e.g. same species, subspecies, and variety) to the plant comprising the polynucleotide construction of the present invention accept the control does not comprise the polynucleotide construct. In some embodiments, the control will comprise a polynucleotide construct but not comprise the one or more R gene sequences that are in a polynucleotide construction of the present invention.

Additionally, the present invention provides transformed plants, seeds, and plant cells produced by the methods of present invention and/or comprising a polynucleotide construct of the present invention. Also provided are progeny plants and seeds thereof comprising a polynucleotide construct of the present invention. The present invention also provides seeds, vegetative parts, and other plant parts produced by the transformed plants and/or progeny plants of the invention as well as food products and other agricultural products produced from such plant parts that are intended to be consumed or used by humans and other animals including, but not limited to pets (e.g., dogs and cats) and livestock (e.g., pigs, cows, chickens, turkeys, and ducks).

The methods of the invention can be used to enhance the resistance of a plant to a rust disease, particularly a rust disease caused by a Puccinia spp., particularly to stripe rust caused by *Puccinia striiformis* f. sp. *tritici*. Preferred plants for use in the methods of the present invention are grass plants, particularly grain plants, more particularly barley and wheat plants.

The present invention encompasses isolated or substantially purified polynucleotide (also referred to herein as "nucleic acid molecule", "nucleic acid" and the like) or protein (also referred to herein as "polypeptide") compositions including, for example, polynucleotides and proteins comprising the sequences set forth in the accompanying Sequence Listing as well as variants and fragments of such polynucleotides and proteins. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of polynucleotides comprising coding sequences may encode protein fragments that retain biological activity of the full-length or native protein. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

Polynucleotides that are fragments of a native R polynucleotide comprise at least 16, 20, 50, 75, 100, 125, 150, 175, 200, 300, 400, 500, 1000, 2000, 5000, 7500, 10000, 12500 contiguous nucleotides, or up to the number of nucleotides present in a full-length R polynucleotide disclosed herein (for example, 12800 nucleotides for SEQ ID NO: 1 and 3126 nucleotides for SEQ ID NOS: 2, 5, 7, 9, 11, and 13).

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the R proteins of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an R protein of the invention. Generally, variants of a particular polynucleotide of the invention will have at least about 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. In certain embodiments of the invention, variants of a particular polynucleotide of the invention will have at least about 80%, 85%, 90%, 91%, 92%, 93%, 94%, 95%, 96%, 97%, 98%, 99% or more sequence identity to at least one nucleotide sequence selected from the group consisting of SEQ ID NOS: 1, 2, 5, 7, 9, 11, and 13, and optionally comprises a non-naturally occurring nucleotide sequence that differs from at least one nucleotide sequence selected from the group consisting of the nucleotide sequence set forth in SEQ ID NO: 1, 2, 5, 7, 9, 11, and 13 by at least one nucleotide modification selected from the group consisting of the substitution of at least one nucleotide, the addition of at least one nucleotide, and the deletion of at least one nucleotide.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, a polynucleotide that encodes a polypeptide with a given percent sequence identity to the polypeptide of SEQ ID NO: 3, 6, 8, 10, 12, or 14 is disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 60%, 65%, 70%, 75%, 80%, 85%, 86%, 87%, 88%, 89%, 90%, 91%, 92%, 93%, 94%, 95%, 96%, 97%, 98%, 99% or more sequence identity. In certain embodiments of the invention, variants of a particular polypeptide of the invention will have at least about 80%, 85%, 90%, 91%, 92%, 93%, 94%, 95%, 96%, 97%, 98%, 99% or more sequence identity to at least one of the full-length amino acid sequences set forth in SEQ ID NO: 3, 6, 8, 10, 12, and 14, and optionally comprises a non-naturally occurring amino acid sequence that differs from at least one of the full-length amino acid sequences set forth in SEQ ID NO: 3, 6, 8, 10, 12, and 14 by at least one nucleotide modification selected from the group consisting of the substitution of at least one amino acid, the addition of at least one amino acid, and the deletion of at least one amino acid.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Such variants may result from, for example, genetic polymorphism or from human manipulation. Biologically active variants of an R protein will have at least about 80%, 85%, 86%, 87%, 88%, 89%, 90%, 91%, 92%, 93%, 94%, 95%, 96%, 97%, 98%, 99% or more sequence identity to the amino acid sequence for the native protein (e.g. the amino acid sequence set forth in SEQ ID NO: 3, 6, 8, 10, 12, or 14) as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant and other variant forms. Likewise, the proteins of the invention encompass both naturally occurring proteins and artificial or non-naturally occurring proteins as well as variants and modified forms thereof. More preferably, such variants confer to a plant or part thereof comprising the variant enhanced resistance wheat stripe rust caused by at least one race of *Puccinia striiformis* f. sp. *tritici*. In some embodiments, the mutations that will be made in the DNA encoding the variant will not place the sequence out of reading frame. Optimally, the mutations will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that are disclosed herein below.

For example, a wheat or barley plant that is susceptible to wheat stripe rust caused by a particular race or races of *Puccinia striiformis* f. sp. *tritici* can be transformed with an Rps6 polynucleotide, regenerated into a transformed or transgenic plant comprising the polynucleotide, and tested for resistance to wheat stripe rust caused by the particular race or races of *Puccinia striiformis* f. sp. *tritici* using standard resistance assays known in the art or described elsewhere herein. Preferred variant polynucleotides and polypeptides of the present invention confer or are capable of conferring upon a wheat or barley plant enhanced resistance to at least one race, but preferably two or more races, of *Puccinia striiformis* f. sp. *tritici* that is known to cause wheat stripe rust in a susceptible wheat or barley plant.

Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 86%, 87%, 88%, 89%, 90%, 91%, 92%, 93%, 94%, 95%, 96%, 97%, 98%, 99%, or greater sequence identity. Functions of orthologs are often highly conserved among species. Thus, isolated polynucleotides that encode R proteins and which hybridize under stringent conditions to at least one of the R proteins disclosed herein or otherwise known in the art, or to variants or fragments thereof, are encompassed by the present invention.

In one embodiment, the orthologs of the present invention have coding sequences comprising at least 80%, 85%, 86%, 87%, 88%, 89%, 90%, 91%, 92%, 93%, 94%, 95%, 96%, 97%, 98%, 99%, or greater nucleotide sequence identity to the nucleotide sequence set forth in at least one of SEQ ID NOS: 2, 5, 7, 9, 11 or 13 and/or encode proteins comprising least 80%, 85%, 86%, 87%, 88%, 89%, 90%, 91%, 92%, 93%, 94%, 95%, 96%, 97%, 98%, 99%, or greater amino acid sequence identity to at least one of the amino acid sequence set forth in SEQ ID NOS: 3, 6, 8, 10, 12, and 14.

As an NLR protein, RPS6, the R protein encoded by Rps6, comprises certain conserved domains. The conserved domains in the amino acid sequence of RPS6 (SEQ ID NO: 3) include, for example, a coiled-coil domain (amino acids 39 to 189), a nucleotide-binding domain (amino acids 190 to 384) and a leucine-rich repeat domain (amino acids 586 to 988). Preferably, variant RPS6 proteins of the present invention comprise a coiled-coil domain, a nucleotide-binding domain, and a leucine-rich repeat domain corresponding to the domains disclosed above.

In some embodiments, variant RPS6 proteins of the present invention comprise a higher percentage of amino acid sequence identity to one, two, or three of such conserved domains than to the full-length amino acid sequence of the RPS6 (SEQ ID NO: 3) protein disclosed herein. Preferably, such variants comprise a corresponding domain or domains having at least 95%, 96%, 97%, 98%, 99%, or 100% sequence identity to one, two, or three of the conserved domains of NLR proteins and further comprise an amino acid sequence having at least 80%, 85%, 86%, 87%, 88%, 89%, 90%, 91%, 92%, 93%, 94%, 95%, 96%, 97%, 98%, or 99% identity to the amino acid set forth in SEQ ID NO: 3.

It is recognized that domains in variant RPS6 proteins corresponding to those conserved domains, as well as any particular conserved amino acids therein, can be identified by methods known to those of skill in the art or disclosed elsewhere herein such as, for example, multiple sequence alignment. It is further recognized that the positions of such conserved domains and conserved amino acids within a particular variant RPS6 can vary from the positions in the amino acid sequences set forth in SEQ ID NO: 3 and that through methods such as, for example, multiple sequence alignment, the corresponding positions of such conserved domains and conserved amino acids can be determined for any variant RPS6 protein of the present invention.

Preferably, the variant RPS6 proteins of the present invention and the polynucleotides encoding them confer, or are capable of conferring upon a barley or wheat plant comprising such a protein or polynucleotide, enhanced resistance to at least one race of *Puccinia striiformis* f. sp. *tritici* that is known to cause wheat stripe rust in a susceptible wheat or barley plant.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire polynucleotide disclosed herein, or one or more portions thereof, may be used as a probe capable of specifically hybridizing to corresponding polynucleotide and messenger RNAs. To achieve specific hybridization under a variety of conditions, such probes include sequences that are unique among the sequence of the gene or cDNA of interest sequences and are optimally at least about 10 nucleotides in length, and most optimally at least about 20 nucleotides in length. Such probes may be used to amplify corresponding polynucleotides for the particular gene of interest from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is recognized that the R protein coding sequences of the present invention encompass polynucleotide molecules comprising a nucleotide sequence that is sufficiently identical to the nucleotide sequence of SEQ ID NO: 1, 2, 5, 7, 9, 11 and/or 13. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 86%, 87%, 88%, 89%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST; available on the world-wide web at ncbi.nlm.nih.gov). Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, Md., USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website on the world-wide web at: ebi.ac.uk/Tools/clustalw/index.html).

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide constructs comprising R protein coding regions can be provided in expression cassettes for expression in the plant or other organism or in a host cell of interest. The cassette will include 5' and 3' regulatory sequences operably linked to the R protein coding region. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the R protein coding region to be under the transcriptional regulation of the regulatory regions. The expression cassette may additionally contain selectable marker genes.

The expression cassette will include in the 5'-3' direction of transcription, a transcriptional and translational initiation region (i.e., a promoter), a R protein coding region of the invention, and a transcriptional and translational termination region (i.e., termination region) functional in plants or other organism or non-human host cell. The regulatory regions (i.e., promoters, transcriptional regulatory regions, and translational termination regions) and/or the R protein coding region or of the invention may be native/analogous to the host cell or to each other. Alternatively, the regulatory regions and/or the R protein coding region of the invention may be heterologous to the host cell or to each other.

As used herein, "heterologous" in reference to a nucleic acid molecule or nucleotide sequence is a nucleic acid molecule or nucleotide sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The present invention provides host cells comprising at least of the nucleic acid molecules, expression cassettes, and vectors of the present invention. In preferred embodiments of the invention, a host cell is a plant cell. In other embodiments, a host cell is selected from the group consisting of a bacterium, a fungal cell, and an animal cell. In certain embodiments, a host cell is non-human animal cell. However, in some other embodiments, the host cell is an in-vitro cultured human cell.

While it may be optimal to express the R protein using heterologous promoters, the native promoter of the corresponding R gene may be used.

The termination region may be native with the transcriptional initiation region, may be native with the operably linked R protein coding region of interest, may be native with the plant host, or may be derived from another source (i.e., foreign or heterologous to the promoter, the R protein of interest, and/or the plant host), or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression of the R protein coding sequences within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Also of interest are the native promoters from other resistance genes from the target species. These promoters are often pathogen-inducible, and are likely to express the resistance gene at appropriate levels and in appropriate tissues. Examples of such promoters are the Sr57/Lr34, Sr33, and Sr35 promoters of wheat (Risk et al. (2012) *Plant Biotechnol J* 10: 447-487; Periyannan et al. (2013) *Science* 341: 786-788; Saintenac et al. (2013) *Science* 341: 783-786).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not intended to be limiting. Any selectable marker gene can be used in the present invention.

Numerous plant transformation vectors and methods for transforming plants are available. See, for example, An, G. et al. (1986) *Plant Pysiol.*, 81:301-305; Fry, J., et al. (1987) *Plant Cell Rep.* 6:321-325; Block, M. (1988) *Theor. Appl Genet.* 76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene.* 118:255-260; Christou, et al. (1992) *Trends. Biotechnol.* 10:239-246; D'Halluin, et al. (1992) Bio/Technol. 10:309-314; Dhir, et al. (1992) *Plant Physiol.* 99:81-88; Casas et al. (1993) *Proc. Nat. Acad Sci. USA* 90:11212-11216; Christou, P. (1993) *In Vitro Cell. Dev. Biol.-Plant;* 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; Guo Chin Sci. Bull. 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; and Wan, Y. C. and Lemaux, P. G. (1994) *Plant Physiol.* 104:3748.

Plant transformation vectors that find use in the present invention include, for example, T-DNA vectors or plasmids, which are suitable for use in *Agrobacterium*-mediated transformation methods that are disclosed elsewhere herein or otherwise known in the art. Examples of such T-DNA vectors or plasmids are the IHP_0205_NLR-A_construct (SEQ ID NO: 15), the IHP_0300_NLR-A_native construct (SEQ ID NO: 34), and the pBract202_TSL_pMla6_NLR-A_CDS_gDNA_tMla6 construct (SEQ ID NO: 35). The IHP_0205_NLR-A_construct (SEQ ID NO: 15) comprises a hygromycin resistance gene driven by a 35S promoter and nos terminator followed by 2.4 kb promoter, exons 1, 2, and 3, intron 3, exon 4, and 1.8 kb terminator of NLR-A, flanked by the left (LB) and right (RB) T-DNA border sequences, and further comprises two replication origin sites (pSa-ORI and colEI-ori) and kanamycin resistance (npt1). The IHP_0300_NLR-A_native construct (SEQ ID NO: 34) comprises a hygromycin resistance gene driven by a 35S promoter and nos terminator followed by the native sequence of NLR-A containing all four exons and three introns that is approximately 17 kb in length, flanked by the left (LB) and right (RB) T-DNA border sequences, and further comprises two replication origin sites (pSa-ORI and colEI-ori) and kanamycin resistance (npt1). The pBract202_TSL_pMla6_NLR-A_CDS_gDNA_tMla6 construct (SEQ ID NO: 35) comprises a hygromycin resistance gene driven by a 35S promoter and nos terminator followed by 1.2 kb of promoter sequence, a 464 bp 5'UTR of Mla6 (GenBank Acession No. AJ302293), the native coding sequence of NLR-A containing exons 1, 2, and 3 and introns 1 and 2 that is approximately 12 kb, 47 bp 3'-UTR of Mla6, and a 1.6 kb terminator from Mla6, flanked by the left (LB) and right (RB) T-DNA border sequences, and further comprises two replication origin sites (pSa-ORI and colEI-ori) and kanamycin resistance (npt1).

The methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.*, 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *Proc. Natl. Acad. Sci. USA* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

If desired, the modified viruses or modified viral nucleic acids can be prepared in formulations. Such formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al. Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, antifreezing agents, for seed treatment formulation also optionally colorants and/or binders and/or gelling agents.

In specific embodiments, the polynucleotide constructs and expression cassettes of the invention can be provided to a plant using a variety of transient transformation methods known in the art. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *PNAS Sci.* 91: 2176-2180 and Hush et al. (1994) *J. Cell Science* 107:775-784, all of which are herein incorporated by reference. Alternatively, the polynucleotide can be transiently transformed into the plant using techniques known in the art. Such techniques include viral vector system and *Agrobacterium tumefaciens*-mediated transient expression as described elsewhere herein.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

In certain embodiments of the invention, the nucleotide sequence of a non-functional allele at an R gene locus of the present invention can be modified in planta to a functional allele that provides resistance to at least one race of a plant pathogen. In one embodiment of the invention, a non-functional allele that is present at the Rps6 locus in a barley plant can be modified to a functional allele that provides resistance to, for example, at least one, two, three, or four races of *Puccinia striiformis* f. sp. *tritici*. In another embodiment of the invention, a non-functional allele that is present at the Rps6 locus in a barley plant can be modified to a functional allele that provides resistance to at least one, two, three, or four races of at least two *Puccinia* spp. that cause rust disease on a barley plant. For example, a non-functional allele at the Rps6 locus can be modified to form whereby the modified allele comprises the nucleotide sequence of Rps6 set forth in SEQ ID NO: 1. In another example, a non-functional allele at the Rps6 locus can be modified to form whereby the modified allele comprises a coding sequence comprising the nucleotide sequence set forth in SEQ ID NO: 3, 6, 8, 10, 12, or 14, or variant thereof and/or encodes an amino acid sequence comprising the amino acid sequence set forth in SEQ ID NO: 3, 6, 8, 10, 12, or 14, or variant thereof.

Any methods known in the art for modifying DNA in the genome of a plant can be used to modify the nucleotide sequences of an R gene in planta, e.g. to modify the nucleotide sequence of a non-functional allele to that of a functional allele that provides resistance to a plant pathogen. Such modifications to the DNA in the genome of a plant include, for example, insertions, deletions, substitutions, and combinations thereof. The insertions, deletions, and substitutions can be made using any method known in the art such as, for example, by genome editing techniques as described elsewhere herein or otherwise known in the art.

The insertions comprise an insertion of at least one nucleotide or base pair (bp) in an allele of an R gene of the present invention. The insertion can comprise insertion of any size DNA fragment into the genome. The inserted DNA can be 1 bp in length, 1-5 bp in length, 5-10 bp in length, 10-15 bp in length, 15-20 bp in length, 20-30 bp in length, 30-50 bp in length, 50-100 bp in length, 100-200 bp in length, 200-300 bp in length, 300-400 bp in length, 400-500 bp in length, 500-600 bp in length, 600-700 bp in length, 700-800 bp in length, 800-900 bp in length, 900-1000 bp in length, 1000-1500 bp.

The deletions comprise the deletion of at least one bp from an allele of an R gene of the present invention. As used herein, a "deletion" is meant the removal of one or more nucleotides or base pairs from the DNA. Provided herein, a deletion in an allele of an R gene can be the removal of at least 1, at least 20, at least 50, at least 100, at least 500, at least 1000, at least 5000 or more bp.

The substitutions comprise the replacement of at least one bp from an allele of an R gene of the present invention with another bp. As used herein, a "substitution" is meant the replacement of one or more nucleotides or base pairs from the DNA with non-identical nucleotides or base pairs. When the substitution comprises two or more nucleotides, the two or more nucleotides can be contiguous or non-contiguous within the DNA sequence of the allele. Provided herein, a substitution in an allele of an R gene can be the replacement of at least 1, at least 20, at least 50, at least 100, at least 500, at least 1000, at least 5000 or more base pairs. In some embodiments, the substitution can be the nucleotide sequence of the entire allele or any portion or portions thereof such as, for example, the transcribed region, the 5' untranslated region, the 3' untranslated region, an exon, or an intron.

In certain embodiments of the invention, the modification of a non-functional allele at an R gene locus is a homozygous modification. By "homozygous modification" is meant that the modification is in both alleles of the R gene locus in a particular genome of a plant. In other cases, the modification of the R gene locus gene is heterozygous, that is, the modification is only in one allele of the of the R gene locus in the genome of a plant. It is recognized the plants of the invention include, for example, crop plants with genomes that are diploid or polyploid (e.g. tetraploid or hexaploid), including autopolyploids and allopolyploids. An autopolyploid is an organism having more than two sets of chromosomes, all of which were derived from the same species. An allopolyploid is an organism having two or more complete sets of chromosomes that are derived from different species. Depending on the particular the crop plant, 1, 2, 3, 4, 5, 6 or more alleles at an R gene locus of the plant can be modified using the methods disclosed.

Such methods known in the art for modifying DNA in the genome of a plant include, for example, genome editing techniques, such as, for example, methods involving targeted mutagenesis, homologous recombination, and mutation breeding. Targeted mutagenesis or similar techniques are disclosed in U.S. Pat. Nos. 5,565,350; 5,731,181; 5,756,325; 5,760,012; 5,795,972, 5,871,984, and 8,106,259; all of which are herein incorporated in their entirety by reference. Methods for gene modification or gene replacement comprising homologous recombination can involve inducing double breaks in DNA using zinc-finger nucleases (ZFN), TAL (transcription activator-like) effector nucleases (TALEN), Clustered Regularly Interspaced Short Palindromic Repeats/CRISPR-associated nuclease (CRISPR/Cas nuclease), or homing endonucleases that have been engineered endonucleases to make double-strand breaks at specific recognition sequences in the genome of a plant, other organism, or host cell. See, for example, Durai et al., (2005) *Nucleic Acids Res* 33:5978-90; Mani et al. (2005) *Biochem Biophys Res Comm* 335:447-57; U.S. Pat. Nos. 7,163,824, 7,001,768, and 6,453,242; Arnould et al. (2006) *J Mol Biol* 355:443-58; Ashworth et al., (2006) *Nature* 441:656-9; Doyon et al. (2006) *J Am Chem Soc* 128:2477-84; Rosen et al., (2006) *Nucleic Acids Res* 34:4791-800; and Smith et al., (2006) *Nucleic Acids Res* 34:e149; U.S. Pat. App. Pub. No. 2009/0133152; and U.S. Pat. App. Pub. No. 2007/0117128; all of which are herein incorporated in their entirety by reference.

TAL effector nucleases (TALENs) can be used to make double-strand breaks at specific recognition sequences in the genome of a plant for gene modification or gene replacement through homologous recombination. TAL effector nucleases are a class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze and Boch (2010) *Virulence* 1:428-432; Christian et al. *Genetics* (2010) 186:757-761; Li et al. (2010) *Nuc. Acids Res.* (2010) doi: 10.1093/nar/gkq704; and Miller et al. (2011) *Nature Biotechnology* 29:143-148; all of which are herein incorporated by reference.

The CRISPR/Cas nuclease system can also be used to make double-strand breaks at specific recognition sequences in the genome of a plant for gene modification or gene replacement through homologous recombination. The CRISPR/Cas nuclease is an RNA-guided (simple guide RNA, sgRNA in short) DNA endonuclease system performing sequence-specific double-stranded breaks in a DNA segment homologous to the designed RNA. It is possible to design the specificity of the sequence (Cho S. W. et al., Nat. Biotechnol. 31:230-232, 2013; Cong L. et al., Science 339:819-823, 2013; Mali P. et al., Science 339:823-826, 2013; Feng Z. et al., Cell Research: 1-4, 2013).

In addition, a ZFN can be used to make double-strand breaks at specific recognition sequences in the genome of a plant for gene modification or gene replacement through homologous recombination. The Zinc Finger Nuclease (ZFN) is a fusion protein comprising the part of the FokI restriction endonuclease protein responsible for DNA cleavage and a zinc finger protein which recognizes specific, designed genomic sequences and cleaves the double-stranded DNA at those sequences, thereby producing free DNA ends (Urnov F. D. et al., Nat Rev Genet. 11:636-46, 2010; Carroll D., Genetics. 188:773-82, 2011).

Breaking DNA using site specific nucleases, such as, for example, those described herein above, can increase the rate of homologous recombination in the region of the breakage. Thus, coupling of such effectors as described above with nucleases enables the generation of targeted changes in genomes which include additions, deletions and other modifications.

Mutation breeding can also be used in the methods and compositions provided herein. Mutation breeding methods can involve, for example, exposing the plants or seeds to a mutagen, particularly a chemical mutagen such as, for example, ethyl methanesulfonate (EMS) and selecting for plants that possess a desired modification in the Rps6 gene. However, other mutagens can be used in the methods disclosed herein including, but not limited to, radiation, such as X-rays, Gamma rays (e.g., cobalt 60 or cesium 137), neutrons, (e.g., product of nuclear fission by uranium 235 in an atomic reactor), Beta radiation (e.g., emitted from radio-isotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Further details of mutation breeding can be found in "Principals of Cultivar Development" Fehr, 1993 Macmillan Publishing Company the disclosure of which is incorporated herein by reference.

The nucleic acid molecules, expression cassettes, vectors, and polynucleotide constructs of the present invention may be used for transformation of any plant species, including, but not limited to, monocots and dicots. Preferred plants of the present invention are grass plants including domesticated and non-domesticated species in the Poaceae family such as, for example, turfgrasses, sugarcane, grain plants, and bamboos. More preferred plants are grain plants including, but not limited to, wheat, barley, oats, maize, rice, sorghum, rye, millet, spelt, and triticale.

As used herein, the term "barley plant" generally refers to a plant that is a member of the species *Hordeum vulgare* L. including, but not limited to, two-rowed barley with shattering spikes (wild barley; previously classified as *H. spontaneum* K. Koch), two-rowed barley with non-shattering spikes (previously classified as *H. distichum* L.), six-row barley with non-shattering spikes (previously classified as *H. hexastichum* L.), and six-row with shattering spikes (previously classified as *H. agriocrithon* Aber).

As used herein, the term "wheat plant" generally refers to a plant that is a member of the *Triticum* genus or a member of another genus within the Triticeae tribe, particularly a member of another genus that is capable of producing interspecific hybrids with at least one *Triticum* sp. Examples of such another genus within the Triticeae tribe are *Aegilops* and *Secale*.

The wheat plants of the present invention include, for example, domesticated and non-domesticated plants. The wheat plants of the present invention include, but are not limited to, the following *Triticum*, *Aegilops* and *Secale* species: *T. aestivum, T. monococcum, T. turgidum, T. boeoticum, T. timopheevii,* and *T. urartu, A. tauschii, S. cereale,* and hybrids thereof. Examples of *T. aestivum* subspecies included within the present invention are *aestivum* (common wheat), *compactum* (club wheat), *macha* (macha wheat), *vavilovi* (vavilovi wheat), spelt (*T. spelta*), and *sphaerococcum* (shot wheat). Examples of *T. turgidum* subspecies included within the present invention are *turgidum, carthlicum, dicoccom, durum, paleocoichicum, polonicum, turanicum,* and *dicoccoides*. Examples of *T. monococcum* subspecies included within the present invention are *monococcum* (einkorn) and *aegilopoides*. In one embodiment of the present invention, the wheat plant is a member of the *Triticum turgidum* species; and in particular, a member of the *Durum* subspecies, for example, a Ciccio, Colosseo, or Utopia cultivar. It is recognized that a wheat plant of the present invention can be a domesticated or a non-domesticated wheat plant.

The present invention also encompasses triticale plants, triticale plant parts, and triticale plant cells comprising an R gene of the invention. As used herein, a "triticale plant" refers to a plant that is created by crossing a rye plant (*Secale cereale*) with either a tetraploid wheat plant (e.g. *Triticum turgidum*) or a hexaploid wheat plant (e.g. *Triticum aestivum*). The present invention also includes seeds produced by the triticale plants described herein and methods for controlling weeds in the vicinity of the triticale plants described herein. As used herein, the term "wheat plant" encompasses triticale plants unless stated otherwise or apparent from the context of use.

Examples of plant species of interest include, but are not limited to, peppers (*Capsicum* spp; e.g., *Capsicum annuum, C. baccatum, C. chinense, C. frutescens, C. pubescens,* and the like), tomatoes (*Lycopersicon esculentum*), tobacco (*Nicotiana tabacum*), eggplant (*Solanum melongena*), petunia (*Petunia* spp., e.g., *Petunia×hybrida* or *Petunia hybrida*), pea (*Pisum sativum*), bean (*Phaseolus vulgaris*), corn or maize (*Zea mays*), *Brassica* sp. (e.g., *B. napus, B. rapa, B. juncea*), particularly those *Brassica* species useful as sources of seed oil, alfalfa (*Medicago saliva*), rice (*Oryza sativa*), rye (*Secale cereale*), sorghum (*Sorghum bicolor, Sorghum vulgare*), millet (e.g., pearl millet (*Pennisetum* glaucum), proso millet (*Panicum miliaceum*), foxtail millet (*Setaria italica*), finger millet (*Eleusine coracana*)), sunflower (*Helianthus annuus*), safflower (*Carthamus tinctorius*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), strawberry (e.g. *Fragaria×ananassa, Fragaria vesca, Fragaria moschata, Fragaria virginiana, Fragaria chiloensis*), sweet potato (*Ipomoea batatus*), cassava (*Manihot esculenta*), coffee (*Coffea* spp.), coconut (*Cocos nucifera*), oil palm (e.g. *Elaeis guineensis, Elaeis oleifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena sativa*), barley (*Hordeum vulgare*), *Brachypodium distachyon* and other *Brachypodium* spp., switchgrass (*Panicum virgatum*) turfgrasses (e.g. *Poa pratensis, Festuca arundinacea, Festuca* spp., *Cynodon dactylon, Cynodon* spp., *Lolium perenne, Lolium multiflorum, Agrostis palustris, Zoysia japonica, Zoysia* spp., *Stenotaphrum secundatum, Eremochloa ophiuroides*), vegetables, ornamentals, and conifers. In specific embodiments, plants of the present invention are crop plants (e.g. maize, sorghum, wheat, millet, rice, barley, oats, sugarcane, alfalfa, soybean, peanut, sunflower, cotton, safflower, *Brassica* spp., lettuce, strawberry, apple, and citrus etc.).

Vegetables include, but are not limited to, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include, for example, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

As used herein, the term "plant" is intended to encompass plants at any stage of maturity or development, any plant part or parts taken or derived from any such plant unless otherwise clearly indicated by context. As used herein, the term "plant" includes, for example, plant cells, plant protoplasts, plant cell tissue cultures from which plants can be regenerated, plant calli, plant clumps, and plant cells that are intact in plants or parts of plants such as embryos, pollen, ovules, seeds, tubers, propagules, leaves, flowers, branches, fruits, roots, root tips, anthers, and the like. Plant parts include, but are not limited to, plant organs, stems, roots, flowers, ovules, stamens, leaves, embryos, meristematic regions, plant tissues, callus tissue, anther cultures, gametophytes, sporophytes, pollen, microspores, plant cells, protoplasts, and the like. The term "plant" is also intended to encompass a seed. Progeny, variants, and mutants of the regenerated plants are also included within the scope of the invention, provided that these parts comprise the introduced polynucleotides. As used herein, "progeny" and "progeny plant" comprise any subsequent generation of a plant whether resulting from sexual reproduction and/or asexual propagation, unless it is expressly stated otherwise or is apparent from the context of usage.

In some embodiments of the present invention, a plant cell is transformed with a polynucleotide construct encoding an R protein of the present invention. The term "expression" as used herein refers to the biosynthesis of a gene product, including the transcription and/or translation of said gene product. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide. Examples of polynucleotide constructs and nucleic acid molecules that encode R proteins are described elsewhere herein.

The use of the terms "DNA" or "RNA" herein is not intended to limit the present invention to polynucleotide molecules comprising DNA or RNA. Those of ordinary skill in the art will recognize that the methods and compositions of the invention encompass polynucleotide molecules comprised of deoxyribonucleotides (i.e., DNA), ribonucleotides (i.e., RNA) or combinations of ribonucleotides and deoxyribonucleotides. Such deoxyribonucleotides and ribonucleotides include both naturally occurring molecules and synthetic analogues including, but not limited to, nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The polynucleotide molecules of the invention also encompass all forms of polynucleotide molecules including, but not limited to, single-stranded forms, double-stranded forms, hairpins, stem-and-loop structures, and the like. Furthermore, it is understood by those of ordinary skill in the art that the nucleotide sequences disclosed herein also encompasses the complement of that exemplified nucleotide sequence.

The invention is drawn to compositions and methods for producing a plant with enhanced resistance to a plant disease caused by a plant pathogen, particularly to compositions and methods for producing a plant with enhanced resistance to wheat stripe rust caused by Pst, more particularly to compositions and methods for producing a wheat or barley plant with enhanced resistance to wheat stripe rust caused by Pst. By "resistance to a plant disease" or "disease resistance" is intended that the plants avoid the disease symptoms that are the outcome of plant-pathogen interactions. That is, one or more pathogens are prevented from causing a plant disease or plant diseases and the associated disease symptoms, or alternatively, the disease symptoms caused by the one or more pathogens is minimized or lessened.

The present invention encompasses the polynucleotide constructs disclosed herein or in the accompanying sequence listing and/or drawings including, but not limited to, a polynucleotide construct comprising a nucleotide sequence selected from the group consisting of SEQ ID NOS: 17-19. The present invention further encompasses plants, plant cells, host cells, and vectors comprising at least one of such polynucleotide constructs, as well as food products produced from such plants. Additionally encompassed by the present invention are uses of plants comprising at least one of such polynucleotide constructs in the methods disclosed elsewhere herein such as, for example, methods of limiting wheat stripe rust in agricultural crop production.

Plant pathogens include, for example, bacteria, insects, nematodes, fungi, oomycetes, and the like. The preferred pathogens of the present invention are fungal pathogens, particularly fungal pathogens that cause rust diseases, including, but not limited to, *Puccinia brachypodii* (purple false brome rust), *Puccinia coronata* (crown rust), *Puccinia graminis* (stem rust), *Puccinia striiformis* (stripe rust), *Puccinia pseudostriiformis* (stripe rust), *Puccinia pseudo-hordei* (barley grass stripe rust), *Puccinia gansensis* (stripe rust), *Puccinia striiformoides* (stripe rust), *Puccinia hordei* (barley leaf rust), *Puccinia recondita* (wheat leaf rust), *Puccinia sorghi* (maize leaf rust), *Puccinia poae-nemoralis*, *Puccinia poarum*, *Puccinia emaculata*, and *Uromyces dactylidis*. It is believed that the Rps6 nucleotide sequences of the present invention are capable of conferring resistance against rust diseases caused by one or more of these fungal pathogens. See Castro et al. (2003) *Theor. Appl. Genet.* 107:922-930, Derevnina et al. (2015) *Theor. Appl. Genet.* 128: 187-197, and Niks et al. (2013) *Eur. J. Plant Pathol.* 136:393-405; herein incorporated by reference. Other plant pathogens of interest for the present invention are *Blumeria graminis* (powdery mildew) and *Magnaporthe grisea* (also known as *M. oryzae*; blast disease). It has been reported that resistance to powdery mildew and blast disease in barley both map in vicinity of Rps6 suggesting that Rps6 may be capable of conferring resistance to powdery mildew and/or blast disease in addition to being capable of conferring resistance to stripe rust. See Schonfeld et al. (1996) *Theor. Appl. Genet.* 93:48-56, herein incorporated by reference.

In some preferred embodiments, the present invention provides plants and methods of producing plants comprising enhanced resistance to at least one race of *Puccinia striiformis* f. sp. *tritici*. In other preferred embodiments, the present invention provides plants and methods of producing plants comprising enhanced resistance to multiple races of *Puccinia striiformis* f. sp. *tritici*. As used herein, "multiple races" is intended to mean at least two races of a particular plant pathogen, but preferably three, four, five or more races of the plant pathogen.

Other fungal pathogens of interest are those that cause diseases in grain crop plants including, for example, *Ustilago nuda* (barley loose smut), *Ustilago triticiv* (wheat loose smut), *Ustilago nigra* (barley false loose smut), *Ustilago avenae* (oat loose smut), *Ustilago kolleri* (oat covered smut), and *Ustilago maydis* (maize smut).

Other pathogens for the major crops include: Soybeans: *Phytophthora megasperma* fsp. *glycinea*, *Macrophomina phaseolina*, *Rhizoctonia solani*, *Sclerotinia sclerotiorum*, *Fusarium oxysporum*, *Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Septoria glycines*, *Phyllosticta sojicola*, *Alternaria alternata*, *Pseudomonas syringae* p.v. *glycinea*, *Xanthomonas campestris* p.v. *phaseoli*, *Microsphaera diffusa*, *Fusarium semitectum*, *Phialophora gregata*, Soybean mosaic virus, *Glomerella glycines*, Tobacco Ring spot virus, Tobacco Streak virus, *Phakopsora pachyrhizi*, *Pythium aphanidermatum*, *Pythium ultimum*, *Pythium debaryanum*, Tomato spotted wilt virus, *Heterodera glycines Fusarium solani*; Canola: *Albugo candida*, *Alternaria brassicae*, *Leptosphaeria maculans*, *Rhizoctonia solani*, *Sclerotinia sclerotiorum*, *Mycosphaerella brassicicola*, *Pythium ultimum*, *Peronospora parasitica*, *Fusarium roseum*, *Alternaria alternata*; Alfalfa: *Clavibacter michiganese* subsp. *insidiosum*, *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, *Fusarium oxysporum*, *Verticillium albo-atrum*, *Xanthomonas campestris* p.v. *alfalfae*, *Aphanomyces euteiches*, *Stemphylium herbarum*, *Stemphylium alfalfae*, *Colletotrichum trifolii*, *Leptosphaerulina briosiana*, *Uromyces striatus*, *Sclerotinia trifoliorum*, *Stagonospora meliloti*, *Stemphylium botryosum*, *Leptotrichila medicaginis*; Wheat: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f. sp. *tritici*, *Puccinia graminis* f. sp. *tritici*, *Puccinia recondita* f. sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea*, *Tilletia tritici*, *Tilletia laevis*, *Ustilago tritici*, *Tilletia indica*, *Rhizoctonia solani*, *Pythium arrhenomannes*, *Pythium gramicola*, *Pythium aphanidermatum*, High Plains Virus, European wheat striate virus; Sunflower: *Plasmopora halstedii*, *Sclerotinia sclerotiorum*, Aster Yellows, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthi*, *Verticillium dahliae*, *Envinia carotovorum* pv. *carotovora*, *Cephalosporium acremonium*, *Phytophthora cryptogea*, *Albugo tragopogonis*; Corn: *Colletotrichum graminicola*, *Fusarium moniliforme* var. *subglutinans*, *Envinia stewartii*, *F. verticillioides*, *Gibberella zeae* (*Fusarium graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum*, *Physoderma maydis*, *Phyllosticta maydis*, *Kabatiella maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganense* subsp. *nebraskense*, *Trichoderma viride*, Maize Dwarf Mosaic Virus A & B, Wheat Streak Mosaic Virus, Maize Chlorotic Dwarf Virus, *Claviceps sorghi*, *Pseudonomas avenae*, *Envinia chrysanthemi* pv. *zea*, *Envinia carotovora*, Corn stunt spiroplasma, *Diplodia macrospora*, *Sclerophthona macrospora*, *Peronosclerospora sorghi*, *Peronosclerospora philippinensis*, *Peronosclerospora maydis*, *Peronosclerospora sacchari*, *Sphacelotheca reiliana*, *Physopella zeae*, *Cephalosporium maydis*, *Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum*, *C. sublineolum*, *Cercospora sorghi*, *Gloeocercospora sorghi*, *Ascochyta sorghina*, *Pseudomonas syringae* p.v. *syringae*, *Xanthomonas campestris* p.v. *holcicola*, *Pseudomonas andropogonis*, *Puccinia purpurea*, *Macro-*

*phomina phaseolina, Perconia circinata, Fusarium moniliforme, Alternaria alternata, Mpolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.; Tomato: *Corynebacterium michiganense* pv. *michiganense, Pseudomonas syringae* pv. tomato, *Ralstonia solanacearum, Xanthomonas vesicatoria, Xanthomonas perforans, Alternaria solani, Alternaria porri, Collectotrichum* spp., *Fulvia fulva* Syn. *Cladosporium fulvum, Fusarium oxysporum* f. *lycopersici, Leveillula taurica/Oidiopsis taurica, Phytophthora infestans*, other *Phytophthora* spp., *Pseudocercospora fuligena* Syn. *Cercospora fuligena, Sclerotium rolfsii, Septoria lycopersici, Meloidogyne* spp.; Potato: *Ralstonia solanacearum, Pseudomonas solanacearum, Envinia carotovora* subsp. *Atroseptica Envinia carotovora* subsp. *Carotovora, Pectobacterium carotovorum* subsp. *Atrosepticum, Pseudomonas fluorescens, Clavibacter michiganensis* subsp. *Sepedonicus, Corynebacterium sepedonicum, Streptomyces scabiei, Colletotrichum coccodes, Alternaria alternate, Mycovellosiella concors, Cercospora solani, Macrophomina phaseolina, Sclerotium bataticola, Choanephora cucurbitarum, Puccinia pittieriana, Aecidium cantensis, Alternaria solani, Fusarium* spp., *Phoma solanicola* f. *foveata, Botrytis cinerea, Botryotinia fuckeliana, Phytophthora infestans, Pythium* spp., *Phoma andigena* var. *andina, Pleospora herbarum, Stemphylium herbarum, Erysiphe cichoracearum, Spongospora subterranean Rhizoctonia solani, Thanatephorus cucumeris, Rosellinia* sp. *Dematophora* sp., *Septoria lycopersici, Helminthosporium solani, Polyscytalum pustulans, Sclerotium rolfsii, Athelia rolfsii, Angiosorus solani, Ulocladium atrum, Verticillium albo-atrum, V. dahlia, Synchytrium endobioticum, Sclerotinia sclerotiorum, Candidatus Liberibacter solanacearum*; Banana: *Colletotrichum musae, Armillaria mellea, Armillaria tabescens, Pseudomonas solanacearum, Phyllachora musicola, Mycosphaerella fijiensis, Rosellinia bunodes, Pseudomas* spp., *Pestalotiopsis leprogena, Cercospora hayi, Pseudomonas solanacearum, Ceratocystis paradoxa, Verticillium theobromae, Trachysphaera fructigena, Cladosporium musae, Junghuhnia vincta, Cordana johnstonii, Cordana musae, Fusarium pallidoroseum, Colletotrichum musae, Verticillium theobromae, Fusarium* spp., *Acremonium* spp., *Cylindrocladium* spp., *Deightoniella torulosa, Nattrassia mangiferae, Dreschslera gigantean, Guignardia musae, Botryosphaeria ribis, Fusarium solani, Nectria haematococca, Fusarium oxysporum, Rhizoctonia* spp., *Colletotrichum musae, Uredo musae, Uromyces musae, Acrodontium simplex, Curvularia eragrostidis, Drechslera musae-sapientum, Leptosphaeria musarum, Pestalotiopsis disseminate, Ceratocystis paradoxa, Haplobasidion musae, Marasmiellus inoderma, Pseudomonas solanacearum, Radopholus similis, Lasiodiplodia theobromae, Fusarium pallidoroseum, Verticillium theobromae, Pestalotiopsis palmarum, Phaeoseptoria musae, Pyricularia grisea, Fusarium moniliforme, Gibberella fujikuroi, Envinia carotovora, Envinia chrysanthemi, Cylindrocarpon musae, Meloidogyne arenaria, Meloidogyne incognita, Meloidogyne javanica, Pratylenchus coffeae, Pratylenchus goodeyi, Pratylenchus brachyurus, Pratylenchus reniformia, Sclerotinia sclerotiorum, Nectria foliicola, Mycosphaerella musicola, Pseudocercospora musae, Limacinula tenuis, Mycosphaerella musae, Helicotylenchus multicinctus, Helicotylenchus dihystera, Nigrospora sphaerica, Trachysphaera frutigena, Ramichloridium musae*, and *Verticillium theobromae*.

Non-limiting examples of the compositions and methods of the present invention are as follows:

1. A nucleic acid molecule comprising a member selected from the group consisting of:
   (a) a barley Rps6 gene;
   (b) the nucleotide sequence set forth in SEQ ID NO: 1, 2, 5, 7, 9, 11, 13, 15, 34, or 35;
   (c) a nucleotide sequence encoding the amino acid sequence set forth in SEQ ID NO: 3, 6, 8, 10, 12, or 14;
   (d) a nucleotide sequence having at least 85% nucleotide sequence identity to at least one of the full-length nucleotide sequences set forth in SEQ ID NOS: 1, 2, 5, 7, 9, 11, and 13, wherein the nucleic acid molecule is capable of conferring resistance to wheat stripe rust to a plant comprising the nucleic acid molecule; and
   (e) a nucleotide sequence encoding a polypeptide having at least 85% amino acid sequence identity to at least one of the full-length amino acid sequence set forth in SEQ ID NOS: 3, 6, 8, 10, 12, and 14, wherein the nucleic acid molecule is capable of conferring resistance to wheat stripe rust to a plant comprising the nucleic acid molecule.
2. The nucleic acid molecule of embodiment 1, wherein the nucleic acid molecule is an isolated nucleic acid molecule.
3. The nucleic acid molecule of embodiment 1 or 2, wherein the nucleic acid molecule is not naturally occurring.
4. The nucleic acid molecule of embodiment 1 or 2, wherein the barley Rps6 gene is the barley Rps6 gene that is located in the region of the genome of a barley plant corresponding to SEQ ID NO: 4.
5. The nucleic acid molecule of any one of embodiments 1-4, wherein the nucleic acid molecule of (d) or (e) encodes a protein comprising a coiled-coil domain, a nucleotide-binding domain, and a leucine-rich repeat domain.
6. The nucleic acid molecule of embodiment 5, wherein at least one of the coiled-coil domain, the nucleotide-binding domain, and the leucine-rich repeat domain comprises an amino acid sequence having at least 95%, 96%, 97%, 98%, 99%, or 100% to the corresponding domain in SEQ ID NO: 3.
7. An expression cassette comprising the nucleic acid molecule of any one of embodiments 1-6 and an operably linked heterologous promoter.
8. A vector comprising the nucleic acid molecule of any one of embodiments 1-6 or the expression cassette of embodiment 7.
9. A host cell transformed with the nucleic acid molecule of any one of embodiments 1-6, the expression cassette of embodiment 7, or the vector of embodiment 8.
10. The host cell of embodiment 9, wherein the host cell is a plant cell, a bacterium, a fungal cell, or an animal cell.
11. The host cell of embodiment 9 or 10, wherein the plant cell is a barley plant cell, a wheat plant cell, or a *Brachypodium distachyon* plant cell.
12. A plant or seed transformed with the nucleic acid molecule of any one of embodiments 1-6, the expression cassette of embodiment 7, or the vector of embodiment 8.
13. The plant or seed of embodiment 12, wherein the plant is a wheat plant or a barley plant and the seed is wheat seed or barley seed.

14. A transgenic plant or seed comprising stably incorporated in its genome a polynucleotide construct comprising a member selected from the group consisting of:
   (a) a barley Rps6 gene;
   (b) the nucleotide sequence set forth in SEQ ID NO: 1, 2, 5, 7, 9, 11, or 13;
   (c) a nucleotide sequence encoding the amino acid sequence set forth in SEQ ID NO: 3, 6, 8, 10, 12, or 14;
   (d) a nucleotide sequence having at least 85% nucleotide sequence identity to at least one of the full-length nucleotide sequences set forth in SEQ ID NOS: 1, 2, 5, 7, 9, 11, and 13, wherein the nucleic acid molecule is capable of conferring resistance to wheat stripe rust to a plant comprising the nucleic acid molecule; and
   (e) a nucleotide sequence encoding a polypeptide having at least 85% amino acid sequence identity to at least one of the full-length amino acid sequence set forth in SEQ ID NOS: 3, 6, 8, 10, 12, and 14, wherein the nucleic acid molecule is capable of conferring resistance to wheat stripe rust to a plant comprising the nucleic acid molecule.

15. The transgenic plant or seed of embodiment 14, wherein the nucleic acid molecule of (d) or (e) encodes a protein comprising a coiled-coil domain, a nucleotide-binding domain, and a leucine-rich repeat domain.

16. The transgenic plant or seed of embodiment 15, wherein at least one of the coiled-coil domain, the nucleotide-binding domain, and the leucine-rich repeat domain comprises an amino acid sequence having at least 95%, 96%, 97%, 98%, 99%, or 100% to the corresponding domain in SEQ ID NO: 3.

17. The transgenic plant or seed of any one of embodiments 14-16, wherein the polynucleotide construct comprises the nucleotide sequence of any one of (b)-(e) and further comprises a promoter operably linked for the expression of the nucleotide sequence in a plant.

18. The transgenic plant or seed of embodiment 17, wherein the promoter is selected from the group consisting of pathogen-inducible, constitutive, tissue-preferred, wound-inducible, and chemical-regulated promoters.

19. The transgenic plant or seed of any one of embodiments 14-18, wherein the transgenic plant or seed comprises enhanced resistance to wheat stripe rust caused by multiple races of *Puccinia striiformis* f. sp. *tritici*, relative to the resistance of a control plant.

20. The transgenic plant or seed of any one of embodiments 14-19, wherein the transgenic plant is a transgenic wheat plant and the transgenic seed is a transgenic wheat seed.

21. The transgenic plant or seed of any one of embodiments 14-19, wherein the transgenic plant is a transgenic barley plant and the transgenic seed is a transgenic barley seed.

22. The transgenic plant or seed of any one of embodiments 14-19, wherein the transgenic plant is a transgenic *Brachypodium distachyon* plant and the transgenic seed is a transgenic *Brachypodium distachyon* seed.

23. The transgenic plant or seed of any one of embodiments 14-22, wherein the polynucleotide construct is a heterologous nucleic acid molecule.

24. A method for producing a plant with enhanced resistance to a plant disease, the method comprising introducing a polynucleotide construct into at least one plant cell, the polynucleotide construct comprising a member selected from the group consisting of:
   (a) a barley Rps6 gene;
   (b) the nucleotide sequence set forth in SEQ ID NO: 1, 2, 5, 7, 9, 11, or 13;
   (c) a nucleotide sequence encoding the amino acid sequence set forth in SEQ ID NO: 3, 6, 8, 10, 12, or 14;
   (d) a nucleotide sequence having at least 85% nucleotide sequence identity to at least one of the full-length nucleotide sequences set forth in SEQ ID NOS: 1, 2, 5, 7, 9, 11, and 13, wherein the nucleic acid molecule is capable of conferring resistance to the plant disease to a plant comprising the nucleic acid molecule; and
   (e) a nucleotide sequence encoding a polypeptide having at least 85% amino acid sequence identity to at least one of the full-length amino acid sequence set forth in SEQ ID NOS: 3, 6, 8, 10, 12, and 14, wherein the nucleic acid molecule is capable of conferring resistance to the plant disease to a plant comprising the nucleic acid molecule.

25. The method of embodiment 24, wherein the nucleic acid molecule of (d) or (e) encodes a protein comprising a coiled-coil domain, a nucleotide-binding domain, and a leucine-rich repeat domain.

26. The method of embodiment 25, wherein at least one of the coiled-coil domain, the nucleotide-binding domain, and the leucine-rich repeat domain comprises an amino acid sequence having at least 95%, 96%, 97%, 98%, 99%, or 100% to the corresponding domain in SEQ ID NO: 3.

27. The method of any one of embodiments 24-26, wherein the plant disease is a rust disease.

28. The method of any one of embodiments 24-27, wherein the pathogen is in the genus *Puccinia*.

29. The method of any one of embodiments 24-28, wherein the plant is a grass plant.

30. The method of any one of embodiments 24-29, wherein the plant is a grain plant.

31. The method of any one of embodiments 24-30, wherein the plant is barley, wheat, or *Brachypodium distachyon*.

32. The method of any one of embodiments 24-31, wherein the polynucleotide construct is stably incorporated into the genome of the plant cell.

33. The method of any one of embodiments 24-32, wherein the barley, wheat, or *Brachypodium distachyon* plant cell is regenerated into a barley, wheat, or *Brachypodium distachyon* plant comprising in its genome the polynucleotide construct.

34. The method of any one of embodiments 24-33, wherein the polynucleotide construct comprises the nucleotide sequence of any one of (b)-(e) and further comprises a promoter operably linked for the expression of the nucleotide sequence in a plant.

35. The method of embodiment 34, wherein the promoter is selected from the group consisting of pathogen-inducible, constitutive, tissue-preferred, wound-inducible, and chemical-regulated promoters.

36. The method of any one of embodiments 31-35, wherein the barley, wheat, or *Brachypodium distachyon* plant comprising the polynucleotide construct comprises enhanced resistance to wheat stripe rust caused by at least one race of *Puccinia striiformis* f. sp. *tritici*, relative to the resistance of a control barley plant, wheat, or *Brachypodium distachyon*.

37. The method of any one of embodiments 31-35, wherein the barley, wheat, or *Brachypodium distachyon* plant comprising the polynucleotide construct comprises enhanced resistance to wheat stripe rust caused by multiple races of *Puccinia striiformis* f. sp. *tritici*, relative to the resistance of a control barley, wheat, or *Brachypodium distachyon* plant.

38. A plant produced by the method of any one of embodiments 24-37.

39. A seed of the plant of embodiment 38, wherein the seed comprises the polynucleotide construct.

40. A method for producing a barley plant with enhanced resistance to wheat stripe rust, the method comprising modifying in a barley plant or at least one cell thereof, a non-functional allele of the resistance gene Rps6 so as to make a functional allele, whereby the resistance of the barley plant to wheat stripe rust is enhanced.

41. The method of embodiment 40, wherein said modifying a non-functional allele comprises introducing at least one genetic modification selected from the group consisting of an insertion, a deletion, and a substitution of at least one base pair in the non-functional allele.
42. The method of embodiment 40 or 41, wherein said modifying a non-functional allele comprises at least one member selected from the group consisting of targeted mutagenesis, homologous recombination, and mutation breeding.
43. The method of any one of embodiments 40-42, wherein the functional allele comprises a nucleotide sequence selected from the group consisting of:

(a) the nucleotide sequence set forth in SEQ ID NO: 1;

(b) a nucleotide sequence comprising the coding sequence for the amino acid sequence set forth in SEQ ID NO: 3, 6, 8, 10, 12, or 14; and (c) a nucleotide sequence encoding a polypeptide having at least 85% amino acid sequence identity to at least one of the full-length amino acid sequence set forth in SEQ ID NOS: 3, 6, 8, 10, 12, and 14, wherein the nucleic acid molecule is capable of conferring resistance to wheat stripe rust to a plant comprising the nucleic acid molecule.

44. The method of embodiment 43, wherein the polypeptide of (c) comprises a coiled-coil domain, a nucleotide-binding domain, and a leucine-rich repeat domain.
45. The method of embodiment 44, wherein at least one of the coiled-coil domain, the nucleotide-binding domain, and the leucine-rich repeat domain comprises an amino acid sequence having at least 95%, 96%, 97%, 98%, 99%, or 100% to the corresponding domain in SEQ ID NO: 3.
46. The method of any one of embodiments 40-45, wherein the barley plant comprises enhanced resistance to wheat stripe rust caused by multiple races of *Puccinia striiformis* f. sp. *tritici*, relative to the resistance of a control barley plant.
47. A barley plant produced by the method of any one of embodiments 40-46.
48. A seed of the barley plant of embodiment 47, wherein the seed comprises the polynucleotide construct.
49. A method of limiting wheat stripe rust in agricultural crop production, the method comprising planting a seed according to any one of embodiments 12-23, 39, and 48 and growing a plant under conditions favorable for the growth and development of the plant.
50. The method of embodiment 49, further comprising harvesting an at least one seed from the plant.
51. The method of embodiment 49 or 50, wherein the seed is a wheat seed or a barley seed.
52. Use of the plant or seed of any one of embodiments 12-23, 38, 39, 47, and 48 in agriculture.
53. A human or animal food product produced using the plant or seed of any one of embodiments 12-23, 38, 39, 47, and 48.
54. A polypeptide comprising an amino acid sequence selected from the group consisting of:

(a) the amino acid sequence encoded by the nucleotide sequence set forth in SEQ ID NO: 1;

(b) the amino acid sequence encoded by the nucleotide sequence set forth in SEQ ID NO: 2, 5, 7, 9, 11, or 13;

(c) the amino acid sequence set forth in SEQ ID NO: 3, 6, 8, 10, 12, or 14; and (d) an amino acid sequence having at least 85% sequence identity to at least one of the full-length amino acid sequence set forth in SEQ ID NOS: 3, 6, 8, 10, 12, and 14, wherein a polypeptide comprising the amino acid sequence is capable of conferring resistance to stripe rust to a wheat or barley plant comprising the polypeptide, and optionally, wherein the polypeptide is not naturally occurring.

55. The polypeptide of embodiment 54, wherein the polypeptide of (d) comprises a coiled-coil domain, a nucleotide-binding domain, and a leucine-rich repeat domain.
56. The polypeptide of embodiment 55, wherein at least one of the coiled-coil domain, the nucleotide-binding domain, and the leucine-rich repeat domain comprises an amino acid sequence having at least 95%, 96%, 97%, 98%, 99%, or 100% to the corresponding domain in SEQ ID NO: 3.
57. The polypeptide of any one of embodiments 54-56, wherein the polypeptide is an isolated polypeptide.
58. The polypeptide of any one of embodiments 54-57, wherein the polypeptide is not naturally occurring.

Additional embodiments of the methods and compositions of the present invention are described elsewhere herein.

The following examples are offered by way of illustration and not by way of limitation.

EXAMPLES

Example 1: Isolation and Fine Mapping of Rps6

Mapping of Rps6: Differential phenotypes were observed between Abed Binder 12 and Russell inoculated with Pst isolates 08/501 and 08/21. Russell rarely showed pustules but had a clear microscopic phenotype of colonization (FIG. 1). We inoculated the Abed Binder 12×Russell $F_2$ populations with Pst isolate 08/501 (AxR-P st). The parents, $F_1$ and 92 $F_2$ plants were phenotyped using macroscopic and microscopic evaluation of Pst colonization (pCOL). Pustule formation was not observed for the AxR-Pst $F_2$ population, although segregation was observed for chlorosis and pCOL (FIG. 2A-2B). A strong correlation between chlorosis and pCOL was observed ($r^2$=0.88) (FIG. 2C). The $F_1$ displayed a similar resistant phenotype to Abed Binder 12. To map resistance to Pst, we genotyped the AxR-Pst $F_2$ population with the barley oligonucleotide assay (BOPA1; 1,536 SNP-based markers; Close et al. 2009). A total of 535 polymorphic OPA markers were identified between Abed Binder 12 and Russell and they were used to generate a genetic map with eight linkage groups. In addition, 26 CAPS markers and 28 Sequenom MassARRAY markers were used to generate a final map consisting of 589 markers over seven linkage groups, representing 362 non-redundant marker haplotypes and a total genetic distance of 1,131 cM. Quantitative trait locus (QTL) analysis using composite interval mapping with chlorosis and pCOL phenotypes on the AxR-Pst population identified a major effect locus on the long arm of chromosome 7H that was contributed by Abed Binder 12 (FIG. 3). The QTL accounted for 57.7% and 69.4% of the phenotypic variation for chlorosis and pCOL, respectively. In both instances, marker U32_7356_p1, positioned at 169.7 cM, was the most strongly linked marker (Table 1)

TABLE 1

Significant QTLs from composite interval mapping of chlorosis and pCOL phenotypes in the Abed Binder 12 x Russell F$_2$ population inoculated with Pst isolate 08/501

| Trait | Chr[a] | cM | Peak Marker | EWT[b] | LOD | AEE[c] | DEE[d] | D/A[e] | PVE[f] |
|---|---|---|---|---|---|---|---|---|---|
| Chlorosis | 3H | 155.7 | 1_0893 | 4.38 | 6.52 | −0.47 | −0.07 | 0.15 | 0.13 |
| Chlorosis | 7H | 169.7 | U32_7356_p1 | 4.38 | 21.57 | 0.99 | −0.51 | −0.52 | 0.58 |
| pCOL | 3H | 158.3 | 1_0694 | 4.20 | 4.60 | −0.12 | 0.03 | −0.21 | 0.08 |
| pCOL | 7H | 169.7 | U32_7356_p1 | 4.20 | 26.59 | 0.40 | −0.15 | −0.39 | 0.69 |

[a]Chromosome.
[b]Experimental-wide threshold.
[c]Additive effect estimate, positive values indicate the contribution of resistance from Abed Binder 12.
[d]Dominance effect estimate.
[e]Estimate of dominance to additivity ratio.
[f]Percent of the phenotypic variation explained.

Figure 4:
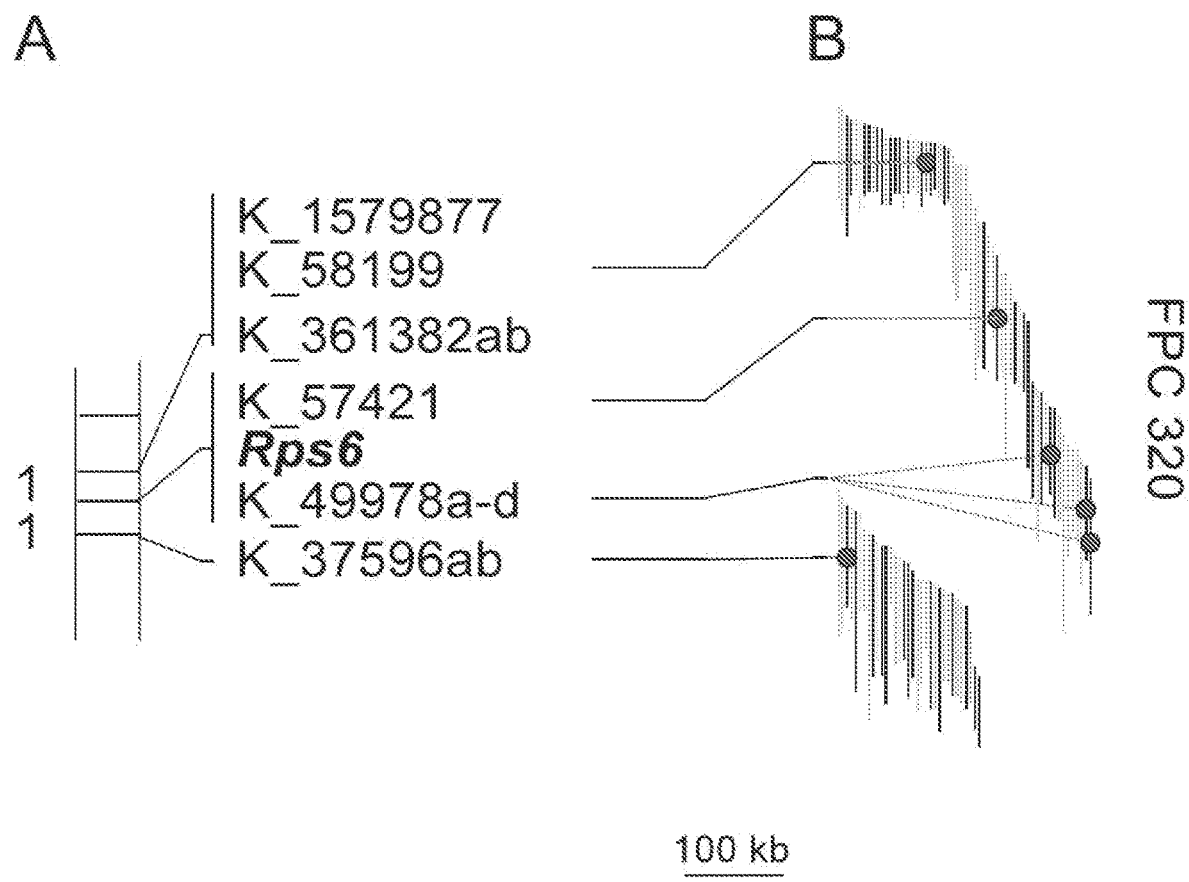
FIG. 4. Fine mapping of Rps6. (A) High-resolution genetic map based on a recombination screen including 2,894 gametes. Numbers shown on left are the number of recombination events between markers. Marker names are shown on the right, with letters after marker names indicating cosegregating KASP markers derived from a single WGS contig. (B) Physical map anchoring based on the high-resolution genetic map. BACs that are sequenced or have BES available are black, otherwise BACs are shown in grey. A truncated FPC 320 is shown based on the anchoring of markers.

Fine mapping Rps6: We carried out a recombination screen and saturated the locus with markers based on the genomic resources available in barley. The recombination screen was carried out using seed bulked from F$_3$ plants that were heterozygous for Rps6 in a F$_{2:3}$ family that segregated only for Rps6. The KASP markers K_2547604b and K_1579285b were generated from Sequenom markers S_43900 and S_3446, respectively, and used as flanking markers that span a 6.0 cM region encompassing Rps6. In total, 2,894 gametes were characterized, identifying 135 recombination events between the flanking markers. Progeny tests were performed using individuals with recombinant chromosomes and scored homozygous or segregating for resistance, or homozygous susceptible. Marker saturation of the Rps6 interval was performed by (1) comparing genomic contigs derived from cultivars Barke, Bowman, and Morex to identify SNPs or (2) by aligning reads from RNAseq on Abed Binder 12 and Russell to whole genome shotgun (WGS) contigs anchored to the Rps6 region (IBGSC (2012) Nature 491:711-716; Mascher et al. (2013) Plant J. 76:718-727). These analyses were performed twice; initially using the anchored contigs from the IBGSC reference anchoring that included 78 contigs between 127.12 cM and 129.21 cM (IBGSC (2012) Nature 491:711-716). Later, a larger interval was investigated including 1,345 contigs between 126.20 cM and 131.44 cM based on an updated anchoring (Mascher et al. (2013) Plant J. 76:718-727). RNAseq data was aligned to WGS contigs and manually curated to identify SNPs polymorphic between Abed Binder 12 and Russell. A total of 102 SNPs were successfully converted into Kompetitive Allele Specific PCR (KASP) markers and surveyed on recombinant individuals in the Rps6 region. In total, 49 KASP markers representing 30 WGS contigs mapped between the Rps6 flanking markers. At a fine scale, contigs mapped in a different order relative to their current anchoring in the barley POPSEQ anchored contigs, although at the rough scale the general order was preserved. The markers collapsed into 18 marker bins and positioned Rps6 in a 0.1 cM region, flanked by K_361382 (proximal) and K_37596 (distal) (FIG. 4). Rps6 is located 0.07 cM from the proximal marker with only two recombination events to be resolved between them. Contrastingly, only a single recombination event differentiates the distal marker with Rps6.

Anchoring of Rps6 to the physical map of barley: The Rps6 locus was anchored to the barley physical map using the available BES and shotgun sequenced BACs in the Rps6 region (IBGSC (2012) Nature 491:711-716). In the proximal region, several KASP markers map to the physical map on FPC 8887 based on BES and sequenced BACs. Using currently available information it is unclear if FPC 8887 is correctly orientated based on our marker order. Marker K_58199 defines a boundary on FPC 320, indicating that K_361382 is located on the physical sequence between K_58199 and K_57421 (FIG. 4). Rps6 cosegregates with markers K_57421 and K_49978, which both map to proximal region of FPC 320. The entire distal region from K_58199 to K_1579285 is well anchored to FPC 320. Annotated genes in the region include MLOC_18254 on contig 1579877 and two NLRs present on contigs 49978 and 37596. The high confidence gene model MLOC_65262 is present on contig 49978 and cosegregates with Rps6 based on the resolution of our recombination screen, whereas the NLR on contig 37596 is separated by a critical recombination event. MLOC_65262 is preferentially expressed in roots, with little or no expression in leaves in Morex (IBGSC (2012) Nature 491:711-716).

Figure 5:
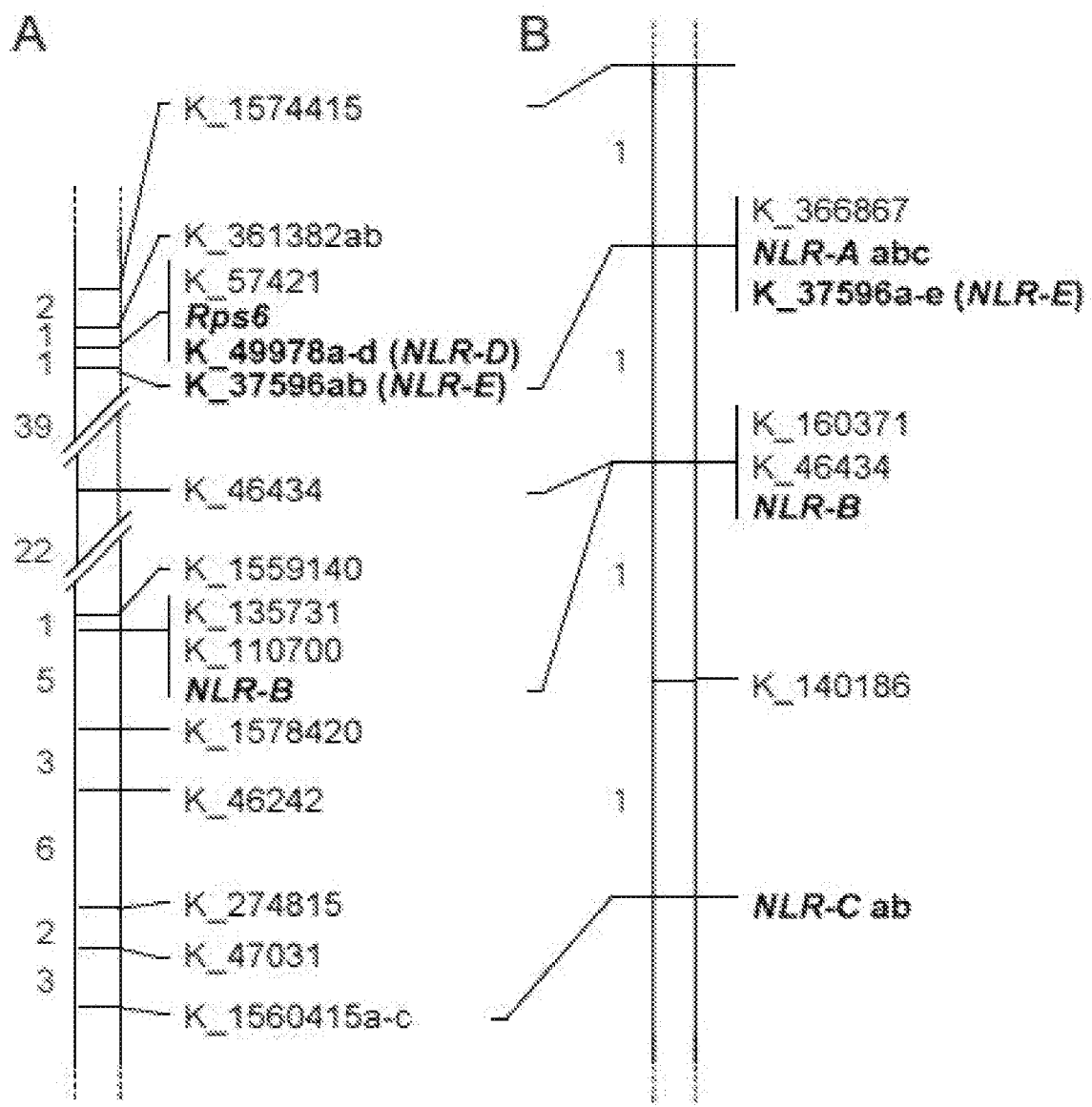
FIG. 5. Identification and genetic mapping of five NLR candidate genes in the Rps6 region. (A) Abed Binder 12×Russell high-resolution $F_2$ map used for fine mapping Rps6. (B) Doubled haploid derived F2 mapping population (DHMP). Numbers on left of linkage group show the number of recombination events between markers.

Candidate gene analysis in the Rps6 region: To identify candidate NLR genes at the Rps6 locus we utilised existing barley genomics resources in combination with transcriptome assemblies from six barley accessions. We selected a region harbouring Rps6 based on linkage mapping of the region (FIG. 5). Using marker colinearity, we identified 665 WGS contigs anchored to the Rps6 region derived from the cultivars Morex, Barke, and Bowman (IBGSC (2012) Nature 491:711-716) (Table 2). The contigs were anchored in 16 genetic bins and each bin contained a variable number of contigs ranging from 1 to 442. To check for the presence of candidate genes in the anchored sequence information, we searched for motifs associated with NLRs using the motif alignment and search tool (MAST) according to the parameters and motifs reported by Jupe et al. ((2012) BMC Genomics 13:75). Eleven WGS contigs contained NLR motifs (Table 3). These contigs were compared to identify whether similar contigs had been identified in each parent. Indeed, we observed redundancy between accessions and the contigs collapsed into 5 homologous groups. We provisionally designated the putative NLRs harboured in the contigs as NLR-A, NLR-B, NLR-C, NLR-D, and NLR-E. The only Morex contig identified via MAST analysis grouped with the NLR-D homologous group and was the high confidence gene MLOC_65262 cosegregating with Rps6 in the high-resolution genetic map (Table 3). The second annotated NLR identified from Morex contig 37596 in the barley physical map was not identified using MAST analysis, as only contigs contained in the original anchoring of IBGSC (IBGSC (2012) Nature 491:711-716) were interrogated. However, BLAST analysis indicated that the annotated NLR on contig 37596 grouped with the NLR-E homologous group. NLR-E was separated from Rps6 by a critical recombination event in the high-resolution genetic map.

TABLE 2

Anchored WGS contigs in the Rps6 region.

| Accession | Contigs | Mean length (bp) | Total Length (kb) |
|---|---|---|---|
| Barke | 213 | 3,239 | 690 |
| Bowman | 215 | 4,008 | 860 |
| Morex | 237 | 3,782 | 900 |

TABLE 3

Identification of five candidate NLR genes in the Rps6 region.

| | | | RNAseq expression analysis[1,2] | | | | | | |
|---|---|---|---|---|---|---|---|---|---|
| | MAST analysis on POPseq | | Rps6 | | | rps6 | | | |
| Gene | WGS contigs | E-value | A | G | B | S | R | M | MLOC ID |
| NLR-A | barke_contig_2780081 | 1.50E−43 | H | H | H | ND | ND | ND | NA |
| | bowman_contig_200425 | 6.80E−43 | | | | | | | |
| NLR-B | barke_contig_268211 | 2 | ND | ND | ND | ND | ND | ND | NA |
| | bowman_contig_856833 | 0.11 | | | | | | | |
| NLR-C | barke_contig_1788934 | 5.40E−36 | L | L | H | L | ND | ND | NA |
| | bowman_contig_874416 | 9.30E−37 | | | | | | | |
| NLR-D | barke_contig_417389 | 5.70E−47 | ND | ND | ND | ND | ND | ND | MLOC_65262 |
| | bowman_contig_852986 | 3.60E−47 | | | | | | | |
| | morex_contig_49978 | 1.40E−40 | | | | | | | |
| NLR-E | barke_contig_480243 | 2.20E−49 | L | L | L | H | H | H | NA |
| | bowman_contig_859170 | 3.10E−47 | | | | | | | |
| | morex_contig_37596[1] | | | | | | | | |

Expression analysis of candidate genes at the Rps6 locus: To investigate the five NLR candidate genes in more detail we established expression profiles for each gene using transcript assemblies for six key accessions harbouring Rps6 or rps6 (accessions Abed Binder 12, Golden Promise, Barke, SusPtrit, Russell, and Manchuria) (Table 3). The WGS contigs harbouring NLR motifs were used to search the assemblies for transcripts corresponding to the NLR candidates. Strikingly, transcripts corresponding to NLR-A were only detected in accessions harbouring Rps6, showing a clear expression polymorphism between resistant and susceptible genotypes (Table 3). No allelic diversity was evident in the NLR-A transcripts found in the Rps6 accessions. Conversely, NLR-E exhibited an inverse expression polymorphism between Rps6 and rps6 accessions. A comparison of the NLR-E transcripts derived from Russell and Manchuria (rps6), and the Barke/Bowman (Rps6) WGS contigs, revealed a single synonymous substitution. This, coupled with the critical recombination event separating NLR-E (K_37596ab) from Rps6 in the high-resolution genetic map, excluded NLR-E as a candidate gene. We did not detect any expression of NLRB or NLR-D. This was consistent with the annotation of NLR-D (MLOC 65262) as a root-expressed gene in the barley high confidence gene assembly (IBGSC (2012) *Nature* 491:711-716). In the case of NLR-C, we did not observe any expression polymorphisms differentiating Rps6 from rps6 accessions.

Figure 6:
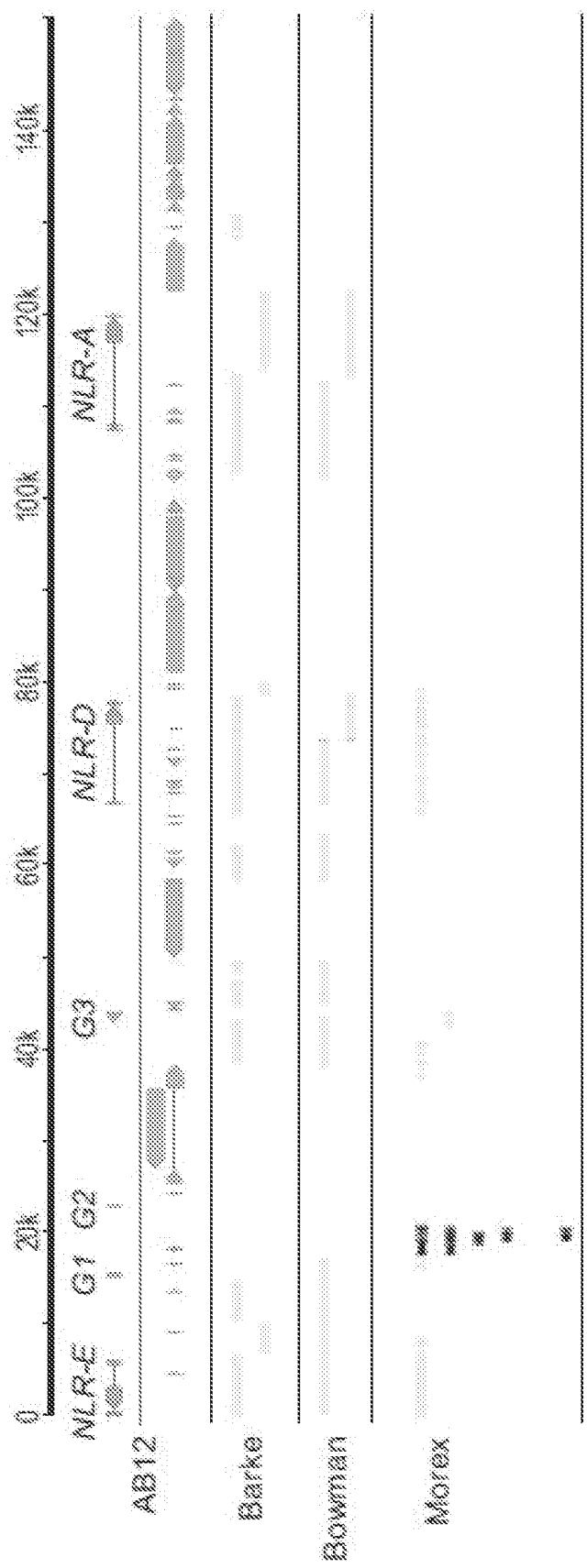
FIG. 6. Physical mapping of Rps6 and gene model of the candidate gene NLR-A. The BAC clone harbouring NLR A, NLR-D, and NLR-E derived from Abed Binder 12 (AB12) is shown on top. The locations of NLR candidates NLR-A, NLR-D, and NLR-E are indicated in the upper AB12 track, as well as additional genes in the locus including MLOC_8985 (G1), MLOC_41646 (G2), and MLOC_19985 (G3). The other grey boxes in the lower AB12 track represent repetitive sequence. The three additional tracks show alignments of whole genome shotgun contigs derived from Barke (Rps6), Bowman (Rps6), and Morex (rps6).

Gene model of NLR-A: We constructed a gene model for NLR-A by aligning the Abed Binder 12 NLR-A transcript to Barke contig 2780081, originally identified as harbouring NLR-A using MAST analysis (Table 3). We observed a perfect alignment with the exception of approximately 600 bp of sequence at the 5' of the Abed Binder 12 transcript. Therefore, we searched the anchored Barke WGS contigs using the unaligned 5' sequence and identified an additional Barke contig (contig 54347) to which the 5' sequence aligned (FIG. 6). We assembled a full gene model for NLR-A by concatenating the Barke contigs and re-aligning the Abed Binder 12 NLR-A transcript (FIG. 6). This model proposed that NLR-A consisted of four exons and three introns. Interestingly, the second intron was approximately 8.8 kbp in length. However, according to POPSEQ anchoring of the Barke contigs, contig 54347 was anchored 4.4 cM distal to contig 2780081.

Figure 7:
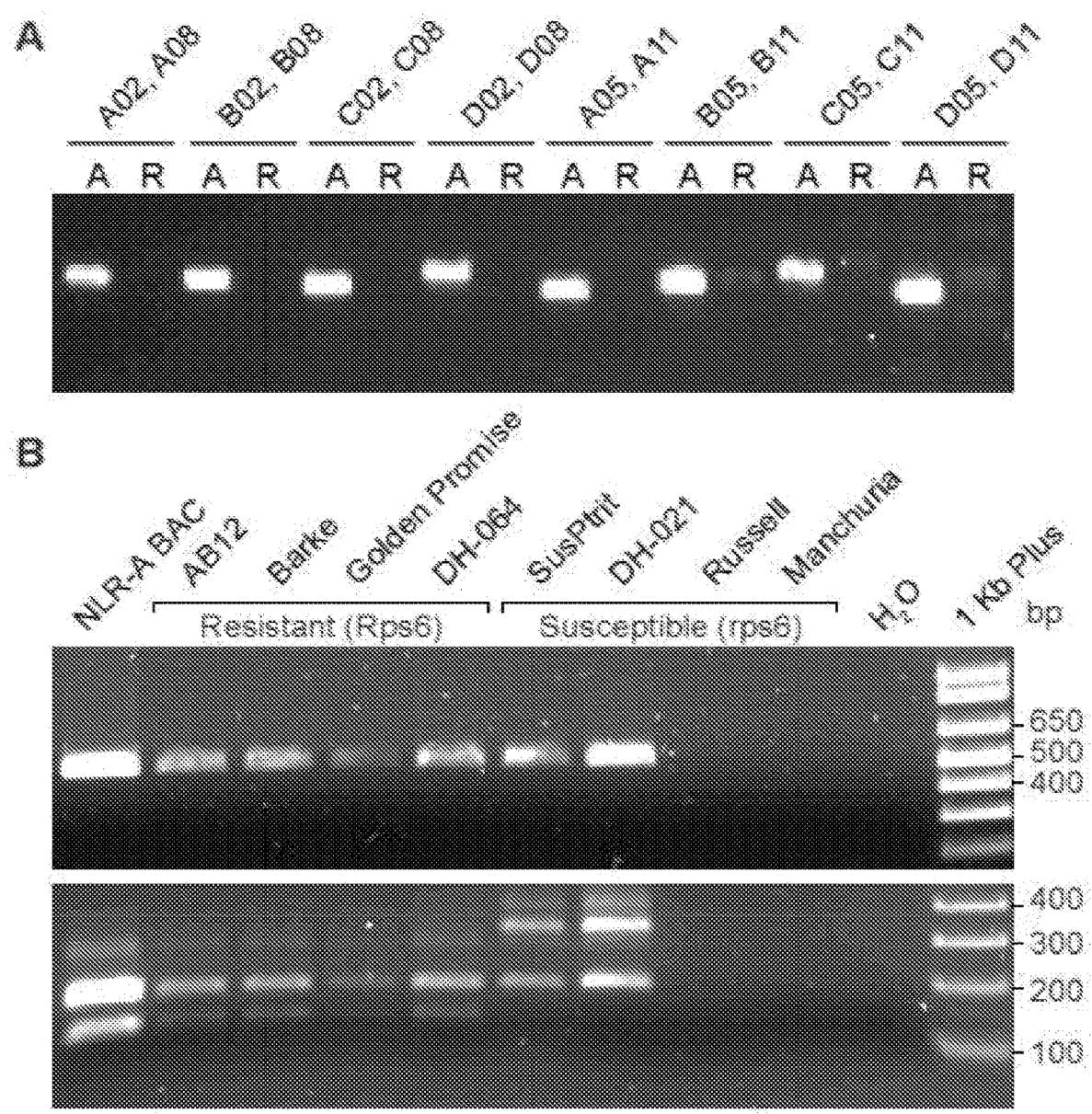
FIG. 7. A single nucleotide polymorphism differentiates three NLR-A haplotypes. (A) gDNA from Abed Binder 12 'A' and Russell 'R' amplified with eight PCR primer pairs specific for NLR-A. (B) Top panel: gDNA from Rps6 and rps6 accessions amplified with primer pair A05/A11; Bottom panel: Digestion of PCR amplicons using Taq$_\alpha$I differentiates three NLR-A haplotypes (NLR-A1, NLR-A2, and nlr-a) in eight Rps6 differential accessions.

Mapping of candidate genes at the Rps6 locus: Genetic mapping had excluded NLR-E as a candidate gene and showed that NLR-D cosegregated with Rps6. We also wanted to map NLR-A, NLRB, and NLR-C into the high-resolution genetic map to see where they were positioned relative to the Rps6 locus. We initiated a PCR based strategy for identifying SNP markers for NLR-A. To do this, we designed PCR primers along the length of the concatenated Barke contigs 54347 and 2780081. PCR amplification using these primers on Abed Binder 12 and Russell genomic DNA, showed a clear presence/absence polymorphism between Abed Binder 12 and Russell (FIG. 7). This result was concurrent with the absence of an NLR-A transcript in the Russell transcriptome. However, failure to amplify NLR-A from Russell gDNA meant it would not be possible to precisely map NLR-A in the Abed Binder 12×Russell mapping population as it is a dominant marker. Therefore, we hypothesised that it may be possible to amplify NLR-A in different accessions known to harbour Rps6 or rps6.

Using the SusPtrit×Golden Promise doubled-haploid (DH) genetic map we identified two DH lines that harboured Rps6 or rps6 in the absence of other genes. Using these lines, and the key accessions used for RNAseq analysis, we PCR amplified gDNA using eight primer pairs that amplified the 5' and 3' ends of NLR-A. We observed three NLR-A haplotypes, in the eight different accessions, which we named NLR-A1, NLR-A2, and nlr-a (Table 4). The Rps6 containing accessions Abed Binder 12, Barke, Golden Promise, and SusPtrit×Golden Promise DH line 64 (DH-064) represented the NLR-A1 haplotype exhibiting 100% amplification of all primers tested. Russell and Manchuria, both susceptible to *P. striiformis* f. sp. *tritici*, showed no amplification of any of the primers (nlr-a haplotype). However, SusPtrit and SusPtrit×Golden Promise DH line 21 (DH-021) showed successful amplification of 50% of the primers tested and represented the NLR-A2 haplotype. Sanger sequencing of the PCR amplicons revealed a SNP in the putative NBS domain of NLR-A between the SusPtrit and Golden Promise alleles. Using this SNP, we developed a CAPS marker that showed clear differentiation of the different haplotypes (FIG. 7). The absence of any amplicons in nlr-a accessions suggested that NLR-A was deleted in these lines. In order to map NLR-A, we crossed DH-021 with DH-064 to create a DH derived $F_2$ mapping population (DHMP). A linkage map was constructed using 43 KASP markers including markers for NLR-A and NLR-E. NLR-A and NLR-E co-segregated with K_366867. This positioned NLR-A and NLR-E at the Rps6 locus based on marker colinearity with the Abed Binder 12×Russell high-resolution mapping population (FIG. 5). NLR-D markers were not polymorphic on the DHMP population and we were unable to determine the position of NLR-D in the DHMP population.

Abed Binder 12 RNAseq reads to the BAC contig differentiated NLR-A, NLR-D, and NLR-E and demonstrated that NLR-A was highly expressed compared to NLR-E and NLR-D (FIG. 6). This result confirmed the earlier expression analysis performed using de novo assembly of the RNAseq data. The physical linkage of NLR-A, NLR-D, and NLR-E was consistent with the genetic linkage of these genes in the high-resolution and DHMP mapping populations. We anchored the BAC clone to the Abed Binder 12×Russell genetic map using markers K_49978 (NLR-D) and K_37596 (NLR-E). A single recombination event separates these markers and defines the distal physical region of the Rps6 locus. The Rps6 proximal marker, K_361382, does not reside within the BAC clone and the boundary of the proximal physical region has yet to be defined. Alignment of whole genome shotgun sequence contigs derived from Barke, Bowman, and Morex found the presence of NLR-A in Barke and Bowman, whereas the region is absent in Morex (FIG. 6).

TABLE 4

Eight primer pairs differentiate three NLR-A haplotypes.

| | | PCR primer combination | | | | | | | | |
|---|---|---|---|---|---|---|---|---|---|---|
| Accession | Allele | A02/A08 | B02/B08 | C02/C08 | D02/D08 | A05/A11 | B05/B11 | C05/C11 | D05/D11 | Haplotype |
| Abed Binder 12 | Rps6 | + | + | + | + | + | + | + | + | NLR-A1 |
| Barke | Rps6 | + | + | + | + | + | + | + | + | NLR-A1 |
| Golden Promise | Rps6 | + | + | + | + | + | + | + | + | NLR-A1 |
| SxGP DH-064 | Rps6 | + | + | + | + | + | + | + | + | NLR-A1 |
| SusPtrit | rps6 | − | − | − | − | + | + | + | + | NLR-A2 |
| SxGP DH-021 | rps6 | − | − | − | − | + | + | + | + | NLR-A2 |
| Russell | rps6 | − | − | − | − | − | − | − | − | nlr-a |
| Manchuria | rps6 | − | − | − | − | − | − | − | − | nlr-a |

In order to map NLRB and NLR-C, we designed markers based on SNPs identified between Barke and Morex WGS contigs harbouring the genes. NLRB mapped distal to Rps6 and excluded the gene as a candidate gene for Rps6 (FIG. 5). NLR-C markers were not polymorphic in the high-resolution genetic map but we were able to map NLR-C distal to Rps6 in the DHMP population (FIG. 5). Taken together, these results excluded NLRB, NLR-C, and NLR-E as candidate genes for Rps6. The presence of a putative deletion region harbouring NLR-A and a clear expression polymorphism between Rps6 and rps6 harbouring accessions supports NLR-A as a candidate gene for Rps6.

Physical map of the Rps6 locus: We initiated physical mapping of the Rps6 region using an Abed Binder 12 BAC library. A PCR screen, using two sets of primers, identified a single BAC clone harbouring NLR-A (primer pairs A02/A08 and A05/A11; FIG. 6). We sequenced the BAC clone with Pacific Biosciences long read sequencing using a SMRT cell with C4-P6 chemistry and were able to construct and annotate a single contiguous BAC sequence (FIG. 6). The clone mostly consisted of repetitive and low complexity sequence (Table 5). However, the clone harboured three CNL genes: NLR-A, NLR-D, and NLR-E (FIG. 6 and Table 5). Signatures of three additional genes annotated in the barley low confidence gene set were identified on the BAC: MLOC_8985.1, MLOC_41646.1, and MLOC_19985.1. All three were annotated as unknown proteins although InterPro scan revealed MLOC_19985.1 contains an F-box domain. Comparison of NLR-A, NLR-D, and NLR-E showed high homology between the genes at the amino acid level (approx. 60%) and in the DNA coding sequence (approx. 70%) (Tables 6 and 7). Despite the similarity, alignment of the

TABLE 5

Annotation of Abed Binder 12 BAC clone 4931-1-11E harbouring NLR-A.

| Name | Length (bp) |
|---|---|
| LTR/Copia BARE1_HV | 3,826 |
| DNA/CMC-EnSpm | 4,601 |
| DNA/CMC-EnSpm | 536 |
| DNA/CMC-EnSpm | 1,229 |
| DNA/CMC-EnSpm | 5,270 |
| DNA/CMC-EnSpm | 1,098 |
| Low complexity A-rich | 94 |
| DNA/CMC-EnSpm | 2,396 |
| DNA/CMC-EnSpm | 1,111 |
| Unknown REP1_SB | 52 |
| LTR/Copia IKEROS_HV | 5,817 |
| Satellite TREP106 | 253 |
| LINE/L1 LINE1-56_SBi | 669 |
| LINE/L1 LINE1-55_SBi | 213 |
| DNA/TcMar-Stowaway | 88 |
| ICARUS_TM | |
| NLR-A | 3,723 |
| DNA-8-1_TA | 138 |
| Low complexity | 89 |
| Low_complexity | 34 |
| LTR/Gypsy SUKKULA1_HV-LTR | 753 |
| LTR/Copia WIS2_TM-int | 1,230 |
| LTR/Copia BARE-2_HV_LTR | 1,356 |
| LINE/L1 LINE1-61_SBi | 98 |
| LTR/Copia BARE1_HV | 8,113 |
| LTR/Copia BARE1_HV | 8,945 |
| LINE/L1 LINE1-20_SBi | 87 |

TABLE 5-continued

Annotation of Abed Binder 12 BAC clone 4931-1-11E harbouring NLR-A.

| Name | Length (bp) |
|---|---|
| LINE/L1 LINE1-47_SBi | 86 |
| DNA/CMC-EnSpm | 49 |
| DNA/TcMar-Stowaway | 145 |
| DNA/PIF-Harbinger HARB-5_SBi | 911 |
| Satellite TREP106 | 531 |
| Satellite TREP106 | 535 |
| Satellite TREP106 | 107 |
| NLR-D | 2,700 |
| LTR/Copia Copia-8_PD-I | 52 |
| Low_complexity GA-rich | 49 |
| LINE/L1 L1_TD | 325 |
| LINE/L1 L1_TD | 976 |
| LTR/Copia BARE-2_HV_LTR | 1,811 |
| LTR/Copia BARE-2_HV | 8,586 |
| LTR/Copia BARE-2_HV_LTR | 1,811 |
| LTR/Gypsy Gypsy-12_TA-LTR solo | 795 |
| DNA IR12_TM | 17 |
| MLOC.19985.1 | 1,212 |
| LTR/Copia WIS2_TM-LTR | 1,753 |
| LTR/Copia Angela | 8,804 |
| LTR/Copia WIS2_TM-LTR | 1,762 |
| LTR/Copia Copia1_HV-int | 3,877 |
| LTR/Copia Copia1_HV-LTR solo | 325 |
| DNA/PIF-Harbinger | 250 |
| MLOC_41646.1 | 296 |
| DNA/CMC-EnSpm EnSpm-N3_TA | 489 |
| DNA/CMC-EnSpm EnSpm-21_SBi | 133 |
| LTR/Copia Copia19-ZM_I-int | 212 |
| MLOC_8985.1 | 462 |
| DNA/CMC-EnSpm | 263 |
| DEIMOS | 275 |
| DNA/TcMar-Stowaway | 258 |
| NLR-E | 3,936 |

TABLE 6

Amino acid and DNA similarity between full length NLR-A, NLR-D, and NLR-E.

| | | Whole length (aa) % similarity | | | | |
|---|---|---|---|---|---|---|
| | | NLR-A | NLR-B | NLR-C | NLR-D | NLR-E |
| Whole length (gDNA) % similarity | NLR-A | | — | 35 | 58 | 63 |
| | NLR-B | — | | — | — | — |
| | NLR-C | 49 | — | | 33 | 37 |
| | NLR-D | 67 | — | 49 | | 67 |
| | NLR-E | 70 | — | 50 | 73 | |

TABLE 7

Amino acid similarity for NBS and LRR domains of NLR-A, NLR-D, and NLR-E.

| | | NBS domain (aa) % similarity | | | | |
|---|---|---|---|---|---|---|
| | | NLR-A | NLR-B | NLR-C | NLR-D | NLR-E |
| LRR domain (aa) % similarity | NLR-A | | — | 49 | 75 | 80 |
| | NLR-B | — | | — | — | — |
| | NLR-C | 38 | — | | 44 | 48 |
| | NLR-D | 59 | — | 41 | | 86 |
| | NLR-E | 57 | — | 49 | 63 | |

Identification of Rps6 from diverse accessions: To investigate the frequency of Rps6 in barley we assembled a panel of 134 accessions that included wild, landrace, elite 2-row, and elite 6-row barleys (Table 8). The panel was inoculated with *P. striiformis* f. sp. *trilici* isolate 08/21 and phenotyped using the macroscopic observations of chlorosis and infection and using microscopic assays pCOL and pPUST. We initiated a crossing block to generate populations segregating for resistance to *Puccinia striiformis* f. sp. *trilici*. Resistant accessions used as parental lines in crosses were selected using the phylogenetic relationships and phenotypic information collected for the barley diversity panel to achieve a representative sample of the diversity. A total of 13 $F_2$ populations and 2 $BC_1$ populations were created and in each case the susceptible parent was Manchuria, a 6-row cultivar (Table 9). Polymorphic markers linked to Rps6 and two additional known loci (Rpst1 and Rpst3) were identified for each population using OPA genotyping data derived from parental accessions. OPA markers were converted to KASP markers and assayed on a minimum of 93 individuals for each $F_2$ population. Each population was phenotyped using pCOL and pPUST and single marker regression was used to ascertain the percent variation explained by Rps6 in each population. In addition, we also analysed three existing populations, including a RIL and two DH populations. In total, we analysed 18 populations that represented diversity from each phylogenetic clade (Table 9). Rps6 was detected in several accessions, contributing to resistance in 40% (6 out of 15) of the populations (Tables 10 and 11).

TABLE 8

Accessions of barley used for inoculation with *P. striiformis* f. sp. *tritici*.

| Accession name | PI/CI Number | Row | Status | Isolate | CHL | INF |
|---|---|---|---|---|---|---|
| Commander | | 2 | cultivar | Pst 08/21 | 0 | 0 |
| Hindmarsh | | 2 | cultivar | Pst 08/21 | 0 | 0 |
| Maritime | | 2 | cultivar | Pst 08/21 | 1.21 | 0 |
| Clipper | PI 349366 | 2 | cultivar | Pst 08/21 | 1 | 0 |
| Finniss | | 2 | cultivar | Pst 08/21 | 1.38 | 0 |
| Q21861 | PI 584766 | 2 | breeding | Pst 08/21 | 2 | 0 |
| Bancroft | PI 605474 | 2 | cultivar | Pst 08/21 | 0.5 | 0 |
| Betzes | | 2 | cultivar | Pst 08/21 | 0 | 0 |
| SM89010 | | 2 | cultivar | Pst 08/21 | 0.5 | 0 |
| Bowman | PI 483237 | 2 | cultivar | Pst 08/21 | 0 | 0 |
| BCD47 | PI 659444 | 2 | genetic | Pst 08/21 | 0.5 | 0 |
| Sebastian | | 2 | cultivar | Pst 08/21 | 0 | 0 |
| Rainbow | | 2 | cultivar | Pst 08/21 | 0 | 0 |
| Fractal | | 2 | cultivar | Pst 08/21 | 0 | 0 |
| Optic | | 2 | cultivar | Pst 08/21 | 0 | 0 |
| Feltwell | | 2 | cultivar | Pst 08/21 | 0 | 0 |
| Saloon | | 2 | cultivar | Pst 08/21 | 0 | 0 |
| Power | | 2 | cultivar | Pst 08/21 | 0 | 0 |
| Henley | | 2 | cultivar | Pst 08/21 | 0 | 0 |
| Tipple | | 2 | cultivar | Pst 08/21 | 0 | 0 |
| Heron | | 2 | cultivar | Pst 08/21 | 0 | 0 |
| Atem | | 2 | cultivar | Pst 08/21 | 0 | 0 |
| Onyx | | 2 | cultivar | Pst 08/21 | 0 | 0 |
| Barke | | 2 | cultivar | Pst 08/21 | 0 | 0 |
| Ria | | 2 | cultivar | Pst 08/21 | 0 | 0 |
| Prisma | | 2 | cultivar | Pst 08/21 | 0 | 0 |
| Triumph | | 2 | cultivar | Pst 08/21 | 0 | 0 |
| Trumpf | PI 548762 | 2 | cultivar | Pst 08/501 | 0 | 0 |
| Diamant | CIho 15226 | 2 | cultivar | Pst 11/08 | 1 | 0 |
| Derkado | | 2 | cultivar | Pst 08/21 | 0 | 0 |
| Heather | | 2 | cultivar | Pst 08/21 | 0 | 0 |
| Tardus | | 2 | cultivar | Pst 08/21 | 0 | 0 |
| Zephyr | PI 339815 | 2 | cultivar | Pst 08/21 | 0.5 | 0 |
| Carlsberg II | CIho 15218 | 2 | cultivar | Pst 11/08 | 0 | 0 |
| Maythorpe | | 2 | cultivar | Pst 08/21 | 0 | 0 |
| Golden Promise | PI 343079 | 2 | cultivar | Pst 08/21 | 0 | 0 |
| Pallas | CIho 11313 | 2 | cultivar | Pst 11/08 | 0 | 0 |
| Siri | | 2 | cultivar | Pst 08/21 | 0 | 0 |
| Sultan 5 | | 2 | cultivar | Pst 11/08 | 0 | 0 |
| Cambrinus | PI 321779 | 2 | cultivar | Pst 08/21 | 1 | 0 |
| Ingrid | | 2 | cultivar | Pst 08/501 | 0 | 0 |
| M1460 | | — | genetic | Pst 08/21 | 0 | 0 |
| Haisa | CIho 9855 | 2 | cultivar | Pst 08/501 | 0 | 0 |
| Varunda | PI 410865 | 2 | cultivar | Pst 08/501 | 0 | 0 |

TABLE 8-continued

Accessions of barley used for inoculation with *P. striiformis f.* sp. *tritici.*

| Accession name | PI/CI Number | Row | Status | Isolate | CHL | INF |
|---|---|---|---|---|---|---|
| Emir | CIho 13541 | 2 | cultivar | Pst 11/08 | 0 | 0 |
| Mazurka | PI 399501 | 2 | cultivar | Pst 08/21 | 1 | 0 |
| Minerva | | 2 | cultivar | Pst 08/21 | 0 | 0 |
| Vada | | 2 | cultivar | Pst 08/501 | 0 | 0 |
| Baronesse | PI 568246 | 2 | cultivar | Pst 08/21 | 0 | 0 |
| Jive | | 2 | cultivar | Pst 08/21 | 0 | 0 |
| Apex | | 2 | cultivar | Pst 08/501 | 0 | 0 |
| Armelle | PI 410855 | 2 | cultivar | Pst 08/21 | 0 | 0 |
| Chevalier | CIho 156 | 2 | cultivar | Pst 08/21 | 0 | 0 |
| Stauffers Obersulzer | PI 467580 | 2 | cultivar | Pst 08/501 | 0 | 0 |
| Malteria Heda | CIho 15224 | 2 | cultivar | Pst 11/08 | 0.5 | 0 |
| Probstdorfer Vollkorn | CIho 15222 | 2 | cultivar | Pst 08/501 | 0 | 0 |
| Heils Franken | PI 327917 | 2 | cultivar | Pst 11/08 | 0 | 0 |
| Haruna Nijo | | 2 | cultivar | Pst 08/21 | 0 | 0 |
| CIho 4196 | CIho 4196 | 2 | landrace | Pst 08/21 | 0 | 0 |
| L94 | | 2 | landrace | Pst 08/501 | 1 | 0 |
| Grannenlose Zweizeilige | PI 548740 | 2 | landrace | Pst 08/21 | 1.5 | 0 |
| Hiproly | PI 60693 | 2 | landrace | Pst 08/501 | 1 | 0 |
| Abyssinian 14 | CIho 7202 | 2 | landrace | Pst 08/501 | 3 | 1 |
| Benton | PI 539105 | 6 | cultivar | Pst 08/21 | 0 | 0 |
| HOR 2926 | PI 548734 | — | — | Pst 11/08 | 0 | 0 |
| HOR 1428 | PI 548708 | 2 | landrace | Pst 11/08 | 0 | 0 |
| SusPtrit | | 6 | genetic | Pst 08/21 | 3 | 4 |
| OWB Recessive | GSHO 3451 | 6 | genetic | Pst 08/21 | 2 | 0 |
| Trebi | PI 537442 | 6 | cultivar | Pst 08/21 | 0 | 0 |
| Steptoe | CIho 15229 | 6 | cultivar | Pst 08/21 | 3.5 | 0 |
| Algerian | PI 539104 | 6 | cultivar | Pst 08/21 | 1 | 0 |
| Abed Binder 12 | PI 327961 | 6 | cultivar | Pst 08/21 | 0 | 0 |
| Duplex | CIho 12420 | 6 | landrace | Pst 08/21 | 0 | 0 |
| Cebada Capa | | 6 | cultivar | NA | NA | NA |
| Psaknon | CIho 6305 | 6 | breeding | Pst 08/21 | 0 | 0 |
| WBDC 350 | | 2 | wild | Pst 08/21 | 0 | 0 |
| WBDC 045 | | 2 | wild | Pst 08/21 | 0 | 0 |
| Spontaneum I | PI 293413 | 2 | wild | Pst 08/501 | 0 | 0 |
| WBDC 259 | | 2 | wild | Pst 08/21 | 1 | 0.5 |
| WBDC 241 | | 2 | wild | Pst 08/21 | 3 | 1 |
| 22 | PI 466309 | 2 | wild | Pst 08/501 | 2.5 | 1 |
| WBDC 085 | | 2 | wild | Pst 08/21 | 0 | 0 |
| WBDC 148 | | 2 | wild | Pst 08/21 | 3 | 1 |
| WBDC 013 | | 2 | wild | Pst 08/21 | 0 | 0 |
| WBDC 334 | | 2 | wild | Pst 08/21 | 2 | 3 |
| WBDC 247 | | 2 | wild | Pst 08/21 | 3 | 2 |
| 32 | PI 466444 | 2 | wild | Pst 08/501 | 1 | 0 |
| WBDC 072 | | 2 | wild | Pst 08/21 | 3 | 0.5 |
| 20007 | PI 284752 | 2 | wild | Pst 08/501 | 0.5 | 0 |
| WBDC 038 | | 2 | wild | Pst 08/21 | 3 | 3 |
| WBDC 199 | | 2 | wild | Pst 08/21 | 0 | 0 |
| 55 | PI 466279 | 2 | wild | Pst 08/501 | 3.5 | 0 |
| WBDC 253 | | 2 | wild | Pst 08/21 | 0 | 0 |
| WBDC 008 | | 2 | wild | Pst 08/21 | 0 | 0 |
| WBDC 110 | | 2 | wild | Pst 08/21 | 0.5 | 0 |
| WBDC 068 | | 2 | wild | Pst 08/21 | 0.5 | 0 |
| WBDC 109 | | 2 | wild | Pst 08/21 | 2 | 0 |
| WBDC 112 | | 2 | wild | Pst 08/21 | 0.5 | 0 |
| OWB Dominant | GSHO 3450 | 2 | genetic | Pst 08/21 | 4 | 0 |
| OUH602 | | 2 | wild | Pst 08/21 | 4 | 3 |
| WBDC 343 | | 2 | wild | Pst 08/21 | 1.5 | 0 |
| G-88 | PI 466211 | 2 | wild | Pst 08/501 | 1 | 0 |
| Spiti | CIho 14349 | 6 | landrace | Pst 08/21 | 1.5 | 0 |
| Black Hull-less | PI 24849 | 6 | landrace | Pst 08/21 | 3 | 3 |
| West China | CIho 7556 | 6 | breeding | Pst 08/21 | 0 | 0 |
| Nigrate | CIho 2444 | 6 | landrace | Pst 08/21 | 0.5 | 0 |
| Durani | PI 125311 | 6 | landrace | Pst 08/21 | 0.5 | 1 |
| WBDC 172 | | 2 | wild | Pst 08/21 | 0 | |
| Multan | PI 57956 | 6 | landrace | Pst 08/21 | 0 | 0 |
| Kwan | PI 39367 | 6 | landrace | Pst 08/21 | 0 | 0 |
| Rupee | CIho 4355 | 6 | landrace | Pst 08/21 | 0 | 0 |
| 15 | CIho 11619 | 6 | — | Pst 08/21 | 0.5 | 0 |
| Long Glumes | CIho 6168 | 2 | genetic | Pst 08/21 | 0 | 0 |
| HOR 3401 | PI 327764 | 6 | landrace | Pst 08/21 | 0 | 0 |
| Hanna | CIho 906 | 2 | breeding | Pst 08/21 | 0 | 0 |
| Dopla | | 6 | cultivar | Pst 08/21 | 0.5 | 0 |
| Regina | | 6 | cultivar | NA | NA | NA |
| Igri | PI 428488 | 2 | cultivar | Pst 08/21 | 0 | 0 |
| DH46 | | — | genetic | Pst 08/21 | 2 | 1 |
| Parasol | | — | cultivar | NA | NA | NA |
| Manas | | — | cultivar | Pst 08/21 | 0.5 | 0 |
| Franger | PI 180669 | 6 | cultivar | Pst 08/21 | 0.5 | 1 |
| Astrix | PI 339826 | 6 | cultivar | Pst 08/21 | 0.5 | 0 |
| Fong Tien | | 6 | — | Pst 11/08 | 3.5 | 2.5 |
| Manchuria | CIho 2330 | 6 | cultivar | Pst 08/21 | 3 | 0.5 |
| Bigo | CIho 13611 | 6 | cultivar | Pst 08/21 | 0 | 0 |
| Foster | | 6 | cultivar | Pst 08/21 | 1.5 | |
| Morex | CIho 15773 | 6 | cultivar | Pst 08/21 | 1.5 | 0 |
| Russell | PI 483127 | 6 | cultivar | Pst 08/21 | 1 | 0 |

TABLE 9

Eighteen structured populations inoculated with *P. striiformis f.* sp. *tritici.*

| Resistant Accession | Cross | Type | N |
|---|---|---|---|
| Abed Binder 12 | Manchuria x Abed Binder 12 | $F_2$ | 96 |
| | Manchuria x (Manchuria x Abed Binder 12 $F_1$) | $BC_1$ | 90 |
| Betzes | Manchuria x Betzes | $F_2$ | 94 |
| CIho 4196 | Foster x CIho 4196 | RIL | 89 |
| Duplex | Duplex x Manchuria | $F_2$ | 94 |
| Emir | Manchuria x Emir | $F_2$ | 94 |
| Golden Promise | SusPtrit x Golden Promise | DH | 122 |
| Grannenlose Zweizeilige | Grannenlose Zweizeilige x Manchuria | $F_2$ | 92 |
| Haruna Nijo | Haruna Nijo x OUH602 | DH | 94 |
| Heils Franken | Manchuria x Heils Franken | $F_2$ | 93 |
| | Manchuria x (Manchuria x Heils Franken $F_1$) | $BC_1$ | 93 |
| HOR 1428 | Manchuria x HOR 1428 | $F_2$ | 94 |
| HOR 2926 | Manchuria x HOR 2926 | $F_2$ | 92 |
| I 5 | I 5 x Manchuria | $F_2$ | 94 |
| Sultan 5 | Manchuria x Sultan 5 | $F_2$ | 190 |
| WBDC 008 | WBDC 008 x Manchuria | $F_2$ | 92 |
| WBDC 085 | WBDC 085 x Manchuria | $F_2$ | 94 |

TABLE 10

Composite interval mapping of resistance to *P. striiformis f. sp. tritici* in several mapping populations.

| Resistant Accession | Cross | Type | Trait | Chr | cM | Peak Marker | LOD | EWT | AEE | PVE |
|---|---|---|---|---|---|---|---|---|---|---|
| CIho 4196 | Foster x CIho 4196 | RIL | CHL | 1H | 8.93 | owbGBS32429_p1 | 20.24 | 3.19 | 0.32 | 0.53 |
| | | | CHL | 6H | 20.62 | 1_0136 | 3.82 | 3.19 | 0.12 | 0.07 |
| | | | pCOL | 1H | 9.50 | 0711N16_R1_p1 | 14.99 | 3.17 | 0.10 | 0.38 |
| | | | pCOL | 1H | 71.06 | 1_0357 | 4.69 | 3.17 | 0.05 | 0.09 |
| | | | pCOL | 7H | 145.28 | 1_0888 | 4.37 | 3.17 | 0.05 | 0.09 |
| Golden Promise | SusPtrit x Golden Promise | DH | CHL | 1H | 12.55 | BOPA2_12_30817 | 19.64 | 3.26 | 0.76 | 0.28 |
| | | | CHL | 4H | 89.12 | BOPA1_4361-1867 | 6.73 | 3.26 | 0.39 | 0.07 |
| | | | CHL | 7H | 161.20 | SCRI_RS_155652 | 18.30 | 3.26 | 0.72 | 0.25 |
| | | | INF | 1H | 14.21 | BOPA2_12_30950 | 4.91 | 3.03 | 0.39 | 0.11 |
| | | | INF | 4H | 89.95 | SCRI_RS_121084 | 4.07 | 3.03 | 0.36 | 0.09 |
| | | | INF | 7H | 164.52 | SCRI_RS_206322 | 5.52 | 3.03 | 0.43 | 0.12 |
| | | | pCOL | 1H | 12.55 | BOPA2_12_30817 | 18.13 | 3.25 | 0.18 | 0.23 |
| | | | pCOL | 4H | 89.12 | BOPA1_4361-1867 | 12.54 | 3.25 | 0.14 | 0.14 |
| | | | pCOL | 7H | 161.20 | SCRI_RS_155652 | 20.20 | 3.25 | 0.19 | 0.26 |
| | | | pPUST | 1H | 14.21 | BOPA2_12_30950 | 4.51 | 3.10 | 0.08 | 0.10 |
| | | | pPUST | 4H | 89.12 | BOPA1_4361-1867 | 3.71 | 3.10 | 0.08 | 0.09 |
| | | | pPUST | 7H | 164.52 | SCRI_RS_206322 | 4.69 | 3.10 | 0.09 | 0.11 |
| Hama Nijo | Haruna NO x OUH602 | DH | CHL | 1H | 13.34 | 1_0419 | 32.80 | 3.02 | −1.23 | 0.69 |
| | | | CHL | 4H | 91.75 | 2_1243 | 4.42 | 3.02 | −0.37 | 0.06 |
| | | | CHL | 5H | 109.89 | 1_1200 | 3.62 | 3.02 | −0.33 | 0.05 |
| | | | INF | 1H | 15.34 | 1_0419 | 7.52 | 2.92 | −0.57 | 0.28 |
| | | | INF | 4H | 91.49 | 1_0785 | 4.54 | 2.92 | −0.39 | 0.13 |
| | | | pCOL | 1H | 13.34 | 1_0419 | 32.88 | 3.12 | −0.35 | 0.71 |
| | | | pCOL | 5H | 97.21 | 2_1168 | 3.59 | 3.12 | −0.09 | 0.05 |
| | | | pCOL | 7H | 164.10 | 1_0454 | 4.05 | 3.12 | −0.09 | 0.05 |
| | | | pPUST | 1H | 15.34 | 1_0419 | 6.96 | 2.81 | −0.14 | 0.27 |
| | | | pPUST | 2H | 74.78 | 2_0528 | 2.81 | 2.81 | 0.07 | 0.08 |
| | | | pPUST | 4H | 87.49 | 1_0785 | 3.66 | 2.81 | −0.09 | 0.11 |
| Barke | Morex x Barke | DH | CHL | 1H | 11.69 | 2_1174 | 16.42 | 3.09 | 0.53 | 0.38 |
| | | | CHL | 5H | 167.68 | 3_0666 | 7.79 | 3.09 | 0.34 | 0.14 |
| | | | CHL | 6H | 45.35 | 1_0061 | 3.28 | 3.09 | −0.20 | 0.05 |
| | | | CHL | 7H | 139.49 | 1_0687 | 6.41 | 3.09 | 0.32 | 0.11 |
| | | | pCOL | 1H | 11.84 | 2_0665 | 20.53 | 3.16 | 0.20 | 0.51 |
| | | | pCOL | 5H | 165.52 | 2_0876 | 7.24 | 3.16 | 0.10 | 0.12 |
| | | | pCOL | 7H | 149.17 | 2_0483 | 5.78 | 3.16 | 0.09 | 0.09 |

Chr: Chromosome.
Cross: Direction of cross is determined by Mother x Father, designation of alleles are A and B for Mother and Father, respectively.
AEE: Allelic effect estimate, negative and positive values indicate resistance is contributed by the A and B alleles, respectively.
PVE: Percent of the phenotypic variation explained.

TABLE 11

Marker-trait association at the Rpst1, Rps6, and Rpst3 loci in diverse barley $F_2$ populations inoculated with *P. striiformis f sp. tritici*.

| Resistant Accession | Cross | Type | Trait | Chr | Marker | LOD | MTT | AEE | DEE | DEE/AEE | PVE |
|---|---|---|---|---|---|---|---|---|---|---|---|
| Abed Binder 12 | Manchuria x Abed Binder 12 | $F_2$ | CHL | 7H | U32_3345_P1 | 8.35 | 1.36 | 0.61 | −0.77 | −1.27 | 0.33 |
| | | | INF | 7H | U32_3345_P1 | 2.29 | 1.13 | 0.24 | −0.24 | −1.00 | 0.10 |
| | | | pCOL | 7H | U32_3345_P1 | 20.09 | 1.35 | 0.26 | −0.20 | −0.78 | 0.61 |
| | | | pPUST | 4H | 3_0718_60_R | 2.12 | 1.35 | −0.06 | −0.04 | 0.55 | 0.09 |
| | | | pPUST | 7H | U32_3345_P1 | 3.21 | 1.17 | 0.07 | −0.05 | −0.82 | 0.13 |
| | Manchuria x (Manchuria x Abed Binder 12) | $BC_1$ | CHL | 4H | 3_0718_60_R | 2.28 | 0.98 | NA | 0.58 | NA | 0.03 |
| | | | CHL | 7H | U32_3345_P1 | 26.32 | 0.85 | NA | 2.72 | NA | 0.67 |
| | | | INF | 7H | U32_3345_P1 | 6.46 | 0.90 | NA | 1.47 | NA | 0.27 |
| | | | pCOL | 4H | 3_0718_60_R | 1.60 | 0.81 | NA | 0.12 | NA | 0.02 |
| | | | pCOL | 7H | U32_3345_P1 | 26.48 | 0.84 | NA | 0.69 | NA | 0.69 |
| | | | pPUST | 4H | 3_0718_60_R | 0.92 | 0.81 | NA | 0.10 | NA | 0.03 |
| | | | pPUST | 7H | U32_3345_P1 | 5.78 | 0.84 | NA | 0.27 | NA | 0.24 |
| Betzes | Manchuria x Betzes | $F_2$ | CHL | 1H | HV5_963924_P1 | 14.19 | 1.35 | 0.95 | −0.52 | −0.54 | 0.41 |
| | | | CHL | 4H | 1_0751_120_F | 7.39 | 1.35 | 0.69 | −0.35 | −0.51 | 0.18 |
| | | | pCOL | 1H | HV5_963924_P1 | 17.74 | 1.43 | 0.29 | −0.13 | −0.44 | 0.45 |
| | | | pCOL | 4H | 1_0751_120_F | 9.71 | 1.39 | 0.20 | −0.14 | −0.69 | 0.20 |
| | | | INF | 1H | HV5_963924_P1 | 2.63 | 1.26 | 0.20 | −0.29 | −1.46 | 0.11 |
| | | | INF | 4H | 1_0751_120_F | 2.36 | 1.24 | 0.26 | −0.18 | −0.68 | 0.10 |
| Emir | Manchuria x Emir | $F_2$ | CHL | 1H | HV5_963924_P1 | 3.19 | 1.32 | 0.28 | −0.05 | −0.16 | 0.08 |
| | | | CHL | 4H | GBS0288 | 1.81 | 1.41 | 0.22 | −0.03 | −0.13 | 0.04 |
| | | | CHL | 7H | U32_2966_P1 | 10.25 | 1.34 | 0.53 | −0.50 | −0.95 | 0.31 |
| | | | pCOL | 1H | HV5_963924_P1 | 2.88 | 1.54 | 0.07 | 0.02 | 0.34 | 0.07 |

TABLE 11-continued

Marker-trait association at the Rpst1, Rps6, and Rpst3 loci in diverse barley $F_2$ populations inoculated with *P. striiformis f* sp. *tritici*.

| Resistant Accession | Cross | Type | Trait | Chr | Marker | LOD | MTT | AEE | DEE | DEE/AEE | PVE |
|---|---|---|---|---|---|---|---|---|---|---|---|
| | | | pCOL | 4H | GBS0288 | 1.66 | 1.44 | 0.06 | −0.02 | −0.34 | 0.04 |
| | | | pCOL | 7H | U32_2966_P1 | 12.68 | 1.37 | 0.18 | −0.16 | −0.88 | 0.39 |
| Grannenlose | Grannenlose | $F_2$ | CHL | 4H | 2_0384_120_F | 1.85 | 1.30 | −0.44 | 0.26 | −0.60 | 0.09 |
| Zweizeilige | Zweizeilige | | pCOL | 4H | 2_0384_120_F | 2.88 | 1.40 | −0.13 | 0.12 | −0.96 | 0.13 |
| | x Manchuria | | INF | 1H | 206D11_T7_p1_281_F | 2.30 | 1.16 | 0.19 | −0.13 | −0.66 | 0.11 |
| | | | pPUST | 1H | 206D11_T7_p1_281_F | 1.22 | 1.18 | 0.02 | −0.01 | −0.45 | 0.06 |
| Heils | Manchuria x | $F_2$ | CHL | 1H | 206D11_T7_p1_281_F | 61.27 | 1.45 | 1.49 | −1.47 | −0.99 | 0.95 |
| Franken | Heils | | pCOL | 1H | 206D11_T7_p1_281_F | 59.08 | 1.34 | 0.44 | −0.41 | −0.92 | 0.95 |
| | Franken | | INF | 1H | 206D11_T7_p1_281_F | 2.82 | 1.35 | 0.30 | −0.24 | −0.81 | 0.13 |
| | | | pPUST | 1H | 206D11_T7_p1_281_F | 2.82 | 1.21 | 0.06 | −0.05 | −0.93 | 0.13 |
| | Manchuria x | $BC_1$ | CHL | 1H | 206D11_T7_p1_281_F | 6.73 | 0.78 | NA | −1.50 | NA | 0.29 |
| | (Manchuria | | pCOL | 1H | 206D11_T7_p1_281_F | 7.89 | 0.86 | NA | −0.29 | NA | 0.32 |
| | x Heils Franken) | | INF | 1H | 206D11_T7_p1_281_F | 3.67 | 0.83 | NA | −0.85 | NA | 0.17 |
| | | | pPUST | 1H | 206D11_T7_p1_281_F | 3.03 | 0.75 | NA | −0.16 | NA | 0.14 |
| HOR 1428 | Manchuria x | $F_2$ | CHL | 1H | HV5_963924_P1 | 2.64 | 1.26 | 0.50 | −0.30 | −0.59 | 0.12 |
| | HOR 1428 | | pCOL | 1H | HV5_963924_P1 | 2.24 | 1.35 | 0.14 | −0.05 | −0.35 | 0.10 |
| HOR 2926 | Manchuria x | $F_2$ | CHL | 1H | HV5_963924_P1 | 12.25 | 1.28 | 0.78 | −0.55 | −0.71 | 0.42 |
| | HOR 2926 | | pCOL | 1H | HV5_963924_P1 | 7.69 | 1.39 | 0.19 | −0.13 | −0.65 | 0.32 |
| | I 5 x Manchuria | $F_2$ | CHL | 1H | 206D11_T7_p1_281_F | 11.71 | 1.27 | −1.02 | −0.54 | 0.53 | 0.44 |
| | | | pCOL | 1H | 206D11_T7_p1_281 F | 14.45 | 1.35 | −0.30 | −0.15 | 0.50 | 0.49 |
| | | | pCOL | 4H | 1_0510_120_F | 1.96 | 1.37 | −0.09 | −0.01 | 0.10 | 0.05 |
| Sultan 5 | Manchuria x | $F_2$ | CHL | 4H | contig_134516_375_F | 6.32 | X | 0.27 | −0.08 | −0.30 | 0.06 |
| | Sultan 5 | | CHL | 7H | BOPA1_4671-856_192_F | 43.54 | X | 0.85 | −0.73 | −0.85 | 0.62 |
| WBDC 008 | WBDC 008 x | $F_2$ | CHL | 7H | SCRI_RS_185445_60_F | 13.49 | 1.32 | −1.61 | 0.21 | −0.13 | 0.49 |
| | Manchuria | | pCOL | 7H | SCRI_RS_185445_60_F | 12.41 | 1.29 | −0.32 | 0.05 | −0.14 | 0.46 |
| | | | INF | 4H | 1_1398_77_F | 2.05 | 1.27 | −0.27 | −0.16 | 0.61 | 0.08 |
| | | | INF | 7H | SCRI_RS_185445_60_F | 3.92 | 1.28 | −0.37 | −0.36 | 0.95 | 0.16 |
| | | | pPUST | 4H | 1_1398_77_F | 1.50 | 1.13 | −0.06 | −0.03 | 0.46 | 0.06 |
| | | | pPUST | 7H | SCRI_RS_185445_60_F | 4.34 | 1.46 | −0.10 | −0.09 | 0.90 | 0.18 |
| WBDC 085 | WBDC 085 x | $F_2$ | CHL | 4H | 1_1398_77_F | 1.60 | 1.38 | −0.35 | 0.54 | −1.53 | 0.06 |
| | Manchuria | | CHL | 7H | OZ_43640_p1_174_F | 3.85 | 1.35 | −0.81 | 0.30 | −0.37 | 0.16 |
| | | | pCOL | 4H | 1_1398_77_F | 1.83 | 1.44 | −0.10 | 0.07 | −0.66 | 0.07 |
| | | | pCOL | 7H | OZ_43640_p1_174_F | 4.92 | 1.43 | −0.19 | 0.08 | −0.43 | 0.20 |

Chr: Chromosome.

Cross: Direction of cross is determined by Mother x Father, designation of alleles are A and B for Mother and Father, respectively.

AEE: Allelic effect estimate, negative and positive values indicate resistance is contributed by the A and B alleles, respectively.

DEE: Dominance effect estimate.

PVE: Percent of the phenotypic variation explained.

Association of NLR-A and Rps6: A total of 38 accessions were selected for transcriptome sequencing (Table 12). RNAseq was performed using either HiSeq 2000 or HiSeq 2500 systems, with paired end reads of length 100 or 150 bp. Transcriptomes were assembled using Trinity and BLAST was used to identify the presence or absence of NLR-A. We identified a strong association with expression of NLR-A and expression of resistance at the Rps6 locus (Table 12). In total, seven accessions were found to express NLR-A and Rps6; and 15 accessions were found to lack expression of NLR-A and Rps6. Tophat alignments were performed on the genomic sequence of NLR-A using the RNAseq derived from 38 barley accessions. The majority of accessions contained the same coding sequence including Abed Binder 12, Aramir, Barke, BCD12, BCD47, Commander, Emir, Finniss, Golden Promise, Pallas, Sultan 5, and WBDC013, whereas accessions Hindmarsh, WBDC008, WBDC085, WBDC109, and WBDC110 contained polymorphisms relative to the Abed Binder 12 allele. In addition, Bowman was found to be identical to Abed Binder 12 based on WGS contigs aligned to NLR-A (FIG. 6). WBDC008 has the most polymorphisms, with 16 synonymous and 5 non-synonymous mutations relative to Abed Binder 12. Non-synonymous mutations include Q95E (WBDC008, WBDC109, WBDC110), N148K (WBDC008, WBDC085, WBDC109, WBDC110), S535P (Hindmarsh), L539S, W665L, and K680E (WBDC008), and A920V (WBDC109 and WBDC110).

TABLE 12

Association of NLR-A and Rps6 in diverse barley accessions based on expression and mapping, respectively.

| Accession | USDA-GRIN | Presence of NLR-A | Presence of Rps6 |
|---|---|---|---|
| Abed Binder 12 | PI 327961 | Expressed | Rps6 |
| Aramir | | Expressed | Not tested |
| Barke | | Expressed | Rps6 |
| BCD12 | PI 659443 | Expressed | Not tested |
| BCD47 | PI 659444 | Expressed | Not tested |
| Betzes | | Not expressed | rps6 |
| Bowman | PI 483237 | Present in genome | Not tested |
| CI 16139 | CI 16139 | Not expressed | rps6 |
| CI 16147 | CI 16147 | Not expressed | rps6 |
| CI 16153 | CI 16153 | Not expressed | rps6 |
| CIho 4196 | CIho 4196 | Not expressed | rps6 |
| Commander | CIho 6011 | Expressed | Not tested |
| Duplex | CIho 12420 | Not expressed | rps6 |
| Emir | CIho 13541 | Expressed | Rps6 |
| Finniss | | Expressed | Not tested |
| Fong Tien | | Not expressed | rps6 |
| Golden Promise | PI 343079 | Expressed | Rps6 |
| Grannenlose Zweizeilige | PI 548740 | Not expressed | rps6 |
| Haruna Nijo | | Not expressed | rps6 |
| Heils Franken | PI 327917 | Not expressed | rps6 |
| Hindmarsh | | Expressed | Not tested |
| HOR 1428 | PI 328669 | Not expressed | rps6 |
| I 5 | CIho 11619 | Not expressed | rps6 |

TABLE 12-continued

Association of NLR-A and Rps6 in diverse barley accessions based on expression and mapping, respectively.

| Accession | USDA-GRIN | Presence of NLR-A | Presence of Rps6 |
|---|---|---|---|
| Igri | PI 428488 | Not expressed | Not tested |
| Manchuria | CIho 2330 | Not expressed | rps6 |
| Maritime | | Not expressed | Not tested |
| Pallas | CIho 11313 | Expressed | Not tested |
| Q21861 | PI 584766 | Not expressed | Not tested |
| Russell | PI 483127 | Not expressed | rps6 |
| Sultan 5 | | Expressed | Rps6 |
| SusPtrit | | Not expressed | rps6 |
| WBDC 008 | | Expressed | Rps6 |
| WBDC 013 | | Expressed? | Not tested |
| WBDC 085 | | Expressed | Rps6 |
| WBDC 109 | | Expressed | Not tested |
| WBDC 110 | | Expressed | Not tested |
| WBDC 172 | | Not expressed | Not tested |
| WBDC 259 | | Not expressed | Not tested |

Molecular cloning of NLR-A: The genomic region encompassing the NLR-A transcript is 12.8 kb in length. This substantial size is primarily due to intron 2, which is 8.8 kb in length. Difficulty has been faced previously with using large T-DNA constructs using *Agrobacterium*-based transformation; therefore we adopted a cloning strategy that would allow for retention of native genomic sequence for the promoter and terminator of NLR-A, but removing either intron 2 or introns 1 and 2. PCR primers were developed to amplify NLR-A into two parts: fragment 1 contained 2.4 kb promoter, exons 1 and 2, and intron 1, and approximately half of intron 2, and fragment 2 that contained a portion of exon 3, intron 3, exon 4, and a 1.8 kb terminator region. Both regions were amplified from the BAC derived from Abed Binder 12 genomic DNA containing NLR-A, cloned into the pCR-XL-TOPO vector, transformed into *E. coli*, and sequenced. In parallel, cDNA generated from Abed Binder 12 RNA was used to amplify the entire coding sequence of NLR-A (fragment 3), cloned into the pSC-B vector, transformed into *E. coli*, and sequenced. The design of the T-DNA construct included a hygromycin resistance gene driven by a 35S promoter and nos terminator followed by 2.4 kb promoter, exons 1, 2, and 3, intron 3, exon 4, and 1.8 kb terminator of NLR-A. Primers were developed that amplified from cloned fragments 1, 2, and 3, ensuring that 40 base pair overlaps existed between all three fragments and the backbone vector pBract202. Fragments were assembled using Gibson assembly and were used for transformation with *Agrobacterium tumefaciens* (FIG. 8).

Materials and Methods

Genetic material: Abed Binder 12 (PI 327961), Russell (PI 483127), and Manchuria (CIho 2330) were obtained from the United States Department of Agriculture, Agricultural Research Service (USDA-ARS) Grain Resources Information Network (GRIN). Accessions SusPtrit and Golden Promise were obtained from Rients Niks (Wageningen UR). Accession Barke was obtained from Nils Stein (Leibniz-Institut für Pflanzengenetik und Kulturpflanzenforschung).

Pathogen material: Pathogen assays were carried out using either *P. striiformis* f. sp. *tritici* isolates 08/501 or 08/21. *P. striiformis* f. sp. *tritici* isolates were collected by The National Institute for Agricultural Botany in 2008. *P. striiformis* f. sp. *tritici* isolates 08/21 and 08/501 uredinio- spores were bulked, and maintained, on the susceptible wheat cvs. Solstice and Victo, respectively.

Inoculation assays: For plant inoculations, seeds were sown a peat-based compost. Plants were grown in a controlled environment chamber at 18° C. day and 11° C. night using a 16 h light and 8 h dark cycle with lighting provided by metal halide bulbs (Philips MASTER HPI-T Plus 400W/ 645 E40). Inoculations were performed on 14-day-old seedlings when the first leaf was fully emerged and prior to the emergence of the second leaf. Inoculum was prepared by mixing fresh spores with talcum powder at a weight ratio of 1:16. A compressed air pump was used to disseminate inoculum onto seedlings positioned on a spinning platform. After inoculation, seedling pots were sealed in plastic bags and stored in the dark at 6° C. in order to achieve the high humidity required for successful germination. Seedlings were returned to the controlled environment growth chamber after 48 to 72 hours post inoculation. Disease symptoms were scored 14 days post inoculation.

Phenotyping: Plants inoculated with *P. striiformis* f. sp. *tritici* were scored using a phenotyping scale that measured the macroscopic phenotypes of chlorosis (leaf yellowing) and infection (pustule formation). Plants were individually scored on a continuous nine-point scale ranging from 0 to 4, with increments of 0.5. Scores reflected the percentage of the inoculated leaf surface expressing the disease symptom. A score of 0 indicated no expression of the phenotype (0% coverage), whereas a score of 4 indicated extensive expression of the phenotype (100% coverage). For microscopic phenotyping, first leaves of inoculated seedlings were harvested with scissors and placed in 15 mL centrifuge tubes filled with 1.0 M KOH and a droplet of surfactant (Silwet L-77, Loveland Industries Ltd.). Tubes were incubated at 37° C. for 12 to 16 hours. The KOH solution was decanted and leaves were washed three times using 15 mL of 50 mM Tris HCL-pH7.5. Leaf samples were then incubated overnight at 4° C. in a 2.0% w/v staining solution containing wheat germ agglutinin conjugated to fluorescein isothiocyanate (WGA-FITC; Sigma Aldrich; L4895-10MG) dissolved in 50 mM Tris HCL. Leaves were washed with sterile water and mounted on microscope slides. Mounts were visualized under blue light excitation using a fluorescence microscope with GFP filter under a 5× objective. Each field of view (FOV) was 2.72 mm×2.04 mm. Data was collected by estimating the amount of colonization and pustule formation in non-overlapping FOVs covering the length and breadth of the leaf. Disease symptoms were estimated to be less than 15%, between 15 and 50%, or greater than 50% by assigning the values 0, 0.5 and 1 to each FOV. Percent colonization (pCOL) and pustule formation (pPUST) scores, ranging from 0 to 100%, were calculated by averaging the values relative to the number of FOVs in each leaf.

DNA extraction: DNA from all populations was extracted from leaf tissue following a CTAB-based protocol adapted for 96-well based format modified from (Stewart and Via (1993) *BioTechniques* 14:748-750) that provides PCR-grade genomic DNA.

Abed Binder 12×Russell $F_2$ genetic map construction: The concentration of gDNA was estimated using the PicoGreen dsDNA quantification assay (Life Technologies; P11496) and was normalized to 60 ng/μL. Oligonucleotide assay (OPA) genotyping using the barley BOPA1 design that includes 1,536 SNP-based markers was performed at the University of California, Los Angeles Southern California Genotyping Consortium (Los Angeles, Calif., USA) (Close et al. 2009). Additional markers were developed as either cleaved amplified polymorphic sequence (CAPS) or Sequenom MassARRAY markers to bridge gaps between unlinked chromosome arms and increase marker density. For CAPS marker development, we identified type II restriction enzymes that digest at polymorphic positions using CAPS Designer (available on the world-wide web at: solgenomics.net/tools/caps_designer/caps_input.pl). CAPS marker PCR reactions were prepared by mixing 2 µL buffer (10×), 0.4 µL dNTPs, 0.4 µL forward primer, 0.4 µL reverse primer, 0.2 µL Taq polymerase, 2 µL gDNA at 10 ng/µL, and 14.6 µL H$_2$O. The PCR cycling started with an initial denaturation step at 94° C. for five minutes and then proceeded through a cycle of 94° C. for 20 seconds, annealing at 56° C. for 30 seconds and primer extension at 72° C. for one minute for a total of 35 cycles. The procedure ended with a final extension at 72° C. for five minutes before being held at 16° C. Digestions were performed according to the manufacturer's instructions for individual enzymes. Electrophoresis was used to resolve restriction fragments using 2.0% TBE agarose gels stained with ethidium bromide. Gel images were taken using a Bio-Rad ChemDoc XRS+ imaging system and markers were scored manually. GBS CAPS markers are described in (Kota et al. (2008) *Funct. Integr. Genomics* 8:223-233). All primers and restriction enzymes for CAPS markers are detailed in ESM 1. For Sequenom marker development, SNP sequences were extracted in IUPAC format with 40 to 60 bp flanking sequence. This sequence was used as a template for primer design using MassARRAY software v3.1 for the multiplexing up to 32 SNP assays. Sequenom genotyping was carried out at the Iowa State University Genomic Technologies Facility (Ames, Iowa, USA). All SNPs and WGS contig source information for Sequenom markers are detailed in ESM 2.

Genetic map construction: A genetic map was constructed using 589 markers including 535 barley OPA (Close et al. (2009) *BMC Genomics* 10:582), 26 CAPS markers, and 28 Sequenom markers. JoinMap v4 (Kyazma B. V., Wageningen, Netherlands) was used using default parameters and an independence LOD threshold of 4.0. Genetic distances were estimated using the Kosambi mapping function. Integrity of the genetic map was evaluated through comparison with the current OPA consensus genetic map of barley (Muñoz-Amatriain et al. (2011) *Plant Genome* 4:238-249) and with two-point linkage tests using R/qtl (v1.33-7).

QTL and ANOVA analyses: Composite interval mapping was performed with QTL Cartographer (v1.17j) using model 6, the selection of five background markers, a step size of 2 cM, and a window size of 10 cM (Basten et al. (1994) "Zmap—a QTL cartographer," in: Smith et al. (eds) *Proceedings of the 5th World Congress on Genetics Applied to Livestock Production: Computing Strategies and Software*, Guelph, Ontario, Canada). Significant QTLs were extracted using the Eqtl module under the H$_0$:H$_3$ model using experiment-wide thresholds (EWT) that were calculated using 1,000 permutations with the reselection of background markers using a threshold of α<0.05 (Doerge and Churchill (1996) *Genetics* 142:285-294; Lauter et al. (2008) *Plant Genome* 1:99-110). ANOVA analyses for testing the linkage of individual markers were performed with R/qtl.

Transcriptome sequencing and assembly: Leaf tissue was harvested from first and second leaves 18 days after sowing for accessions described in Table 12. Samples were flash frozen in liquid nitrogen, and stored at −80° C. Samples were homogenised in liquid nitrogen-chilled pestle and mortars. RNA was extracted from samples using TRI-reagent (Sigma-Aldrich; T9424) according to the manufacturers protocol. DNA was removed by treating samples with RQ1 RNase free DNase (Promega; M6101). Samples were purified using RNeasy mini spin columns following the RNA Cleanup protocol (Qiagen; product No. 74104). The quality and integrity of the RNA samples were assessed using RNA Nano Chips (Agilent Technologies; product no. 5067-1511) on an Agilent 2100 Bioanalyzer. Abed Binder 12 and Russell RNA libraries were constructed using Illumina TruSeq RNA library preparation (Illumina; RS-122-2001). Final library insert sizes were predicted to be 411 and 339 bp for Abed Binder 12 and Russell, respectively. Barcoded libraries were sequenced using 100 bp paired-end reads on one lane of a Hiseq 2000/2500. This generated 32.0 and 59.3 million paired end reads for Abed Binder 12 and Russell, respectively. All library preparation and sequencing was performed at The Genome Analysis Centre (Norwich, UK). RNAseq data quality was assessed with FastQC and reads were removed using Trimmomatic (v0.32) with parameters set at ILLUMINACLIP:TruSeq3-PE.fa:2:30:10, LEADING:3, TRAILING:3, SLIDINGWINDOW:4:15, and MINLEN:100. These parameters will remove all reads with adapter sequence, ambiguous bases, or a substantial reduction in read quality. Transcriptome assembly was performed using Trinity (v2013-11-10) using default parameters.

Marker development for saturation at the Rps6 locus: Initial marker development was guided by two approaches to identify sequences anchored to the Rps6 region. This included the identification of anchored unigenes based on marker colinearity with existing genetic maps (Moscou et al. (2011) *PLoS Genet* 7:e1002208; Muñoz-Amatriain et al. (2011) *Plant Genome* 4:238-249; Potokina et al. (2008) *Plant* 53:90-101) and orthologous rice genes based on the barley genome zipper (Mayer et al. (2011) *Plant Cell* 23:1249-1263). A region on rice chromosome 6 was selected including 38 genes (Os06g43140 to Os06g43900). Best BLASTn hits returned from the cv. Morex WGS assembly (IBGSC (2012) *Nature* 491:711-716) were used as template for PCR primer design using Primer3 (libprimer3 release 2.3.6). All BLASTn queries were performed using blastall (v2.2.23). Abed Binder 12 and Russell gDNA was used as template for PCR amplification and Sanger sequencing. SNPs were identified by aligning sequence files using Seqman software (DNAstar Lasergene v11). SNPs were then used to develop markers using Cleaved Amplified Polymorphic Sequences or Sequenom MassARRAY iPLEX platform as described above.

Subsequent marker development involved either (1) the comparison of genomic contigs derived from cvs. Barke, Bowman, and Morex or (2) the comparison of Abed Binder 12 and Russell RNAseq aligned reads to WGS contigs anchored to the Rps6 region (IBGSC (2012) *Nature* 491: 711-716; Mascher et al. (2013) *Plant J.* 76:718-727). Geneious (v8.1.6) was used for read alignment using Geneious mapping function with default parameters and data visualization (Kearse et al. (2012) *Bioinformatics* 28:1647-1649). SNPs were converted into Kompetitive Allele Specific PCR (KASP) markers using a similar approach as described in (Ramirez-Gonzalez et al. (2015) *Bioinformatics* 31:2038-2039). All WGS contig source information, SNPs, KASP marker template, and primers are detailed in ESM 3. KASP assays were performed at the John Innes Centre Genotyping Facility (Norwich, UK).

Recombination screen and phenotyping: A recombination screen was carried out using seed bulked from F$_3$ plants selected from a single F$_{2:3}$ family that were heterozygous for Rps6. Sequenom markers were converted into KASP markers and used as flanking markers to identify recombinant chromosomes. Two independent progeny tests were performed using individuals with recombinant chromosomes. A total of 16 individuals per family per replicate were scored for macroscopic observation of chlorosis and infection.

Example 2: Transformation of Barley with Rps6 and Testing for Wheat Stripe Rust Resistance Yeo et al. ((2014) *Theor. Appl. Genet.* 127:325-337) previously established the doubled haploid population Sus-Ptrit×Golden Promise (SxGP DH) to identify a transformable barley accession that was also susceptible to several heterologous rusts of barley. We found that the accession SxGP DH-47 was susceptible to wheat stripe rust and had previously been shown to be competent for *Agrobacterium*-based transformation (Yeo et al. (2014) *Theor. Appl. Genet.* 127:325-337). Transformation of SxGP DH-47 barley is performed as described by Bartlett et al. ((2008) *Plant Methods* 4:22) with a modification on the use of immature embryo-derived callus for infection with *Agrobacterium tumefaciens* rather than immature embryos. Briefly, immature embryos are harvested from barley plants grown in a greenhouse, with embryos approximately 1.5 to 2 mm in diameter. In contrast to Bartlett et al. ((2008) *Plant Methods* 4:22), immature embryos with embryonic axis removed are placed on callus induction media for approximately four weeks. Immature embryo-derived calli are inoculated with *A. tumefaciens* strain AGL1 containing: (1) the T-DNA plasmid IHP_0205_NLR-A construct (SEQ ID NO: 15), the T-DNA plasmid IHP_0300 NLR-A native construct (SEQ ID NO: 34), or the T-DNA plasmid pBract202_TSLpMla6 NLR-A_CDS_gDNA_tMla6 construct (SEQ ID NO: 35); and (2) the pSoup plasmid. Calli are co-cultivated with *A. tumefaciens* for two days. All other steps in the transformation procedure are equivalent to Bartlett et al. ((2008) *Plant Methods* 4:22).

Seed ($T_1$) derived from the hemizygous $T_0$ plants containing a T-DNA insert are grown for two weeks, inoculated with *P. striiformis* f. sp. *tritici* isolate 08/21, and then scored for resistance or susceptibility as described above in Example 1 (see "Inoculation assays" in the Materials and Methods section). Several independent T-DNA insertion events are tested. In each experiment, individual $T_1$ plants are scored for resistant and susceptible phenotypes, and confirmation of Rps6 function is established by associating the presence/absence of the T-DNA insert with resistance/susceptibility.

Example 3: Transformation of Wheat with Rps6 and Testing for Wheat Stripe Rust Resistance Transformation of wheat (*Triticum aestivum* 'Fielder') is carried out as described by Periyannan et al. ((2013) *Science* 341: 786-788). T-DNA inserts include the original promoter and coding sequences for NLR-A (SEQ ID NO: 17) from barley contained in one of the T-DNA plasmids (SEQ ID NO: 15, 34, or 35) described in Example 2, as well as the genomic segment of the open reading frame of NLR-A (SEQ ID NO: 2) fused to a promoter and terminator from a highly expressed NLR gene from wheat. Phenotypic screens for resistance or susceptibility of transformed wheat plants to wheat stripe rust will be carried out as described above in Example 2 for barley.

Example 4: Transformation of *Brachypodium distachyon* with Rps6 and Testing for Wheat Stripe Rust Resistance Transformation of the model grass species *Brachypodium distachyon* is carried out essentially as described by Vain et al. ((2008) *Plant Biotechnol. J.* 6: 236-245; doi:10.1111/j.1467-7652.2007.00308.x). T-DNA inserts include the original promoter and coding sequences for NLR-A (SEQ ID NO: 17) from barley contained in one of the T-DNA plasmids (SEQ ID NO: 15, 34, or 35) described in Example 2, as well as the genomic segment of the open reading frame of NLR-A (SEQ ID NO: 2) fused to a promoter and terminator from a highly expressed NLR gene from wheat. Phenotypic screens for resistance or susceptibility to wheat stripe rust will be carried out as described above in Dawson et al. ((2015) *Front. Plant Sci.* 6: 876; doi: 10.3389/fpls.2015.00876).

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A transgenic plant, plant cell, or seed comprising stably, incorporated in its genome a heterologous polynucleotide construct comprising a member selected from the group consisting of:
   (a) the nucleotide sequence set forth in SEQ ID NO: 1 or 2; and
   (b) a nucleotide sequence encoding the amino acid sequence set forth in SEQ ID NO: 3.

2. A method for producing a plant with enhanced resistance to a plant disease, the method comprising introducing a heterologous polynucleotide construct into at least one plant cell, the heterologous polynucleotide construct comprising a member selected from the group consisting of:
   (a) the nucleotide sequence set forth in SEQ ID NO: 1 or 2; and
   (b) a nucleotide sequence encoding the amino acid sequence set forth in SEQ ID NO: 3;
   and regenerating said plant from said pant cell, wherein the regenerated plant comprises said heterologous polynucleotide construct.

3. The method of claim 2, wherein the plant is barley, wheat, or *Brachypodium distachyon*.

4. The method of claim 2, wherein the heterologous polynucleotide construct is stably incorporated into the genome of the plant cell.

5. A method of limiting wheat stripe rust in agricultural crop production, the method comprising planting a transgenic seed and growing from said seed a plant under conditions favorable for the growth and development of the plant, wherein the transgenic seed comprises stably incorporated in its genome a heterologous polynucleotide construct comprising a member selected from the group consisting of:
   (a) the nucleotide sequence set forth in SEQ ID NO: 1 or 2; and
   (b) a nucleotide sequence encoding the amino acid sequence set forth in SEQ ID NO: 3.

6. The transgenic plant, plant cell, or seed of claim 1, wherein the transgenic plant is a wheat or barley plant, the transgenic plant cell is a wheat or a barley plant cell, and the transgenic seed is wheat or barley seed.

* * * * *

SEQUENCE LISTING

```
<160> NUMBER OF SEQ ID NOS: 35

<210> SEQ ID NO 1
<211> LENGTH: 12800
<212> TYPE: DNA
<213> ORGANISM: Hordeum vulgare

<400> SEQUENCE: 1
gtgcaccata catgatatat acatgtaaat tcatgctgtt aatactgcat aaattgtgtg      60
tttgtgtgag agaaactgag agagggagta tcagttccat tttctctctt caccagtgct     120
tgttcatgta tccaagctac caggtcacca ggtgtattag cagagtctat atatatacat    180
```

```
actgcaggct aactagctag ccttcttccc ccctttaac taaggcttgc aaatgccgga    240
tccagttact attagtgctg ctgtaggatg gggcgtatcc gcagtaggct ggctcgcctc    300
tcccatcatt tcaagggttg tcaacaaagg tttcgcccac ctcgacttcg atgcagcaga    360
gaagctgaag atacttgata tacaagttct acaactgcag cgcgtgatag aagtagtcga    420
tgagagcacg tacaggcttc gcttggagcc actgttagac aagcttagat ctgctcttta    480
tgaagccgaa gacatcttgg atgattttga ttatcagcgt ctcgagaagc agatccatgt    540
tgggtctagt tccacacgta aacgcaagat agattcgctg gagaagaatc atcggtctgc    600
catgccgagt tcctccctaa aagataaggt atttccttgc tctcatactt gattttcttt    660
ttctgctttg tcacgggcac catatttctt ccatgtata tatatgtaat aaaaactagg    720
aactgtattc aactttattg tttattcttt ttcccatgat tagatggaaa cattcccgag    780
gatttcatcg aagggaaagg agactatcaa taatttactg agccaggtat ataagcatcc    840
actctgatca tgctgaaatc atacttgcat tattcatatt tttctttagt ttaatgtgca    900
ttattaatat ttaagaaaaa aaatgttatt taatggtaga aattagctat gcacatatac    960
tcttcctcca tctcgaagga atgaatgtat ctagatgcat tctagttcta gatacattca   1020
tttctatcca tctttgtaac aagtaattcc ggacggagga agtatatttc aatttaatat   1080
atcatacatt cataggatca agcacaacca tggtttgatc atcgagtatg accttaaaga   1140
agatttaatt cagaaccact tctcggaggt gatgggaaag gggaatcgac gagacttaga   1200
ccttaactag gatgagttgg accttgtgcc acatgacctc ttggtcttcg agggccaaat   1260 tatgagcat gaggtgttgg aagcaatcac tgatatgcct actgacaagg cccccaggcc   1320
tggtggcttc gccggcctct tttaaaagaa atattgggt aaaatgaggc ataacattgt   1380
gagggtgatt gggctctttg aatgcgtgca tgaggccaac atccattggc tcaagagcat   1440
ctacagccgg acccccttaaa tgaccccctca tacatccgtg gatgcattcg gttagtgacg   1500
ggagagggga gagaaggaaa aaagtgaccc aatcggaccc ctcatatcgt ccctgtatgc   1560
ctgggctgtc catgaaccct catatccatc tcaaataagg ggaggatatg aggcctcgcg   1620
aacgctctcg gtccaccgca taggacgcga ccctacctcg gaccaccttt atctttctt   1680 tattcattct tttctttctc tctcttcctc tccaccaatc acatacaagt gaccgggcct   1740
atgagaaaga aaataaggaa tctggttgcg tggacggaca aataggaaac acgcccggtc   1800
actgatcgcg cgcgtccgcg agtatttgag ggaccggatt tgcaagttct ggctatagat   1860
gattttaatc ccgtgaatac tatgcttta ccaaagacgg atagtttgga gggcattaat   1920
gactataggc ccattagctt tatatattca tgtgattgcc aagctcactg cgatgatctt   1980
cgtcacttgt acacgcctgc acatggacac tctcatatcc aactcacaaa gtgctttcat   2040
aaagaagaga agcattcatg aaaccttcac atatgtgagg aatcttgctc agcagtttca   2100
caaagacaag acctcttctc tcctcttcaa acttgatgta cgtaaggcct tcaacttggt   2160
caagtgggag tacattattg atcttattca aagatgaggc ttcccaagca agttcgcgga   2220
ttggattacc atgctcctct ctatctcctc ctctcggata cttctcaatg tgggggccgg   2280 accgccatc aagcatgatc atgggctacg gcaaagggat tcagtcttgc ttctcctttt   2340
ggtcattgcc attgacccac tccaaaaaaa ccttcatgtt gccaccacca aaattttgct   2400
acacaagatt ctaggtcgac atgccatagt gtagatgtcc ttatatacgg atgatgtggt   2460
ggtatccatg aaacccataa agcgggagag cgacaacctc tctaccatac tcaaatgttt   2520
```

```
tggccaggtc atgtcgccaa gggccttgat acaaacttcc agaggcggat tcaggccctA    2580
ggcagccaag gcctcggcct ggggcgtggt gactgtagca aaaatatcca atgtagcaca    2640
ttgtattata ctatagccat acagcctgcc tgcgaattga tctgattcta gctccgatta    2700
tccacataat taagatgccg tgaaatacaa cttggcccct tcttcaacac ttgctgacaa    2760
gaaaacaacc tttcctatga gatatttggg aagccgcttt tggtctggc  aactcaagag    2820 ggtgaacttc caattcttaa aggacaaggt gggttccaag attccaccct gggacggaaa    2880
aaacatcagc accattggtt gtacagttct tgtcaaattc gtgttatcct ccgaagcggt    2940
ctacctcatc actcccctca ttgcaacacc cagcatccta tgcaacacaa acaagctcaa    3000
gtgtgccttt ctttggtaag gttcaaacaa gattaacggt gcaaattgca aagtgcaaag    3060
ttaacaagga tttcgtatgc tggcaatgtt atgatctcta cacattttgc atagaacttg    3120
aattattcca caatatgcaa gaacaagcat gtagtcatgt aactttcaga tagccgtatt    3180
atgtgcaaac atattgcata gaacttgcat ggttccacaa tattcaagaa caagcataag    3240
tagtgtaact ttgagacaac aatatgattt tcacacagat agcattgaac ttgcatttat    3300
acatccatgc tgtgcacagt gttgaaacaa cataacaaaa acattggcga tcaatcattt    3360
cttgacatgt cgaagatgaa ttgcatccca cgttggtgtt gcctcccaa  tttatgtctt    3420 gctctttctc tcatagaaac gagtgtgcat tcccgcacac acacgcacat acacaacaaa    3480
cagacatagc aaagtacgca aatacacaaa gaaaaaacag ctaacacaag aaaaatctaa    3540
acacaaagaa cttttccaaa atcaatgaac ttttttttaa tccatccatt attttccgaa    3600
agtccatgaa tgttttctca attcatggta tttttcaatt tgtgaacatt tttcctacga    3660
atgaactttt ccaaaaagat gaaccatttg tcaaaaacaa cagtcagatg tcaaacatgt    3720
cagtggtcaa cttatcgccc aggttaccat gaagaagttt ttttgttgaa ccgtgaagaa    3780
gcgatcaggt gtatgatgtt gcgtgttgag cgacagctga tcactggtgt agtggagtgt    3840
tgcatccgct acaaaaagaa ctagacaagt gctgcctagg aggtcccgtt gtacatggaa    3900
aggcatcaca caaaccaaag cgcacaagcc tacatcctgc acctggcctt tttttttttgt    3960 tcttttttt  accttcaaaa aatcagtgca tgaagtagga tttgaaccat ggacctcttg    4020
gattagttcc atccgtaatg aactggaaca tctcacttgt tacgtctaat tactttattt    4080
atttctttta ttgtgaatct ctcagtctg  gttttcttct cgtgttgctt ttgttttgct    4140
tttttctttt agttttttttt ttcatttctc tatatttctt cttctttctc tcttttcttt    4200 tttccttttct ctaaatttat gaacattttc ttaaatttgt gaaaaaaaat tcaatttcaa    4260
gaccttattt tttgaatcca tgtttatttc tcaaataatg aatgttttca agtttgcaaa    4320
cttttgtcaa ttcaatggac tttattttgt caactctgtg aatgttccta aaattgatga    4380 acttttaaa  aatgtgtgaa acttttttgtc aaattctata acttctttga gaaattagtg    4440
acttctttta aagccgatta catattttaa ttttcatggat tattttcaaa tcgctgtttt    4500
ttaaaacaac atttgaactt ttctttaatc taagggttgc gttataaacc gaaaacttga    4560
tttttaccat tcgatttatt ctaaatttttg gttggcaaaa ctataaactg gaatgaatat    4620
ggggaagcaa ataaccaata attccggttca acggcttatt cggtttgatg ttcagtttta    4680
caccgagcaa actcgtcaaa tgtgttgctt tctattagga cactctgtca cattatatag    4740
caaattttgg tcccctattt tagtagctca gccggatttg actaaattgg acgctatgcg    4800
caacttgggt gtacgatgtc accgaaaggc tcgtgcgggt tgtgccttc  gttgtactaa    4860 aatttgcatg gagtactaga atgggaacac caatggcaaa atttaggtaa atttttactaa    4920
```

```
tatccacaag tacatcatgt acaacggagg ggttttggtt taggcggaag agttcgtccc   4980
ctagcacggt ttttagcata catcaaatac tcctaaaaaa acaccctaga attatcatgg   5040
catggaccca tgccaacttc catcgaattt tgactttttt tgtatttcct atggggtttc   5100
cggtcaaaaa acctcaagta ctgaccgaac gggatgcagc gtgcattcgt tcttcgaatt   5160
cgttcaaatt ttgcgtcgag tactagaatg gcatgctcag ctgcctgcaa aagttggata   5220
aatttaatga atgtccacag atacatcatg tacaaccgag cggtttcggt tatagcactt   5280
tttcacatag atctaacaga cgcaaatgtg ttatgttcat ttgacgcatg tcgagtcaca   5340
acatgctctc aaacataggc tatttctttc ggaaaaaaat tcgatctatt cattctcaat   5400
catggtaata caacgaatac cagaaataat aaaaattaca tctagatccg tagagcacct   5460
agcgacgatt acaattactg aagcgagccg aaggcagaaa aaatttcgat ctattcattc   5520
tcaatcatgg taatacaacg aataccagaa ataataaaaa ttacatctag atccgtagac   5580
cacctagcga caattacaat tactgaagcg agccgaaggc acgcctgttg gaaataacca   5640
cgacatgtgt ggtctgtgtc cggttcgtac acacgacaat catcgtatag tggtaggatt   5700
aggattcata gccgtgtagg ttatcttatc taatgtcctg actattatat ataggtagct   5760
atccccttgt aagctgcaac cgtgagatcg tgagatcaaa agatcaaaag caataaaagt   5820
gcaaggcttg gcccagaccc gacgtcgacg ttgttgccgt gtactttccg gcaatacata   5880
cgtacgatac tagctcgagt gctttccgag ctatccgtcg gagaggtaaa cgtagacgta   5940
gacagcaatc gtgcacgtat acacgaaggc tgctggatgg ttcctcctgt gctagctagc   6000
acgtactact gcacgagatc tttggctgat cgatctatgc ggcgagaaca caggaaacac   6060
tcggcgagtt ggccaaaagg agccttgcac ttttattgct tttgatcttt tgatctcacg   6120
atctcacggt tgcagcttac aaggggatag ctacctatat ataatagtca ggacattaga   6180
taagataacc tacacggcta cgaatcctaa tcctaccact atatgatgat tgtcctgtgt   6240
aagaaccgga cacagaccac acatgtcgtg gttatttcca acaacgccgc cgtcattgct   6300
cctccatcac cggagtcgag cacaatttgt tgtagtagac agtcgggaag tcgtcgtgct   6360
aaggccccgt agcaccggtg caccagaaca gcaaccaccg cagatgaaga ataacataga   6420
tcaaaaggat ccaatccgaa gacacacgaa catagacgaa caacgatgag atccgagcaa   6480
atccaccaaa gataaatctg tcggagacac aactccacac gctcaccaac ggtgctaggc   6540
acaccgccgt aatgggggct aggaagggag acctttattc catcttcacg cagccgccgc   6600
cgtctcgtct tcctgagcag gacacaaacc ctagcaaaac tgaaagtaac gactaaaaac   6660
ggagccctcc cgccggcgct tgctgagatc caccgcgctc ccatggccct aggggcaccg   6720
gagtggaggc ggacctgcgg cggcgccggc aggacgcaga aaccctaact ttttttttg   6780 tgaaggagga ggaggcggac ttttgtgtca aacataggct tatggcccac caggccacct   6840
tatattgaac atggtgcttc tttggacatt tttaaaatga cactaagttt tttagtaggt   6900
gggtatgccc ataatttaaa caaaaattta aaactgttat gttgagtttt taacgtaaaa   6960
aatatataga aaaggagaa aaaataaaac agccaatgtt ttgctaaagc taatacatat   7020
ttgaaaaaat gaatataatg tttgacagtt acttaaaact gttattttga tattccaaaa   7080
aatatttcaa tttcgcgaac aagcttcaaa aataaaaata aacctttaaa aggagaaaaa   7140
tgaattaacg gaaaatgaga aaatagaaag aaaataagct taggccttcg cggaactaga   7200
acacgacatc gctcttgtcg ggcggctgtt aggccgaggc aagtgctcgg gatttcaata   7260
```

```
agctcaacga ttcaaaaaat gtccctattt tcaaaattcg tttataaata aaaaaatgtt    7320 cccttttca agcttgtaca taaactgaaa ttcctttgcg ggagtttcta ataatgttcg    7380
tactttcaaa tgattttcct aacttcaaaa atattcctgt tttcaaaagc aatatacaca    7440
aataaaatga tgataggga aattcacaaa ataatgttc gctcttctag aaaaatgttt    7500
ctgttttgtg acttttagga acttaaagac aacaatattt tgaagtaata actataaaat    7560
gtgtaaaaaa gtttgtgagg tctattaaaa tgtttgtcgt tgaaagtgat cattttgct     7620 cttttaaaat gattgaaatg tctatttcaa aatttctata caattttat aatgtgaata     7680 tttttagttt cgtaattata cattttata aattttgaaa aaacaaatac ttgggtctgg     7740
cgatgtcgat ttgaggacct aatagtcagc gctttaagcg ccagttagga agctagcgct    7800
cgagcccagt attgcgcaag cttgcttgct tcacccgatg gctttgacaa aaattcatga    7860
attccaaaac gttaataagt ttgaagtata gtttgtggat ttgaaaattg ttcacgagta    7920
aaatgtaaaa agctcatgat cgtgaaaagg ttcacaaatt tgaaaacaag tttctgaata    7980
ttaaaattgt tgcacgttca aatttcaaaa ttatcatgat tttaaaaaca tttatgaatt    8040
tgaaaactgt tcacgagata tattttataa attttataaa aaaaacatga gtttagacaa    8100
tgttcacaaa tttggaagta gttggcgggt ttgaaacaaa ttttatgaat tttttttaacc   8160 ttgataaaca taaatggaaa ttcatgaaaa aaagtggaaa gggtaaaata aatataaaac    8220
gaaattggca aaaagaaaga gaaaaaaccg agagaaaacc atgcataaaa aacgaaaagg    8280
aaaattgtcc agaaaaacta tgcatagcca gaaccggaaa tgtagagaac aagaagaaaa    8340
agaagtggaa ctatgcagaa catgttatct atccgaggtg gtaattttga atccggacgc    8400
agagtttctg ctcccaagct catttgagct cgatgaaaac atttggcatg aaataacatt    8460
cctacaaagt ttggcaaaaa caaaatcgat gctgtgaaaa gcggattttc agagtgtcca    8520
ttttttttgc tacgaattgt aggaatgtta tttcatacca atttgttttt acacttaaaa    8580
ctttgtcatt gctggtcaca aaaaaaaaat cagaattatt tgaacgtttc ttgatttttt    8640
tttgattttt actgttcacc gagctcaaat gagctcgggg gcagaagggc actttcaaat    8700
cccaagtggc acaatagcca acatcaaata ggagcttcgc tactatacaa caccgtatac    8760
atacaaacat ggatataatt tgtcaaaggt ttatattgcc ctttatacgt tttcattctt    8820
ttataatgca acatgtaagt ggacaatcca gtggtccggc tcagcttgt gcgaaacatg     8880 ctagcacggt gactgtcacc gaaagctggc ttacgaaaac tcctagcttc ctgattagca    8940
gccttcaagc tgactgctca gcaaacgcct tgtttgaat aaagcttaaa attccatgca     9000
aaaaagttat tgccctttat atgttttctg agaggggagg gggaggggt atcaaagcgg     9060 gactagagat ataagcccgc taacctggtc ggggcatttg gaattgcaag aaaaacaggc    9120
acgggttttt agatcttcgg tttgacaaac gaaacatgtg caataaggca gcaaaagtat    9180
atattcaagt tgattcgatt actaatctaa tgatatctat tttttactgg catatctcac    9240
atgttctgtt agtcaaattg aagacctaag aactcatgcg ctccttgaa attgaacaaa     9300 actagttcat ttctaaaact tcaacacaaa atgacctcga tccgaaaata cttcacaaat    9360
tggctccttt ttgcatgacg cccgaggata gggctccatg ctatttagca tgacgcccta    9420
ggccaaggct gtatctacca tgacaccctg gccccggccg gcgtcatgca aagggccag     9480 tttgtgaaat attttgagat ggaggccatt ttgtttgaa gttcagaaa agggctagtt      9540 tcgtcaattt ttactacact ccttaccaac ccggatagag gagtaaatat atattcctca    9600
aatagagcag ttattgatag tttcaactta cctgttattc ggttttatag gggattggaa    9660
```

```
catcaaaagt ggagttgaag aaaagcctag agaaaataga aaataccata aacgatgcat   9720
gtaaagtttt ggaacaactg aacttgccga gtgtatgtaa tgataatggg agacgaggtg   9780
ttgctaccaa ttctcgtagt gcagtcacta ctgcaggtcc tcctctacga gtaattggtc   9840
gagatcagga tcgtgacaag atcatagcaa tgcttcatga aaggatgac cggtgtcaag    9900 tcaatggtac atcttattct gtaattggca ttcatggcgt cgccgggtct gggaaatcaa   9960
cacttgcaca gtatgtttat gatcatgaga aaaagtgcaa gcaaggtaaa agagaaggct  10020
attttgatgt tctcatgtgg attcatgttt ctcaaaaaat cggtttggag tccagtttca  10080
gggacatgtt tgagggggct acagggaaag catgcccgaa ttttaatagt cttaacgtct  10140
taaaggaaaa gttggaggag gaactacgtg gaaaacggat ttttttggta ctagatgatg  10200
tctggtacaa cagtaagaat tcaggagacc gtgaagaact gcagaagtta atttctccgt  10260
tgaatgttgg gaaggcagga agcagaatct tggtgactag tcgaactgaa gctgcattag  10320
tagctctccg tgctgcaaaa gagggatgta tcccaatatc taacctggat gataaagttt  10380
tccttaaaat gttcatgcat tatgcacttc cacatgcatg gccagttggc aatgatcgaa  10440
gaaaacttga aatgattgga gaggacattg caaaaaagct gaagggttca cctctggcag  10500
ctagaatagt gggttcacgg ctcggtgata atccaaatgt tgaattttgg aggagagaga  10560
aagaccggga tcttatgaac gagacgatgg gagcactttg gtggagctac cagtaccttg  10620
atgagcaggt caggcgatgc ttcgcttaca tcagcatttt tcccagacgt catcatttga  10680
aacgtgatga cttaattaac ctatgggtgg ccgaaggatt tataaagaca gtaaagctg   10740 aagaggaaat ggaagatgtt gcctcggaat actttgatga gctgctttcg ttctcatttc  10800
tgcaattagg agggaaagat gagctatttg cacgtgaggt cgattacttt ataattcatg  10860
atctgttgta tgatttagca gaggaggttg ctggaagaga ttgcttcagg atagagaaag  10920
gtttcacagg agaagtccct ccggatgttc gctatctttt tgttgggact tacgataaag  10980
agatgcttac tgagaagata tccaggttgc aaaatttacg cactctcttc gtcgataagt  11040
acatacagat tttatcaccc aagtacgatg attttgttag tatggtgact atgttgatgg  11100
ggctgcggaa attgagggta ctgaatttac atttcactgg atatggtatt cctaaattct  11160
cattgccgga ttctattctt cagtggaagc atctgcgtta ctttgctttt ggggtgtccc  11220
cgtttaccaa gctaaccttta ccatgcgctt ttaccaagct ttaccacttg catgtggtag  11280
atttcggtga ttgcaatagt ttggagtttt ctcgtggtga atacatgatg aacctggtca  11340
atttgcgccg tgtaatctac aagaattatc tcgactttcc gaacattggc aggctgacat  11400
ggctgcaatc gttgccgtgc ttcagaataa ggaagaaaca tgggtatgaa tcacatcagc  11460
tgaaacacct aaacaagctt caaggcaggc tgtacattgg tggtcttcag aatgttgaga  11520
gcaaggagga agctcttaat gtgaaccttg cagccaagga aaaactcaca gaagtggtac  11580
tgcgctggag tgataatagc tgcagtccag aaattcaagc agaggtactt gagggccttt  11640
gtccttcaaa gtatcttgaa atactagaaa tcaagttata caatggcatg aagtttccaa  11700
attggatgac gagtaagcat aagggtgggc caaagaacct gcaagaactt agattcagac  11760
agagcaccct gggatctgct cctgatgttg ggctttcat tcaccttcag tcgttattta   11820
tttatcaatg cagctgggat accttaccag ggaatatgga gcacctcaca gcgctcaaga  11880
aactggagat acggtcatgc aataatattc ggtcgcttcc aacactgccc aagtcccttg  11940
agcagtttgc gatctggtcc tgcagcttgg atgctttacc gggcaatatg gagcacctca  12000
```

| | | | | |
|---|---|---|---|---|
| cagcactcaa | gaaactggag | atacggtcat | gcaataatat | tcggtggctt | ccaacactgc | 12060 |
| ccaagtccct | tgagcagttt | gcgatctcgc | gctgcagctt | ggatgcttta | ccgggcaata | 12120 |
| tggagcacct | cacagcgctc | aagaaactgg | atatatggtc | atgcgagaat | atacggtcgc | 12180 |
| ttccaacact | acccaagtct | cttgaggagt | ttacagtctg | gaactgcact | agtgagttca | 12240 |
| tgcaatcttg | tatgacgact | gatgatccaa | actggcagaa | gattgagcac | gttccaaaca | 12300 |
| aaaaaattgg | atttctatga | aaacgataca | taaagaaggt | acgtatttaa | attcctttga | 12360 |
| cgtcttcgtt | ttccattttt | gcgtgcagta | aatgttactg | caacaattag | ccgttaaggt | 12420 |
| tcctggtatt | tttctgattc | agttgctaac | tattaggcgc | gtgccctttg | gttgaggacg | 12480 |
| ggagatgaag | tcgaagccga | agccgtcaga | atcttgctaa | atttacggtc | tctcttactg | 12540 |
| gatagcctct | tggttgggtt | atgcctactt | tggttggttg | agtcttgcat | gtttacacct | 12600 |
| aaagtggtgc | aaaatgccat | ctctccatgc | agtcacaact | cacaaacagt | ggatttatga | 12660 |
| attgtttaca | atatatggat | ttatggatgc | aataacgtgt | aataatgaac | agctgattga | 12720 |
| tttgccttca | tatatatata | tatatgattt | gtaacactgc | cgtgtggatg | atgaacctgg | 12780 |
| cccaaactgt | ttgattccta | | | | | 12800 |

<210> SEQ ID NO 2
<211> LENGTH: 3126
<212> TYPE: DNA
<213> ORGANISM: Hordeum vulgare

<400> SEQUENCE: 2

| | | | | | | |
|---|---|---|---|---|---|---|
| atgccggatc | cagttactat | tagtgctgct | gtaggatggg | gcgtatccgc | agtaggctgg | 60 |
| ctcgcctctc | ccatcatttc | aagggttgtc | aacaaaggtt | tcgcccacct | cgacttcgat | 120 |
| gcagcagaga | agctgaagat | acttgatata | caagttctac | aactgcagcg | cgtgatagaa | 180 |
| gtagtcgatg | agagcacgta | caggcttcgc | ttggagccac | tgttagacaa | gcttagatct | 240 |
| gctctttatg | aagccgaaga | catcttggat | gattttgatt | atcagcgtct | cgagaagcag | 300 |
| atccatgttg | ggtctagttc | cacacgtaaa | cgcaagatag | attcgctgga | gaagaatcat | 360 |
| cggtctgcca | tgccgagttc | ctccctaaaa | gataagatgg | aaacattccc | gaggatttca | 420 |
| tcgaagggaa | aggagactat | caataattta | ctgagccagg | ggattggaac | atcaaaagtg | 480 |
| gagttgaaga | aaagcctaga | gaaaatagaa | aataccataa | acgatgcatg | taaagttttg | 540 |
| gaacaactga | acttgccgag | tgtatgtaat | gataatggga | gacgaggtgt | tgctaccaat | 600 |
| tctcgtagtg | cagtcactac | tgcaggtcct | cctctacgag | taattggtcg | agatcaggat | 660 |
| cgtgacaaga | tcatagcaat | gcttcatgag | aaggatgacc | ggtgtcaagt | caatggtaca | 720 |
| tcttattctg | taattggcat | tcatggcgtc | gccgggtctg | ggaaatcaac | acttgcacag | 780 |
| tatgtttatg | atcatgagaa | aaagtgcaag | caaggtaaaa | gagaaggcta | ttttgatgtt | 840 |
| ctcatgtgga | ttcatgtttc | tcaaaaaatc | ggtttggagt | ccagtttcag | ggacatgttt | 900 |
| gaggggcta | cagggaaagc | atgcccgaat | tttaatagtc | ttaacgtctt | aaaggaaaag | 960 |
| ttggaggagg | aactacgtgg | aaaacggatt | ttttggtac | tagatgatgt | ctggtacaac | 1020 |
| agtaagaatt | caggagaccg | tgaagaactg | cagaagttaa | tttctccgtt | gaatgttggg | 1080 |
| aaggcaggaa | gcagaatctt | ggtgactagt | cgaactgaag | ctgcattagt | agctctccgt | 1140 |
| gctgcaaaag | agggatgtat | cccaatatct | aacctggatg | ataaagtttt | ccttaaaatg | 1200 |
| ttcatgcatt | atgcacttcc | acatgcatgg | ccagttggca | atgatcgaag | aaaacttgaa | 1260 |
| atgattggag | aggacattgc | aaaaaagctg | aagggttcac | ctctggcagc | tagaatagtg | 1320 |

-continued

```
ggttcacggc tcggtgataa tccaaatgtt gaattttgga ggagagagaa agaccgggat   1380
cttatgaacg agacgatggg agcactttgg tggagctacc agtaccttga tgagcaggtc   1440
aggcgatgct tcgcttacat cagcattttt cccagacgtc atcatttgaa acgtgatgac   1500
ttaattaacc tatgggtggc cgaaggattt ataaagacaa gtaaagctga gaggaaatg    1560 gaagatgttg cctcggaata ctttgatgag ctgctttcgt tctcatttct gcaattagga   1620
gggaaagatg agctatttgc acgtgaggtc gattacttta taattcatga tctgttgtat   1680
gatttagcag aggaggttgc tggaagagat tgcttcagga tagagaaagg tttcacagga   1740
gaagtccctc cggatgttcg ctatcttttt gttgggactt acgataaaga gatgcttact   1800
gagaagatat ccaggttgca aaatttacgc actctcttcg tcgataagta catacagatt   1860
ttatcaccca agtacgatga tttttgttagt atggtgacta tgttgatggg gctgcggaaa   1920
ttgagggtac tgaatttaca tttcactgga tatggtattc ctaaattctc attgccggat   1980
tctattcttc agtggaagca tctgcgttac tttgcttttg gggtgtcccc gtttaccaag   2040
ctaactttac catgcgcttt taccaagctt taccacttgc atgtggtaga tttcggtgat   2100
tgcaatagtt tggagttttc tcgtggtgaa tacatgatga acctggtcaa tttgcgccgt   2160
gtaatctaca agaattatct cgactttccg aacattggca ggctgacatg gctgcaatcg   2220
ttgccgtgct tcagaataag gaagaaacat gggtatgaat cacatcagct gaaacaccta   2280
aacaagcttc aaggcaggct gtacattggt ggtcttcaga atgttgagag caaggaggaa   2340
gctcttaatg tgaaccttgc agccaaggaa aaactcacag aagtggtact gcgctggagt   2400
gataatagct gcagtccaga aattcaagca gaggtacttg agggcctttg tccttcaaag   2460
tatcttgaaa tactagaaat caagttatac aatggcatga agtttccaaa ttggatgacg   2520
agtaagcata agggtgggcc aaagaacctg caagaactta gattcagaca gagcaccctg   2580
ggatctgctc ctgatgttgg ggctttcatt caccttcagt cgttatttat ttatcaatgc   2640
agctgggata ccttaccagg gaatatggag cacctcacag cgctcaagaa actggagata   2700
cggtcatgca ataatattcg gtcgcttcca acactgccca gtcccttga gcagtttgcg    2760 atctggtcct gcagcttgga tgctttaccg ggcaatatgg agcacctcac agcactcaag   2820
aaactggaga tacggtcatg caataatatt cggtggcttc caacactgcc caagtccctt   2880
gagcagtttg cgatctcgcg ctgcagcttg atgctttac cggcaatat ggagcacctc    2940 acagcgctca gaaactgga tatatggtca tgcgagaata tacggtcgct tccaacacta   3000
cccaagtctc ttgaggagtt tacagtctgg aactgcacta gtgagttcat gcaatcttgt   3060
atgacgactg atgatccaaa ctggcagaag attgagcacg ttccaaacaa aaaaattgga   3120
tttcta                                                             3126
```

<210> SEQ ID NO 3
<211> LENGTH: 1042
<212> TYPE: PRT
<213> ORGANISM: Hordeum vulgare

<400> SEQUENCE: 3

```
Met Pro Asp Pro Val Thr Ile Ser Ala Ala Val Gly Trp Gly Val Ser
1               5                   10                  15

Ala Val Gly Trp Leu Ala Ser Pro Ile Ile Ser Arg Val Val Asn Lys
            20                  25                  30

Gly Phe Ala His Leu Asp Phe Asp Ala Ala Glu Lys Leu Lys Ile Leu
        35                  40                  45
```

```
Asp Ile Gln Val Leu Gln Leu Gln Arg Val Ile Glu Val Val Asp Glu
     50                  55                  60

Ser Thr Tyr Arg Leu Arg Leu Glu Pro Leu Leu Asp Lys Leu Arg Ser
 65                  70                  75                  80

Ala Leu Tyr Glu Ala Glu Asp Ile Leu Asp Asp Phe Asp Tyr Gln Arg
                 85                  90                  95

Leu Glu Lys Gln Ile His Val Gly Ser Ser Thr Arg Lys Arg Lys
                100                 105                 110

Ile Asp Ser Leu Glu Lys Asn His Arg Ser Ala Met Pro Ser Ser Ser
            115                 120                 125

Leu Lys Asp Lys Met Glu Thr Phe Pro Arg Ile Ser Ser Lys Gly Lys
130                 135                 140

Glu Thr Ile Asn Asn Leu Leu Ser Gln Gly Ile Gly Thr Ser Lys Val
145                 150                 155                 160

Glu Leu Lys Lys Ser Leu Glu Lys Ile Glu Asn Thr Ile Asn Asp Ala
                165                 170                 175

Cys Lys Val Leu Glu Gln Leu Asn Leu Pro Ser Val Cys Asn Asp Asn
                180                 185                 190

Gly Arg Gly Val Ala Thr Asn Ser Arg Ser Ala Val Thr Thr Ala
                195                 200                 205

Gly Pro Pro Leu Arg Val Ile Gly Arg Asp Gln Asp Arg Asp Lys Ile
210                 215                 220

Ile Ala Met Leu His Glu Lys Asp Asp Arg Cys Gln Val Asn Gly Thr
225                 230                 235                 240

Ser Tyr Ser Val Ile Gly Ile His Gly Val Ala Gly Ser Gly Lys Ser
                245                 250                 255

Thr Leu Ala Gln Tyr Val Tyr Asp His Glu Lys Lys Cys Lys Gln Gly
                260                 265                 270

Lys Arg Glu Gly Tyr Phe Asp Val Leu Met Trp Ile His Val Ser Gln
                275                 280                 285

Lys Ile Gly Leu Glu Ser Ser Phe Arg Asp Met Phe Glu Gly Ala Thr
            290                 295                 300

Gly Lys Ala Cys Pro Asn Phe Asn Ser Leu Asn Val Leu Lys Glu Lys
305                 310                 315                 320

Leu Glu Glu Glu Leu Arg Gly Lys Arg Ile Phe Leu Val Leu Asp Asp
                325                 330                 335

Val Trp Tyr Asn Ser Lys Asn Ser Gly Asp Arg Glu Glu Leu Gln Lys
                340                 345                 350

Leu Ile Ser Pro Leu Asn Val Gly Lys Ala Gly Ser Arg Ile Leu Val
            355                 360                 365

Thr Ser Arg Thr Glu Ala Ala Leu Val Ala Leu Arg Ala Ala Lys Glu
370                 375                 380

Gly Cys Ile Pro Ile Ser Asn Leu Asp Asp Lys Val Phe Leu Lys Met
385                 390                 395                 400

Phe Met His Tyr Ala Leu Pro His Ala Trp Pro Val Gly Asn Asp Arg
                405                 410                 415

Arg Lys Leu Glu Met Ile Gly Glu Asp Ile Ala Lys Lys Leu Lys Gly
                420                 425                 430

Ser Pro Leu Ala Ala Arg Ile Val Gly Ser Arg Leu Gly Asp Asn Pro
            435                 440                 445

Asn Val Glu Phe Trp Arg Arg Glu Lys Asp Arg Asp Leu Met Asn Glu
            450                 455                 460
```

```
Thr Met Gly Ala Leu Trp Trp Ser Tyr Gln Tyr Leu Asp Glu Gln Val
465                 470                 475                 480

Arg Arg Cys Phe Ala Tyr Ile Ser Ile Phe Pro Arg Arg His His Leu
            485                 490                 495

Lys Arg Asp Asp Leu Ile Asn Leu Trp Val Ala Glu Gly Phe Ile Lys
        500                 505                 510

Thr Ser Lys Ala Glu Glu Met Glu Asp Val Ala Ser Glu Tyr Phe
    515                 520                 525

Asp Glu Leu Leu Ser Phe Ser Phe Leu Gln Leu Gly Gly Lys Asp Glu
        530                 535                 540

Leu Phe Ala Arg Glu Val Asp Tyr Phe Ile Ile His Asp Leu Leu Tyr
545                 550                 555                 560

Asp Leu Ala Glu Glu Val Ala Gly Arg Asp Cys Phe Arg Ile Glu Lys
                565                 570                 575

Gly Phe Thr Gly Glu Val Pro Pro Asp Val Arg Tyr Leu Phe Val Gly
            580                 585                 590

Thr Tyr Asp Lys Glu Met Leu Thr Glu Lys Ile Ser Arg Leu Gln Asn
        595                 600                 605

Leu Arg Thr Leu Phe Val Asp Lys Tyr Ile Gln Ile Leu Ser Pro Lys
    610                 615                 620

Tyr Asp Asp Phe Val Ser Met Val Thr Met Leu Met Gly Leu Arg Lys
625                 630                 635                 640

Leu Arg Val Leu Asn Leu His Phe Thr Gly Tyr Gly Ile Pro Lys Phe
                645                 650                 655

Ser Leu Pro Asp Ser Ile Leu Gln Trp Lys His Leu Arg Tyr Phe Ala
            660                 665                 670

Phe Gly Val Ser Pro Phe Thr Lys Leu Thr Leu Pro Cys Ala Phe Thr
        675                 680                 685

Lys Leu Tyr His Leu His Val Val Asp Phe Gly Asp Cys Asn Ser Leu
    690                 695                 700

Glu Phe Ser Arg Gly Glu Tyr Met Met Asn Leu Val Asn Leu Arg Arg
705                 710                 715                 720

Val Ile Tyr Lys Asn Tyr Leu Asp Phe Pro Asn Ile Gly Arg Leu Thr
                725                 730                 735

Trp Leu Gln Ser Leu Pro Cys Phe Arg Ile Arg Lys Lys His Gly Tyr
            740                 745                 750

Glu Ser His Gln Leu Lys His Leu Asn Lys Leu Gln Gly Arg Leu Tyr
        755                 760                 765

Ile Gly Gly Leu Gln Asn Val Glu Ser Lys Glu Ala Leu Asn Val
    770                 775                 780

Asn Leu Ala Ala Lys Glu Lys Leu Thr Glu Val Val Leu Arg Trp Ser
785                 790                 795                 800

Asp Asn Ser Cys Ser Pro Glu Ile Gln Ala Glu Val Leu Glu Gly Leu
                805                 810                 815

Cys Pro Ser Lys Tyr Leu Glu Ile Leu Glu Ile Lys Leu Tyr Asn Gly
            820                 825                 830

Met Lys Phe Pro Asn Trp Met Thr Ser Lys His Lys Gly Gly Pro Lys
        835                 840                 845

Asn Leu Gln Glu Leu Arg Phe Arg Gln Ser Thr Leu Gly Ser Ala Pro
    850                 855                 860

Asp Val Gly Ala Phe Ile His Leu Gln Ser Leu Phe Ile Tyr Gln Cys
865                 870                 875                 880

Ser Trp Asp Thr Leu Pro Gly Asn Met Glu His Leu Thr Ala Leu Lys
```

```
                   885               890                895
Lys Leu Glu Ile Arg Ser Cys Asn Asn Ile Arg Ser Leu Pro Thr Leu
                900                905                910

Pro Lys Ser Leu Glu Gln Phe Ala Ile Trp Ser Cys Ser Leu Asp Ala
            915                920                925

Leu Pro Gly Asn Met Glu His Leu Thr Ala Leu Lys Lys Leu Glu Ile
        930                935                940

Arg Ser Cys Asn Asn Ile Arg Trp Leu Pro Thr Leu Pro Lys Ser Leu
945                950                955                960

Glu Gln Phe Ala Ile Ser Arg Cys Ser Leu Asp Ala Leu Pro Gly Asn
                965                970                975

Met Glu His Leu Thr Ala Leu Lys Lys Leu Asp Ile Trp Ser Cys Glu
            980                985                990

Asn Ile Arg Ser Leu Pro Thr Leu  Pro Lys Ser Leu Glu  Glu Phe Thr
            995                 1000                 1005

Val Trp  Asn Cys Thr Ser Glu  Phe Met Gln Ser Cys  Met Thr Thr
    1010                 1015                 1020

Asp Asp  Pro Asn Trp Gln Lys  Ile Glu His Val Pro  Asn Lys Lys
    1025                 1030                 1035

Ile Gly  Phe Leu
    1040

<210> SEQ ID NO 4
<211> LENGTH: 152228
<212> TYPE: DNA
<213> ORGANISM: Hordeum vulgare

<400> SEQUENCE: 4
cagccgatac cccatcagcc tgatccgtc  cacatcagtg gaggtgggct cctggcaagc     60
atccacaacg aacttgtcat ctccagcacg cactttctt  ctcagaacca cctgcacata    120
ccaagccatg aacatctatt aaagcagagt tcatttctat gtttccaaac ggcacataat    180
taaggttgct acatgaacaa ggttaatcgc ctgatgcttt tgttactaa  cccacgactt    240
agcaatgtat tcaaagtcta caacagagtt agttccaatg tcaaagaact agattattac    300
ttacatacca tagtaaacaa ctacattcag tgttcatcag tcatcactgc atgcagagat    360
ggcactttgc attatccata gtttcacttg agcacttcac ctgcaaacac gcaagaatcg    420
acaaagagac atgatgaaca tggaaatcgc tacccagtaa gtctaagggt ttggactcca    480
tctcacacgt ctgacagttg gcagctacaa tcttgacggc aaatagtagc agtaacattt    540
actgaagaca aaatggaaaa acaagatgc  caaatgaatt taaccacgta ccttcctgta    600
tgggcctttc tcaagaactt ataattgttt tctttggaat gtgctcaatc ttttgccaat    660
ttggatcagc agccgtcgta caagatcgca tgaactcacg gttgcagtac atgagtgtaa    720
actcctcaag agacataggc agcgttggaa gcgaccgtat attcatgcaa actgtgatct    780
ccagtttctt gagcgacgtg agatgatcca tattacctgg taatgcatcc cagctgcatt    840
caacaagaca tagcgaaaga agataaacga aagctccaag gtcaccagca ggtcccagct    900
ggccacagtt cctgaagata agttcttgga ggttctttgg ggagccgcta tgcatacccg    960
caatccaatt cggtaacccc gaagcaaggt aattcctgat ttctagtcgt tcaagatact   1020
tcgatgggca agaccctca  actacctctg cttgaacttc tgggctgcag ctcccccttt   1080
tccattgaag tacaagttct gtgagttttt ccttggctgc aagattgact tcaagagcct   1140
cctccttgct ctcaacattc tcaagaccgc agatgtacag cgtgccttga agcttgttta   1200
```

```
ggtgtttcag ctgatgtggc tcataccct ttttcttcct tattgtgaag aacggtaaca    1260
tttggagcca tgtcagcctg cccacgtctg gaaaatccag acgtgcctca ctgattacac    1320
agcgcaagtt gacgagattc atcatatctt cactactaga aaacgccaaa tcacgacaac    1380
cgccaaaatc taccacctgc atgtggtaca gcttcgtaaa agcagccggt acagttagcc    1440
tggtaagtgc agtcacccaa aaaagaaaat aacgcagatg cttcaactga ccaatagaat    1500
ccgggaatga gaacttgcgg agaccagttc caatgagaca taaattcagt acacgcaatt    1560
tccgcagccc catgaacgta gtgaacatac tcgcaaagac ttggtactcg tttgatttaa    1620
cctctatgta agcatcgatt atgagagtgc gtaagttctg cagtccagat atcttcttag    1680
taagcaattc tctatcataa gtcgcaacaa agagataccg aacatcttta ggaacttctc    1740
ctgtgcagcc tttctcgatc ctgaagcaat ctcttccagc aacctcctct gctaaatcac    1800
ataacagatc atgaatagta aagtaatcca cctcacgttc aaataacttg tctttccctc    1860
ctaattgcag aaatgaggcc gacagcaatt catcaaaata attcttagca acatcttcca    1920
tttcctcttc agccttacca gtctttataa acccttctgc tacccacaac ttaactaact    1980
catcacgttt cagacgatgt cgtctaggga aaatactgca gtaagcgaag catcgcctga    2040
cttgctcatc aagatattgg tagctccacc acagagctcc cattgtgtca ttcaaaaggt    2100
cccgatcttt ctgactcctc caaaactcaa tagtttgtgt ctcacggagc cgtgaaccca    2160
ctgttctggc tgctagaggt gatcccttca gcttttggc aatgtcctct ccgatcattt    2220
caagtattct gcgatcatgt tcacttaccc ttgtatctcg aagtgcataa tgcatgaaca    2280
tttcaaggaa cactttctca tccaagtcag atattggaat gcatcgctct tttacagcac    2340
ctagagttac taatgcagct tcagttcgac tagtcaccaa gattttgctt cccgcctttc    2400
caacattaag tggagaaatc aaaatttgta gctcttcacg atctcccgaa ttcttaatgt    2460
tataccagac atcatccagc accaacaaaa tctgttttcc acgcagttca tcctccagtt    2520
tttcctttag gacgttacga ctactgaagt tatcgcatgc tttccctgta gcccctcaa     2580 acatctctct gaaaatggaa tccaaatcaa atttctgaga acatgaatc cacatgacaa     2640 tatcaaaatg gccttccatt ttctcttgct tgtacttttt ctcatgttca taaacatatt    2700
gtgcaagtgt tgatttccca gacccggcaa taccatgaat gccaattaca gagtagcaag    2760
ttccactaag tgatggagca tcggccgtag caaagcctag ctcagttggt tcagatctat    2820
aaaaccaagc aataagtcca ctacaccaat acaggacata tgctctgaga attttctgaa    2880
aagcccggac cagggcccaa aatggtcccg gtgaggctcc gccactacca ttgacgatat    2940
ttgtttggaa ttggtctttg ttctcattaa gcattgctat gatcttgtca cgatcctgat    3000
cccgaccaat tactcgcgtc ggaggacctg cagtagtgac tgcactgcgt gaattggtag    3060
caatagctcg actcccatta tcattactta cacctagcaa cttcagttgt tccaaaactt    3120
tacatgcatc gcttatagca cttttctatct tctctaggct ctccttcaac tccacttttg    3180
acataccact tttctgcaaa accaaataac aagcgagtcg aggctatcaa gaactcctcc    3240
atttgaaaat aaataaacac ataagtttgc aagttattct ctctctgtgc cctgttaata    3300
tctggtatgg aggcgggtga aaacaaaaga aagccagttg tgttccctgg gtacactata    3360
acgcgctggt agcaagctgg cccctcacat ctggtgttaa gtggccgcaa tagttagatc    3420
cattattaaa agaaaaagga aatccttgttt ctcttttga attttgacaa aactataaat    3480
tatattttat aaaaatattc tggtgctaat gggccgcaac agtgagatcc cttaaaaga    3540
```

-continued

```
tactgttggt tttctttttt tgaaaatttt aacaaaatat ataaattatt atatgtttga    3600
taataactat aatgaaatat tttataagtt tagaagattt ttttaatatt tagtattttg    3660
ataaaaatca tggactttaa aaggtactgc cattttttaa ataatcattt agttcaaagt    3720
tgtttatatg ttttaatttt tttatgtaat ttaacaagat taaaagaaga gtggccacaa    3780
gtgaaaagga accaagaaga ggggccacaa gggagaagga gatgcctacc aggaggtctt    3840
gacaaaatat tgccaatgtg gcgtcagtca acgggccacg cagtttggtc agacttacac    3900
atatatagaa cagatatgtg tgttttcaaa cttttagggc ctggcacacc tcgaatactt    3960
ttaggactgc cggtgtattt tactctgttt aacgttttta atgaatttca ataatgttta    4020 atttaattt aaaattgttc acacatttct ttgaaagttc acatattatt tttacatgca    4080 catatttta taaaagtcca tataattaaa aaatgcgttc atgtattttt tttgaaacat    4140
gtacttaaaa aggtgttcac atatttgttt tctaaatgtt catgtaaaaa gttttttttgt    4200 atttataaag ttttctataa tttttaaaacg ttcttgaagt taacaagctt ttcttgcata    4260
tttaaaattg ttcttgtatt ttagaaatta attatatatt ttataaatgt ttgtgtaatt    4320
tttaaaaatg gttcaaaagc tcttttttaa aatttgaaaa atttctaaaa attaagcagt    4380
ttgtaaaatg atcatgtatt tatcaaaaaa aaatatagtt tttgaatagt atttcattat    4440
tatatttaga aaaatatttg tatacactcc ctccattcta aaatataagg tgcatttgtt    4500
tttcgaaaga caaacatgtg catgtttgat caagattta gaaaaaatat attaatatct    4560
acaatacaag atttatatca ttagatctat catgaaaaca tttcatattt aatttattgt    4620
gtattgtaaa tgttgatatt ttattctatg atcttggcca aacatacact agtttgactt    4680
gcacaaaaat caatgcacct tatattctag aatattggga gtatttgcca aggagcaggc    4740
ctcactggga gaaatcatca attggctccc gggtgaccca ggattcggcc actaagagca    4800
tctccaacag gcgttcaaaa actgctccac gcgttaaaag attcgttttt tggacgccag    4860
acagcttcaa cagacgctgt aaaagagtgc gcgcgctaaa aacttttggg caatcgctga    4920
aaaacgctat cgcccgcagc atattttcga cgccagattg cgcgtgcttc atagtttaca    4980
ctacacgttt ttttgggcgc gcgttttttgg gcaattgcta aagcaatgtt gctcccgacg    5040
cgctaaagtt gctagaatga ctcgctaaaa ctattttaga gcgcggaatt tttgtgcgtt    5100
tgttggagat gctctaagga gatgcatgag atacggcgga agggcccccat gatctcttcc    5160 tggccaccgg acgaattata acgagaccaa cgagatcttg atgaatgcgg taaaacccgt    5220
tcaacaagta tgagtgcacg gaaataccttt atgattttgg gggttggaca tgacagaccg    5280
aacattcttc ttcagcgaat ccaccttact gccatcttga gacttgccat catggatctg    5340
cttcttgaga cgctgatact cgagagcatc caagatgtct tcggcttcgt agagagcaga    5400
tttaagcttg tctaacagtg gctccaagcg aaccctgtaa gtactctcgt cgactacctc    5460
catcacacgc tgcagctgta aaatttgtat gtcgagtatc tttagcttct ccgttgcatc    5520
aaagtcaagg agggcgaaac ctttgttgag gacccttgaa ataatgggcg aggcgagcca    5580
gcctactgcg gatacgcccc atcccacagc agcaccaatg gtaactgcag ccgccattgc    5640
aagctttggg gtgaaggcta gctaggctgc aatatctata cgtaaataaa tcctggtagt    5700
gcacccagta acctggtcac aaccaagaca cacagataag tagcagctga gagagatgat    5760
tcaaccaata cttttgtttcc cactgattag ctttatataa gaaggctaaa ctgacctgaa    5820
catgggagcg cgttctcgct gagggcgagc ccggacctgg tgattcttct ccgcctcccg    5880
cacaaagaac tgatccggcg tcgccgagag gctggacctg gtgtccacct ccgaacgaag    5940
```

```
atgaagaaag cagaacggaa aattgcagaa gagcagtagc gatgatgtgc ggtggaagct    6000
actagcaaag tgcaaaatga atgctggggc aagtgagagg acgggtgtgt gtggttgagg    6060
gatgctttca gtacagcaac ggtgggctaa taagtcttgg tccaacttca gaatggacgt    6120
ctcttgcgtg gccactgtac ctagtgtgac agcgcgcata atagtgacag cactgcacgg    6180
cacatttgac tttgaaggca gtaggaagtt tccagacagg ttctcagttt ctcacagcac    6240
aggtccagtt tcatcatttt gtttagcatg catgaccagt ttcactttca tcgcctcatc    6300
attggtctga gaaagaaggg cgcatctcca aggctaaacc tcaagcgaac actactggaa    6360
ccagcatgtt tgcgtagtgc caatcggcaa tgcgcagaat catctcggcg aagtgttaag    6420
ttgaataagc ctcggccaaa tttcagaacg ggcgattcag gccagctctt ccggaaccaa    6480
atttgaagtt ttcatcacag ataaaacgcg taaacaagta gattggcttt gctttatctt    6540
ataaccaact tgcataatag tactagtata tactactagg attgtagaac tacacatgga    6600
tggcagcaca gttgaccttg aaggcagtaa gaaatttcat catcttcttc ttatcattgg    6660
tgtgagaaat aatgctagcc acgcgacgac acggtctgta tacctgtcta ttaatctata    6720
tgatccacat actacatata ctctacccaa atccaatgaa tgaaaacgcc atagcaaaat    6780
tactcgctcc taaattaatc agtacaagaa caaggcagtg taaaatttct gagagaaaag    6840
gggccgatct actaaatgca tctatcttct gatggaattc gatggtttct caaaaatgtg    6900
gtaatcaaca cttaaaatcc aggagcaaag ctagcacacg ggaatggaaa agggatcgtt    6960
ccagtccgag aactcgctgg tttgcgctgt ttctgacggc gaatcgcctc cggccgccgg    7020
atcgaagctc cgccaagcag cctagaacac gtcggcggcc ttccatcgcc gcagccgact    7080 atgccgagg agacgggagc ttgtggttcg ggcggcccgc tcgcaccctc ttacgatact    7140
tgggccggcc cgattggaat atgaagcgat ttttcctcc ctttttttct taatttattt    7200
tactcccttg agttccaatt acttgtttta aatttgtcta gatatggata tatgaaccca    7260
aagaagtatt ttttttctta ttttatttta tcattcgtca tgttttttt ctatctgcac    7320 tgaaatttac caatgtttga ccactaggat ttgcttcatt cacactagcg agtgaatgtt    7380
tgtatctact cgtgtaagaa aagttcaact acttcatctg gtccttttta ctccgcatat    7440
aaaatttatc tgaaatttta ttgttaaaat tcagcattca caaatgaaa tcaatatcat    7500 taggtgtgtt ctgaatttaa ttttcatatt gtataacttt agtattgtag gtattgatat    7560
ttctttcata taaatatggt caaattttag gaagtttgtc tttataaaaa acttatatga    7620
aaaataaaga agactggatg gattattaaa ctatgcaacg gggaattttg tgtgtgtgtg    7680
tgtgtgagtg tggattttat tttgggtaat agaatttgct agtttgggtt gtacccaagt    7740
tttactttct tgctctataa gaatgtttag ctttcctcac acccgaataa tgaggggtac    7800
cttttgtcta agaagaaata cggaaaagga ttgtctaatc tcgacatttc tccatcctag    7860
ttaggcctcc tgatctccca ttgagcattc gttatcttct tatgacccc tccttcggag    7920 gtggttttct ttccacgtga tatgctctgc tactcttctc tagtgggaaa ctcatccttg    7980
tgcaatgcgg ttctcaataa actctctgct tattgcatca actctcatta ttatcctatg    8040
acattattga ggtggtggaa tgtgtgtagg cttttttgtt agaccagtaa ggacatttgc    8100
tctcatgcac tttgtctaaa agtttgaaac atgtttcgtc ttaatgtgca ggaaggcgac    8160
tctagtaagc gatatcttca tgttcaaaac gggtacttcc tcttgaatta tgtgcacaag    8220
atccatcaga aagggacatg cctgtgcaag tcatgatact tccgtagtct tgaagacgac    8280
```

```
caagaggcgg atcccattga ggttgttcct ggactaggtt gtggcagaat gcttcccaac      8340
ctgttgattc tttagtggct cacttgttcg gaatggcggt cgatgggagc acttcgtttc      8400
attgcgactg gggactttca tggagtgcgc tatgtttatc ctaggtggct ctatattccc      8460
aacgaatcca ccaaatgcta ccatgggtac aatcctcaat ggaggcagat aaggcatgaa      8520
ccacccactc caacatatta gaacctagct agtattgttg aaaagcattg aggatggaga      8580
aacatgcatc cttgtaggac aggtcgctag ccctaaactc aacgatgtac tccctcggat      8640
aaaattagga tgaatactaa tcaaaacagt ggcacagatg accctgctat tttgatcacc      8700 aacaccccc aaagagaccg atgcacggtt gacaaaccat gagatgaaga ggcactatcc       8760
acttgatgaa atcaccacat aatctctaag attgacgttt ttagacttaa gactcaaata      8820
agaaagggaa taaagttgtg gaactttcat ttggtgaaat gttcgtcatc accacataaa      8880
aatggaaaaa ctgcattta gtattgatgt aaggttccac gcatatttcg gtggagccag       8940
aaagacaata caggcaaggg gaactgacag atgcactgac aaaaagccat ccatgagcac      9000
tcgagggcct ttttgattcg cataatttt aaaacacagg aataagaaaa acacataaag       9060
aaggtggcat atcctatagt actctacatg aattgagata atggttgata gcgcatcaaa      9120
aacaatggaa ttctacagca aaaatttagc ggatgaaaaa tttcctccaa aatgtagtac      9180
aaattgatac cgtgggaaaa ttccaaggat ttaaatccta cgaatcaaaa ggccatcaca      9240
aaaaaaatca taagggtccc aatcctgtaa aaattgaacg agattcagtt gaatcaaagg      9300
aacccacaac ttttaatcgc attatatttg tcattagtag aatttgatgt tagaaaatat      9360
tgttcgagac attcaagtac cctacacaca tctctaatta tccacacgag ttcaactatt      9420
tttaggcctg gtagtctgag cgcagcttgt tttctcaaaa ctaagtctaa gttcaactaa      9480
aaaaaaacta gtgtggatta actgaaaaaa cagtctgagc cttgcctttt ttatgcaaat      9540
ttctatttgc catcgcacag ggcagacgga ctaatgaaac gactgggctg gcccagttaa      9600
ccagttcatt cattctggtt ttggttcctt ttttttttctc ctgatcatag tctcagctat     9660
tatttttttt cctgtttctt tttccttgtc ttttccattt tcatttcctt tttgtttaca      9720
tatctatttt aattttgtaa tttaaagaaa ttcgggtttc taataagtaa gtccaaattt      9780
caaaaactgt ttgtgatttc gagaaaatgt tcagaatgtt tagaatgttc tcatttccac      9840
atgttgttat caatttttta aattttctaa aaaatgttca cagattcaaa aactctttgc      9900
gtttccaatt ttttataaat gttttctaat ttattaaatg tttgctattt ggaaaagtgt      9960
ttgtagtgtg aaaatatctt tgggtttcta ataaatatta aaaaatgtac gaaatttcat     10020
aaaaatggtc atcttttga aaaagttca aaatatttt tttaagttct cattttcaca        10080
tgttgttctg aattttttct tttaaatgtt tcaatacttt ttcatggata taaaaacaat     10140
ttgcatttcc aaattttgt ttggagtttt gaaaaatctt ttttatcaaa ttgttttca       10200 catattaaaa agaatgttcg tgagttttat aaaatatttt ctttatcaaa attagttcac     10260
gcgttcaaac aagggaaagt atttttcttca tccggctgat ccgaagatgg ccatctgctg    10320
cctcggacat gcgatgcgtg ttcatgtgga cccattgcac ccttacatct ttctttcctt     10380
atctccttcc ccaactcatg cagcaccatg gccaccacca tatctacctc ctgcaacgcc     10440
gcagcccctc agccctgat gacaggcggc cggccggccc tcccctcccc ctccccccc      10500 cccccgcccc caaccccagt ggacgccggt ttttcccca actcctgcag cgccatggcc     10560
accaccacat caagctccta caacgctgca gcccctccgc cctcgatgtc ggccggccga    10620
ccgaccctct cctccaccac caccaccctc cccccccca cgcgcgcgcg tgagccgaag     10680
```

```
ctgaacgaag acggtggagg ccggaggtga cgatgcattg acaagtttcc gcaacatggc    10740
ctcagtttca aaaaaatgga ataaatatcc ggttgcaaaa gattgttgta acctgtccta    10800
tgttgcaaaa gttttctcta acatggcctt gaccttcgtt gcaaaaattt ctttcgcaac    10860
agtacctatg ttgcagaaag acgaagaaaa aaaatctgca acaaagagat gtttctggaa    10920
actcgaccgt tgtttcagga attaatgggt ccagagctat ttttttttgca acaaatcgat    10980 tatttctgca actcgaccgt tgttttagaa attattgggt gcggggaggc gacggggcga    11040
tatagatcgg acggctgcgc gcgtacatcg aacagccgtc gaggtgacag atgtatatta    11100
aacatccgtc gatagacgcg tagcagctca aaaaacattg ttggtgattt ttatattttc    11160
taaccaaatt taaaaagtat tcgcaatcac tttttccaaa taatgtccaa ctttggaatt    11220
taaagaaatg ttcggatagg acattacctt tatcttcgtg caccatatga aaccaacaaa    11280
acacattttt tcccgttgac aaactacacg tccttaggaa taggaggttg cttgttcgat    11340
ccctcccttg agcacatatt ttggaatttt cactgtgttg cactaatggg acgacccagt    11400
ttggtgtcgt ctgtgtgtcc gctcgcgaca gaaaggagtt tcctggaaaa tcctatatac    11460
tgctcagtgc gtccaattgt caacgctttg tattttatttt gatattttca ctgtgtcgca    11520
ctaatgggcc gacccagttt ggcgtcgtct gtgtgtcaaa aatcctatat gccgttcagt    11580
gcgtccaatt gtcaacgctt cacacagggt gacgtgagcg atggacgcag tgggcccttg    11640
agcacatatt ttgggatttt cactgtgttg cactaatggg ccgacctagt ttggcgacgt    11700
atgtgcgtcc gctcgtgaca cgaaggagtt ttctggaaaa tcctatatgc cgctctgtgc    11760
gttcaattgt cgatacttcg cacttatttt ggtattttca ctgtgttgca ctaatgggcc    11820
gacccagttt gacgtagtat gtgcgtccac tcgcgacaca aaggaatttc ctgaaaattc    11880
ctatatgccg ttcagtgcgt ccaattgtcg acgtttcgca cagggtggcg tgagcgatgg    11940
atgcagtggg ccggcctgtt tagcgttttt cacagataag gttttgggaa ccttctagac    12000
ttttccagct ggttattttc ggtgttcgaa aacttctaac agtttccctg aatctttttt    12060
ttttgttttc ttttttcaaa attctttttgg tttcttttttt tctgttaatg tttcaacaac    12120
gttctgggat ttaaaaaata tcggaatttt caaaaaatgt tctgggtttt aaaaaatttc    12180
cttcaaattc acaaaatgtt cttgatttttt aggaaaattc ttgtcacttt gaaaaaaaat    12240
agttttcaaa aaatgttctt caaatttgga aattgtttct tatttgttca aacaaatatt    12300
ctgtattttc aaaatgtgtt tgggactgtc cgaaattgtt cttcaaataa taaaaatgtt    12360
ttttattttc agaaaaacgt taagaatttt ctaaaaatgt tatggatatt cataaaatgt    12420
tctagatttt ttaaatttat tttcataaaa tgttgttgtt tttcgaaatt tgttctcaaa    12480
attaaaaaac cgttcgaatt ttcaaaaaat gttcacattt ataactttgt tcaggatttt    12540
tcagaattat tcgcatttca aaaattggtt ctcaagatcc aaaagatgtt cgtgctttaa    12600
aaaaattgtt cactcttcca agtttgtttg gggttttcaa aattgttctc catttcaaaa    12660
ttttgttcct aatatgaaaa aatattcacg ccttaaaaat ttgttcccct tcccaaattt    12720
gttcaagatt ttttaaaatt attcatcatt ttaaatttgt tctcgagatt tgaataatgt    12780
cgtgctttaa aaaaattgtt catgcttcca aatttgtttg gtgttttcaa aattttgttc    12840
ttaagaatca aaaatatttt gcgcttccaa aatttattcc ggtaccaaat tgttcaaca    12900 ttttttaaaa ttatttttttt tatttttttt caatattcaa taaatgttcg tgctttcaaa    12960
aattgtttgc attttttaat ttatttttaa aatgttcatg ttttcaaaaa atggttgata    13020
```

```
aattcaacgt tgttcattt tgattttgaa aaagaaaaa atgaaataag caaaaaggg      13080 aaaaaaggaa attatctgtt tttttagaca aaaacaaaag ctgggccggc cgagtcaggg   13140 tgaaccccc gtgcgtgccc ccgactccct gctgcataga gcgaagggta ggagctgccg   13200
agattccttt tttattggaa gaaagtagt ctcaactgag atatcgggcg tgaaaactca    13260
ccacatattt acctagcaag gcccatccgc aagtttttt ccaattctac tcaacatctt   13320
tagtgagcgt accactcaga aaagcaatct cgcgactcag actattcttc agagacccac  13380
atgttaggag ctggacacgt ggctctttct tattggccct atttgcagag tgtcactctc  13440
ggcaaagtta cgtcacgtgg caaccatcgt cccccttcggt cgtccgttgg ctactttatt 13500
ttgccgagag gcactgtttg actctcggca aactgtttgc cgagtatccg tatcctggct  13560
ttcgataaat tcttgtttgc ctgagaggtg tataccggat gccctttgcc gagtgcacca  13620
ctcggcaaag tctttgccgg cagttattgg cccttttgccg agagacactc gacgtatatc  13680
ccgattccag tagtaaatgt aagatgtttt ttcacactat acttgtgcca aaatacgtct  13740
tacattatgg gacggaggga gtagctggtt tgtattttcg agtctgattg tttttcttaa  13800 attttagtt agagttgcta taacaggaat agtctgacta ttggtaaaac ggaaacaacg   13860
gaactgataa ccaacgcaag aacaatatat gcagcaccaa cctgccgctg gagggactct  13920
gagatctatt ttccttgctg ttgcagggta taccctccgg ccttggggct ctaagttcgg  13980
atgaccagta aaagtactga gaattgttcc tcgtgaaatc ttgaatacgc acaaactgct  14040
gggtggaata ttctctgttg tcggacctttt tgtcccttttt tcttcagatt tggcggagct 14100
gtaatcatac ctgtgataga tcccgtggag ctcgagctag gaagaaactt tgcattctcc  14160
cacctgtgat cgttttgctt gcttacaaga cacacacaag acaacatatg taaatttatc  14220
ctctatgcaa tccagccatg aaattttact tgtgctgtcc aagtcgacgc ggattatagc  14280
acatatcaat cagacaacta gccttctcaa actacttcca atgcttacag gaggcaatca  14340
cataagggga taagccggag gggtgaactg aagataagag ccttgacatt taaggcatgt  14400
aaacctcaca tttaccagtt gatgtacacc gctgctcggt tagtgaggta taggaccgta  14460
ggagatgtgc tactgctgcg gtggtggttg cgacgtcgag aaggattgcg gaaaatcata  14520
ggagtatttc ctcgagtctc tcgatcttaa agttaagcac gaggctgatg atcacgtaca  14580
tcatgcacgg atcagataga tgttgaggac ttgacgtaca tctcctggtc cggcggcatc  14640
cctcgtcaat cctgagacaa tattcctcgg aagtgattct gctccacagc ccgtggccct  14700
ggaacattgc cgattggatt ggcgcctctt ggtaatcatc ggccttatgt acgaattctt  14760
gatcaagcat caccgtgaaa tctcgtaccg tctatacgca cgaattagtc tactggatga  14820
ttaccatcag gccagtggcc tctctttcac catcttctgg atgtattcca acgagacaac  14880
agatcgattg atagatgtgt atgtataaat ttggttaata aaacagaaca cagcatccgg  14940
gactgttaag agctctcagg cctaaccaga gtacgtagca agcaaggaca tcgaaataag  15000
caacagggag gccacaaggg gcaccaaata tctacgtagt tttaaaggtt gatattacat  15060
atccattgat caacttgtag cttctgtaag tatcttcatg ggatttggcc cccaccgatt  15120
aagaaaggcc agcgagcgtt gttggcctgc atttgctgct gcatctgagc catgacatcg  15180
tcgaaggtgg tgtccgggtc gtcgtcctgc gagtcgtagc cgtccgagtc cgacccgtac  15240
aacggcctca tggcctccat ccgcgccacg aacgccaccc cctcctcgtc ccgctccaac  15300
tccggcttcc tcttggagcc gcagcccgcc tgcttctccg cctccgcctt ggccttgagg  15360
aacgcctcct ccttctccag ctccgcgatg aacttgatca gcccctcctc cgtcgtgatg  15420
```

```
gtctccacct ccgcctgcgc cttggccttg atcgtcgcct cctccggcgt ggccttcttc    15480
gccttgacct tgaggaccgg cgcctcctgc tgctccgacc tggccatcgg catggcgaac    15540
ggcctcttgt cggcggccat cgccggatcc gctccggctc cctcccctct tctgctggtt    15600
ggtttagggt ttggtggatt tctctgcgtc tctcgtggga tcttctcttc tcaacgaaaa    15660
gctgcgcgcg gctggcgtat atattacgag gggaaccgtc ggctccgagt cggtcttcgt    15720
atcaggagcc cggaccggcc tcttctttcc gctgggctgt gttgggccgg gctgggcacc    15780
atcgattcct tcttttccgtt agcttgtttt cctttttcct ttattctttt gagagagaca    15840
ggtattattc agactagctt tgttgggcaa gtcatgttcc tcggaaaaaa ggtcacattt    15900
ggttgggatt ttgtcccgat gatgccagtg tcattcacat attctcaaag catgaacatc    15960
ttttttaaatt gtgcatttt tataatattt taggaacatt tgttgaaaat gtataaggag    16020
ggaggtagat gcaaatgtac ttcggcttcg ggctttgggt ttcgcgtttt atgcccaccg    16080
tgagagggcg gtagatgcaa atgtataagg aggcatgttt tatgataaat ggattgatca    16140
gagcgtcatg tgatgggcgg catcgctcgc atcctccatc tccaggacgc tggcaccgcc    16200
attccctgcg gcaaacctcc tctgccccgc cacgggccac cgacattccc tattgttaga    16260
agggagtgag agattggtgg aatagttttt atattgcttg agcctcgtag gcatatatat    16320
ggtaggatgt aattttccta tatatatata taagtacatg atctacttga cgtacaagac    16380
aagccagaat acctagtcta tactatgttt ccaatacaat cacgatactc aaaatccccc    16440
cgcagtcaca atagtagcga cacagatggt gagaccggag aagaatccga aggtaagcca    16500
acggtcatcc ctccatagtc gtaacggtcg atgcatggcg gaagttgtga ctggagtgga    16560
aactgacgag gtttctcaag caaggcgata gcccttgtg ccgatgtcga ggtacccgag    16620
agcgtagggt ggtgtagccg tggtcgaggt agccgtgcga agaatgtcat ggtcgatgtc    16680
gagtcggggt agtcggtgtc gaggaagtca tcgtgaagcc gcgggcgcaa gagggcgccg    16740
agtcagtcat gggcgtaatg gcgtcgaagt agtgatgcgc cgggaaggag acgtagttga    16800
cgatacggcg tgcgggtt gccaagcccg gggacacttc gtggacgaag gtacgcatca    16860
gtgttgccat caccgggcat gcatagacgg acgaggacga tgttgacaat gcgtcgctct    16920
aggtttgcca ggcccgggaa cacagcgggg acaaatgcac gcggcggtgt tgccaacatc    16980
gtgcatgcgt agaggaggga cctacacaag ttgtacgtca tgtcgaggag tcggatggga    17040
cagcagagaa gtagactcga caacgatgcg atgcaaatcg gcgggggccg atgccgcccg    17100
cggtggccga agtagatgaa gtggtcgggg tagacgacga agacatttgc gatgagctgg    17160
tgtgatgtac ggttgacgaa gggggtagac gggcgacgca gctcgggcgg gaaagctaca    17220
acaacgccga agaagaggcg cgacatggct cgggtgggcg agccgcaacg tcgccaaaga    17280
ggagtggcgg ccacggtctg acgacggcgg cggctgttgg ttaggagtgc ggcgacgatg    17340
ttcgaagtag gcgagggaga acccgacagc gtgtcgaaga ccggcacgga cgatggcgtt    17400
accatgccaa gataggcatc acgacgcata ccaggtaaag tcgatgtgcg gagacagcga    17460
agtggaccgt gagccgcggt gcaacgcctt gaagggctt cgcagtggcg gcaggtgggt    17520
cggggcgacg gcaggaagac ctcggggtgg cgatgtggac cgcgtgccgc ggcgctacga    17580
cccgaatggg caacgcagcg gcggggcgcg ggtcggtgta ccacgagga tggccccggg    17640
cgacgacggg gaccgcgtgc tgccgcgcta cagcccgatg gggcggtgta gtggcggcac    17700
gcgggtcggg gcaaccgcgg ggagaactac taggcggcgg cgctgcgacc cgacgtggcg    17760
```

```
acgcagcggc agcccgttgc tcgattggta gaggggcgtg ctgtactcgg ggacaacctt   17820
cacatgatat gcggtagccc gttgctcgaa cggtggagag gcgcatgcaa ccgactaatc   17880
aggtcagttg cacggcgtgg atggagtaga tcgcggcagg cgggtgatca attcgatcgc   17940
acgcgaggtc ggggacgctg cttggtgatg atgacggcgt cgtggacaat gaagcggggt   18000
ggtcgagcag accgagggc  cgacggccag cggggaacta cgtgctcgag gcaaccgacg   18060
cccaagcgca aaagctggtg gccactagta gaaaacgggg ctatagtccc ggttggtaag   18120
ggcatataga cccggttctt caaccggtac tattaacttg ggactaaaga ccccctttag   18180
tctcggtttg ccaggaaccg agactaaagg ccctccacgt ggctgatgtg gctcgaggac   18240
ctttagtccc gattggtgtt acctacccgg actaaaagta ttttttttccg attttttaat   18300 ttttttaaa  tatttttttt aaatatgatt ttagaatctt tgaattattt aacaatttaa   18360
tctctcatca cccctactca ctccttcgac gtggcgctta acttttcggt tttatcttaa   18420
atgattttca agtctccact tgttgttttc ttaacaatat agtaagctat caatcctatt   18480
aacccttagg tcttgatgtc acatgattaa attttttgaa ttccaaacaa ttactaaaat   18540
aaacaacaat atttaataaa caacaataat taatttaaaa acttcaaaaa gagaaaataa   18600
taaaaaaact caaataattc ttaaaaagca tacgtctcta ctggatagat cgatgtgcta   18660
gctagtatca actagtacaa atgcccgtgc gttgcaccgg gtaaaaaaat ataggtagta   18720
aacaacatga taatctcaat caatacataa gatcataatc aagcacataa tattgttaaa   18780
gagtacataa tattcagtat ttgtgagact gttagatgca ctcttgcaag cagagtaaat   18840
tctcctctgt agtaggagta tcttgttaat ttttgtgaag tatagcatct actgcctgaa   18900
cctacaactg agaagaaatt gcatcagtgg gatccagtat tgcaaggctt tgtttcaagg   18960
gagtcctgta attcacccat agatcagtac tattaactaa atgctctgag aaggaatcct   19020
acaaaccgag ttcattggat gtgcataaga ttttatttca atgtatgtat ataggaaaac   19080
taaagcttca tgtgatccat aaagttagac aaaagctttc acataggtca ataaagatgt   19140
acctatgtga aaaaaatatg tacctgattc tgctcggttc cggatgggct accgtttggg   19200
cgacgagtct gtgcagggta tgttattggg gttgtaggat catttccccc agcaaatgaa   19260
tcgtattctt tattaccgct tcaaattaga ggctgctcaa catcatttga cgggaactaa   19320
taaaagactt tggaaacaac aagctcctcc tgcttttcac cttgacctac cccaaggtga   19380
tactgatgca ttctccaatt agttttttct gccttgccac ctccttccg  agaacctatg   19440 taaagaacca gtattttctt ccacccttt  atgacaccgt tattatctaa gatagatctg   19500
gattttccaa tcttgtgcca tctgagattc tcgtcacaaa caatgtggtc actatggcta   19560
atcttgcgac gtttacgctt gccaacatcg taggcatttg atattttgtg gaagaaatga   19620
ctggcgactc cgtctaattt gacacctgca gacatatatg aattagctaa cgatgactta   19680
ttctgcatag tatgagctaa ctatttaatt cagaaggccc tgatagcaag tctaagtaag   19740
aatcatgtac cagggagatt ttccagatgg gtatggcaga ttacttcagc ctcctctatg   19800
gttggaataa aaccatctat tagtacatgg gatgctgccc tgccaacctt tccttctaaa   19860
tgttcaagca gatcgaggtc agttggatca aacttaacac cagcagggag tcctcgccac   19920
tgtgataaaa cctgcaatac aaagcaggga tccttcatga acacagggtc gtgtattctt   19980
gttgtgatgg tgtgtgcaga gttatcaccc gaattgatat atatttggaa caaattatga   20040
aaacaagaat gagatgcaat ccggaacagg gggagaacca atagcaaaag ggcccgtgcg   20100
ttgcaacggg aactatatgt tgtatggttt aactaagact accaattatc tatgacatga   20160
```

```
actcttgttc ctccacctgt cgtcctttga aaaaatgtag aagcaaactg tagatttgga    20220
gaataaaaaa tgaagagaat caacagattt gattagatga gcgtgttcct ccttgtatcc    20280
atcaaagtct gatttgtttt tctttcctga acatgtttgc tgtgaaaaga agcgtgctgt    20340
atgaactatc tggtttgatt atctcaagaa aagatggtct gaaccaacta ttacatctag    20400
aaagaaagga aaatacgacc gcaatgccga tccgagtttt cagatccaac tgaggcatag    20460
gttattggtt tcagagtttt tttagatgaa cacggagctc tccctccggt tccattgcaa    20520
gataaaaccc aacaaagtat tatacatcag ctcacataga ggaaaaaatt aaacaatata    20580
tattttaaat tgtgatcatt ctatgaaaac ctcatacata acgacaacca tggtgatcat    20640
tctatgaaaa cctcatgcat atttgttgta caatcaaaaa taaaggttga ggtttaaaga    20700
atgtagcaat aatttataag tactcctaat acttctacca aaatattcag agactgttct    20760 ttttcctaa cgtatactta tttaaccgaa taaatactaa agattttctt atattatttc     20820
ttcctttgtg aaaaatgcag ccaagcaaac atacatgtcc gggcacgcca tctggttctt    20880
ggcgcactcc tcccattccc gcactttgtc tgaccacgcc ccctgcaatc actatatcga    20940
tcagcgtcag ttactacaaa atatcataaa tctaaatagc acgtcaccac ctcatgaacc    21000
accaacatgt agatcagatg aaaaactatt cagaaagatt tcacaccttt atgctcttgt    21060
tcagcgcgtc gacgaatttc cccgcgtctt cgtcgtagta gtccttctcc gccgtctgga    21120
tgatgttcac gtcccagacc tgacaacata caacaaccgg aaggtacaag tttcagcatt    21180
gttgccacac ttctttttt ctaaagtctg aactacatga ggcttacatg gtggagtttc     21240
agataaaatc agttaaggaa aattttaatt atggtttcag ttaaattcag ttgatgtttc    21300
agtaaaggaa aagtttattt atggttttag ttaaagtttg agttaaggaa aagttccatt    21360
tggtgtcatt tggtttcatt ttggccatca tttcagttaa atacagttaa ggaaaagttt    21420
catttggttt catttgtttc tgaaattaga gtaaaagagg agcactattg taagagggga    21480
gcaaatggac tactccaagc tcctacactt aattaacaca aagatgctac tcatacactt    21540
tactggaaaa aggtacaatt aattaaatgg cctagtgctc catacatatg catatggaaa    21600
cacattttaa ttaaattgac tactccatac atatgcaata tgaaacacat tttaactatg    21660
ggagtacatc attccataaa caaagaaaat gccaacaaga gtatgatcag attttgattg    21720
gtcacagagt gaaaaaaatg caacatcgca cagaacttgg atagatgctg ctaagctcac    21780
atgcctgacc atagttttta ttttctttgc tttattttgt tcagaaggag gaagaacag    21840 atggagcaaa aggaacaatc tgttgcacat attggacaag cgccactact ttgaatttac    21900
acacacattc gacatgaaca atctatttgc ctacaacttt acttttgaa accaccataa     21960 ttttggacca ctgtattctt cgactaattt tgttactaaa atttgaatgt gttcaatagg    22020
ctatgctgat tgacctgggg aatgacctgg ggaatgacaa cgatattttt ggagaagctt    22080
cagaaagtac atcaacttct gttaatcagc ttctcgaaaa cagtatgtcc ttgtcagaat    22140
cccatgcttt tatttaggta ctgtcatgac aagataacct ggcatgagtt aattaccggt    22200
tttgtaagca attatctgtc ttctagtagc atatctaaaa aaatagcaca tctagacaga    22260
agacggtcaa ggtttagcag gattgaaatt gcacaatctg aacagaataa ccgcttcatt    22320
aacttacatt tgtcatcatt ttgccatctc ataggttggc gcagacccta cacatcatac    22380
agaaagatct caagtgtcag cagacatgcc attcatggaa atgaccagcc aatgcgaagc    22440
tctgacggtg gggaaacaac agaagatgtc taccttcatg agcttctaga ggaacatgca    22500
```

```
agcggctccc ctgccaagcc atcagcccaa ccagatggag ctggctctct tccatgatcc   22560
accggtgcct gaggtatcaa ctctcaatgc ctctgagaaa agcatattcg tacattttag   22620
caagatacta aaatatcacg gattaacata tcagctgcgg ccaagaaact tgaactgtag   22680
tggagattaa ccaaggtgat gcaccaacga cgaatttggc tatagctctg accgatgaac   22740
atcatgtgga ggcgtagttg acctgcagta gtatggggga gatctcgatg ggaggaggaa   22800
gagggtcacc ccggtcggcg atgaagctcc ggctggtgct ctcccgacg gacaccgagc   22860 tgtggccggc gaggaccgct ccttgatggg tgtcagctcc ttgagggcga gctggtggcg   22920
gcggatctgg gagtcgaagg tggttgggaa ggaggcggcg gacccgggag gcgaaggtgg   22980
ttgcggagga ggcggcggcg ggaggcgacg ttgttgggga cgaggcggcg gatccgggag   23040
gcgacggtgg ctggggtctt cagatccacg tcgaggcgg cgcgcgtcac cattgtcggc   23100
gggggtggtt tggtggcctg ggagccgcat gtggtgggcg cggtggcccg cggggctgt   23160 ggccaacagc caccgggaac acgggagggc ggaggtccct ctgcgcccgc cggagccggc   23220
ggcgtcgcca tttgcggggt gggggttgtgg ggagagaggg gggaaggagg gacgagttag   23280
tttagataaa atataggggtg ttttgtgcaa aacataaaat aacggttcaa cttgacttac   23340
agaaggactg cgggttgaat cctcgaaaac gaagggcttt ttatgcaaaa atgccacgac   23400
ggacgcgacg gacgacagaa gcgttcggcg ctttattatt aggggagatt tatgtcacac   23460
gattttgatg accaaaagaa gatggattcg gagagacgaa cgagccagtt tcttggttt   23520 gaaaaaaag gtcgggacct atttttatata tatcacataa gagcatcttc aacagccggc   23580
gtggcgcgct atgcgtttgc agctcgttga tcgcctgttt tggggtggca gggaccgctg   23640
gctcgagcgg gcgctgtaaa ctttaacgtg cgcgcgtagc ttcaacatgc atgctaaaat   23700
gcaatgagcg ctctcacaca aacaacatat gcgctccaaa cgtacaagca aaagatcga   23760 gcacaaataa aataaatcaa taaaaatagt tcagtttcgt tattcaaact caaacaaata   23820 gttttctt cgatacaaca aatatttaa caatacaaca aatagttcaa caatacaaca   23880
tcaaaggcac aaatcatgat gctctttgtc ggtcattcaa tgtccaccac tcttcaatga   23940 gatcttctg aagatgcgtt tcggcaagtc gaatgacatt ataggaggca acaaaacggg   24000
ccaccctttc agccctccgc cgcactcgta ccggatgtcc caagagctca tagtaagagt   24060
agtctaaatc ttggccacgc tcattctcga tgatcatgtt gtgcatgatg tatcaaagta   24120 tctttgatc ccaaaatcta gccggtcctc tcacaatagc aaattaggct tgcaaaatct   24180
caaaagctct ctccacatct ttcctagccg ccgtgtgaac attttcgaaa tcaagatttt   24240
tcttaccttt cggttttttc aacggcttca caaatatttg ccactatggg tagatgcgga   24300
gataccgtat gtcaatatac gcaaagcgat agtcaccttc tgaaaggtgc tatgcctgag   24360
ctctccggcg gcattcctcc tttgctgaaa aaaccggtca tggctcgcta gtttctctgc   24420
aatgcacctg aacaactcag cgctcatcct aaaccggcgc cagaagaacg actcaggtac   24480
atgggattat ccgcaaaata gtgcttgatc aatctattgt gggcatcgat cctatcccctt   24540 taaattttct gccgacccat aactgaacca ctgcgcttcg gttttttatt gatgtgcata   24600
gctaggatca ttgcaagatc ctcctcctct tccatatcaa attcttttc ggaagaatca   24660 tatgacgaac tcatctataa tgttcaattt aaactaggat ataaaaacta caaacaacat   24720
gcagcaaatt catgtaaaaa acgtggagtt tcgtcgaaca ccttgcgggc gccgagcggc   24780
agtgggcggt cggacgctgt ttgtcggagg actgccgcgc gcgaggggtg gcggtgacta   24840
gagggagacg gggaagtagc ggcggagctg ggatagaccg aggaagcacc ggaatggtcg   24900
```

```
ccggaagaaa tggggtggtg cggacggcag cgacggcaac gcgagcagct ggatggggta   24960
ggtggagttg cgagcgggtg ctcgagtgtc cagcgcgctg gagcgggcgc ggcaaacaaa   25020
cggcgtgcga tggcgtttcg gcctacatgt tgaactagtt atgtcgcccg tgcggttttt   25080
gtggctcctc tggagcgtgc gggacggtag cgcgcgcaaa acactaatt tttcagcgcg    25140 gcgctcatat agcgcgtctg ttgaagatgc tctaaagacc acagttttag ggatactatg   25200
gtttgttaat ctcgagtatt tgtttcatcc aaacaactca aagtattgga aaccacaata   25260
ttccttcaaa actgcaaaga tactttagct cccaaacgca ccgtgagatg attacataca   25320
tgttgtgtag aagttaatca tgttgtttct ttaggattag gaaagaaagc caaaccgagt   25380
cctagtagta ttaggatttc tagtcctagt ctatttccat agtcccttgt ggacgtgtat   25440
aaaatacacc ctagggtgt tgattgtaac accagatcga aaaacgaaaa gcaatacaaa    25500
tcaaaggctc gacacgggcc tttagccatc aaatccatcg atcagtttta ttcgtgtcgc   25560
tagttacgca agttccgtca agtagccggt cgaagcaaga atcgcgtagg cacgcctgta   25620
cagctgcata cgcacgttca aaagccaaca attggtatct agagcctcga cgatctacga   25680
tctacgatga cggacatcaa cgttgagtcg gtcaagtccg gcaagggcgg tgccaaggcg   25740
aataagaacg gcgacaaggt gaagaagggc gtcaagtcag caacgagtgg tggaggaatg   25800
agcggcgcca acgtccaggt gcatcgcaac atccccatcc agtacccgat gttcaccggt   25860
gccaactacg ccgtgtgggc agtgaagatg aaaattattc tccgaacccct tcgagtgtgg    25920 caggcaatca cggacgacga cgtcgatgac gagtccgacg aaggtgccat ggccgccata   25980
gcccagtccg tgctggattc cgtgctaatg acattggcgg agttcgagac ggcaagagag   26040
gtgtggaacg cactcaagga gatgaggatc ggagaagatc gcgtcaccaa ggctcgggca   26100
caagtgctga agcgccaatt tcacaagttg cagatggagg aaactgaatc ggtgaacgac   26160
tatgccatgc gtcttactac tttggtggga gagatccatg cgcttggtgc aaagctcgat   26220
gagaccgaga ttgtggagaa atttttcagt tcggtgctga taaattcacg tacatcatcg   26280
gcacgctcga gaagctttat gacatcgatg acatgaccat aacgagacaa atcggacgct   26340
tgcggacatg ggaagagaat gctcgtggct gtcggaaagg caaggagga ggtagcgacc     26400 aactcatgta ctcgcgcgca gattgggagg ccccaagtag caaaggaagg cgtgatggtg   26460
gcgaaggctc aagcaacggg aagcgcgacg gacaaaccgg aaaaggcaag ccacaaggtc   26520
gtggtaaggc ggaccaatct aaagggcgga agccacgaaa cttggattta tccgaggtta   26580
agtgctataa ctacaacgag atgggtcact ttgcaaagga ttgtccgaat cctaacaagc   26640
gggagatcaa ggcaaatttg gcaaagcagg aagacgaagg tccaggtctt ctgatggccg   26700
aagtttgtga tctcgctgaa acggtggttg tgaaaccaac ccggaaggtg ctacatcatg   26760
agaagaatgt gacacctaag ttatccgggg atcacaatgt atcgtggtat ctcggcacgg   26820
gtgccagtaa ccagatgacg ggatgcaagg agaaatttct cgagctgcaa tatgatgttc   26880
aaggctcggt caagttcggt gatggttctg ttgggttacg tagcataaat tcaaaaaact   26940
tcctacgcat gttcagatct tcctatggag agaccagcaa cgagagaggg gtaagagcat   27000
cttcgtacct ttgaagatcg ctaagcggaa gcgttgctag aacgcggttg atggagtcgt   27060
actcgtagcg attccgatct agtgccgaac aacgacacct ccgcgttcaa cacacgtgca   27120
gcctggtgac gtctcccgca ccttgatcca gcaaggagga gggagaggtt ggggaagaag   27180
tccagcaaca cgacggcgtg gtgtcggtgg agagacgagg tctcccggta gggcttcgcc   27240
```

```
aagcaccggc agagaggagg aggaagaaga gcagggctgc gccgagagag agggaaaacc    27300
gtgtgtcaaa cagccccgaa ccctcatcta tatataggg aagagggagg gggcgcagcc    27360
cttagggttc ccaccccaa ggggtgcggc agcccagat gggagagggg gtggcggcca    27420
gggcagggag gaggggtggc gcaccctct ggtgggcctt aggcccacct atgctagggt    27480 tccccttcc cccctttctc tgatgcgcat gggctgggtg ggggcgcac cagcccacct    27540 aggggctggt tcccttcccc acttagtcca tctagcctcc cggggtcgtt gccccttc    27600 ggtggtcccc cggaccacc tccggtggtc ccggtggtcc cggtacgtta ccggtgatgc    27660
ccgaaacact tccggtgtcc aaaaccatcc gtcctatata tcaatcttta cctccggacc    27720
attccggagc tcctcgtgat gtccgagatc tcatccggga ctccgaacaa ctttcagtaa    27780
cctcgtacaa caattcccta taaccctagc gtcatcgaac cttaagtgtg tagaccctac    27840
gggttcggga gacaggtaga catgaccgag acacctctct agccaatagc catcagcggg    27900
gtctggatac ccatggtggc tcccactagc tccacgatga tctcatcgga tgaaccacga    27960
tttcaaggat tcaatcaatc ccgtatacga ttccctttgt ctgtcggtat agaacttgcc    28020
cgagattcga tcgtcggtat acctatacct tgttcaatct cgttaccggt aagtctcttt    28080
actcgttccg tagcacgtca tcgtgtgact aactccttag tcacattgag ctcatgatga    28140
tgttctaccg agtgggccta gagatacctc tccgtcacac ggagtgacaa atcccgatct    28200
cgattcatgc caacccaaca gacactttcg gaggtacccg tagtgcacct ttatagtcac    28260
ccagttacgt tctgacgttt gatacaccca aagcactcct acggtatccg agagttgcac    28320
aatctcacgg tcgaaggaaa agatacttga cattagaaaa gcattagcat acgaacaata    28380
cgatctagtg ctaggcttag gattgggtct tgtccatcat atcattctcc caatgatgtg    28440
atcccgttat caatgacatc taatgcccat gatcatgaaa ccatgatcat ctattgacta    28500
acgagctagc caactagagg cttgctaggg acacattgtg atctatttat tcacacatgt    28560
attactgttt cctgttaata caattatagc atgaacaata gacgattatc atgaacaaga    28620
aaatatgata ataaccattt tattattgcc tctagggcat atttccaaca gtctcccact    28680
tgcactagag tcaataatct agttacattg tgatgtatcg aacacccata gcattatggt    28740
gttgatcatg tttgctcgt ggaagaggtt tagtcaacgg gtctgcaata ttcagatccg    28800
tgtgtacttt acaaatatct atcattccac tctggacatg gtcctggatg gagttgtagc    28860
ggcgcttgat gtgcttcgtc ttctggtgaa acctgggctc cttggctatg gcaatggctc    28920
cagtgttatc acagaagagt gtcataggac cggacgcgct tggaaccact ccaaggtcgg    28980
tgatgagctc cttcatccaa attcctccat gagccgcttc tgaagcagct atgtactccg    29040
cttcacatgt agatgctgcc atgacttctt gtttgctgct gcaccagctc actgccccac    29100
cattcaacac atacacgtat ccggtctgtg acttagagtc atccggatct gtgtcgaagc    29160
tagcgtcgac gtaaccctt acgacgagct cttcgtcacc tccataaatg agaaacattt    29220
ccttagtcct tttcaggtac ttaaggatat tcttgaccgt tgtccagtgt tccgcaccgg    29280
gattactttg gtacctccct accaagctta tggcaaggtt tatatcaggt ctggtacaca    29340
gcatggcata cattagagag cccatggctg aagcgtaggg gacagaactc atcttctctc    29400
tatctgctgc cgtggtcggc gactgagtct tactcaatct cataccttgc aaaactggca    29460
agaacccttt cttgagtttt tccatattga acttcttcaa tatcttgtca aggtatgtac    29520
tttgcgaaat acctatgagg cgtctcgatc tatccctata gatcttgatg cctaatatgt    29580
atgcagcttc tccaaggtcc ttcattgaaa aactcttgtt caaataggcc tttatgctct    29640
```

```
ccaacatctc tatatcattc cccatcaata atatgtcatc cacatatagt acgaggaaag    29700
ctacagagct cccactcact ttcttgtaca gacaggcttc tccataaacc tgtatgaacc    29760
caaacgcttt aatcacctca ttaaagcgaa tgttccaact ctgagatgct tgcaccagcc    29820
catagatgga gcgctagagc ttgcacactt tgttagcatc ctcagggtcg acaaaacctt    29880
ctggttgcat catatacaac tcttccttaa ggttcccgtt aaggaacgcc gttttgacgt    29940
ccatttgcca aatttcatag tcataaaagg cggcaattgc taacatgatt cggactgatt    30000
tcagcttcgc tacgggagag aaagtctctt cgtagtcaac tccttgaatt tgtcgaaaac    30060
cctttgcgac aagtcgagct ttgtaaacgg ttacattacc gtttgcatca gtcttcttct    30120
tgaagatcca tttatttttct atggctcgcc ggtcatcggg caagtccacc aaagtccata    30180
cttttttctc atacatggat cctatctcgg atttcatggc ctcaagccat tgttggaat     30240 ccgggcccgc cattgcttct tcatagttcg aaggttcacc gttgtctaac aacatgattt    30300
ccatcacagg gttgccgtac cactctcgtg cggagcgtac ccttgtggac cttcgcggtt    30360
caggagtaac ttgatccgaa gcttcatggt catcatcatt aacttcctct tcagtcggtg    30420
taggtgccac aggaacaact ttcctgcgct gcgctacttt cctgttcgag agggggtgta    30480
attacctcat caagttctac cttcctccca cttacttctt tcgagagaaa ctctttctct    30540
agaaaggatc tgttcttggc aacaaaggtt ttaccttcga atctaagata gaaggtatac    30600
ccaatagttt ccttagggta tcctatgaat acgcatttct ccgctttggg ttcgagcttt    30660
tctggttgaa gtttcttcac ataagcatcg caaccccaaa ctttaagaaa cgacaactta    30720
ggtttcttgc caaaccatag ttcatacggt gtcgtctcaa cggatttaga cggtgcccta    30780
tttaaagtga atgctgcagt ttctaatgcg tatcccaaa atgatagcgg taagtcggtg     30840
agagacatca tagatcgtac catatctaat aaagtgcggt tacgacgttc agacactctg    30900
ttgcgctgcg gtgtgccagg cggcgtcagt tgtgaaacga ttccacactt ccttaggtgt    30960
gtgccaaact cgtgactcaa atattctcct ccacgatcag atcgtagaca tttaatttttt   31020 ctgtcatgtt gattctcaac ctcactctga aattccttga acttttcaaa cgtttcagat    31080
ttgtgcttca tcaagtagat ataccatac ctactcaaat catcggtgag agtgagaaca     31140
taacgataac caccgcgagc ttcaacgttc attggaccac acacatcagt atgtattatt    31200
tccaataagt cggttgctct ctccattatt cctgagaatg gagtcttaat catcttgccc    31260
atgaggcacg gtttgcatgt gtcaaatgat tcaaagtcaa gagactctaa tagtccatca    31320
gtatggagct tcttcatgcg cttaacgccg atatgaccaa ggcggcagtg ccacaagtat    31380
gtgggactat cattatcaac tttgcatctt ttggtactca cactatgaat atgtgtaaca    31440
tcacgatcga gattcatcaa gaataaacca ttcaccagcg gagcatgtcc ataaaacata    31500
tcactcgtat aaatagaaca accattattc tctgacttaa atgagtagcc gtctcgcatt    31560
aggcaagacc ctgatacaat gttcatgctt aaagctggta ctaaataaca attattaagg    31620
tttaaaacta atcccggcgg tagatgtaga ggtagcgtgc cgacggcgat cacatcgacc    31680
tttgaaccat tcccgacgcg catcgtcacc tcgtccttgg ccagtctccg cttattccgc    31740
agttcctgct ttgagttgca aatgtgagca acagcaccgg tatcaaatac ccacgagcta    31800
ctacgagcgt tggtaaggta cacatcaata acatgtatat cacgtatacc ttttacgttg    31860
ccggccttct tgtccgctaa gtatttgggg cagttccgct tccagtgacc ctttcccttg    31920
caatagaagc actcagtctc aggcttgggt ccgttctttt tcttcttccc ggcatctggc    31980
```

```
ttaccgggcg cggcaacagt tttgccgtct ttcttgaagt tcttcttacc cctgcctttc   32040
ttgaaactag tggtcttgtt gaccatcaac acttgatgct ctttcttgat ttccactcct   32100
gcagacttga gcatcgagta caactcggga atggttttct ccataccttg catgttgtag   32160
ttaagcacaa agactttgta gcttggtggg agagactgga ggattctgtc aatgatagca   32220
tcatccggaa gttcgactcc aagtgaagtc agatgaccgt gtaacccaga cagtttgagt   32280
atgtgctcac tgacagaact gttctcgtcc atcttacagt tgaagaactt gtcggagact   32340
tcatatctct cgacacgggc atgagattga aagactagct tcagctcctg gaacatctca   32400
tatgccccgt gttgctcaaa acgcctttgg agccccgttt ctaaactgta taacatgcca   32460
cacctgacca gagagtagtc atcactccgc gcttgccaga cgttcagaat gtcctgggct   32520
gctgcgggag cggagggtc acctagcggc gcattaagga cataagcctt tttagctgct   32580
tcaaggatga gcttcaagtt gcaaacccag tccgcatagt tgctaccatc atctttcagc   32640
ttgtttttct ctaggaatgc gttgaagtta aggttgacgt tggacatcta caatatttat   32700
aaagacaact tttagactaa gttcatgaca attaagttca tttaatcaaa ttaagtgatga  32760 actcccactt aaatcgacat ccctctagtc atctaagtga tacatgatcc atgttgacta   32820
acccgtgtcc gatcatcacg tgagacggac tagtcaccat ggtgagcaac ttcatgctga   32880
tcgtattcaa ccatacgact catgttcgac cttcggtgt cttgtattcg aggtcatgtc    32940
tgtacatgct aagctcgtcg agtcaaccta ggtgtttcgc gtgtgtaaat ctggcttaca   33000
cccgttgtat gcgaacgtaa gaatctatca cacccgatca tcacgtggtg cttcgagaca   33060
acgaaccttc acaacggtgc acacttaggg gaatacgttc tcgaaatttt aagagggatc   33120
atcttattat gctaccgtcg ttttaagcaa taagatgtaa aacatgataa acatcacaat   33180
gcaatcatat agtgacatga tatggccatt atcatctttg ctctttcgat ctccatcttc   33240
aggcatcgca tgatcatcat cgtcaccggc gtgacaccat gatctcaatc atcatgatct   33300
ccatcatcgt gtctccgtga agtcgtcacg ccaactacta ctatcactac tactatggct   33360
aaccgttagc aatgaagtaa aagtagtaag cacatggcgt tgcatctcat acaagaaatt   33420
aaaacaactc ctatggctcc tgccggttgt catactcatc aacatgcaag ttgtgaaacc   33480
tattacaata acatgatcat gacatacatc atacatgcaa catcacaact ttggccatat   33540
cacatcacat gtcaaaaccc tgcaaaaaca agttagacgt cctctaattg ttgttgcaag   33600
ttttacgtgg ctggtttggg tttctagcaa gaacgccttc ttacctacgt gacagccaca   33660
acgatgatat gccaaagcta tttacccttc ataaggaccc ttttcatcaa atccagtctg   33720
actagagtag gagagacaga caccgctag ccacattat gcacgatgtg catgtctgtc     33780
ggtggaacca gtctcacgta agcgtacgtg taaggtcggt ccgggccgct tcatcccaaa   33840
ataccgcctg aaaagaataa gactagtaac ggcaagcaaa ttgacaaacc atcgccccca   33900
acttttgtgt tctactcgtg catagaatct acgcatagaa aacctagctc ggatgccact   33960
gttgggttac gtagcataaa ttcaaatttt ttcctacgca tgttcagatc ttcctatgga   34020
gagaccagca acgagagagg ggtaagagca tcttcgtacc tttgaagatc gctaagcgga   34080
agcgttgcta gaacgcggtt gatggagtcg tactcgtagc gattccgatc tagtgccgaa   34140
caacggcacc tccgcgttca acacacgtgc agcccggtga cgtctcccgc accttgatcc   34200
agcaaggagg agggagaggt tgggaagaa gtccagcaac acgacggcgt ggtgtcggtg    34260
gagagacgag gtctcccggc agggcttcgc caagcaccgg cagagaggag gaggaagaag   34320
agcagggctg cgccgagaga gagggaaaac cgtgtgtcaa acagcccga accctcatct    34380
```

```
atatataggg ggagagggag ggggcgcagc ccttagggtt cccaccccca agggtgcgg    34440
cagccccaga tgggagaggg ggcggcggcc agggcaggga ggaggggtgg cgcacccctc    34500
tggtgggcct taggcccacc tatgctaggg ttcccccctt cccccctttc tctgatgcgc    34560
atgggctggg tgggggcgca ccagcccacc taggggctgg ttcccttccc cacttagccc    34620
atatagcctc ccggggtcgt tgccccctt cggtggtccc ccgggaccac ctccggtggt     34680
cccggtatgt taccggtgac gcccgaaaca cttccggtgt ccaaaaccat ccgtcctata    34740
tatcaatctt tacctccgaa ccatttcgga gctcctcgtg acgtccggga tctcatccgg    34800
gactccgaac aactttcggt aacctcgtac aacaattccc tataaccta gcgtcatcga     34860
accttaagtg tgtagaccct acgggttcgg gagacagaca gacatgaccg agacacctct   34920
ctggccaata gccatcagcg gggtctggat acccatggtg gctcccacta gctccacgat    34980
gatctcatcg gatgaaccac gatgtcaagg attcaatcaa tcccgtatac gattcccttt    35040
gtgtgtcggt atagaacttg cccgagattc gatcgtcggt ataccatac cttgttcaat     35100
ctcgttaccg gtaagtctct ttactcgttc cgtagcacgt catcgtgtga ataactcctt    35160
agtcacattg agctcatgat gatgttctac cgagtgggcc cagagatacc tctccgtcac    35220
atggagtgac aaatcccgat ctcgattcgt gccaatccaa cagacacttt cggaggtacc    35280
cgtagtgcac ctttatagtc acccaattac gttgtgacgt ttgatacacc caaagcactc    35340
ctacggtatc cgggagttgc acaatctcac ggtcgaagga aaagatactt gacattagaa    35400
aagcattagc atacgaacaa tacgatctag tgctaggctt aggattgggt cttgtccatc    35460
acatcattct cccaatgatg tgatcccgtt atcaatgaca tctaatgccc atgatcagga    35520
aaccatgatc atctattgac taacgagcta gccaactaga ggcttgctag ggacacattg    35580
tgatctatt attcacacat gtattactgt ttcctgttaa tacaattata gcatgaacaa    35640
tagacgatta tcatgaacaa gaaaatatga taataaccat tttattattg cctctagggc    35700
atatttccaa caggttcagt tgtggagatt tgcgtgcaag gatctgtcct cttcgagggt    35760
ctcacaggcg aacatcgcat actcaccgga gtgtactaca tcccacggct tcgcaacaac    35820
attatctcta ttgggaagct tgacgagaat ggatgcaagg tgaatatcga aacggagtg    35880
atgacgatct tcgacaacct ccgaaaagtg ctagctcgtg ttaatcgcac acggaatagc    35940
ctctatatcc tcaaccttga tcaatctcaa ccggagtgtt gtctcgccaa gactgatgat    36000
gattcgtggt tatggcatgc tagatttgga cacgttaact tctacgcctt gaagaagatg    36060
tcaaagatgg agatggtatc cgggatgcca tttatcgacc atgttgaccg agtatgtgac    36120
gggtgcttgg ttgcaaaaca gcaccgcagg ccgttccttg ctcagtctac ctatcgtgca    36180
agtgatgcac tcgagctgct ccatggtgat ctatgtggcc ctatcacccc agaaactcac    36240
gcgggaaaga agtatttatt cctcgtggta gacgactact cgagatatat gtgggtcgtt    36300
ctcctacgat ctaaagatga ggcgtttgaa gcattcaaga agctgaaggc tacaacgaag    36360
atggaacaca agttgaaggt tcgcgctcta cacacagatc gcgacggaga atttacgtcg    36420
aacgaattca acgattactg cgagaagatt ggcataaaaa ggttcctcac ggcaccttac    36480
acgccgcagc agaacggggt cgttgaaagg cgcaatcgaa ccgtcgttga catggcaagg    36540
agtttactca agagcaagaa cctgccgggg acttttttggg gagaagctgt ctcgacggcg    36600
gtctatcttc tcaaccgggc tccaacgaag gcggtgatcg acaagactcc gtatgaagca    36660
atttacggac gtaagccgaa tgtgtctcat ctacggacgt tcgggtgtgt ggcacatgtg    36720
```

```
aagacggcgg agccgcatct ctcaaagctt gccgatcgta gcaccaagat ggtgttcatc    36780
ggctacgaga ggagttccgg caccaaagca taccgcttct acgatccaca aaccaagcgt    36840
ctacggattt cacgcgacgt cgtgtttgaa gaaaaccaag cgtggaattg gagcgccgca    36900
gccgacaatg ctccaaacag taacatattc acggttgaat ttccaactga tgatgatgca    36960
cgggaggatg tccaagtggt tgataagacg ctcaaccaag gtgaccacaa tggtagtgat    37020
catcatggtg ccgacaccga cgacgacgcg cataggtcgc aaggagatag cgacaacgaa    37080
gcgcacggca caggtggaga tcttgacgac aacatcgaca acgaggcaca tagtgacgat    37140
gacaatcaag atgatgatca tgatcacgac cactacgccg acgacgcgga tgtcgatgac    37200
acgcccgaga ctcagccgtc ttcctcaagt gcatcaacac tgacataatt tgtgtcgcct    37260
ccttcgcaag ccacaacgga ttcctcaggg cctcgtcgct acaagaccct caagaaagtc    37320
tacaagtaca caaagccagt tacactcgaa tactccggac tatgtctttt cggagttgag    37380
gagccggcga acttcgtaca ggcgagaaaa agccgtagtt ggacgcacgc cttggatgag    37440
gagatgaagg ccattgagag caatggcacg tggactttga taacccgtcc tctaaaccaa    37500
aaggcgttag gtttgaagtg ggcttacaag ttaaagaagg acacacaagg tgccattgtg    37560
aagtacaagg caagactcgt tgcaaagggc tacgcacaac gtcaaggagt tgactatgat    37620
gaggtgtttg caccggttgc tcgaatcgag acggtgagag tgctcctagc tttggcagca    37680
caagaggatt ggaaggttca tcatatggat gttaaatccg cttttctcaa cggcgatctc    37740
acagaagaag tgtatgtgga caaccccctc ggctacgaga agaaaggtga agaagggaaa    37800
gtttacaagc tcaagaaggc actttacggg ttgaagcaag cgccaagagc ttgaaactca    37860
aaattagacc ggagtttggt ctcgttcggg ttcaagagat gtcccctcga gcacgcagtc    37920
tatacaaaga actccaaagg ctcaaacctg ctagttggga tttatgtcga cgatctgatt    37980
atcaccggag atagcgtaca agaaattaaa cgtttcaaga cgcaaatgaa gaacaagttt    38040
agcatgagcg atctgggatt actcagctat tacttgggca tcgaagtgaa gcaaagctcc    38100
ggagagattt ccctatgtca atcggcttat gcggtcaagt tattggaaaa gtgtggcatg    38160
tcagattgct acgagacaca agttccattg gaccaacgtc acaagttgag caagggtagc    38220
tcaaattcgc cggtggacac cacaatgtat caaagcgttg tgggcagtct aagatatttg    38280
gtgcataccc gacctgactt ggcttattca atcgggatcg tgagtcgttt ccccacccac    38340
atcccctttg tgccgctggc aaatgacgtc gggcaaagcc tgccgacggc tggcagcgac    38400
gggatccgct ctctttgatg gagctcgaca tacaatatcc ccgtttccac actccacctc    38460
gcaccacacc ggccatctct ttcacttgca gacttccgca tgtcctcccc actcacacgc    38520
ctcagtgctc accggatctg gccgaggccg cccattgcgg catgtggctg ccttcggttc    38580
ggtaccatac gcagatccag atcatttttgc tccgcgagct ctttacgctc gatctgctcc    38640
gcccttcctg gcttcgcccg cattggctgc gcggcgcgtg ctccgggtgg catcccttg    38700 ttcagtgcgt gcccctaac catgctggtc atccggctgg ctagaggtcc tccacctctg    38760
ggctcatgcc ccgaatccct ccgctccggc aaactcccct ccaacgtatc gtgcatccgg    38820
acgttcgtgg cctgctgctc atttgagctg ctacgccacc caggcgggc ttcgttgtcg    38880 ccggcgtggc acgtgcgtcg gccgtcgcgc cctccaccc ctccctcaga tccatgctca    38940
tgggtgctcg atggattgtc gcgatcccct acctcagtag ggctatgtgg ctgtggtgcc    39000
atcaacctgt tcacttcccg cggccaagca ttgcggttgc gtctccggtt tgttccgcat    39060
cagccgtgtc tagcatggag cacgatttg tatttcggcc gtaaaaatca aatttcggcc    39120
```

```
gaattttcac catctgggcc tgtggcgaga aatatctatt gggcgaaaag aatgattttt    39180
ggtcaaattt cagtcaaatg ctgattaaat tttggtctaa tttcaaccga ttttttttta    39240
aatgactgaa attcggccat ctcggcctgg ggcgagaaaa aatacaatac gaaaatcaaa    39300
acactggcat ggaggactgt tggccatggc cgcagatccc tctgaccttt ggctctctgt    39360
ctccgcgaga aatcccctcg ctggttcctt gccaccggac gcaacggcga cgaattcccg    39420
gcgccacttc atcttcttgg aggcgctggt gtggagattc agtgcagcta cgggtttgga    39480
tgaaagtcct gcgatgatgg cgcatgtggg cgtcattcaa ctttcctaaa ggtatcgcaa    39540
aaatccatgc tttagtcgac tcgcctacgc ccgtccatcc ttccatcgac atagtctctc    39600
cgtcgagcca cttgccgcca tctatccatc ctcctggtgt gttcttcatg ttgttttgct    39660
tgctcaggtc cctcccatgg ctgccgttct ctcgcaacag gttgcagtct atagtggtt     39720 tgtgttgcaa ttaccctgct tcctatgttt tcgtattcta tgatgtaccc cggtgtcagc    39780
catattgttg tgcatgttca tgaccctccc atggtggtca ttttattatg gtgagcttag    39840
tgctcttggt gttgtttcgg ctcatctttg ctcttcgaca acgcaagatg cctccccaat    39900
ttgctaatcg tcctgaattc ccgtggcgga gctcccactc aaggttcgtg ttatcactcg    39960
ttggttgtga atgctcctga gtagtgtcgt gaggttcggt atgcacgctg gtgcggtgtg    40020
gtaggttgct tgcttagtct gggtattgtg atcccttgac gacacccctc ttctagttgt    40080
gcctccgtgg tgatggtcct tcggtctagt tatgtcgtgc cttgttctgg gcatcctttt    40140
tcttatcttc tttagtcatt gttgtgtgtc ttttttctca cctagtgtgt tggtataaca    40200
aacttcaact gaaaaaaatg taagaaactg ggtgtatttc atagcaagaa gcaacacact    40260
aggtgtcgtc cgtcgtccca gtataaaaat gactcaccaa tacgacagaa atccacattc    40320
atcgtacaga attgctaatg cgcaatcacc tgatgaggca ttttgtttgg gagctaactg    40380
ttgtgttgtt gtatatgatg tcaatgttac caagtcattt gaaagagtca acaactggtg    40440
taagggagtc ctaattctag taatttactt agttgctggt gaaccaaatt tagtgcaata    40500
tgttatattg aaagttttgtc ctgtcatcga tattgcaggc taatccatca gatgcagaca   40560
atctcccttt tatttgacat ggaaataaga ttgatgctca ttgtggtaac agtaggagtg    40620
tgagtatttt tcacaaaaaa tgctatgttc ccttgctttt agactatttg ttttcaggtt    40680
gcttatgaaa ataaaaaaag gctgaagctt ggtgtgcctc caaggggatg tttgagtcga    40740
tcatctcacc cagatgattt tctttgaaat taaggagaac caccatgaca cgaagatcta    40800
agagcagtca agattgactg aattaaacaa gaatttggt tgcttgcacg atgataagca     40860
ttccggtgat cttatgaggc tgatttcaga taaaacatct tgtgagcata cgatgttctt    40920
attgtttaga tcagtgactg gggatcttgg ttatgactgt accgctatgg atctatttca    40980
aaataacatc atgagataaa attatacatg tggaggagac agaaaagctt cctttgagtc    41040
atcttcggta ctccttatt taagaagaaa aaagtagttg cagatacaaa gcagcagcag     41100
gagcagctag ctttacccac agcagcacgg aaccggatcc tctcacttat acaagggatg    41160
tcaaggagca gccgacgaca tcctgatttg gagcagatgc tacgatgctc cgtctcggga    41220 tcgactttg tccatccacc tctttttcct ttcggtcctc tactctagtt gcggattgtt     41280
ttctttcctt ttccccgctt cttacagtgt ttttttttaa tctttttgat gaaaaacaat    41340
gtataagtca ttcgagtaat ataacaaacg gtggggcaca atccccgctc ccgcgcaca     41400 ccattccgtc aggtgaagca atgtacattg tgttgttgtc tagacaaggt gaagacgtct    41460
```

```
gcaagaactc cgagctattg aaaccacggt cgctttgaat tatgaatgct gatctgatta   41520
tgcaaggctc ggtcaactaa atgaacaagc cagaagttta gacaccagag aagaatttat   41580
gattttcttt tgctttagca atttagaaga atttacgatc taagaaggaa cacattatac   41640
gtggttaggt acagggagat gcagaatacc attgtcacat tggtaatatt catctaaact   41700
gaatttgaaa catgtgactg aaaacactcg cttcattgtg tgcctagcgt cagaatttga   41760
aatacaagtt gaaatacatc aacacacaga aacaattcgt gaaaaactga agtcatacag   41820
aattggtaca tttgtgttgc ataagttcat actacctaac cacctagaag tataaaaaag   41880
tttctagcga aaaaaagaa agaaactgga ggcatcagtg gtaaaaccaa cacactagct   41940
ccaaccgagt ataaaattga tgcacaaaca gcaaagaaaa acaaaacagg ctgccgcatt   42000
taatttattt ttacgagaat tgctaatatg caatccggat acttcttaag tttcagtcaa   42060
tcatctcaac caatatgatc tgctttcaga ttaggagaac aaccatgata tgaggatcta   42120
agggtgatgg agattcactg caataaagaa gaaattcaat tgcatgtcca gacttcagat   42180
agaacaactt gtgaggacaa gcagtccctt ttaatatgta gagcattgac tcgggatttt   42240
atgagacaac atcatgagat caaattatac acgcaaaaac aactaaagga aactcctccg   42300
actccttgta tccattgaca aaatgagttg tgcttgatta gataaatttt ctcgaggtga   42360
aatgatccaa ggtaaactca ttccacacat gcattccatc aagttacctt gaccatcaca   42420
attactccga aatatttatc gtggtctttt tttttgtgat tccatcagaa cacatgaata   42480
aactactcat agtgtggaag atatattttt tcgtaccaac cacattctct tatatggcaa   42540
ttggaacaaa caagacagca aaacacaatt atatatgttc ccaagcttgc tttgtcttct   42600
cgcgaataaa cactactact aagtcataaa caagaattat aaattatatt aacaaacaat   42660
caagcaatag acaagtttta cgataatttt gaagggaatg agataacaag gatgcaatat   42720 aaatttttacc acttcatatt gtccgtgaag acaacgatgg tgggaaattg gtatatatgt   42780
gtgtccaacc gtacatccgc ctggattgtt tcgcacaaac cctctgaagc tgcaacgtct   42840
tgacgttgat tgagaaataa tcaaagagtg gatgctctgg gacgaggct tctgtctttg   42900 tcaagagcaa gtacctctct gttgcatctc tgatatggta tttgtaccca gaatctagtg   42960
agattgtttt ttccatctgc cactggacgg gactcttgcc tttgttccgc gcaatggtat   43020
agctgagatg agatgcaaat tcaccatgga aaccaaacat cccaagcttg ccttcacctg   43080
cctccacaat ggctattccc tctgcactcc attcgccggg tgggaggtca gcaatggaga   43140
actccatccg cctggtgtcc agcaccagca acttttttcct cccaatcatt acccagtccc   43200
agtagaagca tccataagca taatggctgc tgagaaaaag tgggttggtc cgtgacatca   43260
cagtcttgtc ggccatgcca tgaaccaaag cactccaatc cttggattca gtggcttgcc   43320
attgcccggt gctcgaagag aagactaagg catccagctt agttttgcta tatgccatcc   43380
agatcactct gaatgctttc tcttccgccg ccgccgccgt ctccgtgtcc tcctcgcaga   43440
ggggaacgag gaaaggtatc cggcggagcc ttagtgccat gggatcgggg tgattcaccg   43500
aatcggctaa gtcatctggt actggaggaa gcaggacgta cagccggtgc aagggatcgc   43560
acaccacagc tcctggaag accgggcct gctcctcgtg tttgtataga cgatgaagga   43620
ggacgcggcc gtcgtgggtg tcctggacgg cccatcggca gcgggagggc aggaaggaga   43680
aggagaagtc ggcggcaacg gcgagcgcgc gagcggcggg agcggagggg tgaggcggga   43740
gggccgggtg gaacctgtcg tagtcgagga agccgaggaa gggcgggggcg tgcaggcggc   43800 ggaagcgtcg gaggaaggag ccctcggtgg ccagctggcg gaagggggacg caggcggcgg   43860
```

```
aggcgcggac gaggtccgcc ggctccggaa gccggaggaa gatctccgtc aagaggtggt   43920
cggggatcgc cgtcagcggc gaggccattt cctttcgcgg ccgtcgggat ccgttgacta   43980
gatgcgaagg gggcggctgg gtgctgatgg atttgggaat gtgctgatgg attcgtaagg   44040
agaaaaaaaa caagtttact tatttccagt gtgaaattta acaacaacac ccccctccgg   44100
tccgtcgccc tcctctggcg acacggggga gacctagccg ccgcgacgga ccccgggaag   44160
gtggcagcgg ggcggatcta ggttcctcat gccccaccac ccaaccccgc ggcccggcca   44220
cgcctctacc gcggcggcga ccctccctcc cgctggttcg gcggtgacgc atccggcttc   44280
ctcccgggca atctggccct gcacgtctct ggctgacgtg gcccctcctc cgtcatcctt   44340
gtccaccccc tccacacgtg tgatgaccca taagtgtagt ggatttatcg tagccttta    44400 gatgagtaag agtgtcgaac ccaacgagga gcagaaggta ttaacaagtg accttgagca   44460
aatattaact gcaagtattg aaaggtagct tttatgggtt ttctagtata agcaactagt   44520
aaataaatgg aaggaaagta aatagtgccg aggtgcagca agtggtccaa tccttttaaa   44580
cacaaaagga taagccaagg gactaaactt ataaagacta tggcgttttt gaggacacac   44640
aggagagatc gtcaagtgct ttcgtcatat tccgtctagt actatgtttt gtattgataa   44700
gtgttatccg cgtggatctt aactagtgca ccgtctaggc taagacaagt acactcttat   44760
gattaacccc tcttgcaagc atccgcaaat acaagagata aattaaggta aagcttaacc   44820
ataacagtaa gctttaggat ccaatactcc ctcatgcaaa agtatgcgaa ctcgggttca   44880
ggtttctgtc actgtggcaa cccaccataa tcattcttta tacacgatgc attttcatag   44940
gtccttaaaa aggcgaagta ttatgtagtc gacgttcaca aaacaccact agaagaataa   45000
tagcgtaact taaatatcaa tcaacaaata ttacttcaac atcatatgac tactagcatc   45060
tagacttttc ccatgtcctc aagaactaat ggaactactc acaagacata aaaagatca    45120 tgatcagagg tgatgaaaat atgattaaaa aagatctggg tgacctggcc ctgcacgtct   45180
ctagctgacg caaccccttc cgtcctcctt ccggcgacct ggccctgcac gtctctggct   45240
gacgcaaccc cttccggcct ccttccgggc gacctggtcg tccccccac cagctgatgt    45300 tttgtgtcta ctagctgaag gcaattccgg cgctcctggt tgttaccacg atcgccaccc   45360
atggagcttc aaccccaccc cctagtccag tcgtgctggt gcttgtcgcc cacggttggg   45420
ggttgtggtc tgcactctac agccggttac tttcgtgaga catagctaca tgtacttcca   45480
tgtcgacatt gattttgagc ttccatgaga ctcatgactt tcatgagac aactcgtgct    45540 tccatgtact ccacgaaaag ggaaaaacat atagttgtac tttcacgaaa aaatacgttg   45600
atttgctttc ataagaacca taagttgggc atttcctatt tagcgttgta ggcgccggtt   45660
tcttcatgtt ttaatcggcg cctgcagcag ggttagttgg gctcggccca ctctattttt   45720
tttctgtttt ctaaaccaaa aattgtgtga ctactaagat tcaaacctgc aacctcgtca   45780
cccataccat ggtgcgctca gtccactaac cgacaggctg gagttacctt aactgtttaa   45840
tttcaccttt ccatcccttt cttcttatat ccatttttcct atttatccat ttttattttc   45900
tttcttggac gattttcttc gattttttct acaaatagaa tgaacttgct ttcaaaaaaa   45960
ctgatgaact ttttgcacaa ttgatgaact ttgtttcaaa atcgattggt ttttagaaaa   46020
aaataaattt ttatttaaaa ttcgtaattt tcttttattt aaaatgaact tttctaaaat   46080
ccggtgtact ttttaaaaac ttgatcaact ttttaaaaat acttatgaac ttttactaaa   46140
ttcggtgaac ttttttaaaa tttgatgaac ttctttggaa aacttattaa gttttctaa    46200
```

```
attggatgga cttttttctaa aattccatta attttttaaaa aattgatgaa cgttttttcaa   46260 aatcgctaaa cttttttaaa aatttgatga atgttttttca aaatctatta acttgtttga   46320
aaatttgatg aacattttc aaaaactctg aaccttttta aaaatttgat gaacgttttt   46380
ataattgcat taactttttt aaaagttcga tgaacctttt tcaaaatcgc tgaactattt   46440
ttaaatccaa ttaaccttt tccaaattga taaactttgt ttttcaaaac aggtgaaccc   46500
ttttttattt gcttaataaa tctatgaatt ttttaattt gacaatatat tcaaaattgt   46560
aaaaattcga acttggtctt tttcccaaac taatactgca ggtcggccga aaaaaaacag   46620
caagtcaaga gaaagctaac ggattttcat aatgggccgc ggcccactgc taggctttgt   46680
aggcgccact tccccaacga gctactacag tggcctatag gaggtcctga tgtccaatgc   46740
agctcggccg aaaataaaac agcgagtcaa gagaaagcta acggattttc ataatgggcc   46800
gcggcccact gctaggcgct gtaggcgcca cttctccaat gagcgccac agcgcccaat   46860 aggaggtccc cataaattat gctttaaaaa agtgaaaacc gcaaccatac atctgggctt   46920 cgtcttttt ttctggtatt tgggtattt gttttttccgt tacccttttt ttctttttttt   46980 ttggttttttt aatgatttgt ttcgaaaccc attaacacac acggtatgtc ggtatctact   47040
ttcaaagacc tcgactctaa aatccaacaa caattttatt tgatatttgg acgcacattt   47100
cagaagataa agcaatttga ataaatgaat caatgagaaa actttgagg ttgcgttaaa   47160 cggctatagt gtgccacttg ttagttaccg aggatatgaa cagtgacctt tgcaactggt   47220
aacatttact agtgattttt ttttgaaatg acaagttacc tttgcaagtg gtaacgttta   47280
ctagcgatct aaaaaaaatt gacaagtgac ttttgcaagt ggtaacattt actagcgatt   47340 taaaaaatc gatatttggc tggggaaaag gagaaaaaaa gtcacggatg ctccatgggc   47400
tgcaaagttt ttgtgccgga gataaaaact ttataaaccc ttgaaatatt taaaatgtac   47460
ttggattagt atctttgttt ccacatagct ttactatatc agctcacctg ttattttgtt   47520
ttgcaggaga gtggtctgcc aaaagggtag taggagaaga gcctaaagaa gatcaaacgt   47580 tcttttaagag gtgcacggtt ttttttttcc agaacaattg cacttgatat gtgtaagtct   47640
ctatttctaa taataaagca aatactgttt gtggtcttac atcatagttt tttttgcaaa   47700
aaagccctta tagttttcag aattcaaccc gcggttcata taataagtca atcgaagcgg   47760
tatgcacgag ataaaagaaa aaaactacct cccgatccca tttcgacctc aaggctcgag   47820
cgcgccacca cctcttgccg accgctaccc tcaccccaa cgccgcgtgc cgccacggac   47880
accgagcacc ttcatggatg ctgaaaccgt tggcggctcc ccaccggccc ctgggagagg   47940
acgcgcacgg gctagcaacc gctgccttcg ccagcagcgg cagcaggcgc ggacgaagat   48000
cccctcgtgg ggccgacgcc ggtcaagaag ccagcgatcg atggcaatag gagcaagggc   48060
gtcaccaacc cggacaccca ctcgccttcc ccaaggacaa gaagcacgat gaggcggcaa   48120
cagcggagga cgaggccaag gccagcgccg aggacaaggt gagccgtcgg gtcacgagag   48180
ctacacctcc ccacctccat ccgccaattc ggcctacttt gatttcgatt tcttgctgca   48240
tctgcttgtt gtcgcgaata atcaggggt agcggcaggg catcatctgc agctgcaccg   48300
attcgaccac ccccagatgt actaccagca gcatagtgga ggccgcaaac gcatgccact   48360
attcacgcac gacggtcgtg gccagaagca cttctacgtg ccaccacccc ttcaggcggg   48420
tgcgccggcg ttttcacagg tatgaggtgc tcatggaggt gggccgcctt gctgccgagt   48480
acctggtagc caaaggcatg ctccctccgg catcgctgca aggcggcggt agtgttgggt   48540
ggggctagat gtcgcctaag cctctgttgc cgacaacatc ttgatgacaa gtaaggtaac   48600
```

```
caatggcgga gctatgggcc atggttgggc aggcaaggta gagcaaagca catgattttt    48660
tttcacgcat gacctatttc tctctcaggc acaccgattt gaagcatggt ggattgtggt    48720
ggaaaagctg gctgagagca tgtttgaata acagctgcaa ctctcgcacg ggtggtggaa    48780
aagctggtcg agagcaagtt tgagtagcag ctgcaactct ggcactctga attccctgag    48840
ctctcctctg gcctaagtcg tcgttctact tccgtacagt taattttagt agaaactggt    48900
tgtttgtgca aacacaaggt gtagtgataa tagatgatta gagaaaaaca agtaaaagta    48960
tgtgcaaaaa aatgatagat ttaactccag ccattgcatt cttatattgt gttgtgctgt    49020
tctaaccatg aattatatgt agcagactgt atgttcagcc tccatgttca tgtctttgat    49080
ctccttaggt tgcacaaagg ctttagttgt acatatgtgc caataatgta cctaggagag    49140
cctccctaaa atatgtcgat atctgtgaaa ctttgttatt cttcctcgcc ataataacca    49200
tgaccttcag ggggatattt attacaattt tggtatatat ttagtgtgat ctctgcttag    49260
gaataagggt aaaaggtcaa catatcaaag cctgattcca aattatgttg gtactatata    49320
atagttctct aataaaggat ctctgcaatg gattcttttt gatttaataa gctaacaaaa    49380
ggcaatcggc cccatttata ctggtatttt tcatggcacc caaacttttt atcttctctc    49440 attattttg tgaaaataac tttaccatgg aattgtttga tatggcctgt gatgtgttgg     49500
ttctgattct gttgcaattg aatttgtgct gagaacgcgg aaaatattgt tctcacttat    49560
ggtgattcga ttatgcaagt ataatatgtc ctttgttctg tagcaaaacg cgggagtttg    49620
ttctattatt ttcatctgaa gtctttacaa aggagttggg actgagtgag tgacatatat    49680
ttgcttgagg ttattaatta attttgctat tacttgcatc ttatttgaa gtattttctt      49740 caagttcttt ctgttttcca catcgtctac tctatagaag ctgtcacatt aaattaagta    49800
agtacatgct tctttcttgt ccaattttgt tctattctat tactcggaag cctgcacaag    49860
agagtgaagc agatttgaat tatttttga tgtggggtct gtatgttatt gttggggaac     49920
gttgcatggg aaacaaaaat tttcctacgc gcacgaagac ctatcatggt gatgtccatc    49980
tacgagaggg gatgagtgat ctacgtaccc ttgtagaccg tacagcagaa gcgttagaga    50040
acgcggttga tgtagtggaa cgtcctcacg tccctcggtc cgccccgcga acaatcccgc    50100
gatcagtccc acgatctagt accgaacgga cggcacctcc gcgttcagca cacgtacagc    50160
tcgacgatga tctcggcctt cttgatccag caagagagac ggagaggtag aagagttctc    50220
cggcagcgtg acggcgctcc ggaggttggt gatgatcttg tctcagcagg gctccgcccg    50280
agctccgcag aaacgcgatc tagaggaaaa gctatggagg tatgtggtcg ggcagccgtg    50340
agaaagtcgt ctcaaatcag ccctaatacc tccgtatata taggtgggag gggagggaa     50400 gaggcagcct caaaccctca agggttggcc gaaattggag gtggaggagt tctactccaa    50460
tcctacttgg agtaggattc caccttccca cttggaaact cttttccacct tgtgtttttt    50520 ccttctcaaa ccttatgggc cttagtggga acttattcca gcccactagg ggctggttta    50580
tctcttccca tagcccatga gacccttgg ggcgtgacac ccctcccgac ggtccccggc      50640
acccctcccg gcactccggg tacactaccg atgagcccga aacttttccg gtaatgcacg    50700
aaaaccttcc ggtaaccaaa tgaggtcatc ctatatatca atcttcgttt ccggaccatt    50760
ccggaaaccc tcgtgacgtc cgtgatctca tccgggactc cgaacaacat tcggtaacca    50820
accatataac tcaaatacgc ataaaacaac gtcgaacctt aagtgtgcag accctgcggg    50880
ttcgagaact atgtagacat gacccgagag actcctcggt caatatccaa tagcgggacc    50940
```

-continued

```
tggatgccca tattggatcc tacatattct acgaagatct tatcgtttga acctcagtgc    51000
caaggattca tataatcccg tatgtcattc cctttgtcct tcggtatgtt acttgcccga    51060
gattcgatcg ttagtatccg catacctatt tcaatctcgt ttaccggcaa gtctctttac    51120
tcgttccgta atacaagatc ccgcaactta cattaagtta caatgcttgc aaggcttgtg    51180
tgtgatgttg tattaccgag tgggcccega gatacctctc cgtcacacgg agtgacaaat    51240
cccagtcttg atccatacta actcaacgaa caccttcgga gatacctgta gagcatcttt    51300
atagtcaccc agttacgttg cgacgtttga tacacacaaa gtattcctcc ggtgttagta    51360
agttatatga tctcatggtc ataggaataa atacttgaca cgcagaaaac agtagcaaca    51420
aaatgacacg atcaacatgc tacgtctatt agtttgggtc tagtccatca catgattctc    51480
ctaatgatgt gatcccgtta tcaagtgaca acacttgcct atggccagga aaccttgacc    51540
atctttgatc aacgagctag tcaactagag gcttactagg acagtgtttt tgtctatgta    51600
cccacacaag tattgtgttt ccaatcaata aaattatagc atggataata aacgattatc    51660
atgaacaaag aaatataata ataactaatt tattattgcc tctagggcat atttccaaca    51720
gtctcccact tgcactagag tcaataatct agttcacatc accatgtgat tccaatgaat    51780
ccaacaccca tatagttatg gggtctgatc acgtcttgct cgtgagagag gttttagtca    51840
acggttctga aactttcaga tccgtgcgtc ctttacaaat ctttatgtca tcttatagat    51900
gctgctacta cgtgctattc ggaaatgctc caaatatcta ctctactata cgaatccgtt    51960
tcactactca tagttattcg gattagtgtc aaagcttgca tcgacgtaac cttttacgac    52020
aaactcttta accacctcca taatcgagaa aaatcccttt gtccattagt tactaaggat    52080
aaattttgac cgctgctagt gattcaatca tggatcactc tctgtacctc tcaacatatt    52140
ttgagtcaag gcacatatca ggtgcggtac acagcatggc atactttaga ttctacggct    52200
aaggcataga agacgacctt cgtctattct ctttattctg ccgtggtcgg gttttgagtc    52260
ttactcaaat tcacacctta caacgcaacc aagaactcct tctttgctga tctatttga    52320 actccttcaa aaacttgtca aggcatgcat cttgttgaaa cttccattaa gcgctttcga    52380
tctatctcca tagatctttg atgctcaacg ttcaagtagc tcaatccagg tattcctttg    52440
aaaactcctt tcaaacaact ttgtatgctt tacagaaatt ctacattact tctgatccac    52500
aatatgtcaa ccacatatac ttatcagaaa ttctatagtg ctcccactca cttctttgga    52560
aatacaagtt tctcataaac cttgtacaaa cccaaaatct ttgatcatct catcaaagtg    52620
tatattccaa ctccgagatg cttgcaccag tccattgaag gatcactgga gcttgcatac    52680
ttgctagtat ctttaggatc gacaaaacct tctggttgta tcacatacaa tgtttgctca    52740
aggaaaccgt cgaggaaaca atgttttgac atcctacgtg caatatttca taaataatgc    52800
atcaacaact aacataattc taacagacct ttagcatcgc tacgagtgag aaagtctcat    52860
catagtcaac tgtttgatct tatcgaaaac atctttgcga caagtcgaac ttttcttaat    52920
agtgatttat caccatcatc gtctgtcttc ttttaaagat ccatctttac tcaatagtcc    52980
tctgaccatc aagtaattct tccaaagtct acactttgtt ttcatacatg gatcctctct    53040
cggatttcat ggcttccagc catttgtcgg aatccgggcc caccatcgct atctccataa    53100
ctcgtaggtt cactgttgct cgacaacatg acctccaaga cagggttacc gtaccactct    53160
gtagtagtac gcgaccttgt caacctacga gacttgtagt aacttgatcc gatgctcgat    53220
gatcaccatc atcagcttcc acttcaattg gtgtaggcgc cacaggaaca acttcctgca    53280
ccctgctaca cactggttga agtgatggtt caataacctc atcaagttct actaccctcc    53340
```

```
cactcaattc tttcgagaga aacctttcct cgagaaagga tccgtttcta gaaacaaaca   53400
ctttgctttc ggatctgaga taggagatgt acccaactgt tttggatatc ctatgaagat   53460
gcatttatcc gctttgggtt cgagcttatc agactgaaac ttttcacat aagtgtcgaa    53520 gccccaaact ttcaagaaac gacagtttag atttctctaa accttagtct atactgtgtc   53580
atctcaacgg aaatacgcgg tgccctattt aaagtgaatg cggttgtctc taatgcataa   53640
cccataatcg ataatggtaa ttcgataaga gacatgacag catgcaccat actaaacagt   53700
gcgtggctat gacgttcaga cacatcatca cactatgatg ttccaggtgg catgaactgt   53760
gaaacaattt ccacattgtc ttaactgtgt accaaaaact cgcaactcag atattcattt   53820
ctatgatcat atcgtagaca gttcatcctc ttgttacgac gaacttcact ctgaaacgga   53880
attgaacttt tcagtatttc agactgtga ttcattaagt aaatactcct gtatctactc     53940
aagtcgtcag tgaagtaaga acataatgat atccactgcg tgcctcagca ctcattggac   54000
tgcatacatc aaaaatgtat cacttccgac aagttactat cttgtttcat ctcaatgaaa   54060
acaaggcctt gctcatgtgg tatgatctgc atgtcactag tgattcgcaa tcaggtgagt   54120
aaagatccat cagcatggac cctcttcatg caatttatac taacatgact caagcggcag   54180
tgccacaagt aagtggtact atcatcatta actcgtatct tttggcacca atgtgtaaca   54240
ctacaatcga gattcaataa accattgaag gtgattattc aagcaaatag agtaaccatt   54300
attctctttg aatgaataat cgtattgcaa taaacacgat ccaatcatgt tcatgcctaa   54360
cgcaagcacc aaataacaat tatttaggtt caacaccaat cccgatggta gagggagcgt   54420
gcgacgtttg atcatatcaa ccttggaaac acttccaaca cgtatcgtca cctcgccttt   54480
agctagtctc cgtttatgtc gtagcttta tttcgcgtta ctaatcactt agcaaccgaa    54540
ccggtatcca atacccttgt gctactagga gtactagtaa agtacacatc aacattatgt   54600
atatcaaata tacttctctc gactttttgcc agccttctta tctaccaagt atctagagtt  54660
gctctgcctc agtgactgtt ccccttatta cagaagcact tagtctcggg tttgggtttg   54720
ggtctcttca ttagcgcagc aactgttttg ccgtttcacg aagtatccct tctagccctc   54780
gcctttcttg aaacttagtg gttttccaaa ccatcaacta ttgatgctcc ttcttgattt   54840
ctactttcgc agtgtcaaac gtcgcgaatc gctcaaggat cattgtatct atccttgata  54900
tgttatagtt catcacgaag ctctcaaagc ttggtggcag tgactttgg agaaccatca   54960 ctatctcatc tggaagatta gctcccactt gattcaagtg attgtcgtac tcagacaatc   55020
tgagcacatg ctcaatgatt gagcttttct cctttacttt gtggacaaag aatcttgttt   55080
ggaggtttcc tacctcttaa caagggcaca agcatgaaat cacaatttca tctcttcgga   55140
acatcactta tgttccgtga cgttttacaa cgttttcggc gccttgcttc taagccatca   55200
agtatcttgc actgaacaat cgtgtagtca tcagtaacgt gtatgtcgga tgttcatagc   55260
atccacagac gacgctcgag gtgcagcaca ccgagtggtg cattaaggac ataagccttc   55320
tgcgtagcaa cgaggacaat cctcggtttt acagactcag tctgcaaagg ttgctactat   55380
caattttcaa ctaaattttc tctaggaaca tataaaaaca gtagagctat agcgcaagct   55440
acatcgtaat tcgcaaagac cattagacta tattcatgac aattagttca attaatcata   55500
ttacttaaga actcccactc aaaaagtaca tctctctagt catttgagtg gtacatgatc   55560
caaatccgct atctcaagtc cgatcatcac gtgagtcgag aatagtttca gtggtaagca   55620
tccctatgct aatcatatca actataagat tcatgctcga cctttcggtc tcatgtgttc   55680
```

```
cgaggccatg tctgcacatg ctaggctcgt caagcttaac ccgagtgttc cgcgtgtgca    55740
actgttttgc acccgttgta tgtgaacgtt gagtctatca cacccgatca tcacgtggtg    55800
tctcgaaacg aagaactgtc gcaacggtgc acagtcgggg agaacacaat tttgtcttga    55860
aatttcagtg agagatcacc tcataatgct accgtcgttc taagcaaaat aaggtgcata    55920
aaaggattaa catcacatgc aattcataag tgacatgata tggccatcat cacgtgcttc    55980
ttgatctcca tcaccaaagc accggcacga tcttcttgtc accggcgcca caccatgatc    56040
atccatcaac gtgttgccat cggggttgtc gtgctactta tgctattact actaaagcta    56100
catcctagca aaatagtaaa cgcatctgca agcacaaacg ttagttataa agacaaccct    56160
atggctcctg ccggttgccg taccatcgac gtgaaagtcg atatttctat tacaacatga    56220
tcatctcata catccaatat atcacatcac atcgttggcc atatcacatc acaatcatac    56280
cctgcaaaaa caagttagac gtcctctaat tttgttgttg catgttttac gtggtgacca    56340
agggtatcta gtaggatcgc atcttactta cgcaaacacc acaacggaga tatatgagtt    56400
gctatttaac ctcatccaag gacctcctcg gtcaaatccg attcaactaa agttggagaa    56460
accgtcactt gccagtcatc tttgagcaaa gggggttact cgtgacgatg aaaccagtct    56520
ctcgtaagcg tacgagtaat gtcggtccaa gccgcttcaa tcaaacaata ccgcggaatc    56580
aagaaaagac taaggagggc agcaaaacgc acatcaccgc ccacaaaaac atttgtgttc    56640
tactcgagaa gacatctacg catgaaccta gctcatgatg ccactgttgg ggaacgtcgc    56700
atgggaaaca aaaattttcc tacgcgcacg aagacctatc atggtgatgt ccatctacga    56760
gagggggatga gtgatctacg tacccttgta gaccgtacag cagaagcgtt agagaacgcg    56820
gttgatgtag tggaacgtcc tcacgtccct cgatccgccc cgcgaacaat cccgcgatca    56880
gtcccacgat ctagtaccga acggacggca cctccgcgtt cagcacacgt acagctcgac    56940
gatgacctcg gccttcttga tccagcaaga gagacggaga ggtagaagag ttctccggca    57000
gcgtgacggc gctccggagg ttggtgatga tcttgtctca gcagggctcc gcccgagctc    57060
cgcagaaacg cgatctagag gaaaagctat ggaggtatgt ggtcgggcag ccgtgagaaa    57120
gtcgtctcaa atcagcccta ataccctccg atatataggt gggaggggga gggaagaggc    57180
agcctcaaac cctcaagggt tggccgaaat tggaggtgga ggagtcctac tccaatccta    57240
cttggagtag gattccacct tcccacttgg aaactctttc caccttgtgt tttttccttc    57300
tcaaacctta tgggccttag tgggaactta ttccagccca ctaggggctg gtttatctct    57360
tcccatagcc catgagaccc cttggggcgt gacacccctc ccgacggtcc ccggcacccc    57420
tcccggcact cccggtacac taccgatgag cccgaaactt ttccggtaat gcacgaaaac    57480
cttccggtaa ccaaatgagg tcatcctata tatcaatctt cgtttccgga ccattccgga    57540
aaccctcgtg acgtccgtga tctcatccgg gactccgaac aacattcgat aaccaaccat    57600
ataactcaaa tacgcataaa acaacgtcga accttaagtg tgcagaccct gcgggttcga    57660
gaactatgta gacatgaccc gagagactcc tcggtcaata tccaatagcg ggacctggat    57720
gcccatattg gatcctacat attctacgaa gatcttatcg tttgaacctc agtgccaagg    57780
attcatataa tcccgtatgt cattcccttt gtccttcggt atgttacttg cccgagattc    57840
gatcgttagt atccgcatac ctatttcaat ctcgtttacc ggcaagtctc tttactcgtt    57900
ccgtaataca agatcccgca acttacatta agttacaatg cttgcaaggc ttgtgtgtga    57960
tgttgtatta ccgagtgggc cccgagatac ctctccgtca cacggagtga caaatcccag    58020
tcttgatcca tactaactca acgaacacct tcggagatac ctgtagagca tctttatagt    58080
```

```
cacccagtta cgttgcgacg tttgatgcac acaaagtatt cctccggtgt tagtaagtta    58140
tatgatctca tggtcatagg aataaatact tgacacgtag aaaacagtag caacaaaatg    58200
acacgatcaa catgctacgt ctattagttt gggtctagtc catcacatga ttctcctaat    58260
gatgtgatcc cgttatcaag tgacaacact tgcctatggc caggaaacct tgaccatctt    58320
tgatcaacga gctagtcaac tagaggctta ctagggacag tgttttgtct atgtatccac    58380
acaagtattg tgtttccaat caatacaatt atagcatgga taataaacga ttatcatgaa    58440
caaagaaata taataataac taatttatta ttgcctctag ggcatatttc caacagttat    58500
agtgttgatg aatgaaaact gatgaaaagt agtggcaaac atttgattga gtgaactact    58560 agtttttttac cagtaataca cagtagtttc ttggaatata ctctgcatgc caaacaacat    58620
ccatatttga ttttcctctg tgattgggac aaatatcact ttttgggcta aagctggtta    58680
atttattatt tggatatgag tagtagtatc aacacaaata acttaaaaga tggttctttc    58740
atggctccaa agtttattgg taatgctttg tttcaggata tgtcaagagg ctatttgcac    58800
tgcagtttaa ggcagctaat agaatacagg ctaagtagct cacttatatt tgcactccag    58860
ttgaaatggt tatctattct gccggctagg tcacacgtca tattaatttc agaagaaaat    58920
tttctaattt agtgttgtgc ttgcttgtat tgtgagtcac agtttatatt tccacactgt    58980
aaaatggatg tttcaatcac taaattgaac taaggctttt agaataaatt gtggcatcta    59040
agcttgtgtg tagtcattac taaatgtgta atattagcac ggctatttct taagtgcagc    59100
atgtcaccag tttcatttga ttaggattaa tatattattt atatactcat tgagatatta    59160
tgttcatgag ggattggctt gaatgcatat aatttttatga ccctgttgta acgcacgggc    59220
ccttgtgcta taatgataat gagagaagag ttgtcactac caattcaagc agtgcagtca    59280
ccactacaga tcctctgcta tcagtaatta gtagagacca ggttcgtgac aagatcatag    59340
caatgcttca tgagaagaaa gaccaagtgt gaagcaaata ttgtcagtgg tccacacatt    59400
ttcataattg tcattcatgg catcaccagg tctaggaaat aaacgattgc acggtgagct    59460
tatgatcatg cgaaaaagta caagcaagag aaaatggaag gccatttgat cttcttatgt    59520
ggattcatgc ttctaaaaaa ttcaatttgg attccctttt agggagatgt ttgacagggg    59580
tacacaaaag gattgcctca aattcaatag tcgtaatgtc ctaaaagaaa atctgtagga    59640
gaactgcatg aaaacggaat tttttggtac tagatgatgt gttatacaac cataggaatg    59700
tgagagacca tgagaaaata gtttctgcgt tttttttaaag gaggatcacc ccggcctctg    59760
catcatgatg atgcatgcat ccatttatta aaacacggaa atagaggtcc cacaaaagtg    59820
atcaatctaa aagagttcac aggttgaact cgcaaaacaa aataacaata aaagccacaa    59880
ccggctaaga caacaataag tttgatgact aaacacctag cctattagtt agtcgccatc    59940
caaaccggtt gaagatagct cgtgctaccg tctcccaccg gttgcaccca gtagccaaaa    60000
gctccatgga ctccacagtt gtgagtaatg accatgtacg gatccacgtc gtagctctat    60060
agataacctg caaaaagttc ttgaagtttt tgttgttaaa tatgatatca ttttttggagt    60120 tccatatagt ccagaataaa gcacatattc ctatccgaat atgacccgca atatttgttt    60180
gcactccatt tagccacgtc tcaaataacg tgttcatact gattgaaggc ccaatgttaa    60240
aggctatata tatagtatgc caaagcaatt gggcaagcgg acagtcaaga aagatgtgtt    60300
taatagtctc attatgatcc caaaacaac atgtggtgtt tcctacccag cttctcttaa    60360
tgagattgtc cttcgtcaaa atcactccct tgtgaacgaa ccacatacat tttttgattc    60420
```

| | |
|---|---|
| ttaatggtac tttaaccttc caaatgtgag gtgatgtcag taatgtccta gaatcaataa | 60480 |
| gatctagatg catcgatttc acggaaaagc tgccattcgc ggttagtttc cagtgaatag | 60540 |
| tatcttgctg gtccctgagt tgaacttcct tcaacctacg gactaagtgt agtcaagaat | 60600 |
| cccatagccc ccccaccaaa gatctcctga attgtacatt tagaggaatc gaaccatgtg | 60660 |
| taatattgta gcaacataat cttctttagg ttcaacaatc ttctatttct aaatagctat | 60720 |
| aacccactag ctattttttt agacatgtaa gtacgccaca tgagcaactc atacatgtaa | 60780 |
| gccataaatt acattttcat tactctatgc atgcaaacat cacatcatta attcatgcat | 60840 |
| gttactctta agttacttttt tgcatcagat tttgtattga taatatatgt gttggttaca | 60900 |
| tgtaccatat atctgtagtt cacattcaca ttgttgttaa aattgatatt cttttttactg | 60960 |
| tatttttttct gttttttaaac tcttttatatt tctttttcat ttgtaagctt acatttgctt | 61020 |
| gccataagtt atagctgttt ttttagcaac tttcatgctc ttttagcaag ttttccgtaa | 61080 |
| caaaattctt taacacgttt cccgcagcaa cgtgccaggg catcatctag tattatataa | 61140 |
| ggaggaatat tgtagagcca aagggcatct ccccctagcca tgtatcttcc caaaatttag | 61200 |
| tagtggcgcc attaccatca ttaaaattta ccctatgaaa aataataatt tttttcatctt | 61260 |
| cattaacccc ttctagaaag gtgaatcaaa gggtctaatt gtaacctgta ccaaagtctt | 61320 |
| agactgtagg tatttattcc gaagaattttg tacccacatt ccttccgtct caacagccaa | 61380 |
| tctgaagagc catctactag gaaggcatct atttttaatt tctaagttct caatccctaa | 61440 |
| ccaaccttgg tctgcgttga acgttggaaa ggcaggaagc ggaatcttgg tgactagtga | 61500 |
| aactaaagat gcattattag ctctggatgc tgtaaaagag agatatattt caatatctaa | 61560 |
| ccaggatgat gtagtagtcc ttcaaatgtt catatattgc acttggaggt gcaatggtag | 61620 |
| gtggacatta ccaaagaaaa cttgaaataa ttggaggga catttcagaa aagctgaaga | 61680 |
| actcgcatct ggcaaccacg cgcgacagtg gatgcacggc tccgtaaaac ctcacaaggt | 61740 |
| gagatttaga tgaaaatttt gactagaagt agccccaca ccccgttgca tagttaaaaa | 61800 |
| agcaattttt cataggaagc aattcatagg gttgcctatt ataaatactt gtagaaataa | 61860 |
| aagaaaaaca gaataatgaa aaagaggaat taatttttt gagtgctgag taaatttgt | 61920 |
| tttgagaggt aaaagatgaa aatagtattt atttttttgaa aaagtgtcta tttcaaccga | 61980 |
| ctgatttctt cctcgcatca gccgcgtcgc gaagcgtccg atccaggtgg accatgcggt | 62040 |
| gctcgtgtct ctcgcgggca ctcgcgtcaa gtggctgcaa acacgccatg cttttcatca | 62100 |
| gctccacaca ccgcaaccctt tacacatcaa gtgaaggcgt tccgagggcg cgacgagtcg | 62160 |
| aggggcggtg atgctgcatt gaagcttcga tcatatcgtg gccaaatcca acatgaggaa | 62220 |
| ggaagcagaa tgtcgttgtg cattgaccaa atccaatgac catacatcat gcagatcatc | 62280 |
| caaatcagac gatcattgac ccgactgatt tttcgggaaa tcagtcgatt aacatgtagc | 62340 |
| atgcgcccta ttttttcaagg atgttttttt agcggtgttt taggaataaa cgaaaatagt | 62400 |
| acaaaaagca acgcttcata ctctaactgg cccggcacaa gtggtgtgag agggtgcgag | 62460 |
| ctggtcgtcc ggacgggacc tcctactgaa cgcattttgc gtccaatagc gatggcttcg | 62520 |
| cataggaggc acgaagcgac tgggccgccg tcgctatcga aactacttgt ccggccagtt | 62580 |
| aaccctctcg ggtattttcg cctattttag ttattttcct ttttttctttt tttctcttct | 62640 |
| tccttatttt cttttgtgtt tctctttctc tttttttctag aaggttacat ttttttttaa | 62700 |
| tttatgaaac ttaaacagcc tttgtattta cgaataaaat ttccaaatga aaatctttt | 62760 |
| gactttctga agaattaata agaacacaaa atttttttgaa aacaagagca ttttaaaaac | 62820 |

```
ttagaacaat tgtttttaga aaagaacaat ttttgaaatt tataaacatg ttttaaatca    62880
ggaacatttt ttcaaattgt gtacactttt tgaaacacga atattttga acttacgaac     62940 atttttgaa aatacaaaaa ttctttagag aatgaagaac attttgcaaa tgtcagaaca     63000 tttttcaaa ttatgaatca ttttttcaaa ttctagaaca ttttccaaat tccagaacat     63060 tttccaaat tccggaacat tttttcaaat tccgaaacat ttttcaatt tccaagacat      63120 tttttaaaaa tccggaacat tttttcaagt tctgcaacat cttttcatat tccaaaacat    63180 ttttcgaat tccaaaacat gtttcaaatt ccggaacatt ttttaaaatt ccaaaaaata     63240
attcgaattc tggaacattt ttttcaaatt ccggaacatc ttttcaaatt ccaggacatt    63300
ttttcaaatt ccaaaatatt ttttcaaatt ctggaaattt ttggaacaga aaagaaaaaa    63360 gaaaaagaa aaaccacttc ggagaatctt ttaaaaagtt cccaaaacca gaaaacaaaa     63420
ccgactgaga aagtatagaa ggtcccaaaa ccgacatccc cgcacttgtt aatgggtcgg    63480
cctagatcat gttagctcgc aatctctgtg tgcgaaggcg cgacaatttg tcgtaagagc    63540
aactccaatg tggcgaccca tttcgtccgc cgtcgaccgt ttgggtcagt gcagacaaaa    63600
atgatggccc aacgcgtcga tccattgcca aaacgcgtcc cgccgaccc atttccgacc     63660 caaatttggg actgaaatgc gtcagcacgg acgcgaagca gactcgcgcc cgcccctcgg    63720
tgtctgcccc caataccgc ggtcaacatt atttatgacg gccgccatgc tcgggccac      63780 gcgtcagcga tcgcggccgg tcttttttaa tctgagcgtg cggtgggttc cgctatctgc    63840
ttccaaaacc ctgcccgtcc acatccagcc ccgtccttgg cgaccaaaac catagcacac    63900
caaggcatgc ggcttcccaa acaagggcaa agccctgctc tacacccgcg ccatctcctc    63960
gtcgccgtct tcccaccggc atcgccagcg cgtgagcgtc ccggtgcacc aagcgcgatg    64020
gcactgggag caccgcatgc cactccctta ccccgatgtc acgctgccgc acgacgggca    64080
tatggatccg gagaggattc cggtgccggc cgagccgcgg tcagcgcagt tgcatgcaga    64140
ggaagtgagc cgccgtcgtc gtctgctgac gacggagcag tggcaagacc ctcatacgcg    64200
gttgactccc ctaaccggga ggtgtggttc gcggtggagc acgaggcgca gagccgtcgt    64260
ggtgtgcgtg aagtgcagcc aggaggccct ccgccgcccc cgcctgtcgt caacgacgag    64320
gaccaggagg ctgaggccgc ataccaggca tcgctcgcag ctgtcctccg cgacggcaag    64380
gaggaagcgc ggcgcagggc cgatgaggag tcggcgtacc aggagcaagc ctacctcgag    64440
cattggaggt cgcaacacct gccggcggag cgcgtcgaag gccttcggct catggaggtg    64500
gagaaggagg cgaaggagga cgacgggaa cggaggagg agcgtgcccg tgctgctgca      64560
ctgccaccgt caccagcaca gcccgcgtcg gcgggataga cgacggaggc gcaggcagct    64620
gcgttctgga acacgcgtt tccctggacc ggccctgcgc ctacgctggt cgacctcacc     64680
gacctcgatg acgaagacaa cgacgcttag ggctgccctc ctagttttag ttttttttat    64740
gtttaattaa tgtaacgcgg atccgtggac tctcgccggc cttcgtgacc ggcttttgat    64800
gtttaattat gcatttcgta gccaactttc tattttttt gaacgttagt aaaaatgggt     64860
ctggtcaacg ttggacgaat gccgacccat ttacaaaagc ggatatttgt gagggtgttt    64920
gttttcaggg acttattggt ttagggactt aaaaaagtcc gtataagtcc cacctaaacc    64980
aaacacaagg gacttattgt ggtgatttgg gacttatcaa ataagactct caggaggag     65040 cttattggga cttatcccgg gccggaccta ccccgcgtcg ctccaggctc gttccccgca    65100
cgccgccccg cctctcggtc caatcgccgc cgccgccccg cctctcgccc cgtcgccgcc    65160
```

```
ccgtcgccgc cccacctctc gctccggtcg ccgccccgcc tcggttcgtt ctgcctcagt    65220
tcgccgcccc gcctcggttc gttctgcctc ggttcgttgc agcggtgcct ccaatcgccg    65280
gacaggccct ctcccgagcc tcgttgcagc ggtgcttatc ctgtgtgccg tacgcgttgg    65340
ctgataacaa ttcatgtgaa caagtgtatt attatgtgca acatgaactt ataagtccct    65400
gtaactgtaa acaaacaggt agggacttat gacttataag ttaagactta aaaagttct    65460 aggacttatg aaacaaacag ggcctgtgtc tgcttgatgg acccaaacaa acaaaaagcg    65520
aacaatggcc ttcacgttgg agttgcccta acccgcggca aatagggctt tcccgtccaa    65580
cgccgaccca tttatgaaaa cggatatta tgtccgtttg attcacccaa acagataaaa    65640
aacggacaaa atcgcgtggc gttggagttg ccctaagccg tggcaaatag ggctttcccg    65700
tccggaccac aagcttcccg tttcctccgg cagcagtcta gcggcgatgg aaggcggccg    65760
acgtctccga tgctggtcgg cggaacttcg atccgccggc gggagccgac tcgccgtccg    65820
aaactcgagc tgcctatggc gacaccgccg ccacaggtct ccggcaggtg agcgcaaaac    65880
cagcgagttc tctgactcgg ataatccctt ttccattccc gtgtggcagc tttactcttg    65940
gactaatagt taatttccaa atttctgaga gaccttcgaa tttcatcaga ggacagatgc    66000
aactcgattt aggggtaatt gtttctctga gaaatttcgc actgtactgt tttgtacagt    66060
ttaagtttga tctttctttt taattcgctg gaatagggta aagacagtat atatatctgg    66120
agtatgcagt tagaactgga ccgtgttgtg tggtcggcaa taattttcag acaaatgaca    66180
agaactgacc gttctgtgta agaacctacc tggaaacttc ctgctgcctt cagggtcaag    66240
cgtaccgcgt gtccgcgtag tactgtccta gtatatatgt ttatactact gcattatgca    66300
ttatgcgtgc tgttaatcag ataaccttgt cgtatgtaaa gcaaggcagt gggtaccaac    66360
cagagtggtt acacatgagt cgtccaatct gaaattggac cgagtcttgt tcatcttata    66420
ttagttcatg attcgtcatt atcttttttg ttttttcgtt agtagtataa tactgacatg    66480
atgggatcca tttggcctta ttataaaagc acaccagaag gaagcaaagc attagttcaa    66540
gcatctctct caactgctac tacttgttta tgggtcttag ctagctgtca ccgggtgcat    66600
taccaggagt tatgtattgt acatacaagg tcctgcagcc aagctatcta gccttctatc    66660
ccctctctga aagcttgcca tggcggatcc agtttccatc ggtgctgctg taggatgggg    66720
cgtatccgca gtaggctggc tcgcctctcc catcatttca agggtcctca acaaaggttt    66780
cgcccacctc gactttgacg cgacagcgaa gctgaagata ctcgatatac aaattttaca    66840
gctgcagcgc ataatggagg tagtcgacga gagcacttac agggttcact tggagccact    66900
tctaaacaag cttagatccg ctctctacga agccgaagac atcttggatg ctgttgaata    66960
tcagcgtctc gagaagcaga tccaagatgc caagtcagaa ggaaacatac ctccaactcc    67020
aagtattatg gattcgctgt ggaggattct ttggtctttc atgcccagct ccctactaaa    67080
agataaggta tttccctgcc ctcatacttg gatgtttact tttttttact gcaggtcctt    67140
catcttttta tgccatgtaa atactccctc agttcctaaa ttaatatgag gtctgcttca    67200
gtagaccccg tctcacaaac cgtataaaga taatatgacc gacctcgtaa tctaacaaga    67260
accacactaa ccaactagga cagcctaatg gttgtgtcta tttacttctt tttcttatct    67320
gatgctaacc agtccttta tcactattct tttttgtctt ttctattcgt ttttctttt    67380 ttcatttctt ttattttttt tttaaatctc acatttacaa aatttgttc agatttcaaa    67440 aaaatgtccg cttagtaaaa ttttgttcat aaagtacaaa tatttgcatt ataaaaaatt    67500
aaagatatgc caaaaaaata ttttttaat aaaaaaatgc tcacatcata taattaaatt    67560
```

```
tctgaacata tattaaatag aaaatctgtt tgtttaaaag ataatcgttt atttcttgtt   67620
tcaatagaaa cacgctcaca taagaaaaat caaacacaat caaacaattt taagttattt   67680
attaaataga aaagtaaaaa gtcaaactat ataaatcagt gacttgttta ttatccattt   67740
ttttgttcct tttactttct tgttgttctt cgttttgcct tattttcttt cctttccctt   67800
ttcaaaaaat gctcacatca atagaatgga cctaaatttt tccacacaca ctagcatcat   67860
catgccaggc atacatcata aaatttattg tgttctcaca ctttacgcat tttctaaggt   67920
ttttcgggtg aaaaaccota aaacactaac cttacacatg ttgtgtcatg tttggccggt   67980
gttttagggc atttttctcc gttgtgcatg catacaatgt atttttttaaa attacatgga   68040 tattgtgatg atgatgacag cgtgtgaaaa acaattgagt gcgtttcatg gatgtaaaac   68100
gggaaacatt ttagacgtga cctatcggca cactaagacg gcactgcttg tacatgatct   68160
acgtcacttt attcatgtaa tgacaccaac ttttggcgtg aacatgcatt ctagccccca   68220
cgtgaggaat gaacaaattc ggacaccaaa tgcacgttgt gccacgtcta gttggccttt   68280
agggcatttt cctcttgaaa actataataa atgcatacaa tgtagaaaat tattaaaaat   68340
tgacatggat gcttgtggtg atgatgaaag cctgtggaaa taattgtgtg catttcatgg   68400
atatgaaacg gagaacgtgt tggacacttg tcctaccagc acaataagac ggtgctgctt   68460
gtacatggca tgcgttacgt tgttcatgaa atgacaccaa cttttgacat catatgtgaa   68520
caaccattct agtcccacac gcaagaaatg aacgaattcg gtcaccgaac acacgttgcg   68580
tcacgtcagg tcggtgtttt agtgcatttt cctctagaaa accgtagtaa atgcatacaa   68640
tgtagaaaat tgttgaaaat tgacatggat gcttgtgatg atgatggcag catgtgaaaa   68700
aaattgagtg cgtttatgga tatgaaacgg agaacgtgtt ggacacgtgc cctaccggta   68760
cagtaagacg gtactacttg tacatttttct tcgtcatgtc atttatagaa tgataccaac   68820
ttttgacatc gtgtgtgtac attcattcta gccacacacg caaggaacga acgaactcgg   68880
acaccgaacg cacgttgcgt cacgtccggg cggtgtttta gtgcattttt ctctagaaaa   68940
ccgtaataaa tgcatacaat atagaaaatt cttgaaaatt aacatggatg cttgtgatga   69000
tgattctagc gtgtgaaaaa aattgagtga gttttatgaa tgtgaaacgg agaacgtatt   69060
gaacacatgc cctaccggaa tagtaagacg gtacaacttg tatacattat gcgtcacatc   69120
attcatggaa tgacatcaac ttttttttcat tatgtgtgaa catttattct accccctcacg   69180 caaggaatga acgaattcgt acaccgaacg cacgttgcgg tcacgtccag ccgatgtttt   69240
atgacatttt tctctaaaaa cccatagtaa atgcataaaa tgtagaaaat tgttaaaaat   69300
taacatgtat gcttgtggtg atgctagaaa aaaattgatg tcatttcatg catgtcaaga   69360
agcatatcgt attcaaaggc gaggattaag gtaggcccat agggcaaggc atttgttatt   69420
cgcaatccct gtcattatca atcaaaatga acattttctt atttcctatt tacttttga   69480 aaattttcaa caattttagg attcaaattt tgtgtgattt gttttaaca tgaacacttt   69540 ttccaaaatt gttaataagt cccaaatatt gatgttgtac gcgaattaca aaccgcatac   69600 ttttttaaaat ttatcatcat ttttaaaaca caaacacttc ttaaatttat gatttgtctt   69660
tcaaaaattg gtacatttt tggaacttag aaaataatct tgtattcaaa ttgtttctac   69720
acaaaaacta aaaatgttca cgaaaattta aaataaattg gtgtcaatgt tttgttcata   69780
ttttcggatt ttttagttaa attttatatt tcatagtatt ctccaaaaaa tgttcgtgtc   69840
aaaatatttt tcgctgtttt taaagtatgt tcgtgttatg acatgctgag caattttgaa   69900
```

```
atgcgcaaac aatattttga catatttata caattgtttt tcaaaatact atattagtac    69960
tttatgaata aaatttaaga aaatcaaact ttttagaaaa aaattacaac aattttaagc    70020
gtgagtattt aaaaaaaaat aagagacgaa tttcaaaaaa aaatagtgat aaagtgcaga    70080
tttatcaatg ggccggccag ctgtgaatta agtagaaca aaacataaaa aataagtaaa    70140
tatgaacaag cattaggatg tcctagttgg ttagagcatc tctagcagac cccgtataaa    70200
gtcaacccac ataagtcgtt tataattcac aaaaaaaaag gttttacggg ctgacgcggg    70260
cgcggacaga gtctgatccc gcaaatcaaa cccgtaaaaa ggatattcgt agaagatgtt    70320
tttttacgga tcggcaatgc ggggtctact cggacggcac cgcgtcggcc ccgcaaaccg    70380
aagaccacgt aaatcagaat tagtaatgtg caatataagt aaaattcaat attacaaata    70440
cagtaatcat ccaaaatgca acaattattc aaatcatcat agcaaactaa ataattcaat    70500
acaaaagttg tcccgcatac gaatcacaca cgaatgaaat gaaatgaat ggaaaatgg    70560
aatgtgttac tgcccagccc tttgtcaatg gtgctcaatg agatcttttct gaagttgaca    70620
gtgggtgatt gcattttcaa tctccctgta ggtttgaaga aaagctctaa tttggttagg    70680
gcctctagct gttttgacac ggctgcccac attgtcatag aaaactctaa gttcatgtct    70740
ctctcatctt cgagaatcat attgtgaaga ataacacatc atgtcatgat gttttttcaag    70800
gaccgcttgt cccaaaatcg agcaagacca cgaacattgg caaacctaga ttgcaaagcc    70860
gcaaatgcaa tttcaatgtc ttttcgggcc gcctcctgtg cctttgcgaa ttcaaactct    70920
ttcctacttt gggggtcttt gatgctcttc ataaatgtgc accaaaaagg gtatatacca    70980
tctgcaagat agtatccttt tgtgtattca tgtcaattga tagtgtagtt gcaagatgga    71040
gcatcaccgt gcaagcctag caagcaaatg agaccgttgc aacacattga tatcatttag    71100
gttaccggc atataccgaa aaagcaatcc caaatccata aatcatgtga agctacaacc    71160
tctagcacaa ttattgcatt acgagacttg ccatgctttt ggaaaatttt ccgtgccatg    71220
cttttgggca attttcaaag tgcaatgtat acaatctatg cttcctagca tgccaggcca    71280
acctcttctt tcattaaatg ccatcaattt cgttgtgtct tcctcgttcg gtgcctgaag    71340
atattcagga tcaaaggcac ggacaatcac tttgacaaac ctacgcactg actcagttgt    71400
actatcttcc ccaatgcgaa ggtactcatc gctatagtta gccggaaggc cgtatgaaat    71460
tacccacata gttgccgaga tttttttgata tgcactaaat cctttcaagc ccgcaaaatt    71520
ccttctttga gtaatatatc gacaattggc ctcgcaagct tgaatttttt tacaaagagg    71580
gatctacaca tacggtacct tctccagaaa aggttcagcg ggtatattgg attggcggca    71640
aagtagtctt gcatcaacat ctcattcccg agatggcggt gacggccgat agtcgatcct    71700
cgccgcctct ttcgatgctc gtcttcgtgc tccttcacgg caatgccat caccaaactc    71760
tgccggcgaa gtgtgagaag catcgtctca atatccgagt catacgaatc ggatgaatcc    71820
tcgagcagaa acttctcgca catgctcaac tccatctccg gtggtggctc tcccaccacg    71880
atggattggc agatccgggg aactggtgca acggctcggc ggaagacggc aggggcgccc    71940
aaccggcgcg attcgcccca cagatttggc ggagtcgccg gcggtggact ggcggaacca    72000
atggcgggc ggcgacggaa gtggttgggg aaaaggggcgc gggctgaaat ttccgtcccg    72060
ccaaccgctt ccttgggata cagggcactg tataggcgag gcagaaacct gtgttttcac    72120
gggttgggaa ggggattttg ccgccccctc aaaaacaatt acgggtcgga cgcgtttgca    72180
gggtctggtt tggcagcatt ttccgcgcgg accccttattt tggtggttat tttacgggtc    72240
aaggtattat acgggatcta ctacagatgc tcttagtgat tttatcaact ataaggtctt    72300
```

```
gagttcaact cttattgctt gcacagtttt tttcttttaa aaaaacgtgc aaactgttga    72360
ggttgcacaa taagagaaag acaccccgag aaaaaaatgg atgtcgcgta tatgtatatg    72420
tgagcaggcc acgtatcgtg cacgtgaaaa gaccatccta tcctttatta tgaaggggta    72480
tagagagatc tcaactgtca gtgtgtttag agggtttact gaagcaaaaa agtgaattaa    72540
tatatgacct tttagagatt tcactataga ttacgtattg atgtatatag acatattcta    72600
aagtgtagat tcactcatct tgcttcgtat gtagtctata gtaaaatctt taaaagatct    72660
tatatttagg aatggaggga gtatatctta cttggaaaaa agaggcaact ttagctccca    72720
atcagaatgg attctcactt atttgccata attatttaaa tagagagatg ataagatttt    72780
gaagtacagt aagagatacg ataccggttg gtaggaaaag taggatttgt ttccttggat    72840
ccaccaatat cactacatga tggagacgtg tgcggtgtgc cctatatcaa ttcagcaatg    72900
aatcaagagt ttatatatta ggagtacttc ttagagtaga ttggcctagt tatcctggaa    72960
ggatccaaga ttgttccact ctcccattag aagtgttctt cctcaagctc atcttccctg    73020
tgtagccctg aaatactatt tggtcctctc gtgatgggac aacggtgcct cttgatgcac    73080
tcccgtctcg cacgacaccg aactcaatgt cgaaccagga ccccaaacgg cgtcatagag    73140
ttaccaaagt ccctcgaaac aggttttcat ctcacttata aagcaacaac cgaagaaaga    73200
ccacgaccga atgataaagg tggtgagatc accctctttc aaagccgatc ccagaataat    73260
cggatcatgc agaatgcaag cgactacgct accaaccaag aacacatgaa tacctagaca    73320
caccgtcaca ctacaaccta atacaccttc acgacaacgg tctcaagagg gagaacggca    73380
ccgagagtca ccactgccga gtccacaatg gacaaatgtc tttaccccta tccctagcac    73440
ggagagaaga accacggcga cgtcttcaag aagagtgcga caccctggt attgccgccg    73500 ttgacgccaa aggcgcagat ttttcgctcg gcaactcacc ggcaccacca caaggccgtc    73560
aggacgacac cctagaggag gatacgcccg agccacccc ctctacacct cccgtcgccc    73620
acacgaccat gaaggagagc tactaccgcc gcaatggtcc gtgtcgacaa actatgtgga    73680
ccaccattcg gggccgttgc cctagcatcc ctgccacgag acaccgtcca caacgcactt    73740
cacaactcat tccgtcatga tagaaagagc ataggcacgt ccctaaccc tagcccgaca    73800 tgagtctggg taggagcctc ctgtgtaaga ggcacccacg cctaggtcct accaaattcc    73860
tgttgattgg ggggggggc acaactccat gactgctgac gagcatcgat aagaagccca    73920
tgtcgtggcc caagctagca cgcatgacgt cgtgtccatg gccaccgacg acgatccgcc    73980
aagcaatgca acggtatcat gaccaccacc agcgaccacc gcgcccgcga gcacaacccg    74040
aaccgctccc cacctgacct atgtggagca agctctccga tttgcttcgg gcccaaatcc    74100
ccccagcaca aaccctaggt cgtggccacc acgacgagtg cgagcccgca cccgtttgc    74160 atgtacccag tagaagggag gttgtcaccg ccacccgcac cccattgcca agcaacaaac    74220
ggcgtgccat atccacacca acgtgcacag ctagcaagct agcaagatgg ttgatcgatc    74280
cgaagcaaca cacacaggta gccggcatat atcaacaggc tggtatcgag ccttcttcgt    74340
tttcttattg atctggttcg gttacagagg aggttacaag aatatatata ggagctaaaa    74400
ccaacatcac ctaactatat agaggatata gaattaggat tcctatatta tacaattatt    74460
tcttcgagtc ctagccgcac aggacacagg tgtacttcgt gtttaactcc aacaaggagg    74520
agggaaggag gaggtcccgc cgtcgccaac gccgaccagg cttttcccgg cgatgcgccc    74580
ctgtggcggc gagaaggaga ggtaggagaa gaggcgcgag cctgacggtg ctagagttgc    74640
```

```
cgaaggagct gaaaacattg gacgcatttg ggatgctagc gcccacgtga gtctccgaca    74700
accaccacat gtcagagttt gtgttttgaa tttcggcaaa aagaatagat ttcggccatc    74760
tcgacctata gtgaaaaatc ttggtcaatt tttggtcaaa attgagccaa atatattttg    74820
gtcaaaactg agccaaattt tagtcaaatt tggtcaaat tgcagccaaa atttttataa     74880
atggccgaaa ttcggccatc ttggcctaga gcgaaaaaat tcacaaacca aaaatcaaaa    74940
tcttggtcgg actcgagaca tatcacccat gacacgcaca atggaggatc gagatcgaca    75000
taaggtgccc tgggattgcc cagatgagct agtgacctca tcgacgcact tgggaccgga    75060
ggggaacacc aacatcgtac ttcttatcta gcatgcctcc gttacggagc tgccttgtcc    75120
ttctatggcc tggattctct tcacccggtg ttcacttttc tctagatatt aacagggcat    75180
agaaagaaaa agaaaaactt acttcgcact gtattattaa taaatctata tgggtgagaa    75240
ataaatacgc tacatatatt cttcaaacgg aattgttctt gatacccctca agacctcaac   75300 atacctgtta tttggctttg caggagagtg gtttgccaaa actacagttg cagaagagcc    75360
taaagaagat agaaagttct ataagtgatg catgtaaagt gttagaacaa ctgaacttgg    75420
caggtgcaag taatgataac gggagtagag ctgttgctac caattcactc ggtgcagtca    75480
ctacggcaga tcctccaata agagtaattg gccgagatca ggatcgtgac aagatcatag    75540
caatgcttca tgagaaggaa gaccactgtc aagcaaacac cgtcagtggt acatgttatt    75600
ctgtagttgg cattcatggc attgccgggt ctggaaaatc aacacttgca cagtgtgttt    75660
atcatcttga gaaaaagtac aaccatggga caatggaacg ccatttcgat attgtcatgt    75720
ggattcatgt ttctcagaaa tttgatttgg actccatttt tagggaaatg tttgagggg    75780 ctacagggga accatgtgat gacttcaata gtcgtaacgt cctaaaagaa gtgctggaga    75840
agaaactttg tggaaaacgg gttttgttgg tgctggatga tgtctggtac aacattagga    75900
attcaggaga ccgtgaagaa ctacaaaagt taatttctcc attgaatgtt ggaaaggcag    75960
gaagcataat attggtgact agccgaactg aagctgcatt agtatctctg ggtgctgtaa    76020
aagagagatg tattccaata tctgacttgg atgatgaagt gttcctcgaa atgttcatgc    76080
attatgcact tcgagatgca agggtaagtg accatgatcg aagggtactt gaattgattg    76140
gagaggacat ttcgaaaaag cttaaaaggt caccctagc agccagaaca gtgggttcgc     76200
ggcttcgtga gacgcagact gttgagtttt ggaagagtca gaaaaatctg atcttatga    76260 actcgactat gggggctttg tggtggagct accagtatct tgatgaacag gtcaggcgat    76320
gctttgctta ctgcagtatt tttcctagac gacatcgttt gcaacgtgat gagttaatta    76380
agttgtgggt ggcagaaggg tttataaaga ctagtaatcc tgcagaggaa atggaagatg    76440
ttgctaagag ttattttgat gaactgttat cggcctcatt tctgcaatta ggaggaaaag    76500
aaatggtaaa tggacgtgag gttgattact ttacaattca tgacctcctg tgtgatttag    76560
cagaggaggt tgctggaaga gattgcttca ggattgaaaa aggtttcaca ggagaagttc    76620
ctcaagatgt tcggtatctt tatgttggga cttatgatag agaaatgatt actgagaaga    76680
tatgtggatt gttaaattta cgcactctca tcattgatga ctacataagg cttgaatcaa    76740
atgagtgtga agtctttgcg agtatgttca ctatgctgac ggggctgtgg aaattgcggg    76800
taatgaaatt gcgtttcaga ggacttggtc ttcgcaaatt ctcgttcccg gattctattg    76860
gtcagttgaa gcatctgcgt tattttgctt tcatggtggg tggacttacc aagctaaagt    76920
tgccatgtgc tttcaccaag ctttaccata tgcaggtcgt agattttggt aattgcacga    76980
aattgaaatt tgctagtagc gaagatatgg tgaacctcgt gaacttgcga tgtgtaatca    77040
```

```
gcaacgcaga tctggagttt ccgaacgttg gcaggctgac atggctccaa atgttaccgt    77100
cctttacaat taggaagaaa gagggtatg  agccacatca gcttaaacac ttaaacaagc    77160
ttcaagacaa gctgcagatt tttggtcttc agaatcttcg gagcaaggac gaggctctcg    77220
aactcaatct tgctggcaag ggaaacctca gagaactggt acttcgatgg aataatagct    77280
caaggaactc catagaagtg aaagaggagg tacttgaggg tctttgccca tcaaagtatc    77340
ttgaaatact agaaattcat tcgtactacg ggaggttacc aagttggatg atgggtatgt    77400
atggaggccc aaagaaccct caagaactta gattcctgtc ctgttaaccg gaaattgctt    77460
ctgaccttga ggttttcatt cgtcttcgtt ccctagaatt tcatgcgtgc aactgctttg    77520 tcttttccagg caacatggac cacctcacgt cgctcaagaa actggagatc gatggccgtg    77580
agtatatagg gtcgctccca atactgccca agtctcttga ggagattaaa gacacagaat    77640
cttgtgctac ggttgctgat ccaattggta gaagattggt gagattgcca cttcaagcca    77700
gacattctta tgaagaaggt ccatacagaa ggtacgtatt tatatttctt tgatgtcttg    77760 ttttcattg  tgtgttaaat aaatgttact tcaacagtta gccattaaga atgctgctat    77820
gtttctgatt cgtttgctaa ttgccagatt caggcccttt tggtgaggac gggagccaga    77880
ggagatagag ttgccaaacg aacagggcca tttctgtgct cttgtgtctt tgttcagttt    77940
tatatactcc ctccattcca taatccttac gagtttcatg ggaaggaagg agcactttgg    78000
tttgcatgcg tgtttgctaa aatgccatag ctgcatgcag tggcggacaa tgggtgtagt    78060
cgtctactgt ggtagtatat atcaatatat gtaatgtaat gtggaatgat gaacaccgga    78120
ttcatttgct tcctatgtac tatatgattt ataacactgt tgaatgcatg atgaacctta    78180
aactgtatga tttctgtcgt ttttaatact cactatggaa tggtgaacat tgaatgtgtt    78240
tgtttcctgt tgttcgtaaa attgtcagtg cattaactcc cccgcggctg ccatgcgtcg    78300
cctccacccg gtgctgccac cgctggtgtg tggccttttct cctcggcttt ccagtaaaga    78360
cgatgatgat tgcggacccg ttgagggaac agaggcgact caggcgaggg atgccgctgt    78420
actccctcct tccatccgtg ggcaggccag gaagcgagtg gtaaaagcgg tgagttcctg    78480
tggagtccgc ctccgtaata gaattgtttg atgcggtaca ttttttggaa caatcggggc    78540
tgtggtcacg gtggacgtag gactcagctt aaggaatact cctatatggc aaaagaatga    78600
atagatgtgg tagctttgca ggagacgatc aaataaatag acttttcttt tcgcgacctg    78660
cttgcttttg atcctatgca gcgttttgag tggcattggc tgcctccctc cggacactca    78720
gaatgtcaac ttatctctat ctagagatac cattgaatgg atctggacgg agaacaaaag    78780
ttacaccgcc aagtcagcat attcctgcca gttcattggc tctgtcgcca aacctgaggc    78840
taacagcatc tggagactca agattgaaaa aaaagtgcag ttctttatt  ggacgttggc    78900 tcaaaacaga ctgccaacca tcgacagatt gagagcacat ggaagtgatc acaccgcgat    78960
gtgctctctc tgccgccagc tccctgaaac tgccctccac ctcttcagcg catgctcttt    79020
ctccatggag gttcgaaaca gattacacct agcgcggcct ttgagctacc caacactgtc    79080
agcaaaccct cagtcaatct cacaatggtg gcgcaaccac tcccagaact ccagagaaat    79140
agctgctgct gctgctgcct actttgcttg gcacatctgg aacgagagga acagacgggt    79200
cttcaacact atatctattg cgacggatgg tgtggcctct ctgatcaaag ccgatcttga    79260
tgttgtaaga ctagcgctgt agaatcttat tatgtacggg caacgtccac tggacgactg    79320
ctcactcttt tgtatatccc taatctctaa tgaaaagaga gagcacctgt cgtttcctaa    79380
```

| | |
|---|---|
| tctctaatga aaagagagag cacctgtcgt tttaattcaa aaaaataaag acatttgtga | 79440 |
| ggttaccatg tgggaatcag agattttttt ttttcatttt tttaggggtt tgggGatttt | 79500 |
| ttttcattgc cgcgacggtt aaacaccgcg tttcagggct gtcttgggtg acggtgtgtg | 79560 |
| tttatggccc gccagatcac tcgagatgtg ttgatctcct caatgaaatc tctagcctgg | 79620 |
| taggggccaa aaggggggca aatctccggt gatcattggt ggcgacttta acttgatccg | 79680 |
| ctcaggagcg gacaagaata atggcaacgt ggactggtct agggtggccc acaatgccat | 79740 |
| cgcctcggca gtgcttcggg aaatcgcgtg atcgggtgct cgttgcacat ggaccaacaa | 79800 |
| atagccggcg ccgatccgta gtatcctaga ccgcgttttt gctctctaga gtgggagctt | 79860 |
| ctctttccca tgtgctcccc cgtggctgag actcagatcg gatccaatca cgtccttcta | 79920 |
| attctgtcct cgggggagga tatgagacat cgaaacaaga ggttcttctt tgaaactgcg | 79980 |
| tggttcgagg cggagggctt cgagaacctg gtctctgacc gctgggcatt aatcgtgtct | 80040 |
| cagaccggcc ccagcgaggc cctcttgagg tatggaataa agcggccgcc gctttgcgtt | 80100 |
| ctttccttag gggctggggc gccaatcaag gcagcgaatc caagcgggaa cgagcatgtc | 80160 |
| tggtggttga aattgcgggg ctagacgtgc aggccgtgtt ggggaacgtc gcatggaaac | 80220 |
| aaaaaaaatt tcctacgtgc acgaagacct atcatggtga tgtccatcta cgagagggga | 80280 |
| tgagtgatct acgtacccTT atagaccgta cagcagaagc gttagtgaac gcggttgatg | 80340 |
| tagtggaacg tcctcacgcc gcgatcagtc ccacgatcta gtgccaaacg gacggcacct | 80400 |
| ccacgttcag cacacgtaca gctcgacgat gatcttggcc ttcttgatcc agcaagagag | 80460 |
| acggagaggt agaagagttc tccggcagcg tgacggcgct ccggagtttg gtgatgatct | 80520 |
| cgtctcagca gggctccgcc cgagctccgc agaaacgcga tctagagtaa aaaccgtgaa | 80580 |
| ggtatgtggt cgggctgccg tggaaaagtc gtctcaaatc agccctaaaa cctccgtata | 80640 |
| tataggtggg agagggggga ccttgccttg gggctcaagg agccccaagg gggtcggccg | 80700 |
| agccaaaggg gggaaggact ccccccaaac cgagtcctac ttggtttggt gggtggagtc | 80760 |
| cttcttTccT ttcccacctc ctccttttTT TtttctcTTt gattTttctt ccaatgcgca | 80820 |
| tagggcccTT ttgggctgtc ccaccagccc ttagtcccac cagcccacta agggctggtg | 80880 |
| cgccatcctc aaggcctatg gcttccccg gggtgggttg ccccccggtg aactcccgga | 80940 |
| acccattcgt cattcccggt acattcccgg taactccgaa aaccttccgg taatcaaatg | 81000 |
| agtgttggaa ttatgcccta gaggcaataa taaatgtata gttattatta taattcctgt | 81060 |
| atcaagataa tagtttatta tccatgctat aattgtattg aatgaagact catttacatg | 81120 |
| tgtggataca tagacaaaac accgtcccta gcatgcctct agttggctag ccagttgatc | 81180 |
| gatgatagtc agtgtcttct gattatgaac aaggtgttgt tgcttgataa ctggatcacg | 81240 |
| tcattgggag aatcacgtga tggactagac ccaaactaat agacgtagca tgttgatcgt | 81300 |
| gtcattttgt tgctactgtt ttctgcgtgt caagtattta ttcctatgac catgagatca | 81360 |
| tataactcac tgacaccgga ggaatgcttt tgtgtatca aacgtcgcaa cgtaactggg | 81420 |
| tgactataaa gatgctctac aggtatctcc gaaggtgtta gttgatttag tatggatcaa | 81480 |
| gactgggatt tgtcactccg tgtgacggag aggtatctcg ggcccactc ggtaatacaa | 81540 |
| catcacacac aagccttgca agcaatgtaa cttagtgtaa gttgcgggat cttgtattgc | 81600 |
| ggaacgagta aagagacttg ccggtaaacg agattgaaat aggtatgcgg atactgacga | 81660 |
| tcgaatctcg ggcaagtaac ataccgaagg acaaagggaa tgcatacgg gattatacga | 81720 |
| atccttggca ctgaggttca aacgataaga tcttcgtaga atatgtagga tccaatatgg | 81780 |

-continued

```
gcatccaggt cccgctattg gatattgacc gaggagtctc tcgggtcatg tctacatagt   81840
tctcgaaccc gcagggtctg cacacttaag gttcgacatt gtattatgcg tatttgagtt   81900
atatggttgg ttaccgaatg ttgttcggag tcccagatga gatcacggac gtcacgaggg   81960
tttccataat ggtccggaaa caaagattga tatataggat gacctcattt gattaccgga   82020
aggttttcgg agttaccggg aatgtaccgg gaatgacgaa tgggttccgg gagttcaacg   82080
ggggggggg ggggcaacc cacccgggg aagcccatag gctttgggga gacacaccag   82140
cccttagtgg gctggtggga cagccccaag ggggcctatg cgccaagaga aggaaatcaa   82200
aggaaaagaa aaaaaagag ggaggaagtg ggaaggagg gggactcctc ccaccaaacc   82260
aagtccaact cggtttgggg ggggagtcct ccccccttg gctcggccga ccccttgagg   82320
gtcccttgga ccccaaggca aggtccccct ccctcctcct atatatatgg ggcttttagg   82380
gcagatttga gacgactttc tcacggctgc ccgaccacat acctccatag ttttttcctct  82440
agatcgcgtt tctgcggagc tcgggcgag ccctgctgag acgagatcat caccaacctc    82500
cggagcgccg tcacgctgcc agagaactct tctacctctc cgtctctctt gctggatcaa    82560
ggaggccgag atcatcgtcg agctatacgt gtgctgaacg cggaggtgcc gtccgttcgg    82620
tactagatcg tgggactgat cgcgggattg ttcgcggggc ggatcgatgg acgtgaggac    82680
gttccactac atcaaccgcg ttctctaacg cttctgctgt acgatataca agggtacata    82740
gatcacgcat cccctctcgt agatggacat caccatggta ggtcttcgtg cgcgtaggaa    82800
attttttgtt tcccatgcga cgttccccaa cagtggcatc atgagctagg ttcatgcgta    82860
gatgtcttct cgagtagaac acaaaaggtt ttgtgggcgg tgatgtgcgt tttgctgccc    82920
tccttagtct tttcttgatt ccgcggtatt gttggattga agcggcttgg accgacatta    82980
ctcgtacgct tacgagaaac tggtttcatc gttacgagta accccctttg ctcaaagatg    83040
actggcaagt gacggtttct ccaactttag ttgaatcgga cttgaccgag gaggtccttg    83100
gatgaggtta aatagcaact catatatctc cgttgtggtg tttgcgtaag taagatgcga    83160
tcctactaga tacccttggt caccacgtaa acatgcacc aacaaaatta gaggacgtct    83220
aacttgtttt tgcagggtat gattgtgatg tgatatggcc aacgatgtga tgtgatatat    83280
tggatgtatg agatgatcat gttgtaatag aaatatcgac ttgcatgtcg atggtacgac    83340
aaccggcagg agccataggg ttgtcttat actaacgttt gtgcttgcag atgcgtttac    83400
tattttgcta ggatgtagct ttagtagtaa tagcataagt agcacgacaa ccccgatggc    83460
aacacgttga tggatgatca tggtgtggcg ccggtgacaa gaagatcgtg ccggtgcttt    83520
ggtgatggag atcaagaagc acgtgatgat ggccatatca tgtcacttat gaattgcatg    83580
tgatgttaat ccttttttgc accttatttt gcttggaacg acggtagcat tatgaggtga    83640
tctctcacta aaatttcaag acgaaattgt gttctccccg actgtgcacc gttgctacag    83700
ttcgtcgttt cgagacacca cgtgatgatc gggtgtgata gactcaacgt tcacatacaa    83760
cgggtgcaaa acagttgcgc acgcggaaca ttcgggttaa gcttgacgag cctagcatgt    83820
gcagacatgg cctcggaaca catgagaccg aaaggtcgat catgaatcat atagttgata    83880
tgattagcat agggatgctt accactgaaa ctatactcaa ctcacgtgat gatcggactt    83940
gggatagtgt aagtggatca tgaaccactc aaatgactag agagatgtac ttttttgagtg   84000
ggagtttagc atataaattt g attaagttga actctaatta tcttgaacat agtctaagtc   84060
cactttgaat atatttgtgt tgtagatcat ggctcacgca agtgtcatcc tgaattttaa    84120
```

```
tacgttccta gagaaagcta agttgaaaga tgatggaagc aactttgtag actgggctcg    84180
taatcttaag ctaatcttac aagctggaaa gaaggattat gtccttaatg ctgcgctagg    84240
agatgaacca tccgctacgg ctgatcatga tgttaagaac gcttggttag cacgtaagga    84300
ggactactca atagttcaat gtgcagtctt gtatggctta aaccgggac ttcaatgtcg     84360 ctttgagcgt catggagcat ttgagatgtt ccaggagttg aattttatct ttcagaagaa    84420
cgcccggatc gagaggtatg agacctccga taaattctat gcttgcaaga tggaggaaaa    84480
ctcgtctgtc agtgaacatg tgctcaaaat gtctgggtac tcaaaccgtc tagctgaact    84540
ggggattgaa ctcccgcaag aagctatcac tgacagaatc cttcaatcac tgccgccaag    84600
ctataaaggc tttgtgttga actacaacat gcaagggatg aacaagtctc ccggcgagtt    84660
gtttgcgatg ctgaaagtcg cagagtctga actccgtaaa gagcatcaag tgttgatggt    84720
gagcaagacc actagtttca agagaaacgg caaaggcaag aagggcaatt cgaagaagag    84780
cggcaagcct gttgccaatc cgccgaagaa acccaaggct ggacctaagc ctgaaacaga    84840
gtgcttctat tgcaagggta tgggtcactg gaagcgcaat tgcccccaagt atctggcaga   84900 taagaaggcg ggcaaagaaa aatcaggtat atttgatata catgttattg atgtgtactt    84960
aaccggctct cgtagtagtg cctgggtatt cgataccggt tctgttgctc acatttgcaa    85020
ctcgaagcag gaactgcgga atagacgaag gctggcgaaa gacgaagtga cgatgcgcgt    85080
aggaaacggt tccaaggttg atgcaatcgc cgtcggcaca gtgtcacttc aactaccatc    85140
gggattagtg atgaacttaa atcattgtta tttagtgcct gcgttgagca tgaacattat    85200
atctggatct tgtttattgc gagacggtta ctctttttaac tctgagaata atggttgttc    85260
tatttctatg agtaacatct tttatggtca tgcaccgaat gtgagaggat tgttcatatt    85320
gaatcttgat agcgatacgc atatacataa cattgagacc aaaagagtta gagtaaacaa    85380
tgatagcgcc atatttttgt ggcactgccg cttgggtcat attggtgtaa agcgcatgaa    85440
gaaactccat gctgatggac ttttggagtc acttgacttt gattcacttg acacgtgcga    85500
accatgcctc atgggcaaga tgactaagac tccgttctcc ggaacaatgg agcgtgcaag    85560
tgacttgttg gaaatcatac ataccgatgt gtgtggtcca atgagcgtgg aggcacgcgg    85620
tggatatcgt tattttctca ccttcactga cgatttaagt agatatggtt atgtctactt    85680
gatgaagcac aagtctgaaa catttgaaaa gttcaagcaa tttcagagtg aagtggaaaa    85740
tcatcgtaac aagaagatca agttcctacg gtctgatcgt gggggtgaat atctgagttt    85800
cgagtttggt actcacttaa gacaatgtgg aattgtttcg cagttaacac cgcctggaac    85860
accacagcgt aatggtgtgt ccaaacgtcg taatcgtact ttgttagaga tggtgcgatc    85920
tatgatgtct cttactgatt tgccgttatc attttgggt tatgcattag aaacagctgc     85980 attcactttta aatagggcac catcgaaatc cgttgagacg acaccatacg aactgtggta    86040
tggcaaaagg ccaaagttgt cgtttcttaa agtttgggga tgtgatgctt atgtcaaaaa    86100
gcttcagcct gaaaagctgg aacccaaagc ggaaaagtgc gtcttcatag gttacccaaa    86160
agagacagtt gggtacacct tctatctcaa atccgagggc aaagtgtttg ttgctaagaa    86220
cggaactttt ctcgagaagg agtttctctc gagagaattg agtgggagga agatagaact    86280
tgacaaggtt gtcgaacctc tcatccctct ggatggtggc gcagggcaag gggataccte    86340 tgtcgttgcg acgccggttg aggaggaagt taatgatgat gatcatgaaa ctccagttca    86400
agtttctgtt gaaccacgca ggtcgacgag atcacgcgct gctccagagt ggtacggtaa    86460
tcccgtctta tcaatcatgt tgttagacaa caatgaacct acaaattatg aagaagcaat    86520
```

```
ggtgggccca gattccaaca aatggctaga agccatgaaa tccgagatag gatccatgta   86580
tgagaacaaa gtgtggactt tggagatact acctgagggc cgcaaggcta ttcagaacaa   86640
atggatcttt aagaagaaga cggacgctga cggtaatgtg accgtttata aagctcgact   86700
tgtggcaaag ggtttttcac aagttccagg agttgactac gatgagacct tctcacccgt   86760
agcgatgctt aagtccgtca gaatcatgtt agcaatagct gcatctttcg attatgaaat   86820
ctggcagatg gatgtcaaaa cggagttcct taacggtttc cttaaggaag agttgtatat   86880
gatgcaaccc gaaggttttg tcgatcctaa aaatactgac aaggtgtgca agctccagcg   86940
atccatttat gaactggtgc aagcatctcg gagttggaac aaatgctttg atgaggtgat   87000
caaagcattt gggtttatac aagtggttgg agaatcttgt atttacaaga aagtgagtgg   87060
gagctctgtg gcgtttctga tattatatgt ggatgacata ttactgattg gaaacaacgt   87120
agagcttttg gaaagcataa aaggttactt gaataaaagt ttctctatga aggacctagg   87180
agaagctgct tacattctag gcattaagat ctataggggat agatcaaagc gcctgatagg   87240
actttcacaa agcacatacc ttgataaagt tttgaagagg ttcaaaatgg aacagtccaa   87300
gaaagggttc ttgccagtgt tacaaggtac gagattgagt aagactgagt gcccagcaac   87360
tgataaagat agagagcata tgcgctccgt cccctatgct tcaaccatag gctctatcat   87420
gtatgcaatg ctgtgcacta gaccggatgt tagcctggcc ataagtatgg caggtaggtt   87480
ccagagtaat ccaggagtgg atcactggac ggcggtcaag aatatcctga agtacctgaa   87540
aaggactaag gagatgtttc tcgtgtatgg aggtgacgaa gagctcgccg taaaaggtta   87600
cgtcgatgca agctttgaca cagatccgga cgactctaag ttgcaaaccg gatacgtatt   87660
tattcttaat gggggtgcag taagctggtg cagttccaag caaagcgtcg tagcagattc   87720
tacatgtgaa gcggagtaca tagctgcctc ggaggcggct aaggagggtg cctggatgaa   87780
gcagttcatg acggatcttg gagtggtgcc aagtgcactg gatccaataa ccttgttatg   87840
tgacaacact ggtgccattg ccttagcaaa ggaaccaagg tttcacaaga agaccagaca   87900
catcaaacga cgcttcaacc tcatccgcga ctacgtcgag gaggaggacg taaatatatg   87960
caaagtgcac acagatctga atgtagcaga cccgctgact aaacctcttc cacggccaaa   88020
acatgatcga caccagaact gtatgggtgt tagatttatt acaatgtaat tcacatggtg   88080
atgtgagggc tagattattg actctagtgc aagtgggaga ctgttggaat tatgccctag   88140
aggcaataat aaatgtatag ttattattat aattcctgta tcaagataat agtttattat   88200
ccatgctata attgtattga atgaagactc atttacatgt gtggatacat agacaaaaca   88260
ccgtccctag catgcctcta gttggctagc cagttgatcg atgatagtca gtgtcttctg   88320
attatgaaca aggtgttgtt gcttgataac tggatcacgt cattgggaga atcacgtgat   88380
ggactagacc caaactaata gacgtagcat gttgatcgtg tcattttgtt gctactgttt   88440
tctgcgtgtc aagtatttat tcctatgacc atgagatcat ataactcact gacaccgag   88500 gaatgctttg tgtgtatcaa acgtcgcaac gtaactgggt gactataaag atgctctaca   88560
ggtatctccg aaggtgttag ttgatttagt atggatcaag actgggattt gtcactccgt   88620
gtgacggaga ggtatctcgg ggcccactcg gtaatacaac atcacacaca agccttgcaa   88680
gcaatgtaac ttagtgtaag ttgcgggatc ttgtattgcg gaacgagtaa agagacttgc   88740
cggtaaacga gattgaaata ggtatgcgga tactgacgat cgaatctcgg gcaagtaaca   88800
taccgaagga caaagggaat gacatacggg attatacgaa tccttggcac tgaggttcaa   88860
```

```
acgataagat cttcgtagaa tatgtaggat ccaatatggg catccaggtc ccgctattgg    88920
atattgaccg aggagtctct cgggtcatgt ctacatagtt ctcgaacccg cagggtctgc    88980
acacttaagg ttcgacattg tattatgcgt atttgagtta tatggttggt taccgaatgt    89040
tgttcggagt cccggatgag atcacagacg tcacgagggt ttccggaatg gtccggaaac    89100
gaagattgat atataggatg acctcatttg attaccggaa ggttttcgga gttaccggga    89160
atgtaccggg aatgacgaat gggttccggg agttcaccgg ggggggggg gaagccacc    89220 ccgaggaagc ccataggctt tggggagaca caccagccct tagtgggctg gtgggacagc    89280 cccaagggggg cctatgcgcc aagagaagga aatcaaagga aagaaaaaa aagagggagg    89340 aactgggaag ggagggggac tcctcccacc aaaccaagtc caactcggtt tgggggggga    89400 gtcctcccc ccttggatcg gccgacccct tgagggtccc ttggacccca aggcaaggtc    89460
accctccctc ctcctatata tatggggctt ttagggcaga tttgagacga cttttctcacg    89520 gctgcccgac cacataccct catagttttt cctctagatc gcgtttctgc ggagctcggg    89580
cggagccctg ctgagacgag atcatcacca acctccggag cgccgtcacg ctgccggaga    89640
actcttctac ctctccgtct ctcttgctgg atcaagaagg ccgagatcat cgtcgagctg    89700
tacgtgtgct gaacgcggag gtgccgtccg ttcggtacta gatcgtggga ctgatcgcgg    89760
gattgttcgt gggtcggatc aagggacgtg aggacgttcc actacatcaa ccacgttctc    89820
taacgcttct gctgtacgat ctacaagggt acgtagatca ctcatcccct ctcgtagatg    89880
gacatcacca tgataggtct tcgtgcgcgt aggaaatttt ttgtttccca tgcgacgttc    89940
cccaacaatg aggtcatcct atatatcaat ctttgtttcc ggaccattcc ggaaaccctc    90000
gtgacgtccg tgatctcatc cgggactccg aacaacattc ggtaaccaac catataactc    90060
aaatacgcat aaaacaacat cgaaccttaa gtgtgcagac cctgcgggtt cgagaactat    90120
gtagacatga cccgagagac tcctcggtca atatccaata gcgggacctg gatgcccata    90180
ttggatacta catattctac gaagatctta tcgtttgaac ctcagtgcca aggattcata    90240
tattcccgta tgtcattccc tttgtccttc ggtatgttac ttgcccgaga ttcgatcgtc    90300
agtatccgca tacctatttc aatctcgttt accggcaagt ctctttactc gttccgtaat    90360
acaagatccc gcaacttaca ctaagttaca ttgcttgcaa ggcttgtgtg tgatgttgta    90420
ttaccgagta ggccccgaga tacctttccg tcacacggag tgacaaatcc cagtcttgat    90480
ccatactaac tcaacgaaca ccttcggaga tacctgtaga gcatctttat agtcacccaa    90540
ttacgttgcg acgtttgata cacacaaagt attcctccgg tgttagtaag ttatatgatc    90600
tcatggtcat aggaacaaat acttgacacg cagaaaatag tagcaacaaa atgacacgat    90660
caacatgcta cgtctattag tttgggtcta gtccatcacg tgattctcct aatgacgtga    90720
tccagttatc aagcaacaac accttgttca taatcagaag acactgacta tctttgatca    90780
actggctagc caactagagg cttgctaggg acagtgtttt gtctatgtat ccacacatgt    90840
gaatgagtct tcattcaata caattatagc atggataata aacgattatc ttgatacagg    90900
aattataata ataactatat ttactattgc ctctagggca taattccaac agtctcccac    90960
ttgcactaga gtcaataatc tagccctcac atcatcatgc gaattacatt gtaataaatc    91020
taacacccat acagttctgg tgttgatcat gctttggccg tggaagaggt ttattcagcg    91080
ggtctgctac atttagatcc gtgtgcactt tgcatatatt tacgtcctct ccttcgacgt    91140
agtcgcggat gaggttgaag cgtcgtttga tgtgtctgga cttcttgtga aaccgtggtt    91200
cctttgctaa ggcaatggca cccgtgttgt cacagaacaa ggttattgga ttcagtgcgc    91260
```

```
ttggcaccac cccaagatcc gtcatgaact gcttcatcaa gacaccctcc ttagccgcct    91320
ccgaggcatc catgtactcc gcttcacatg tagaatctgc tacgacgctt tgcttggaac    91380
tgcaccagct taccgcaccc ccattaagaa taaatacgta tccggtttgc gacttagagt    91440
cattcggatc tgtgtcaaag cttgcatcga cgtaaccttt tacggcgagc tcttcgtcac    91500
ctccatacac gagaaacatc tccttagtcc ttttcaggta cttcaggata ttcttgaccg    91560
ctgtccagtg atccactcct ggattactct ggaacctacc agccatactt atggccaggc    91620
taacgtccgg tctagtgcac agcattgcat acatgataga acctatggct gaagcatagg    91680
ggacggagcg catatgctct ctatcttcat cagttgctgg gcactgagtc ttactcaatc    91740
tcgtaccttg taaaactggc aagaacccct tcttggactg ttccattttg aacctcttca    91800
aaactttatc aaggtatgtg ctttgtgaaa gtcctatcag gcgttttgat ctatccctat    91860
agatcttaat gcctagaatg taagcaactt ctcctaggtc cttcatagag aaactttat    91920 tcaagtaatc cttatgctc tccaaaaact ctacgttgtt tccaatcagc aatatgtcat    91980
ccacatataa tattagaaac gccacagagc tcccactcac tttcttgtaa atacaagatt    92040
ctccaaccat ttgtataaac ccaaatgctt tgatcacctc atcaaagcat ttgttccaac    92100
tccgagatgc ttgcaccagt ccataaatgg atcgctggag cttgcacacc ttgttagcat    92160
tcttaggatt gacaaaacct tcgggttgca tcatatacaa ttcttcctta aggaaaccgt    92220
taaggaacgc cgttttgaca tccatctgcc atatttcata atcgaaaaat gcagctattg    92280
ctaacatgat tctgacggac ttaagcatcg ctacgggtga gaatgtctca tcgtagtcaa    92340
ctccttgaac ttgtgaaaaa ccctttgcca aaagtcgagc tttataaacg gtcatattgc    92400
cgtcagcgtc cttcttcctc ttaaagatcc atttgttctg aatagccttg cggccctcag    92460
gaagtacctc caaagtccac actttgttct caaacatgga tcctatctcg gacttcatgg    92520
cttctagcca tttgttggaa tctgggccca ccattgcttc ttcataattt gcaggttcat    92580
tgttgtccaa caacatgatt gataagacgg gattaccgta ccactctgga gcagcacgtg    92640
gtctcgtcga cctgcgtggt tcgacagaaa cttgaaccgg agtttcatga tcattatcat    92700
taacttcctc cacaaccggc gtcgcaacta cagaggtttg cccttgccct cgccaccat    92760 ccagagggat gagaggttcg acaacctcgt caagttctat cttcctccca ctcaattctc    92820
tcaagagaaa ctccttctcg agaaaagctc cgttttttagc aacaaacact ttgccctcgg    92880
atttgagata gaaggtgtac ccaactgtct cttttgggta acctatgaag atgcacttt    92940 acgctttggg ttccagcttt tcaggctgaa gcttttttgac ataagcatca catccccaaa    93000
ctttaagaaa cgacaacttt ggccttttgc cataccacag ttcgtatggt gtcatctcaa    93060
cggattttga tggtgcccta tttaaagtga atgcagttgt ttctaatgca taaccccaaa    93120
acgataacgg caaatcggta agagacatca tagattgcac catctctaat aaagtacgat    93180
tacgacgttc ggacacacca ttacgctgtg gtgttccagg cagtgtcaac tgtaaaacaa    93240
ttccacattg tcttaagtga gcaccaaact caaaactcag atattcaccc ccacgatcag    93300
accgtaggaa cttgatcttc ttgttacgat gattttcaac ttcactctga aatttcttga    93360 actttcaaa tgtttcagac ttgtgcttca ttaagtagac ataaccatat ctactcaaat    93420
cgtcagtgaa ggtgagaaaa taacgatatc cgccgcgtgc ctctacgctc atcggaccac    93480
acacatcggt atgtatgatt tccaaaaagt cacttgcacg ctccaatgtt ccggagaacg    93540 gagtttagt catcttgccc atgaggcatg gttcgcacgt gtcaagtgaa tcaaagtcaa    93600
```

```
gtgactccaa aagtccatcg gcatggagtt tcttcatgcg ctttacacca atatgaccta   93660
agcggcagtg ccacaaaaat atggcgctat cattgttaac tctaactctt ttggtctcaa   93720
tgttatgtat gtgtgtatcg ctatcaagat tcaatatgaa aaatcctctc acattgggtg   93780
catgaccata aaagatgcta ctcatagaaa tagaacaacc attattctct gacttaaaag   93840
agtaaccgtc tcgcaataaa caagatccag atataatgtt catgctcaac gcaggcacta   93900
aataacaatg attcaagttc ataactaatc ctgatggtaa ctgaagtgaa actgtgccga   93960
cggcgattgc atcaaccttg gaaccatttc ctacgcgcat cgtcacttca tctttcgcca   94020
gccttcgtct attccgcagt tcctgtttcg agttgcaaat atgagcaaca gaaccggtat   94080 cgaatacccca ggcactacta cgagagccgg ttaagtacac atcaataaca tgtatatcaa   94140 atatcctga ttttttcttt g gccgccttct tatctgccag atacttgggg caattgcgct   94200
tccaatgacc cataccgttg caatagtaac actctgtttc aggcttaggt ccagctttgg   94260
gtttcttctt ccgattggca acaggcttgc cgctcttctt tgaattaccc ttcttgcctt   94320
tgccgtttct cttgaaacta gtggtcttat tcaccatcaa cacttgatgc tctttacgga   94380
gttcagactc tgcgactttc agcattgcaa acaactcgcc gggtgacttg ttcatcccctt   94440 gcatgttgta gttcaacaca aagcctttat agcatggcgg cagtgattga aggattctgt   94500
cagtgatagc ctcttgcggg agttcaatcc ccagctcagc tagacggttt gagtacccag   94560
acattttgag cacatgttca ctgacagacg agttctcctc catcttgcaa gcatagaatt   94620
tatcggaggt ctcataccctc tcgatccggg tgttcttctg aaagataaac ttcaactcct   94680
ggaacatctc aaatgctcca tgacgctcaa agcgacgttg aagtcccggt tctaagccat   94740
acaagactgc acattgaact actgagtagt cctccttacg tgctaaccaa gcattcttaa   94800
catcctgatc agccgtagcg ggtggttcat ctcctagcgc agcattaagg acataatcct   94860
tcttcccagc ttgtaagatt agcttaagat tacgagccca gtctacaaag ttgcttccat   94920
catctttcaa cttagctttc tctaggaacg tattaaaatt cagggtgact gtcgcgtgag   94980
ccatgatcta caacacaaat atattcaaag tggacttaga ctatgttcaa gataattaga   95040
gtttaactta atcaaattat tcgctaaaact cccactcaaa aagtacatct ctctaatcat   95100
ttgagtggtt catgatccac ttacactagc tcaagtccga tcatcacgtg agttgagtat   95160
agtttcagtg gtaagcatcc ctatgctaat catatcatct atatgattca tgatcgagct   95220
ttcggtctca tgtgttccga ggccatgtct gcacatgcta ggctcgtcaa gcttaacccg   95280
agtgttccgc gtgcgcaact gttttgcacc cgttgtatgt gaacgttgag tctatcacac   95340
ccgatcatca cgtggtgtct cgaaacgacg aactgtagca acggtgcaca gtcggcgaga   95400
acacaatttc gtcttgaaat tttagtgaga gatcacctca taatgctacc gtcgttctaa   95460
gcaaaataag gtgcataaaa ggattaacat cacatgcaat tcataagtga catgatatgg   95520
ccatcatcac gtgcttcttg atctccatca ccaaagcacc ggcacgatct tcttgtcacc   95580
ggagccacac catgatctcc atcaacgtgt cgccatcggg gttgtcgtgc tactcatgct   95640
attactacta aagctacatc ctagaaaaat agtaaacaca tctgcaagca caaacattag   95700
tataaagaca acccctatgga tccttccggt tgccgtacca tcgacgtgca agtcgatatt   95760
atctattaca acatgatcat ctcatacatc caatatatca catcacatcg ttggccatat   95820
cacatcacaa gcatacccctg caaaaacaag ttaggcgtcc tctaatttttg ttgttgcatg   95880 ttttacgtgg tgaccatggg tatctagtag gatcgcatct tacttacgca aacaccacaa   95940
cggagatata tgagttgcta tttaaccctca tccaaggacc tcctcggtca aatccgattc   96000
```

```
aactaaagtt ggagaaaccg acacttgcca gtcatctttg agcaacgggg ttactcgtag    96060
cgatgaaacc agtctctcgt aagcgtacga gtaatgtcgg tccaagccgc ttcaatccaa    96120
caataccgcg gaatcaagaa aagactaagg agggcagcaa aacgcacatc accgcccaca    96180 aaaactttg tgttctactc gagaagacat ctacgcatga acctagctca tgatgccatt    96240
gttggggaat gtcgcatggg aaacaaaaaa tttcctacgc gcacgaagac ctatcatggt    96300
gatgtcaatc tacgagaggg gatgagtgat ctacctaccc ttgtagatcg tagagcagaa    96360
gcgttagtga acgcggttga tgtagtggaa cgtcttcacg tccctcgatc cgccccgcga    96420
actatcccgc gatcagtccc acgatctagt gccgaacgga cggcacctcc acgttcagca    96480
cacgtacagc tcgacgatga tctcggcctt cttgatccag caagagagac ggagaggtag    96540
aagagttctc cggcagcgtg acggcgctcc ggaggttggt gatgatctcg tctcagcagg    96600
gctccgcccg agctccgcag aaacgcgatc tagaggaaaa accgtggagg tatgtggtcg    96660
ggctgccgtg gaaaagtcgt ctcaaatcag ccctaaaacc tccatatgta taggtgggag    96720 aggggggggac cttgccttgg ggctcaagga gccccaaggg ggtcggccga gccaaagggg    96780
ggaaggacac cccccaaaac cgagtcctac ttggtttggt gagtggagtc cttctttcct    96840
ttcccacctt cgccttttt tttctttct ctttgatttt tcttccaatg cgcatagggc    96900
ccttttgggc tgtcccacca gcccactaag ggctggtgct ccatcctcaa ggcctatggg    96960
cttccccggg gtgggttgcc ccccggtga actcccggaa cccattcgtc attcccggta    97020
cattcccggt aactccgaaa accttccggt aatcaaatga ggtcatccta tatatcaatc    97080
ttcgtttccg gaccattccg gaaaccctcg tgacgtccgt gatctcatcc gggactccga    97140
acaacattcg ataaccaacc atataactca aatacgcata aaacaacatc gaaccttaag    97200
tgtgcagacc ctccgggttc gagaactatg tagacatgat ccgagagact cctcggtcaa    97260
tatccaatag acggacctgg atgcccatat tggatcctac atattctacg aagatcttat    97320
cgtttgaacc tcagtgccaa ggattcatat attcccgtat gtcattccct ttgtccttcg    97380
gtatgttact tgcccgagat tcgatcgtca gtatccgcat acctatttca atctcgttta    97440
ccggcaagtc tctttactcg ttccgtaata caagatcccg caacttacac taagttacat    97500
tgcttgcaag gcttgtgtgt gatgttgtat taccgagtgg gccccgagat acctctccgt    97560
cacacggagt gacaaatccc agtattgatc catactaact caacgaacac cttcggagat    97620
acctgtagag catctttata gtcacccatt tacgttgcga cgtttgatat acataaagta    97680
ttcctccggt gttagtaagt tatatgatct catggtcata ggaacaaata cttgacacgc    97740
agaaaacagt agcaacaaaa tgacacgatc aacatgctac gtctattagt ttgggtctag    97800
tccatcacgt gattctccta atgacgtgat ccagttatca agcaacaaca ccttgttcat    97860
aatcagaaga cactgactat ctttgatcaa ctggctagcc aactagaggc ttgctaggga    97920
cagtgttttg tctatgtatc cacacatgta aatgagtctt cattcaatac aattatagca    97980
tggataataa acgattatct tgatacagga attataataa taactatatt tattattgcc    98040
tctagggcat aattccaaca ggccgatccc agaatcttct cggaagcaga gtgggcccat    98100
ttagaacaaa gtgttgggta tcctccttgt ggaggaggaa tactgacgtc gtaggggcga    98160
tttcgagtgg gttacaaggg gggtgcaaac acagactaat ttcatgcctt tgcgaatggg    98220
cggaaatgca aaggatctat catgcgtgtg cagggcgata atggcctcct cctctcgcag    98280
agtgcgatcg tttcccacat ctacgagttt ttcattggcc tgctggggac ggaggatgag    98340
```

| | |
|---|---|
| aaactactta gacttcgagc ggatttgtgg gatccatcgg agcaggtgtc gccacgggaa | 98400 |
| aatgaggttt tagccctatc gcaggagatc gatgtgcccc tgggagaaac gaaatataat | 98460 |
| acggcaccgg gccttgacgg cgggcttgtc gtattttta aaaagttctg gccttgcatc | 98520 |
| cgacacctat tttgtgagat tattaatgga ttttctcttg gcacgatcga tagcgcgg | 98580 |
| ttgaattacc gtgtcattag cctcattcct aaggtgaaag gtacgaataa cattaggctg | 98640 |
| tttctgttgg aaatatgccc tagaggcaat aataaattgg ttattattat atttccttgt | 98700 |
| tcatggtaat cgtttattat ccatgctaga attgtattga ttggaaactc aaatacatgt | 98760 |
| gtggatacat agacatcaca ctgtccctag tgagcctcta gttgactagc tcgttgatca | 98820 |
| aagatggtca aggtttcctg gccatagaca agtgttgtca cttgataacg ggatcacatc | 98880 |
| attaggagaa tgatgtgatg gacaagaccc aaactatgaa cgtagcatac gaccatgtca | 98940 |
| gtttattgct actgttttct gcatgtcaat gtatctgttc ctatgaccat gagatcatgc | 99000 |
| aactaccgga caccgaagga gttagtcaca tgatcttgta ttaaagaacg agtaaataga | 99060 |
| cttgctggta acgagattga actaggtata gagatatcga cgatcgaatc tcgggcaagt | 99120 |
| aacataccga aggacaaagg aaacaacata cgtgattaaa tgaatccttg acatagaggt | 99180 |
| tcgactgata gaaatctttg tagaatatgt aggagccaat atggacatcc aggtaccgct | 99240 |
| attggttatt gaccacagag tgtctcaggt catgtttgca tagttctcga acccgcagga | 99300 |
| tctgcacact gaagttttgg tgatgtttca gtatagttga gttataggtg ttggtgaccg | 99360 |
| aaggttgttc ggagtcccgg atgagaccct ggacgtcacg aagagcttca gaatggtccg | 99420 |
| gaggtaaaga ttgatatata ggaagtcctg ttttggtcac cggaaaagtt tcgggataat | 99480 |
| cggtagtgta ccgggagtgc cgggagggta ccggggacc accgggaggg ttgtgacgac | 99540 |
| ccaaaggctt catgggctgt gataggaggt agaccatccc gtagtgggct gaacaaagcc | 99600 |
| tcccctaagg gcccatgcgg ctaggagaag agataaaagg ctaaattcct ttaaaagaaa | 99660 |
| gggaaggagg agtcctccca aagtagtcca cattccttgt gggaaggtga actctttctt | 99720 |
| agggttcggc cgaacctctc ctctgaggag gggccaaggc agcatcccct cctctccctc | 99780 |
| ctatatatac tagaggtttt aaaggtaagg gctaaccctg attgccacgt gctccctcta | 99840 |
| cttcatctag atcggtttct cctctactct agtttcggca gcgcttaggc gaagccctat | 99900 |
| tggaatagtt caccaccacg ccgccgtgct ggagaactca tctagctctc cgcccctctt | 99960 |
| gctggatcaa gaaggcgggg atcgtcataa ggatgtacat tacgctgtag ctctactgtt | 100020 |
| ttagatatgt tcctagagaa aatttagttg aaagttgata gtagcaatta tgcggactgg | 100080 |
| gtacgtaaac tgaggattgt cctcattact gcgcagaagg cttatgtcct taatgcaccg | 100140 |
| ctcgatgtgc tgaacctcga gcgtcgtttg tgaatgttgc gaacatctaa catacgcgtt | 100200 |
| ttttatgact acgtgatagt tagtgcgtaa tgcttaacgg cttagaatta aggcgccgaa | 100260 |
| gacattttga acgtcacgga acatatgaga tgttccaaga gatgaaattg ggatttcatg | 100320 |
| ctcgtgccat tgctgagagg tatgagacct ccgacaagat tctttgtcta caaagtaagg | 100380 |
| gagaaaagct caatcgttga acatgtgctc agattgtctg agtgctacaa tcgcttgaat | 100440 |
| cgagttggag ttaatcttcc aagtgagata gtgatggttc tccaaaatca ctaccaccaa | 100500 |
| gctactagag cttcatgatg aactataaca tatcagggat agagatgatg atccttgaga | 100560 |
| tattcacgat gtttgacacc gcgaaagtag aaataaaaaa ggagcatcaa ttgttgatgg | 100620 |
| ttagtaaaac cactagtttc aagaagggca agggctagaa gggatacttc atgaaacggc | 100680 |
| aaaccagttg ctgctctagt gaagagaccc aaggttgaac ccaaacacga gactaagtgc | 100740 |

```
ttctgtaata aggggaacag tcagtgaaga ggaactaccc tagatacttg gtagatgcga 100800
aggctggcaa agtcgacaaa tgtatattgg atatacatga tattgatgtg tactttacta 100860
gtactcctag tagcatgagg gtattagata ccagtttggt tgctaagtgt tagtaactcg 100920
aaataaaagc tacggaataa acaaagacta gctaaaggcg aggtgacgat atatgttgaa 100980
agtgttccca aggttgatgt gatcaaacat cgcacgctcc ctctaccacc gggattagtg 101040
ttaaacctaa ataattgtta tttggtgttt gcgttgagca tagacatgat taggttgtgt 101100
ttatcgcaac acggttattc atttaaagag aataatggtt actctgttta tttgagtaat 101160
accttcaatg gtcttgcacc taaaatgaat agtttattga atctcgatcg tagtggtgca 101220
catgttcata atatgttggg ccttggcagc gggggcttcg gctcaccttg ggccttggcc 101280
tggcccggct ccggggcttg ataggccaag gtggatctgg ccaagccggg tcttgggcgt 101340
atggagcagg ctggctactg ggtccacgcg gggaggccgg cccagttgcg gcggctgctg 101400
gcgaggctct gccccttgct cgacaggagc catggcgctg gaaccgccgg cgaaggcgag 101460
gcactagggt ggcatcctgg cgagggggcg gctgcaggcg gcgagggagg tcgagggtgg 101520
tgggatccgg tctgaatttg acccgaggcg gcggcaggag ggagatcggc ggcggaggag 101580
cttcagcggc attcatggtc gttctgcaca agagggagac gggagaggtc agaggatgga 101640
ggataagacc gggcttggcc ttggccaccc gcaacgggt gctcacccgc gggaggagag 101700
gctctagcgc ggccccatgg tggtacaccg ggaagaggcg agggcacaag aaaggcgtga 101760
cctgcttgtc cccgagctca ccacgggagc tcgcggtggc cgctgcagat ctgggcccgg 101820
atgggcttcc atggcctcga tctgggcttc caaggctcgc gggaggagag agaggtggga 101880
gagagagtcg gctagggtta gggttttggt gggcacggat cccgaggcac gatgatggct 101940
gcctatttat agaaaaaggg ctagggttgg ggttttttgca ccattttttga accgttggat 102000
tgcgatccga cggctccgga agcggagggg cttaggggttg gcttaggtgg tctgacaggc 102060
tgtgttagag aggctagttg gggaagagag gggagatttg cggcccgaca gaaggttttg 102120
aaacaccgaa aaacgtccgg cgataaaccg atgacggtgc cgctacggtc gaccgttcgg 102180
gtatcagacg gactccgatt gcgacgacat ttggcacgcg gtctacctac actaaaataa 102240
gaccgcacgc caagtttcaa cccaatccaa gaatattttt cggacacctt taaaaacaat 102300
attttaacga tgtcgtgggc gcctgcgtgt gtgattggtc tcgaaatggt caacgatgat 102360
aatgaagaga accaacaact aataacggat gcaagtttga aaaccggcga caacggagtg 102420
ccgatgcaat acgatgatg cgaatgatgt gatgatgaat gcgacaggcg acctaatcat 102480
acggcgacaa cataataaga ggggaatcct atggagcgtc ggtctcgggc tgtcacaacc 102540
catgcgagga ggcgtttctc ctcgtagggc tccactggca tcccgcaact gcaacacgca 102600
gactgctccg cttacctctc ctatgctcgt tgcctctcac ggcctgcggc gtgcgcctcc 102660
acttccggag tgcacgtgca ggccaacgac gcggacacta ggacccaatg ctaccctcgt 102720
ggaggagcgg ctagcggggg aagaacatcg cgtgggcat gtgcggactg tgcagtccta 102780
gtggagctgc acatggcccg aagggtccaa ctccggtgtc atagctccgc cgtcacggga 102840
gctacgacta tgctccagat gtgaagcttt cgtgtgtctc caccattgat cgctccaagg 102900
agatgcggag ggccagctcc ttggagccga cgtccgagcc atcggagccg gagaccctgt 102960
cggagctcga cattggaccc gatgggatcg aactcggaga gggagaggaa gggacgaagc 103020
gagagggagt gagctagggt tcaaaacgag gcgcatggag tgaggatttt gtggaaccgc 103080
```

```
ggtgaggtca gtggagggcc aggcctgtca gccccatatc cgccatatat tttggctgga 103140
tatgaggggt gccggtcagc ccagacgttt aagacgagta taaaaggtcc ggttagatca 103200
cgcttttgtg accaataaat gaccgaacgg cctcttcgaa cgtttgagac aatacaagcg 103260
gcctatatat taggtgtatc tacacctatg agccaaaaca tcattttga aatggactgt 103320
gttgcgtggt caacagtaat tctctaacca atgattagat ggcatgtttt cttttttacgc 103380
aatgataaaa agacacgggg tgctccttta cagcattaca ggcgcccgtt cccgctttcg 103440
gtgcgttcat cgcccatgc tgggccggcc caataagaag gtggctgctc gatcccatac 103500
atcagtcgtt gaattttcaa aaagtaaaat tgtcacggct gatctattga ccgtcggtca 103560
accgttggat ttttcattat tatttcaaaa tcataaaaat aaaaaaatgt tcatcatcaa 103620
aaagaatat ctcgaattta aaattatttt taaaaaatat gaatagttca tcaaatcttt 103680
cgaaaaaag ttcaccaatt caaaacaat gtccaagaat tttgaaaaaa attcacaaaa 103740
acagaaacaa gtttataaaa tttgaaaaac aatcatcaaa attgacaaaa aatcattgaa 103800
tttcaagaaa gttcatcaaa tttgcaagaa ggtcataaag tttggaaaac attcatagaa 103860
tgtgaaaact agttcaccga atttgaaaag aaatatttt ttcaaaggtt cactaaattt 103920
gaaagaaatt cataaaaat aaaaaaatca tgtatgtttt caaagtgcg ttgaactgaa 103980
aaaaatttc aaaatctttt caaaagttca tccatttcaa aaaaaataat caaatttcaa 104040
aacaattcct gaaaatttg aaaatgttca tcaatataca aaagtttcat agatcttaa 104100
tagaaattcg tacaattttg aatatgtttc attgatttga aaaaaaagat tgctctttg 104160
aaaaatagtt cataaaaaa tgctgcactt tttcgataaa aataaaaaa attaaatgg 104220
aaatgaaaaa aaaacaataa gagtaaagaa aagaagaaaa caaaaaatat ataaacaaaa 104280
aaaaccagtt ctgagagaaa ctaaatgaaa aaactggaaa tacctctgtc ccgctggaag 104340
tttactgggc cggcccatga tcgaaagctg aaggcatcgt caacaaaaat gcactttaac 104400
atgcgcctgc agcgtcaaat aggatttacc gatgagacgt gatgtgtaag aaaagaccat 104460
acctgagaaa acaatagggc tggcccaagt ggtgtgacag ggtaggagcg ggacgtccga 104520
accacaagct tccctctttc ctttcgaaat cacgagttag cgatacacct ttcaaccatt 104580
acttccacat tcatagattg cgacaagtgg cgcagtgcat gcatgtcact tgtcgcaacc 104640
tgaaagtttt tccttttttt cgtagatccg tattttgaaa atattttatc tcctaaaccg 104700
tgcgtccaaa tctcgaaccg ttttcaccgt tggctttctc acgccgagat cttcaaaact 104760
agatcccatg ttggtaggtt ttaacaaact ttttttttca cgaaaaaaca gaaagaaaaa 104820
aacctgacga aaaaccgtg cctcatgcaa tagaaaataa aacataaaac atgttttttt 104880
tttcattctg aaaggcacgg gtcatgcctc ttgcgaaggc aaaaccgtgc ctctcgcgga 104940
aaaaagaga gcagaaaacg tgttttccc cttttcagaa gaggcacgga cgtgtctctc 105000
gcgaaggcaa aaccgagact ttcgcggaag caaaagtgtg tctctcgcaa aagaaaaaca 105060
cgttttttcc ctttcgggag aaaaccgtgc ctctcgcaga aaaacaaaca aacagaaaac 105120
gcatttttt tcattcagga gaggcctctc gcaaaggtaa aactgtgcct ttcgcaaaag 105180
gaaaccgtg cctctcgcag aaaaataaac aaacagaaaa cgcgttttc tttcttccg 105240
aagaggcacg gtcgtgcctc tcgcgaaggt aaaatcatgc ctttcgcgga agcaaaaccg 105300
tgcctctcgc aaaaaaacaa aaaacacgtt ttttttcct ttcagagagg cacgaccgtg 105360
cctctcgtga tagcaaaacc gtgtctcgca aaaaaaagt ttttcacgt acaaataaaa 105420
gaaaatgtgt ttttcacca aaataaagta cgaatttctt ttcgttcaaa agttacgaaa 105480
```

```
gatcggtgaa aaaccataac acaatttttt cgaaaaaatc actcaaaaaa ggagaaaacg 105540
cgtgcgaaaa atatttaaaa aaaaatttaa aggaaacgtt cagaacacga cacgtggcga 105600
cggctggaaa cgcgtcaact ggcgacgcgc gggagcaatc gctgggaggc tcccgaaaaa 105660
gcactcgcta actagttgct tcttttcct ccagcataat ccacaacggt tcgctgaaaa 105720
gaaaagttta atcaacacca gaggcaatgt gaggccaccg acgtctctga tgctgcttgt 105780 cggggggcatc aatccggcgg acggggggcga caacccgtca gaaactcgag ccatccatgg 105840
tgaagacgtc gacacaggtc tccggccggg aggtctacgc caaccagcga cttcttcatt 105900
cgtaaaacaa acaaacaaac aaacaaacag ctgttggatc agagaccgga aaaacacagg 105960
cgaccacaaa ggctgtgaac gaatggaaca cgagcacaga acaaccata ttttgcgagg 106020 cccaactgcc gtcctctttt cttgtttttt ttttctttta ttctattaac gtaacaaaca 106080
aagagattac aaagcatgtg taacagccgg acgactgggc cgactccaac gccacgatcc 106140
gtccatatcg tgccatccca cgattgactt ggtgatcatg actaacaaac tacttctact 106200
tacatgcagc gactcgaagt gcatgtacac acccatcata tctgtatagc gtacgtacta 106260
aatacatgca actagcacat gcaccaccag gatgtgatcc tgtctaacaa cctaacctag 106320
ctgctaaaaa caactgaata tgcatgacac agaccttgta acaagattag caccaacaac 106380
agcgagctct aggactcgaa ccattctgag agaaatttca tcggaggaga gatatgcata 106440
ccaaccggct cctttttatc tcggaaattc catccaatat tcatgtcttg ttcttgtact 106500
gaatagttta ggagcaattt ctgtctagct ttttcattag ttagaacagg gcagaggata 106560
gatacatagt gggacaaatg ataagatgag atactgacct gtgctgtgta agaaaagaac 106620
ctgcctaagc tactcgagtc gtccattccg aaattggacc gactcttcat tcagcatttg 106680
accttcaaag gcagcaggca gcaggccaga gagtggtacc gacgcgagga tgtgaagaga 106740
agaaatacaa tacgcatttt tcgctccaag caaagaaaac aaatacggta tatatgtcga 106800
aaatgagtgg atgaaagctc gttcggaata gtattcgccg tcgacatcta gtcttgagta 106860
gacaaggatg agaaaaggcc gatcgatgtg cagcatccag ttaccattga cctgcatgta 106920
gtacgtcaat gattccttag gttcacacct ctagtgcatg ggaaaagcct agatattata 106980
acctacaaat tcaaggaggc aaatttatgg gcttttgtct aatttaaca tttactggta 107040 ggtgtcgatc catcggaaat tcccttgaag catccatgcc aattcgtcaa gtcttgaatt 107100
aatagatagc gacttgagag gatgtggaaa gaaagaaat acagacatta tcgttctaag 107160
caaagaaaag aaatatatat gatatagctg taaaatgagt ggaggaaaat gtgtgtggaa 107220
tagtattcgt cgtcatcatc tagtcttgag tggataaagg tgcgagagga tgtgcaccat 107280
acatgatata tacatgtaaa ttcatgctgt taatactgca taaattgtgt gtttgtgtga 107340
gagaaactga gagagggagt atcagttcca ttttctctct tcaccagtgc ttgttcatgt 107400
atccaagcta ccaggtcacc aggtgtatta gcagagtcta tatatataca tactgcaggc 107460
taactagcta gccttcttcc cccttttaa ctaaggcttg caaatgccgg atccagttac 107520
tattagtgct gctgtaggat ggggcgtatc cgcagtaggc tggctcgcct ctcccatcat 107580
ttcaagggtt gtcaacaaag gtttcgccca cctcgacttc gatgcagcag agaagctgaa 107640
gatacttgat atacaagttc tacaactgca gcgcgtgata gaagtagtcg atgagagcac 107700
gtacaggctt cgcttggagc cactgttaga caagcttaga tctgctcttt atgaagccga 107760
agacatcttg gatgattttg attatcagcg tctcgagaag cagatccatg ttgggtctag 107820
```

```
ttccacacgt aaacgcaaga tagattcgct ggagaagaat catcggtctg ccatgccgag 107880
ttcctcccta aaagataagg tatttccttg ctctcatact tgattttctt tttctgcttt 107940
gtcacgggca ccatatttct ttccatgtat atatatgtaa taaaaactag gaactgtatt 108000
caactttatt gtttattctt tttcccatga ttagatggaa acattcccga ggatttcatc 108060
gaagggaaag gagactatca ataatttact gagccaggta tataagcatc cactctgatc 108120
atgctgaaat catacttgca ttattcatat ttttctttag tttaatgtgc attattaata 108180
tttaagaaaa aaaatgttat ttaatggtag aaattagcta tgcacatata ctcttcctcc 108240
atctcgaagg aatgaatgta tctagatgca ttcagttct agatacattc atttctatcc 108300
atctttgtaa caagtaattc cggacggagg aagtatattt caatttaata tatcatacat 108360
tcataggatc aagcacaacc atggtttgat catcgagtat gaccttaaag aagatttaat 108420
tcagaaccac ttctcggagg tgatgggaaa ggggaatcga cgagacttag accttaacta 108480
ggatgagttg gaccttgtgc cacatgacct cttggtcttc gagggccaaa ttatggagca 108540
tgaggtgttg gaagcaatca ctgatatgcc tactgacaag gcccccaggc ctggtggctt 108600
cgccggcctc ttttaaaaga aatattgggg taaaatgagg cataacattg tgagggtgat 108660
tgggctcttt gaatgcgtgc atgaggccaa catccattgg ctcaagagca tctacagccg 108720 gacccccttaa atgacccctc atacatccgt ggatgcattc ggttagtgac gggagagggg 108780
agagaaggaa aaaagtgacc caatcggacc cctcatatcg tccctgtatg cctgggctgt 108840
ccatgaaccc tcatatccat ctcaaataag gggaggatat gaggcctcgc gaacgctctc 108900
ggtccaccgc ataggacgcg accctacctc ggaccaccct tatctttcct ttattcattc 108960
ttttctttct ctctcttcct ctccaccaat cacatacaag tgaccgggcc tatgagaaag 109020
aaaataagga atctggttgc gtggacggac aaataggaaa cacgcccggt cactgatcgc 109080
gcgcgtccgc gagtatttga gggaccggat ttgcaagttc tggctataga tgattttaat 109140
cccgtgaata ctatgctttt accaaagacg gatagtttgg agggcattaa tgactatagg 109200
cccattagct ttatatattc atgtgattgc caagctcact gcgatgatct tcgtcacttg 109260
tacacgcctg cacatggaca ctctcatatc caactcacaa agtgctttca taagaagag 109320 aagcattcat gaaaccttca catatgtgag gaatcttgct cagcagtttc acaaagacaa 109380
gacctcttct ctcctcttca aacttgatgt acgtaaggcc ttcaacttgg tcaagtggga 109440
gtacattatt gatcttattc aaagatgagg cttcccaagc aagttcgcgg attggattac 109500
catgctcctc tctatctcct cctctcggat acttctcaat gtgggggccg gaccgcctat 109560
caagcatgat catgggctac ggcaaaggga ttcagtcttg cttctccttt tggtcattgc 109620
cattgaccca ctccaaaaaa accttcatgt tgccaccacc aaaatttttgc tacacaagat 109680 tctaggtcga catgccatag tgtagatgtc cttatatacg gatgatgtgg tggtatccat 109740
gaaacccata aagcgggaga gcgacaacct ctctaccata ctcaaatgtt ttggccaggt 109800
catgtcgcca agggccttga tacaaacttc cagaggcgga ttcaggccct aggcagccaa 109860
ggcctcggcc tggggcgtgg tgactgtagc aaaaatatcc aatgtagcac attgtattat 109920
actatagcca tacagcctgc ctgcgaattg atctgattct agctccgatt atccacataa 109980
ttaagatgcc gtgaaataca acttggcccc ttcttcaaca cttgctgaca agaaaacaac 110040
ctttcctatg agatatttgg ggaagccgct tttggtctgg caactcaaga gggtgaactt 110100
ccaattctta aaggacaagg tgggttccaa gattccaccc tgggacggaa aaaacatcag 110160
caccattggt tgtacagttc ttgtcaaatt cgtgttatcc tccgaagcgg tctacctcat 110220
```

```
cactcccctc attgcaacac ccagcatcct atgcaacaca aacaagctca agtgtgcctt    110280
tctttggtaa ggttcaaaca agattaacgg tgcaaattgc aaagtgcaaa gttaacaagg    110340
atttcgtatg ctggcaatgt tatgatctct acacattttg catagaactt gaattattcc    110400
acaatatgca agaacaagca tgtagtcatg taactttcag atagccgtat tatgtgcaaa    110460
catattgcat agaacttgca tggttccaca atattcaaga acaagcataa gtagtgtaac    110520
tttgagacaa caatatgatt ttcacacaga tagcattgaa cttgcattta tacatccatg    110580
ctgtgcacag tgttgaaaca acataacaaa aacattggcg atcaatcatt tcttgacatg    110640
tcgaagatga attgcatccc acgttggtgt tgcctcccca atttatgtct tgctcttcct    110700
ctcatagaaa cgagtgtgca ttcccgcaca cacacgcaca tacacaacaa acagacatag    110760
caaagtacgc aaatacacaa agaaaaaaca gctaacacaa gaaaaatcta aacacaaaga    110820
acttttccaa aatcaatgaa ctttttttta atccatccat tattttccga aagtccatga    110880
atgttttctc aattcatggt atttttcaat ttgtgaacat ttttcctacg aatgaacttt    110940
tccaaaaaga tgaaccattt gtcaaaaaca acagtcagat gtcaaacatg tcagtggtca    111000
acttatcgcc caggttacca tgaagaagtt tttttgttga accgtgaaga agcgatcagg    111060
tgtatgatgt tgcgtgttga gcgacagctg atcactggtg tagtggagtg ttgcatccgc    111120
tacaaaaaga actagacaag tgctgcctag gaggtcccgt tgtacatgga aaggcatcac    111180
acaaaccaaa gcgcacaagc ctacatcctg cacctggcct ttttttttg ttctttttt    111240 taccttcaaa aaatcagtgc atgaagtagg atttgaacca tggacctctt ggattagttc    111300
catccgtaat gaactggaac atctcacttg ttacgtctaa ttactttatt tatttctttt    111360
attgtgaatc ttctcagtct ggttttcttc tcgtgttgct tttgttttgc ttttttctt    111420 tagtttttt tttcatttct ctatatttct tcttctttct ctcttttctt ttttcctttc    111480
tctaaattta tgaacatttt cttaaatttg tgaaaaaaaa ttcaatttca agaccttatt    111540
ttttgaatcc atgtttattt ctcaaataat gaatgttttc aagtttgcaa acttttgtca    111600
attcaatgga cttatttttg tcaactctgt gaatgttcct aaaattgatg aactttttaa    111660
aaatgtgtga aacttttgt caaattctat aacttctttg agaaattagt gacttctttt    111720
aaagccgatt acatatttta atttcatgga ttattttcaa atcgctgttt tttaaaacaa    111780
catttgaact tttctttaat ctaagggttg cgttataaac cgaaaacttg attttacca    111840 ttcgatttat tctaaatttt ggttggcaaa actataaact ggaatgaata tggggaagca    111900
aataaccaat aattcggttc aacggcttat tcggtttgat gttcagtttt acaccgagca    111960
aactcgtcaa atgtgttgct ttctattagg acactctgtc acattatata gcaaattttt    112020
gtcccctatt ttagtagctc agccggattt gactaaattg gacgctatgc gcaacttggg    112080
tgtacgatgt caccgaaagg ctcgtgcggg tttgtgcctt cgttgtacta aaatttgcat    112140
ggagtactag aatgggaaca ccaatggcaa aatttaggta aatttactaa atatccacaa    112200
gtacatcatg tacaacggag gggttttggt ttaggcggaa gagttcgtcc cctagcacgg    112260
tttttagcat acatcaaata ctcctaaaaa aacaccctag aattatcatg gcatggaccc    112320
atgccaactt ccatcgaatt ttgacttttt ttgtatttcc tatggggttt ccggtcaaaa    112380
aacctcaagt actgaccgaa cgggatgcag cgtgcattcg ttcttcgaat tcgttcaaat    112440
tttgcgtcga gtactagaat ggcatgctca gctgcctgca aaagtggat aaatttaatg    112500 aatgtccaca gatacatcat gtacaaccga gcggtttcgg ttatagcact ttttcacata    112560
```

```
gatctaacag acgcaaatgt gttatgttca tttgacgcat gtcgagtcac aacatgctct  112620
caaacatagg ctatttcttt cggaaaaaaa ttcgatctat tcattctcaa tcatggtaat  112680
acaacgaata ccagaaataa taaaaattac atctagatcc gtagagcacc tagcgacgat  112740
tacaattact gaagcgagcc gaaggcagaa aaaatttcga tctattcatt ctcaatcatg  112800
gtaatacaac gaataccaga aataataaaa attacatcta gatccgtaga ccacctagcg  112860
acaattacaa ttactgaagc gagccgaagg cacgcctgtt ggaaataacc acgacatgtg  112920
tggtctgtgt ccggttcgta cacacgacaa tcatcgtata gtggtaggat taggattcat  112980
agccgtgtag gttatcttat ctaatgtcct gactattata tataggtagc tatcccttg   113040 taagctgcaa ccgtgagatc gtgagatcaa aagatcaaaa gcaataaaag tgcaaggctt  113100
ggcccagacc cgacgtcgac gttgttgccg tgtactttcc ggcaatacat acgtacgata  113160
ctagctcgag tgcttttccga gctatccgtc ggagaggtaa acgtagacgt agacagcaat  113220
cgtgcacgta tacacgaagg ctgctggatg gttcctcctg tgctagctag cacgtactac  113280
tgcacgagat ctttggctga tcgatctatg cggcgagaac acaggaaaca ctcggcgagt  113340
tggccaaaag gagccttgca cttttattgc ttttgatctt ttgatctcac gatctcacgg  113400
ttgcagctta caaggggata gctacctata tataatagtc aggacattag ataagataac  113460
ctacacggct acgaatccta atcctaccac tatatgatga ttgtcctgtg taagaaccgg  113520
acacagacca cacatgtcgt ggttatttcc aacaacgccg ccgtcattgc tcctccatca  113580
ccggagtcga gcacaatttg ttgtagtaga cagtcgggaa gtcgtcgtgc taaggccccg  113640
tagcaccggt gcaccagaac agcaaccacc gcagatgaag aataacatag atcaaaagga  113700
tccaatccga agacacacga acatagacga acaacgatga gatccgagca aatccaccaa  113760
agataaatct gtcggagaca caactccaca cgctcaccaa cggtgctagg cacaccgccg  113820 taatggggc taggaaggga gacctttatt ccatcttcac gcagccgccg ccgtctcgtc   113880
ttcctgagca ggacacaaac cctagcaaaa ctgaaagtaa cgactaaaaa cggagcccctc 113940 ccgccggcgc ttgctgagat ccaccgcgct cccatggccc taggggcacc ggagtggagg  114000
cggacctgcg gcggcgccgg caggacgcag aaaccctaac ttttttttt gtgaaggagg   114060 aggaggcgga cttttgtgtc aaacataggc ttatggccca ccaggccacc ttatattgaa  114120
catggtgctt ctttggacat ttttaaaatg acactaagtt ttttagtagg tgggtatgcc  114180
cataatttaa acaaaaattt aaaactgtta tgttgagttt ttaacgtaaa aatatatag    114240 aaaaaggaga aaaataaaa cagccaatgt tttgctaaag ctaatacata tttgaaaaaa  114300
tgaatataat gtttgacagt tacttaaaac tgttattttg atattccaaa aaatatttca  114360
atttcgcgaa caagcttcaa aaataaaaat aaacctttaa aaggagaaaa atgaattaac  114420
ggaaaatgag aaaatagaaa gaaaataagc ttaggccttc gcggaactag aacacgacat  114480
cgctcttgtc gggcggctgt taggccgagg caagtgctcg ggatttcaat aagctcaacg  114540
attcaaaaaa tgtccctatt ttcaaaattc gtttataaat aaaaaaatgt tcccttttc    114600 aagcttgtac ataaactgaa attcctttgc gggagtttct aataatgttc gtactttcaa  114660
atgattttcc taacttcaaa atattcctg ttttcaaaag caatatacac aaataaaatg   114720 atgataggg aaattcacaa aaataatgtt cgctcttcta gaaaaatgtt tctgttttgt    114780
gacttttagg aacttaaaga caacaatatt ttgaagtaat aactataaaa tgtgtaaaaa  114840
agtttgtgag gtctattaaa atgtttgtcg ttgaaagtga tcattttgc tcttttaaaa   114900 tgattgaaat gtctatttca aaatttctat acaattttta taatgtgaat atttttagtt  114960
```

```
tcgtaattat acatttttat aaattttgaa aaaacaaata cttgggtctg gcgatgtcga  115020
tttgaggacc taatagtcag cgctttaagc gccagttagg aagctagcgc tcgagcccag  115080
tattgcgcaa gcttgcttgc ttcacccgat ggctttgaca aaaattcatg aatttcaaaa  115140
cgttaataag tttgaagtat agtttgtgga tttgaaaatt gttcacgagt aaaatgtaaa  115200
aagctcatga tcgtgaaaag gttcacaaat ttgaaaacaa gtttctgaat attaaaattg  115260
ttgcacgttc aaatttcaaa attatcatga ttttaaaaac atttatgaat ttgaaaactg  115320
ttcacgagat atattttata aattttataa aaaaaacatg agtttagaca atgttcacaa  115380
atttggaagt agttggcggg tttgaaacaa attttatgaa ttttttttaac cttgataaac  115440 ataaatggaa attcatgaaa aaagtggaaa agggtaaaat aaatataaaa cgaaattggc  115500
aaaaagaaag agaaaaaacc gagagaaaac catgcataaa aaacgaaaag gaaaattgtc  115560
cagaaaaact atgcatagcc agaaccggaa atgtagagaa caagaagaaa agaagtgga   115620 actatgcaga acatgttatc tatccgaggt ggtaattttg aatccggacg cagagtttct  115680
gctcccaagc tcatttgagc tcgatgaaaa catttggcat gaaataacat tcctacaaag  115740
tttggcaaaa acaaaatcga tgctgtgaaa agcggatttt cagagtgtcc attttttttg  115800
ctacgaattg taggaatgtt atttcatacc aatttgtttt tacacttaaa actttgtcat  115860
tgctggtcac aaaaaaaaaa tcagaattat ttgaacgttt cttgatttt ttttgatttt    115920 tactgttcac cgagctcaaa tgagctcggg ggcagaaggg cactttcaaa tcccaagtgg  115980
cacaatagcc aacatcaaat aggagcttcg ctactataca acaccgtata catacaaaca  116040
tggatataat ttgtcaaagg tttatattgc cctttatacg ttttcattct tttataatgc  116100
aacatgtaag tggacaatcc agtggtccgg ctcagctttg tgcgaaacat gctagcacgg  116160
tgactgtcac cgaaagctgg cttacgaaaa ctcctagctt cctgattagc agccttcaag  116220
ctgactgctc agcaaacgcc tttgtttgaa taaagcttaa aattccatgc aaaaaagtta  116280 ttgccctta tatgttttct gagaggggag ggggaggggg tatcaaagcg ggactagaga    116340
tataagcccg ctaacctggt cggggcattt ggaattgcaa gaaaaacagg cacgggtttt  116400
tagatcttcg gtttgacaaa cgaaacatgt gcaataaggc agcaaaagta tatattcaag  116460
ttgattcgat tactaatcta atgatatcta tttttttactg gcatatctca catgttctgt   116520
tagtcaaatt gaagacctaa gaactcatgc gctcctttga aattgaacaa aactagttca  116580
tttctaaaac ttcaacacaa aatgacctcg atccgaaaat acttcacaaa ttggctcctt  116640
tttgcatgac gcccgaggat agggctccat gctatttagc atgacgccct aggccaaggc  116700
tgtatctacc atgacaccct ggccccggcc ggcgtcatgc aaaagggcca gtttgtgaaa  116760
tattttgaga tggaggccat tttgttttga agtttcagaa aagggctagt ttcgtcaatt  116820
tttactacac tccttaccaa cccggataga ggagtaaata tatattcctc aaatagagca  116880
gttattgata gtttcaactt acctgttatt cggttttata ggggattgga acatcaaaag  116940
tggagttgaa gaaaagccta gagaaaatag aaaataccat aaacgatgca tgtaaagttt  117000
tggaacaact gaacttgccg agtgtatgta atgataatgg gagacgaggt gttgctacca  117060
attctcgtag tgcagtcact actgcaggtc ctcctctacg agtaattggt cgagatcagg  117120
atcgtgacaa gatcatagca atgcttcatg agaaggatga ccggtgtcaa gtcaatggta  117180
catcttattc tgtaattggc attcatggcg tcgccgggtc tgggaaatca acacttgcac  117240
agtatgttta tgatcatgag aaaaagtgca agcaaggtaa aagagaaggc tatttttgatg  117300
```

```
ttctcatgtg gattcatgtt tctcaaaaaa tcggtttgga gtccagtttc agggacatgt    117360 ttgaggggc tacagggaaa gcatgcccga attttaatag tcttaacgtc ttaaaggaaa    117420
agttggagga ggaactacgt ggaaaacgga ttttttttggt actagatgat gtctggtaca    117480
acagtaagaa ttcaggagac cgtgaagaac tgcagaagtt aatttctccg ttgaatgttg    117540
ggaaggcagg aagcagaatc ttggtgacta gtcgaactga agctgcatta gtagctctcc    117600
gtgctgcaaa agagggatgt atcccaatat ctaacctgga tgataaagtt ttccttaaaa    117660
tgttcatgca ttatgcactt ccacatgcat ggccagttgg caatgatcga agaaaacttg    117720
aaatgattgg agaggacatt gcaaaaaagc tgaagggttc acctctggca gctagaatag    117780
tgggttcacg gctcggtgat aatccaaatg ttgaattttg gaggagagag aaagaccggg    117840
atcttatgaa cgagacgatg ggagcacttt ggtggagcta ccagtaccct gatgagcagg    117900
tcaggcgatg cttcgcttac atcagcattt ttcccagacg tcatcatttg aaacgtgatg    117960
acttaattaa cctatgggtg gccgaaggat ttataaagac aagtaaagct gaagaggaaa    118020
tggaagatgt tgcctcggaa tactttgatg agctgctttc gttctcattt ctgcaattag    118080
gagggaaaga tgagctattt gcacgtgagg tcgattactt tataattcat gatctgttgt    118140
atgatttagc agaggaggtt gctggaagag attgcttcag gatagagaaa ggtttcacag    118200
gagaagtccc tccggatgtt cgctatcttt ttgttgggac ttacgataaa gagatgctta    118260
ctgagaagat atccaggttg caaaatttac gcactctctt cgtcgataag tacatacaga    118320
ttttatcacc caagtacgat gattttgtta gtatggtgac tatgttgatg gggctgcgga    118380
aattgagggt actgaattta catttcactg gatatgtat tcctaaattc tcattgccgg    118440
attctattct tcagtggaag catctgcgtt actttgcttt tggggtgtcc ccgtttacca    118500
agctaacttt accatgcgct tttaccaagc tttaccactt gcatgtggta gatttcggtg    118560
attgcaatag tttggagttt tctcgtggtg aatacatgat gaacctggtc aatttgcgcc    118620
gtgtaatcta caagaattat ctcgactttc cgaacattgg caggctgaca tggctgcaat    118680
cgttgccgtg cttcagaata aggaagaaac atgggtatga atcacatcag ctgaaacacc    118740
taaacaagct tcaaggcagg ctgtacattg gtggtcttca gaatgttgag agcaaggagg    118800
aagctcttaa tgtgaacctt gcagccaagg aaaaactcac agaagtggta ctgcgctgga    118860
gtgataatag ctgcagtcca gaaattcaag cagaggtact tgagggcctt tgtccttcaa    118920
agtatcttga aatactagaa atcaagttat acaatggcat gaagtttcca aattggatga    118980
cgagtaagca taagggtggg ccaaagaacc tgcaagaact tagattcaga cagagcaccc    119040
tgggatctgc tcctgatgtt ggggctttca ttcaccttca gtcgttattt atttatcaat    119100
gcagctggga taccttacca gggaatatgg agcacctcac agcgctcaag aaactggaga    119160
tacggtcatg caataatatt cggtcgcttc caacactgcc caagtccctt gagcagtttg    119220
cgatctggtc ctgcagcttg gatgctttac cgggcaatat ggagcacctc acagcactca    119280
agaaactgga gatacggtca tgcaataata ttcggtggct ccaacactg cccaagtccc    119340 ttgagcagtt tgcgatctcg cgctgcagct tggatgcttt accgggcaat atggagcacc    119400
tcacagcgct caagaaactg gatatatggt catgcgagaa tatacggtcg cttccaacac    119460
tacccaagtc tcttgaggag tttacagtct ggaactgcac tagtgagttc atgcaatctt    119520
gtatgacgac tgatgatcca aactggcaga agattgagca cgttccaaac aaaaaaattg    119580
gatttctatg aaaacgatac ataagaagg tacgtattta aattcctttg acgtcttcgt    119640
tttccatttt tgcgtgcagt aaatgttact gcaacaatta gccgttaagg ttcctggtat    119700
```

```
ttttctgatt cagttgctaa ctattaggcg cgtgcccttt ggttgaggac gggagatgaa   119760
gtcgaagccg aagccgtcag aatcttgcta aatttacggt ctctcttact ggatagcctc   119820
ttggttgggt tatgcctact ttggttggtt gagtcttgca tgtttacacc taaagtggtg   119880
caaaatgcca tctctccatg cagtcacaac tcacaaacag tggatttatg aattgtttac   119940
aatatatgga tttatggatg caataacgtg taataatgaa cagctgattg atttgccttc   120000
atatatatat atatatgatt tgtaacactg ccgtgtggat gatgaacctg cccaaactg   120060 tttgattcct agctatatat gatttgtaac actttggaat gattatcact gaattcgttc   120120
ctttcctgtc gttgtttgta tcatggttca aaaaaaagta tccgatttga ttgcgaggaa   120180
ttgggggcta cataagcatg gtatggtatg aggttaccag attgggcgaa gctaacccga   120240
ggaactgctc ctgacattga ggcttccatt cattttcagt aatagaatgc taaaaggctt   120300
tagtggttgc aatcaacgtg cattgtaatt agtgattgca ttttttttc tactggttgc   120360 ccattcaggg aaagtgctct cacacggtgg catgttctct gttctgcaca cgctctcgtt   120420
ttgggcagac gcaagctttg atgtgtccgc ttgggccttc aaacacgatg caacatattc   120480
tgcaaacact attgagtatt ttcttctca atttttgctc atcttaggag ctgttcggta   120540
accatccaga tccatgaaat ctgagaatct gcggagtacc tcttgtccag ctctgcaatt   120600
tttacctgct gctcctccaa ctccgggagt gaagatgcgg agtggaggac atccgaacag   120660
gcctttaatc aatgaaagca tcgctagctg ctacctttcg ttcacaaaaa tgttttaaag   120720
aaggatgcga cctgtagcat gaaaacaaga acgacataga cttctgacca ctgccaagtg   120780
aaattctgta gatcatcaga acacgctata ttgtcagaaa gatgatcaca tctgtgacaa   120840
gtccacgcgc tcgaaacaac aaccactttg aactctgaaa gctgatctca tgacgactcc   120900
accaaattgg gtccaacttg tacacatatt cgagaccttta tgatcgagcc agtatgaaac   120960
gaacaaattc caggcgctca tgtagtatct cattggtaat gctaccacac aggttggact   121020
acatagccag aggcacgcca acataaggaa accgagtcgt gaaaaactcg agattcgcgg   121080
aattggtacg ttgatgttct aggagtcaat atactacctg accacgtggc agtataacaa   121140
acaaacttga actgaagaaa aaacagggaa agaaactggg tggttgggat acacagcaag   121200
acagaggcac atgaacataa aggaattcgg tcaagaaaaa ctcgtacgga attggttttg   121260
caggagttca tttactgcct aggcacattc tatcagtata acaaactaca aaggaaaaga   121320
accaaactgg gggtgttggt agtgaggaaa aacagcacaa tcgcccgaaa ctttacgttt   121380
cagtccgtca tctcaatcaa tatgatttgc attgagattc agagcacaac tatgatactg   121440
agattcaaag agtggtggag acattgactg caataaagag caatttcagt tgcccgtgct   121500
gataagcact cacttcgatc tcatgaggtt gattcacata aaacaacata cgtgggataa   121560
catttcagtt tcctgtgagc acaagttatg caggtttatc tcgaaacagc aacgtaagat   121620
aaaattatac atctgaagat gaagacaaga gaacttctct gcttccttac atctatcata   121680
aggactgtac aaaatgaaca atctttgact tgaacgaatt ttcttgaggt gaaacaatcc   121740
aaggtaaaac aggatataaa gttgtattcc ttctacattt atcttgacca tcagaactac   121800
tactcaataa taataataat aataataagc tggtgtttct agtgattcca tcaggaattc   121860
aggactcatg cataagctac tcatagcgta caagatcatt ccccttacta accgcattct   121920
cttaaaatgg cgatcgaaac aaacaacaca agaaacccaa ttatgatcct gagctttctt   121980
agttttccca atgagcacag gaaattaaac actactaaat caaacaagat ataccaattg   122040
```

```
ccataatata aacattgaag caatagacaa gtcgtgttat tattatgaag ggaaggactg   122100
agataacttg gaagcgatag aaactttacc attttatatt ctccttgaag acagcaatga   122160
tggtgggaag ttgatatatg ggtacgtctc atgcaaacga taataatgtg tctcataaac   122220
cctctgaatc tgcaacgtct tgacatccat tgagaaatat ccagtaagtc gatcctttag   122280
agatgatgag gcttctagcc ttgtgaagac caagtacctc tgtgttgcat ctctgataaa   122340
atatctgtac ccagaatcta gtgagatcgt cttctccacc tgccagtggc tgggaatctc   122400
gcctttgttc cgtgcaacgg tatagctgag aatggatgag gttttaccat ggaaaccaaa   122460
gatcccaagc ctgccttccc ctgcttccac aatggctatt cctccttccg tgctccattc   122520
tccaggcggg aggtcaacaa tggagtgtta ggttgatctc tttacccaat gggcccaacg   122580
gcccattggg ccttgactca cgccctgatc ggggcgtcc agcccaagta aggctggtgg     122640
gcccctgtcg cgcagtgcta tatgtagagg aggtgtggac catggcacgt gttacgaggt   122700
tcgccgccgc cactggttcc ccactcctaa ccctaatccg atctagaggg atgcactgaa   122760
gtgacgggaa gtccaccgcc gccgctgcca catctctctc cttcctcacc gtcgtcacca   122820
cctcaccatg gacgaccgga gggagctcat cgagtacggg ataaggtaac gtaccactac   122880
tctcatcgaa cacatctagc cttgtcgatc cacaggatct atcaatggta tcatgagcaa   122940
ggttggtatt aaatgtgttt ttggttgaag ataacgaaag cgataaagtt tcccctcccc   123000
gatatgaacc ctagaagagg gcaaagatcg agctgaaaaa aaaaagaaaa aggaagtcac   123060
cggatttcca tccggcaaag aagcgccgcc gcaaggccgc gccaaccctc tcgatctcga   123120
cgcgcatcgg caagccgagg cgtcggacga aggtaccacc tcttcggagg caaagaaaag   123180
gtcggattga atccgaaaaa gaaaacaaaa aaaggggga ggagggggaac acgcaaagac     123240 acaacaaagg aaagccaaga aaagccaccc ctcctcggag gcaaagtatg gatctagatc   123300
caaaaggaaa ataagaaag caaacggatc ggatccggaa aaggcaaaca aaggaaggg       123360 caaatgcaaa caaggataa gaaaatccac ccctcccggg gcaaagggcg ccaccaccga    123420
gccgtttgac ggcggcgtgt tcaccctaga ggtgctcgcg ctgctgccaa aggggacggg   123480
gatggcgccg acgagttcac gcatccggac ctctttttgg tagtatggtg aacgtcaata   123540
cggaaaagaa aacagaacca tagccaaccg ctcgacggcg gcgcacccac cgcaaggcgt   123600
gtgcgcagcc ggcgagggga aggccacgac cccggcaaga agtaacatgg ggcggactcg   123660
ggagaagggg ccagatccgc gcggggcaga gagccaccac aggatccctc tcggcggggc   123720
ttgagagcca ccgcgcgagg ggaaggctcg gccacaccgc agtaggaggg cgcgcgcggc   123780
gtggggcttt cagccgccac cgcccggcca accatggcca caggagagga aaggccatg    123840 ctctctctcg agagagagtc acgagagagg agagagctgc ggcgctgggg gggggatga    123900 ctagggtttt cctcccccac ccggccggct gcccttttgt ctccccgagg gccgcggcgc   123960
gccatcggat caccaaggac aaccaggatc tctcctgagc cgaacccag gccaggcagg     124020 ccattgggcc accaggccgc aagtagcagg ccggcccaag ccggcgggag gaggaccagg   124080
ccacgggcca acaggagggc gatggcccag gccgaaaggg gaaaggccga agccggccca   124140
aggaagaaaa ggccttggcc attttctttt ttaaggaatt ttaggttttt gtctattaat   124200
aggcagattt aaaagacttt tctaggcatt ttttcctacg aaaatatgtt tagaaaatag   124260
caaaagaaaa tgttcaaagt ttctgtcaat ttagacagaa ttgttaattt attttttctga  124320 aaagaaaagt aaaagatt ctgagaacaa aatagttttc tcagaaaagg aaagttcat      124380 gatctttata aaagcattaa taatgttcat gaattctttt aattatgaca aaatatattt   124440
```

```
ttctataata gtgacataat atttttctga aaagaaaaat aaaaggttct aaaaataaaa    124500
gaaagatttt cagaaaaaga aaagttcatg gatttttataa aagggattat aaagttcatg   124560 aattttaat tatgcagaa tatttttctg taatagtaac atgattttc tgaaaagaaa      124620 ataaaagatt ctgaaaataa aagaaagatt ttcagaaaga gaaagttca tggattttat    124680 aaagggatt ataaagttca tgaattttta atttaacag aatattttc tgtaaaggtg      124740 catgaatttt atattcacgt ttttccgctg caaagtaaaa aggtttagtc ctccaattaa   124800
attgaaacca acgggaaaat ttaattggaa gaactgttat tagcaaattt tttcccttgt   124860
aggagaaatg agattcaaac agtttccgct atgacaatac aacgaagttt gttttaaagt   124920
taaaatatgg tattgttgtt ttctcaccaa cgttgatgat aacagtacta taattgtatg   124980
agtcatttta tgtttaaggc ttaaatcttt gatatatttt gtatcaaagt gatcaatttt   125040
cggagcacag atagagaaat gcatatttct atttctgctg caatatggtt aatgatgatg   125100
attatttatt agcaaagttg ttcaataaga atactatcat cacattgttt atgagttgta   125160
tgcattattt ccatttctgc ccaacggtga tactagaagg atgatgtttt attctaattc   125220
tgccaccacg gtcatttaga atatttcaga aagttttaaa aggtttaatg tgcatggttt   125280
taatcagacc aacgtagggt tattttcatg ctcattaccg ttgtttattg gctaagtatt   125340
ctcagactaa aagttattca agctttcact catgaaagcg aatgttttgg gtactagtga   125400
cccgaaagat ggaaaagaaa ggtcataact tgagggaata aattctctct aaagaatggc   125460
ttcaaaagaa aataactctt ggatattaat tcaagaaaag aaaagagata gatcattgag   125520
agtcttggtt gacgaatgtc tttcatgtac tctctatgat ggagtctcct ttttttcagt   125580
caacatgatt gaaatgaaac aagcaacatg catgtttaat ttgaccaacg tcggatcaaa   125640
catgtgtgtc aaggataatt cagatttatt tctgaattta atgaagtcaa aagagccaat   125700
tatggcattt atgtcccctta cagggaatta cccgcatggc gggaaaagtc agggaagaat  125760
gcctgcgtaa ctgggtaaag ttgacattgt attatgtcaa caatccgtgt atggcgggag   125820
aaatcttggt aaaggcctta tcctgtatga caggagaaag ttatgatgac tcatgtgcgg   125880
ttaatgtgtc ccactatggg agaaaagtat ggagtagcta ttaagctttc ctattatcga   125940
ccgtacactt tatgtgtaac ggtcattatg caatcactaa atccagaaag gataaaagta   126000
acagacgaac ctaaagacaa gaatgatatg caagtgtgac ttgcaaaaga gacaatgata   126060
gagaactcta ttgagtttct gaaatgtaat gaggaaaaag tactcccata ctagctaact   126120
tataacttca ttttacatga agtgataaga tgaatgagct agataatcga agtttcctca   126180
ttacacaaga gctatgaatg ggtttcgaaa ttgtggcaca aaagttcttg ccacatttcg   126240
aggggagaaa gagacatgaa atacattgta gtgtatttca tgactcctct gtactttaga   126300
tgatgtaatg cacattatgc atctaaagtg atccattaat gaagaatgtg attgtcaagg   126360
ggagtacgac agtcatctga ataccgtcat tatgataccc ctaaagaaaa gaaacagttg   126420
tattttcgga tctttatagt tccgaatgca gactaaggaa tacaacggtg gtgcttaaag   126480
tgtcataaag aagaaagttt aaagatacac catttcttca gtgaagatgg agtaatctgg   126540
gggagcatgt tatatgacct atacaacacc tgttgttagc tctacaaggg atcttgtgat   126600
acaggtccct gtaaaaccta ttgccttttg gaaatgggtg actatagaat gaatttgcct   126660
cttggcaatg acagagcaac gacaacccca tatgaaataa gtgccagtac ctgagatttt   126720
gatggtctct aggcatgtga aaatcagata cttgtgacta ctataaagtc tatgttagtg   126780
```

```
gaattccatc atttgaattt cactaacata gactttatga agggtctaca aggcaaatgt 126840
gactccaaag gaaatatgta aatgcgtaaa acatgactta aatcaaaaga ttttgtgcaa 126900
agaaaatgag aggacaattg cattcatgca aagttataga atgggaaatt cgtttcacaa 126960
ttcctatgca tgtggatgat gtcctacttg ctagtggtga tgtcaatcta ctgcaggagg 127020
agaaaagaag ttcttgtcct caaagttcaa aagaataaaa gggggtatta ggaatgtcgc 127080
atggacatgc taagaaagat ctctaaagca tgcatacgag aaaacctacg cctgttctca 127140
tagtcaaggg taatggaagt ggaaactatg gtgttccaaa agttaataag aaaagattgt 127200
aaacggatat ggtaccatat gcttcagttg ttggaagctc aagatattac cctgacacag 127260
ttcacgtata tattcgggtt gtcttggcaa tgtccagtcc atagataaat caatggaatg 127320
gattcaaaga tatcggcctc atgctgaaag aaataagtgc tctcaaaaca ttgtgagtac 127380
aaaggaggac ttgtgaaatg tatagcaaaa tccacaattc tcgctaactt tcatactcgg 127440
agttttgtgt ggaaaatctc caaatgagtg aaaccattgt catcaatgtg atgcaatgat 127500
atgttatggc ttgatatgag gctgaggat aggcgaaatg gttaatggct acctataccc 127560
ggagttgata atggttgaca acaacgataa ccatttaaaa ttctttcgct cctgtcacaa 127620
cgagtcaagt gttgatgcca aacacactga caaagagtta cgtgttgtga aggagaaagt 127680
ccggaattat ggaaaaatgc ttgaagcata aaagcaacaa acaagtgttt gtagatctgc 127740
tcatcaaagg cttaccgccc agtgtgttcg gagaacacac agtcgacatg ggttttatgt 127800
tatagtctaa tatttctgga caacaaaggg cccaaggtta aagaatctgt ttcaaaatag 127860
agaggtacat tgtggctgtc tgattccatc ggcaattgag ccgtgacgat gaaacatgcc 127920
ctatgtattg atctgttacg aaacgggtaa agttaaaagt atatgatgag atcaagggg 127980 agaatgttag gttgatctct ttacccaatg agcccaacgg cccattgggc cttgactcac 128040
gccctgatcg ggggcgtcca gcccaagtaa ggctggtggg cccctgtcgc gcagtgctat 128100
atgtagagga ggtggggacc atggcacggg ttacgaggtt cgtcgccgcc actggtttcc 128160
cactcctaac cctaatccga tctaagggat gcactaaagt gacgggaagt ccaccgccgc 128220
cgctgccaca tctctctcct tcctcaccgt cgtcaccacc tcaccatgga cgaccagagg 128280
gagctcatcg agtacgggat aaggtaacgt gccactactc tcaccgaaca catctagcct 128340
tgtcgatcca catgatctat catggagaac tccatcttcc tggtcctggt gtcaagcaag 128400 agcaatttt ccctcccgaa ttccacccag tcccagtaga agcagccata agcatgatgg 128460
cgcctgagaa tgaaagggtg gacagacaca tgacatcttg gccatgtcgc gctcgccaag 128520
gccgaaatca ctccaaccct tggatgcagc ggcttgccat tgtccagtgc ttgaagagaa 128580
gaggaaggca gcgagactag ttttgcaatt tgccatcaag atcaccctga atgatgtctc 128640
tcccgccgct gcctgctcct catcgagggg aacgaggaag gccttgcacg cggcctcgct 128700
taccatgggg aacgggtggt caagcgaggc ggcaaggccg tgaggtagtg ggggagcag 128760 gacgtagcct aatcatgttg ccggaggtcg cggtctctga agaccggggg ctgctcatgt 128820
tgccggaggt cgcggtcgag gaggacgcgg ccgtcgcgga cgtcctgcac ggtccattgg 128880
cagtaggagt cggagaggat gaaggagaag tagaagtcgg cggcgacctc gagcgcgcgg 128940
gctgcgggcg cggatgggtg cggcggcaga gcgggacgga acctgccgta gtcgaggaat 129000
ccgaggagtg gtggtgcgtg gaggcggcgg aatctgcgga ggatggagcc gtcggtggcg 129060
agtcggtgga aggagacgca ggcggcgcg gcacgggcga ggtcttcagg gtcgggcagg 129120
cggaggaaga tctcggccag tatgtggccg gggaactccg tcagaggcga cgccatctcc 129180
```

```
cgagcgtccg gcagaagagc tggccgccgg gaaccctcga cgggaggtgc gggtgccggc   129240
ggcgggtgct gctgcggaaa tgggctttgg tcgggccgtt ctagtgccca aaaatgttca   129300
aaacgatcca aactagagca gaatttagaa ttctcgacta actggccact aatcttcagc   129360
gtgtctgcac ttgtcatctc tttctagcct aaaaaagaa aaacttgtta tctctttctt   129420
tatacatact aggaaatgtg cccgtacgtt gcaacggaaa aaacaaaatg ttgcacactc   129480
ctagctaccc atctaatttt gttgttattt tttctattcg ttgtaatcgc taatgacgtt   129540
catattgtcc attatacttt tcactatcgc taactatcaa tttcaagatg atgtgctttt   129600
cattatactt tggcacaaca taggagcatc gctatagagt aaacaacttc tgataaggat   129660
ttttgtaatg tggtcagtgt tcaccaaata tcgtatgccc catgatcgcc gtgctctaag   129720
ctgaggacgg cacttgttgt ttatggagag gagaccgcca tggtaagatt atatctgttg   129780
tataatgcag attttcgatt ttttttttgtt tcggtgaaca ttttttaaaa tttcttacac   129840
attttctccg aattcaagga tatgttttga atacatgatc attttcaaaa tcatgaatgt   129900
tttatatttg ctgaatatat ttttcgaaaa tgtgaaattg tgaattcttt tacaatatca   129960
aaacagtttt tttaatcatc aacattttt gagtccatga acattttatg atttcgcgaa   130020 ccttttttttg aattgccaaa catttatga tttcatcagt atttttaaa tccgtgaacg   130080 ttttatcatt gcctaaacct tttttgaaa tcccaaaaca tttatgatt tcatgaatat   130140 tttagctcaa aactcaaaag cttttaatt tggaaatttg caaattccga attcatttaa   130200
agaagataaa aaataaacgg aaataataaa acagaaatgt gtgaccaaaa aaatgtaggt   130260
tccaggtatc gaacccgggt cacctaggtg gagtaccggc gctccaacca ctacgcgaag   130320
cacgccaggt tttttattcg ggacctcatc gtataagtac cgcaacgggc gatgactttg   130380
actgaaaaaa attcgaatcg tttttcact tatgggtggc atagtgggta atttaggaca   130440
acattggggg taattttagt gatgtacggc agaagcactg agtgctttat tattagggag   130500
agagatatga aaaatacatc ctactacccg gggatagtta ccccacatgt tccatatatt   130560
accatacggg agtgtatata ctaatttatc attgtattta tgttcatata ctatatataa   130620
gattttcaaa gggagttaca tgaataaatt ataatagaaa gtctactcat catccaggtg   130680
cagaataagt tattcttcat ctgaggtaat cttacgatcg cttcataaat aaattacatt   130740
taaaatgcaa atatttacat ttatattgat tcattacgta aagtttgata ttaaaaaaca   130800
aaaatataga tcgtaagacc agaaaaatca cattttatgt atactttaca ctatgtgttt   130860
tgtgtttgta attttacatg acatatagta tttttttactt tgactatata ttttttgcga   130920
tctgttttta cgtatgaaat aagacaaaat ttacgaaaca taaaattatg ctgcattgat   130980
atgaaaatag aagggggtgaa gaatatatat atatatatat agggaaaata gattctacca   131040
tctagtggta gttaccatca tactcgctgc cctccgatct aattagatcc aagcgttgat   131100
caacgggttt gattttagaa tttctctatc cgtcaagaca accagcccgt accccaccta   131160
ccaacccgat ttatgtggga agataacact agtagaaaac agggctaccg ttcggccctc   131220
gccggcccat tagtcccggt tcttcaagaa ccaggaccaa tggggggtat tagacccggt   131280
tcgtgagccc aggggggcgg ccgggcctc gtggcattg tcccggttc gtgtggaacc   131340 attagtcacg gttcgagcca cgaaccggga ccaatggtcc tcgctgctcg cccacaacca   131400
ttggtcccgg ttcgtggctt gaacagggac agaagggttg gctttagtcc cggtttgtgc   131460
cacgaaccgg gacaaataac ttgcctacat atacccaccg ccgcggcaga gcactccata   131520
```

-continued

```
gtgctatgtt tttgtcaagc cggcgagggg agggcatttg ggtgctctag ttcacctcct    131580
atgcacatga ggtgttcgat gaaatgccca agccacacta gttaagcttt ctcctctcga    131640
aactcgacct ccgagctcca ttttcaacga gatttatcta gatttagtgg tccgtcacgc    131700
cctgtcccg ccccgtcttc accgtcgtcg atccccgca ccgatctcgt cgccggcacc      131760
accgtggtga gcctcttgtt cttatcttct ttctgaaaga aaaaattctg acttcagata    131820
gatacttgtc tattttcttc acttttatta ttccttgtta ttatatagtg cgatggtttt    131880
ggtatccgcc cccgtcggcc ctcgtcctgt ctatgattca gatgtggtat atattatctt    131940
ttcataacta tttggttcat ttattgttta tgacaattat gctgaccaat gtgacatata    132000
ttttatttat ctaggaggtt gtcgaaccag aaattccaac cgaccctatt gtcgagaggt    132060
taaatttagt tgaagaagaa acaattact tgaaggaaaa aataagaaaa attgaggagg     132120
agaagatgat attggagttg catgttgtgg atgtcgtcga tgatcacaac atcaagatgg    132180
atgcaatgcg gttgaagatt aaaaagatta gaaaatatgc cattcatacc gaggcttggt    132240
atcattatgc agttggatca gttgttacct tggttgcggc tatgattgca tttgttttg     132300
cattgaaatg ttttacataa tttcaatgta tggtttaatt agatgctctg tagagctata    132360
tgttgttcaa tgagaactat gtatgtactt tggttttaat gctctagaga actatgtatg    132420
tactttagtt tcagagttca tttcaaatgc ttttcaactt catggtctta cagctttgaa    132480
tggtgcattt tgaacacaga aaacaagag agttcaaata agttcaaaaa aattgaaatc     132540
cctttgtaac agacgagttt ccgtatgaaa ccctaatact tcgaaagaga ttgtctgttt    132600
tgtacacgaa gtgcatccag tttttgccgt aagcctctct actttcttgc acatgctatg    132660
tgggtgaaat gatgatacca tgccaacttg gaacctttt agaattcatt tcaaatgctt     132720
ttcaatttca tggtcttata gctcaaaata accagtaaat gcatgaaaaa taacaaatga    132780
agtcagaaag ggttgtaaat tgatgatttg gcttggaatg gtgcattttg aacatagaaa    132840
aacaaggggg ttcaaataaa ttgaaaaaaa ttgaaatccc tttgtaacag acaagtttcc    132900
gtatgtaacc ctgatacttc gaaggagatt gtctgttttg tacacgaagt gcatccagtt    132960
tttgccgtaa gcctctctac tttcttgcac atgctatgtg ggtgaaatga tgataccatg    133020
ccaacttgga accttttcag agttcatttc aaatgctttt caatttcacg gtcttatagc    133080
tcaaataat cagtaaatgc atgaaaaata acaaatgaag tcagaaaggg ttgtaaatta     133140
atgatgtggc tttgaatggt gcattttgaa cacagaaaaa caaggggggtt caaataagtt   133200
caaaaaaatt gaaatccctt tgtaacagac gagtttccgt atgaaaccct catacttcga    133260
aggagattgt ctgttttgta cacgaagtgc atccagtttt ttgccgtaag tctctctact    133320
ttcttgcaca tgctatgtgg gtgaaatgat gataccatga caacttggaa tcttttcaga    133380
gttcatttca aatgttttc aatttcatgg tcttatagct caaaataatt agtaaatgca     133440
tgaaaaataa caaatgaagt cagaaaaggt tgtaaattga tgatgtggct ttgaatggtg    133500
cattttgaac acagaaaaac aagggggttc aaataagttc aacaaaatg aaatcccttt     133560
gtaacagacg agtttccgta tgaaaccctg atacttcgaa ggagattgtc tattttgtac    133620
acgaagtgca tccagttttt tccgtaagcc tctctacttt cgtgcacatg ctatgtgggt    133680
gaaatgatga taccatgcca acttggaacc ttttcagagt tcatttcaaa tgcttttcaa    133740
tttcacggtc ttatagctca aaataatcag taaatgcatg aaaaataaca atgaagtca    133800
gaaagggttg taaattaatg atgtggcttt gaatggtgca tttgaacac agaaaaacaa     133860
gggggttcaa ataagttcaa aaaaattgaa atcccttgt aacagacgag tttccgtatg     133920
```

```
aaaccctcaa acttcgaagg agattgtctg ttttgtacac gaagtgcgtc cagttttttg    133980
ccgtaagcct ctctacttc ttgcacatgc tatgtgggtg aaatgatcat accatgccaa    134040
cttggaatct tttcagagtt catttcaaat gttttcaat ttcatggtct tatagctcaa     134100
aataatcagt aaatgcatga aaaataacaa atgaagtcag aaaaggttgt aaattgatga   134160
tgtggctttg aatggtgcat tttgaacaca gaaaaacaag ggggttcaaa taagttcaac   134220
aaaaatgaaa tcccttttgaa acagatgagt ttccgtatga aaccctgata cttcgaagga   134280
gattgtctat tttgtacatg aagtgcatcc agttttttgcc ataagcctct ctactaccgt   134340
gcacatgcta tgtgggtgaa atgatgatac catgccaact tggaaccttt tcagagttta   134400
tttcaaatgc ttttcaattt cacagtctta tagctcaaaa ttatcagtaa atgcatgaaa   134460
ataacaaatg aagtcagaaa tggttgtaaa ttaatgatat ggctttgaat ggtgcatttt   134520
gaacacagaa aaacaagggg gttcaaataa gttcaaaaaa attgaaatcc ctttgtaaca   134580
gacgagtttc cgtatgaaac cctcaaactt cgaaggagat tgtctatttt gtacacgaag   134640
tgcatccagt ttttgccgt aagcctctct actttcttgc acatgctatg tgggtgaaat    134700
gatcatacca tgccaacttg gaatctttc agagttcatt tcaaatgctt ttcaatttca    134760
tggtcttata gcttaaaata atcagtaaac gcatgaaaaa taacaatga aacaaaataa    134820 aataaatacg taatttgaaa caaaataata taaactttaa taaatagat aagtagaaac    134880 aaaaaaactt taataacata aataaaaatt ttgaaactaa aattatcaaa gtattttctg   134940
ttcaaaacat tataagcaac ttctagtatt attgaaacta aaattattta aaattcatga   135000
aactaaaatt atcaaagtat tttctgttca aaatcattaa aagcaaaaag aattttcata   135060
aaaaactttt tttgttagaa actttaatag caataagaat tatcataaaa taaaattaat   135120
aagtaattag aaacaaaata aaataaaata aataagtaga aacaaatggg aaaaaataaa   135180
aaaattgcca ccaactgggc caccacagcg taaatacgac tagaaacccca tccatgggcc    135240 acgattcagg cccgtagtag gcccagaagg cccatcaggc aaagcagtag caagtaggcc    135300
cgtaagcctg cagtggagag gagctcgaga ggggtgcggc agtggggctt ataaaccact   135360 gcgcgccct ctcaactagc gaggtgggac taaacttcgg ccgcgacgcg ggcagcacac    135420
gggcctttgg tcccggttgg tggcaccaac tgagactaaa ggggggtgca ttggtaccgg   135480
ttcgtggtac caaccgggac caaaggccgt cgattcccgc cctttgggct gctgaaaagt   135540
gacatttagt cccggttggt gccaccaacc gggaccaaag gccgccactt cccgcccttt    135600
gggctgctga aaagtgacct ttggtcccgg ttggtggcac caaccgggac taaggggggc   135660
attggtaccg gttggtgcca cgaaccggta ccaatgcctt gggtatataa gaaacactta   135720 gcagttttg caaaaatcac ttcttctccg ccccgacgcc ccacgatgc tcctcgtccc    135780 cgtcgccgcc gagccctgcc ccgacgccgt cgcccgctcc ctcgcccgac accgtcgccg   135840
ctcgccgccc tgcccgacgc cgttgcccgc gccctcgctc gacgccgtcg ccgctcggca    135900
ccctgccccg acgccgtcgc tgtcgcgctg ctcgccgccc taccccaacg cgcgccgccc    135960
cggccctgcc ccgacgcacg ccgccccggc cctgccccga cccgtcgcc gtcgccgctc     136020 gccgcctgc cctgacccccg cgccctgcc cctcctcacc ttggtccggc ggcgccctcc    136080 cctgttttt taatatatgt gataattgtt tttgttcata tatgatga ttttttttata    136140 gaatatgatg ttttttttct gattatatgt atatgatttt tttataaaat atgatgtttt    136200 tgcttttta taaaaatgta tatatgtttg tatgttcttt gtgtatatat gttcatatat    136260
```

```
gcaaaagtta gatttagtac attttaggtt agtttaattt ttagaaaaaa tttaaatatc    136320
tagctaggaa aggaagaaga agaaaaagaa tgagaggaga aaaaggaaaa taagaagagt    136380
tagaaaggag aagaagagga gaaataaata agaagaggaa aaaagaagaa aaagaagagg    136440
tttctatttt tttcttcttt ctcctctatt gctttcttct tctccttttt tttcttttat    136500
ttttcttcga ttgcttctct tctattcctt tcttcttctc ctcttttat ttcttctttt     136560 gtcttcttat tttttatcgg gtatgtcgtt gtcgatatac cccctcccga tcgaacttca    136620
acatgagggg gggtaccgat atacccctc cccgataata ttattttccc atgtatatgt     136680
atgtcgtgtc gttgtcgata taacccctc ccggataact cgacatgag gggcggtcga     136740 tatatatacc cactctcggc cgtgataact tataccacgg gagcaccccc ctcggccctc    136800
tcgctcgacc aaaactctcg aggacaccca aaccctagag aaaaaacgat gttggtctcc    136860 tacccctcc cgccgtaccc ctacccgaca aactctctcg aggctatcca aatttaccaa     136920
gttaaaagag cgttgtcgtc gaggccaccc caaaccttg aagcgttgtg tcgaggccac     136980
cccaaaccct tgaagcgttg tcgaggccac cccaaaccct agaagcaa cgtcgaggcc      137040 actaacatga ttccttattg tgattagcta gctagttcta cgtttgccac taatatatat    137100
ccatctgtac catgtgtgaa taataattga catgttgtaa atatttgcag aaactatgga    137160
tcactcccga gacgaagcaa cagaagcgat gttggggag ataatcgcac aaggaagaag      137220
tgatgccgtt gcgttgtttc tctacgacac cgatggtcag gaaggaccgg gtgaagaaga    137280
gggctatgtt tatgatggct ccggtgaccc attaatgctg gtacaagaag aggtctatgt    137340
tcatgatggc tccgatgacc caatggaggt acaagaagga gaccgtggtg acggctccgg    137400
tgaccgaacc gagtccggcc aggtatatat atatatatta gttaagcccg tgctgactag    137460
ttaattgatg cattcattgt tttcatatgt acacatatta attaactctc gtctttctta    137520
tttttctcta gcccttcgga tcgagctcaa cttcggtaaa gaaacgaggc ccgaagaaaa    137580
agttgcgctc ggatgaaagg tttgagatca cagcaatcgc gcgcgatggc aagccgattg    137640
aacccatccg gacaagggat gcctttcgtg ctcagtgcgg ggttcttgtt agggacaaga    137700
tcccgatcag tatccagcaa tggttaaagt caaagaagga agaccctgag gtgccgacgt    137760
cttatgtgtc cgatatgcag aaagaagatc tttggacaac gcttaaggca aatttcaccc    137820
taccgctaga ggaggatcca gagaagccag ttaaagagga attgatcaag tctaatgctc    137880
ttaagaagat ggaagaacta ttcaggaggt ggaagaatga gctgaaaacg tttgtcgaca    137940
aagaagagac accagaattc accggccggt ttgagaagat cagagatcaa tggcccgcat    138000
ttgtggccca caagacatcg gaaaagcgta agaagatgtc agcgaaaaac aagaaaaatg    138060
ccgcgaagaa gtagcatcac catcgcacgg ggtcaggtgg ttacctcaaa gcccgacctt    138120
tgtgggacaa gggtgagaat gacctgattg ctaaagggat cgaaccagag acattgagat    138180
ggccagaccg ttgccggact tggttcttcg gggttggcgg aaccttggac cctgtatcac    138240
ggaagtgcgt ttggacggaa gagcaactgc aaatacccgt caggaagctt cggcactata    138300
tcgccacagc acaggaaggg acgttcgttc cacacaaaga aaggacgag ctcacaatgg      138360 ccctcgggaa tcttgagcac cctggacgga cacgaggcat gccaggctcc cttccgtgga    138420
acggtgggtt tccggacgca gggggttacg aaacccagga gaggaggaag aaagtggagc    138480
atagccaact gcaggcgctg cacgaaaggg tacaagggct agaggaacga gaaatagatc    138540
gcagcaaacg acctgccaaa gattcccctg aagctacccc gccatctcag cggagaagca    138600
gtgtggcttc caccgagcag actcagcagc tggagcatgt cttcacggac taccccgtgg    138660
```

```
atgctatcac atagtctcaa cattgccacc ttatgacgcg atggatgaca ttgaaagtca  138720
aggcggctgt tggctctgtt atacctaatg aacctggctc aacctaccac agccagccga  138780
ttccagaagg atatgctagg gtgatggtgg atcaaataac ggacggattt gaggacctta  138840
agcttgacca ccctacgggt gaaggggaga ttcggctggg ttcttcactg aagactccat  138900
gcctatggcg gaaggagctc atcaaccttc cgaactggac gcctcctcct cctccggcga  138960
gtcagggcac tccgcctcct ccgacgagtg atcagggcac tcagcctcct tctccggcgc  139020
gtggcgacac tccgcctcct tctccgcctg tgccgacgcg cccgagcagc cagctgcctc  139080
ctccttctcc gcctcgtcaa caagggagga agagacccgc cgccgctccg gctcctccgg  139140
cgcgtcgtcc ttctcctccg cctcataaga aaggaaagac agccgcatcc gctccgtctg  139200
ctccggcgtc tagcagtaca gccagaggca gacaatacag atacggtcct tctctgaaga  139260
ctccaaagaa gttaccatac gagaggagcc aggaggaaaa cgcgaagatc gtgcaagccg  139320
aagtgactaa cttctttgaa ggggtcaaag caagaaaaa tacacctccg gaggagaaga  139380
tagatccgat aaaagcaaag cgtactctgg ctgccatgac gaaaccacca aagtctccgg  139440
tgaaagacaa ctatgagcgc attcttacaa agtcatttat cgaagcggag cggtcgagaa  139500
gtactgtcag tgctcaaagg ttagcagaac gacgagctgg gaaaaaagtt gcccagctcg  139560
gctaacaagc gaaccaatca ttgcccccgc tccaggtgtc tagcatcgtc gcgaatcatc  139620
cgggcgggat ggtgcccggt tataacgatc ttggagatta cctgcccgac gatgcacatt  139680
ttgatttctt ggaggtggac gaacacagat acgtgtacgg gaagcctctc gtcaaagatg  139740
aaaaatctct aacaacgatg atgcaaagat tccatgattg gtatatgaaa acctgcagag  139800
agtctgaggg gaggaatatt ttgacgctca gagttaaaga ggagcatgac ctcgttggaa  139860
ttgatctgtt gaatgttcca tttgaggagt tcttcgagtt tttcaatcta aaggccctcg  139920
ataagttaat gatcacttgc tactgcctgt aagtagttgt acttctgtca ttaagtctct  139980
atatataggt cagctctttc aatgcatcta tccttaatta ttctcactgt attatgcaga  140040
ttgaagatcg tcgaattgaa gaaaagacaa atcggtgata ttgggttcat taacacaaat  140100
ctcatagatg catatatggc taaatttcag gccaaagata ccgaggccaa gctgctacaa  140160
tcgtttatat aaatcaaaaa caaagctata atactcttcc cttacaactt cgagtgagtg  140220
ttactgtctt atgcatattc ggttttcctt attagtcgag gttatagtaa tgtaattgat  140280
gagttatgca tgcgtgcgca ggttccacta tattctccta gagattaagc ttgagcaggg  140340
acttgtaacc atcttagact cgagacgaaa agatcccaag aagtacgcgg acatgactga  140400
aattctagag aagtaagtta aatctatcat tatcgcacca tatcggcaac ttcaatttgt  140460
tcatttcctg atatcaagta attgtttcct ttgtctggca gggtttagag taaattcacc  140520
tcaaaaactc cgggactgcc aaagaagctg cagtttagac aaccgaaagt aagtactata  140580
gtagcatata tgttccacgc atctcgtagt gattcaagcg ctagtttcat caataccatt  140640
tagcatgctt gctaattatc agtttgattg acctctattt cttgtaaagt ggttgtggca  140700
ggaagaagga ctaattactg tggatactac atttgcgagt ccatccgcca cacgacctat  140760
gagcgaggct actccaagaa acaatatgaa gtgcgtaaaa aattatattc acaatttat  140820 tttattacca tcatttgtgt tcagtttcat ttattcatat atatgtattg acccccttctt  140880 caaattagat atttcggatg cgagatgaac tcctagcacc agatcgtatg cgaggaattc  140940
aagaggaatt ggcagcattc tttcttgacc acgtgatcgc taaagacgga gaatactatg  141000
```

```
tggaccctgc agggttcaat tttaattagg agattatatt gtaaaagata cttatattgt  141060
atatatgtag ccagtagcgt cggatagata tacgggaact tgttgttcga ccaatctctc  141120
agagaaggag aggtggttga tatcacttct ctttgtatgc atctgttcat gacgatcttc  141180
tgtttacttc atttgcttaa ctagctagcg tgtctagtcc tctctatacg tatagtacgt  141240
agcgtcgacc aagcacggag ataagaaagg acacttctct ctattaatta gcatgctaac  141300
acaatatatg aaacacctaa attaaccacc caaaacccc aaaccccccc ctttcaaaaa  141360
aaaacccagc acctgagatg ctgacgcgtg gatgcctatt ggtgctacca accgggacca  141420
aagggcctcc tgcctgggct cgccgcaccg gccacgtgga ggcccatctg tcccggttta  141480
tgcaagaacc gggactaaag gtttagggca ttagtaccga cactttagtc ccgcttcaaa  141540
aaccggaaca aatggccctc acaaaccggg acaatagatc cttttttctac tagtgtaatt  141600
accataacta cctggtgccc aatgagcaag ctatatttga aaatgtaatc accggccgtt  141660
ggtgcgaggc atccttcctt ctcaagtttt agatacgtag gttaaccggt gatccatcct  141720
tttgttagat ttagcctatg tatatccata ttagaatcga tctaatgctg atgcatgtag  141780
gatttggatt attaatttac aagagacggg tttatggatg catgcattga ccggcggata  141840
tctggacgat ggaatgaaag aagagacact agtggaaaat gggccttttgg ccgggaccct  141900
ttagtcccgg cctgcctctg ggccgggact aaaggcccgg ccacgtcacc ccaattctca  141960
atgcctccct cgaggcttta gtcccggccc gtaaggagcc tttagtcccg gttcgtgtcc  142020
caaaccagga ctaaagggct acgcggtggg cagtggtggt ggcaaccgtt cgtatccccc  142080
tttagtcccg gttgttggct caaaccggga ctaaaggtct gacacgtggc ctgccgtagt  142140
ggtggcaacc gttggtatcc cgctttagtc ccggttggtg gctcaacccg ggactaaagg  142200
cccaaacggt ttgcatccct ctgcccaaaa ccaaaaccga ggcagagtct gtgtcgcgtc  142260
gccatttctc tgttcttcct cctctctcgc ttccctctc tccgttcttc ccctctcttc  142320
ttcccttctc ttcttccacc atgccaactc gctttggaga ggtgctcgca catggcaaga  142380
ccaagctcaa tgtcgtgtac acgaacgaga gcagggaggt gccgcatttt cttagaaagt  142440
tgaaggaacg atggtttgac gccgcagtgg atcatgagaa gttcttgggg cttgatctgg  142500
agtacacggc cgatcaatgc ggtgttgccg tcatccaact atgtttcaaa caccatgtct  142560
tgatcttcca atgggcgagg taagttttca ggctttcttt gatccaaggt aatgacattg  142620
taagtttatt tgtttcactc atagttggtt cccttcaaat atttgtagtg aaacaatttt  142680
gattagttga aggggaacac aatctgattg gaatagtgtt ccataatcta aaaaattgta  142740
ttagaatcaa ctagttttta atatgttcca ttggaatcat agttggttcg cttcaaatag  142800
ttgtagtgaa acaattttga ttagttaaag ggaacacaat ctgattggaa tagtgttcca  142860
caatctaaaa aatctgattg attcaatatg ttccattgaa atcatagttg tagtgataca  142920
attttatgcg gtgttctttg atccaaggtt atgaaaattg catatagcta gtgatctctc  142980
taggtttcat tggatagcaa tatgatatgt catagtgatg aaaattgcat atagctagtg  143040
atctctctag gttccattgg atagctatag tgatctctct aggttccatt ggatagcaat  143100
atgcaatatg tctagcttat tgaatatttg caaaaccgtg ggagaatata tatatatata  143160
tatatatata tatatatata tatatatatg tcatagttaa tttacggttt cttgatcaat  143220
tcgtaggata tgaaaattgc ataggatagc aatatgttct atttgaatcc taaagataat  143280
tttctcttta gttgtagtga acatgtttc cttattgcag cagtatgtaa catttgttcc  143340
attttaattt gtttctgttg cagtagtgac aagcattgtc cagaactcat ggacttcctt  143400
```

```
cgcagcggca tcactttttgc taccgttgac ataatgaacg acaagctgaa gatgaggtac 143460
aacttcggtc ttgagatacc aactggttgc ctcattgatc tccaaatggt attgaggctt 143520
cgacatgtca ggacttcgat ggctcatatg gcagttgcct tgatcgacga ggaatatggt 143580
aatatgaaga ccaatttccc aaagtctcag cacaaacttt gggagaaggc cccacttgat 143640
cgtatcaaca ttgagtatgc agcaaaagat gcatacgttt catacaagtt gtaccacaag 143700
attcgagtcg tcaactatgg ccagcgtcac ctcgaataag gtggacattc cgattcgagt 143760
cgtcaactat ggccagcgtc acctcgaata tatatctatg acactagtgg ggacagggcc 143820
tatagccccg acccgtaagg ggctttagtc ccggttcacc aacccgggact aaaggggcgg 143880
gactaaaggc ctaaccttttt cgtcccggcc ctcttacacg ccgggactaa aggtgctcca 143940
cgtgggcgcc tcgtagcgcc cgaggggcag gccctttagt ccccgttcgt tacacggtcc 144000
gggactaaag attttcagat tctgctggct tttggttttt tttttgaatg aaattatttt 144060
tgggttttag ggtttaggg tttaggtgtt caggagatta acgtgatgcc tcgttttgtg 144120
ttcgggaatt agttttcata taatttaaaa tagaaataat tatgcatata tatataagat 144180
taacttatct tacaagcgat catatatata taattatatg gagatatgaa ttgtcgggac 144240
tagagcccgt ctattcgatt acatggacga acatcagtaa tggcccttag ctacactaaa 144300
tcgtcctttg tcttctatag cttccgtcct cagaaatccc gcaagctcct ctgcaatagc 144360
aatcgcgcgt tgctctggta ggacctccgt cctcatggcc gtgtgctata taagaagagg 144420
agatgaatat gaatatcaat catgataaca aagaatgacg ggtaaaatag aggtgtgaat 144480
gttcattgct tacgtcgaat ctgtgctcct tgaactcaga ggtaaacgtg cgaatggtct 144540
cgcaaacata gtatccgcat agatgcgttc cccgtggctg ctggtcgcac tttacgagaa 144600
tggaatatat ataatcaaaa taataatcta gcatcataaa tgtattgaaa attaatagaa 144660
gtatatcata ctactactta cctgagccgc tctaaaggtc agcttctcag gaaagttacc 144720
gggagtcacg cacttgaacc gattccaaac cctgcccgac aaggataatg atttgctaag 144780
tttttcatta attgatatat cagaaaatca tcgaaagaga ctgattgagc gcaagaatga 144840
ttaaaattac ccttggagca tgtcctgcag gctttagaac tgttccaagg gtctcgataa 144900
tgggtcaaag gcatcaactc ttcccttatc aatttgaatg tccaacagaa tccaatggaa 144960
gctgcacatg tctatatata tatatatatg tgtgtgtgtg tgtgtgtgag agagagagag 145020
agagagagag taacttatca attcacttta taagtgaatg gacacaacag agtaaagacc 145080
ctcacctgaa gttctatgga aagagtatgt ggtcacagaa attttgatct cttagaaacc 145140
ttagaaggtt ttcctctgtc tccttgggat aattagttag cgtcgctata tgtattttag 145200
ctagatcaat aaaccgaata tttaggatgc tcttactttt acactccaga atcttcattc 145260
tgcataatag agtacaagtt atatatagac aatgaattga ataactaaa caagttatat 145320
gtagacaacg aattgaaaaa cttacagaca atagcaactc ataagcgatt tgtcgagggc 145380
gtcgccattg tacatctgga agagttcatc aaagtcgata tgaatttctt cggagcggcc 145440
gtagtactcc tgtgggacat tcagcacgat catcgttctc ccattctttg attcacttaa 145500
gtaccattta tgcaagtaac gcatatttgt tgggagatca tctttgcaga ccaaaggctc 145560
tcccatgaca aactgtggct taggggctac cacagccttg ggtatcctgt cgttttggga 145620
agccagcaaa tttcaaccca agataccata atcatctacc aactcctttg cttttttcaaa 145680
agcttgcccc tgcaccggag ggggaacatt ctcggttaac accttgaggg gtgggatcga 145740
```

```
ctgtttggcc tgttgtccaa gctgaggaac gtctgatttt tcttgcttg  tagttgaact    145800
tgatttgctc ccacttgcac ttgcatgtga cctgctcttt ttcacttcct tctgcaatgt    145860
gcgtgtatag tcatcaggct tatagtgtaa ttcatactgt gatggagtgg ttatgaagtc    145920
ttttgcccat gctatgttct tctcggtgta tttcgggcgg ggctcgggtt ccttcctttt    145980
catctgcgca tcatgctgtt cctttgctac ctggcgtttt actcggggt  acgatcataa    146040
ggtctgatag gaagattagc atgaggtacc tttgggaggg gcgacagttt gcgctttggg    146100
gagctccaac ccttagaaat catcgatgaa gcgttcttgc tggcacgctt ccgcttagta    146160
tcatgtgcgg gcggcggcag agacggacga cccaagtccg gcggcggtga tcgagatgga    146220
ctcgtgttgt gctggctgac gtcatgtgca gggcttggag gtaatggagg tgtaggtgac    146280
ctgcgacgac tcggaggcag tgttgtcctt ggggccgagc ctggaagctt gatgtagttc    146340
ttgtcccata gggtgactcc acccagtact tctccgagtg ccctctcatc ttcgggtcca    146400
gctatgtcga gctccatatc attaaacccc gtcatgattt catccacccc gactttagta    146460
aagccagctg gaatctcacg gccatgccag cgtgcatcag ggccagaagg taaagcttgt    146520
ccgacggcca ccttcataga tatgttcttg aatttctgat ggagttcaca tgatgttgac    146580
tccttgattc catccacagg gtagccggga ccgccctcta tcattcttcg ttcatcgttg    146640
ggcgggcct  cagattcagc catgctgctt ttccgcttag atggggtgcc gataatatca    146700
actgcaggat cttcctggcg cggtactcct ctaagctcat caatctgctt ctgttgctcg    146760
ttaatcttgg caagcaactg gttgaacttg tcattctcct catcctgttg ccgcttcttt    146820
gctctctctc ggcttctgta agtgtcttgg tctctggcaa acccaagcca ccacggataa    146880
aaggaccgaa gcctcgcgtt catcctccat gttcgtcatt gccgaggacc agtgtgagca    146940
aatcttctc  tctatctgcg gtgaacttt  ttcttccctc cttaatttct ttcactatcc    147000
ttttccaatt ctccctgggt atcctaagat tgtcattgca gatgaggtcc cctgttgttt    147060
cgtcgtacga cccatcatgc gcaaggaacc aatttcttgc tctcaattcc cactcatcac    147120
ggagtggttc aggtacgacg cctttatcta tcagatcttg ctctttctta tcccactttg    147180
ggatggcagt ctcatagccc cctggcccca gcttgtggtg atatttcttc ttgtcggcat    147240
ttatcttgtt cttttctgat aatgcctggg catcttctga ctccttatac tcttgaaatg    147300
ccttccagtg attcgcctgc ttggccagat acccctcgaa tactggcact ttctgtgtct    147360
tcagatagtt tttccatagc ttctccttcc agctacggaa tagttcgacc atcttcttca    147420
gagtccactg cttgactttg gccctcagtt tgtctgcggc gtcttcattc tcacattctg    147480
gcagtttgaa atgtgacatg agatcattcc aaagattatc tttgtacctt tcggcgacat    147540
agtcactatc ggctgcccct ttgcgcttgt tccattcccg aacgctgatc gggacgtgat    147600
ccctaacgag gactctgcat tgcttcttga atgtgtcagc atcattctta ggaagcttgg    147660
gttcgcccgt aggaaatatc acctcaaatg tgtaatgcgt ccgtgcatcc aactttctag    147720
tcgggcctgg tttcatagtt ttgctcgatg tggaggccta agaggagaa  acattcgtca    147780
aatgaatgta tatgtataca gtatagagct atctccaata tttttcacat attacaagtg    147840
attgtcaaac ttcatatgta tacctcgccg gacttctcct cttcaccggc ttctccatca    147900
gtggagctat caccttctcc gtcattggac ctatctcctg ccccatcggc ttcatcttcg    147960
tgtcgctcga cctctattcc aacgtctgg  tttagatatg acgacggata ttcggctggt    148020
tcaacgtcgg ggccgtcttt gattatatct tccagaagtt cttcctcttc gaggttcctg    148080
atatgtggat ccatagttct gcaaaaaacg gattctctta acctttgtac caaaaaccaa    148140
```

```
agtaggagta cttttccaat ttgacactcc tagatttctg catagtattc aaagtaggag   148200
tacttttcca atttgagcat tcaataagca aaaccaaaac ataaaataaa atagtattca   148260
aattagcatg cattcaatta taagctaata catcatcact tttgtccgta catcgtcgaa   148320
tattatcatt aatactcctc gaatactatc atatatatag catcactaat acatctagaa   148380
ccgtagcgcc cgacgggtat cgtgttgggg aacgtcgcat gggaaacaaa aaatttccta   148440
cgcacacgaa gacctatcat ggtgatgtcc atctacgaga ggggatgagt gatctacgta   148500
cccttgtaga ccgtacaaca gaagcgttag tgaacgcgat tgatgtagtg aacgtcctc    148560 acgtccctcg atccgcccag cgaacaatcc cgcgatcagt cccactatct agtaccgaac   148620
ggatggcacc tccgcgttca gtacacgtac aactcgacga tgatctcggc cttcttgatc   148680
cagcaagaga gacggagagg tagaagagtt ctccggcagc gtgacggtgc tccggagatt   148740
ggggatgacc ttgtctcagc agggctccgc ccgagctccg cagaaacgcg atctagagga   148800 aaaccgtgg aggtatatgt tcgggctgcc atggaaaagt cgtctcaaat cagccctaaa    148860
acctccgtat ataggtgg gagaggggc cttgccttgg ggctcaagga gccccaaggg     148920
ggtcggccga gccaaggggg aaggtctccc cccaaaccga gttggacttg gtttggtggg   148980
ttggagtcct tccttccctt cccacctcaa ttttttttctt tctctttgat ttttcttcca   149040
atgcgcatag ggcccttttg ggctgtccca cgagcccact aagggctggt gcgccaccct   149100
caaggcctat gggcttcccc ggggtgggtt gcccccccgg tgaactccg gaacccattc    149160 gtcattcccg gtacattccc ggtaactcca acaaccttcc ggtaatcaaa tgaggtcatc   149220
ctatatatca atcttcgttt ccggaccatt ccggaaaccc tcgtgacgtt cgtgatctca   149280
tcagggactc cgaacaacat ttggtaacca accatataac tcaaatacac ataaaacaac   149340
gtcgaacctt aagtgtgcag accctgcggg ttcgagaact atgtagacat gacccgagag   149400
actcctcggt caatatccaa tagcaggacc agcatgccca tattggatcc tacatattct   149460
acgaagatct tatcgtttga acctcagtgc caaggattca tataatcccg tatgtcattc   149520
cctttgtcct tcggtatgtt acttgcccga gattcgatcg tcagtatcca catacctatt   149580
tcaatctcgt ttaccggcaa gtctctttac tcattccgta atacaagatc ccgcaactta   149640
cactaagtca cattgcttgc aaggcttgtg tgtgatgttg tattatcgag tgggccccga   149700
gatacctccc cgtcacacat agtgacaaat cccagtcttg atccatacta actcaactaa   149760
caccttcgga gatacttgta gagcatcttt atagtcaccc agttatgttg cgacgtttca   149820
tacacacaaa gtattcctcc ggtgtcagtg agttaaatga tctcatggtc ataggaacaa   149880
atacttgaca cgcagaaaac agtagcaaca aaatgacacg atcaacatgc tacatctatt   149940
agtttgggtc tagtccatca cgtgattctc ctaatgacgt gatctagtta tcatgcaaca   150000
acacattgtt cataatcaga agacactgac tatctttgat caactggcta gccaactaga   150060
ggcttgctat ggacagtgtt ttgtctatgt atccacacat gtaaatgagt cttcattcaa   150120
tacaattata gcatggagaa taaacgatta tcttgataca ggaattataa taataactat   150180
atttattatt gcctctaggg cataattcca aaagtctccc acttgcacta gagtcaataa   150240
tctagccctc acatcatcat gggaattaca ttgtaataaa tctaacaccc atacagttct   150300
ggtgttgatc atgctttggc cgtggaagag gtttagtcag ggtctgctac attcagatct   150360
gtgtgcactt tgcatatatt tacgtcttgt ccttcgacat agtcgcggat gaggttgaag   150420
cgtcgtttga tgtgtctgga cttcttggaa accgtggttc ctttgctaag gcaatggcac   150480
```

-continued

```
ccatgttgtc acagaacaag gttattggat tcagtgcgct tggcacgact ccaagatccg    150540
tcatgaactg cttcatccag acaccctcct tagctgcctc cgaggcagcc atgtactccg    150600
cttcacatgt agaatctgct acgacgcttt gcttggaact gcaccagctt accgcacccc    150660
cattaagaat aaatatgtat ccggtttgcg acttagagtc atccggatct gtgtcaaagc    150720
ttgcatcgac gtaaccttt acgacgagct tcgtcacctc catacacgag aaacatctcc     150780
ttagtccttt tcaggtactt caggatattc ttgaccgctg tcgagtgatc cactcctgga    150840
ttactctaga acctgcctgc catacttatg gccaggctaa cgtccggtct agtgcacatc    150900
attgcataca tgatagagcc tatggctgaa gcataggga cggagcgcat atgctctcta     150960
tcctcatcag ttgctgggca ctgagtctta ctcaatctcg taccttgtaa aactggcaag    151020
aaccccttct tggactgttc cattttgaac ctcttcaaaa ctttatcaag gtatgtgctt    151080
tgtgaaagtc ctatcaggcg ttttgatcta tccctataga tcttaatgcc tagaatgtaa    151140
gcagcttctc ctaggtcctt catagagaaa cttttattca agtaatcctt tatgctctcc    151200
aaaaactcta cgttgtttcc aatcagcaat atgtcatcca catataatat cagaaacgcc    151260
atagagctcc cactcacttt cttgtaaata caagattctc caaccacttg tataaaccca    151320
aatgctttga tcacctcatc aaagcgtttg ttccaactcc aagatgcttg caccagtcca    151380
taaatggatc gctggagctt gcacaccttg ttagcattct taggatcgac aaaacctacg    151440
ggttgtatca tatacaattc ttccttaagg aaaccgttaa ggaacgccgt ttttgacatc    151500
catctgccag atttcataat cgaaaatgc agctattact aacatgattc tgacggactt     151560
aagcatcgct acgggtgaga atgtctcatc gtagtcaact ccttgaactt gtgaaaaacc    151620
cttttccaca agtcgagctt tataaacggt cacattgccg tcagcgtccg tcttcctctt    151680
aaagatcctt ttgttctgaa tagccttgcg gccctcaggc agtaccctcc aaagtcgaca    151740
ctttgttctc atacatggat cctatctcgg acttcatggc ttctagccat ttgttggaat    151800
ctgggcccac cattgcttct tcataattcg caagttcatt gttgtccaac aacatgattg    151860
ataagacggg attaccgtac cactctggag cagcacgtgg tctcgtcgac ctgcgtggtt    151920
cgacagaaac ttgaaccgga ggttcatgat catcatcatt aacttcctcc tcaaccggcg    151980
tcgcaataac acaggttttc cccttgccct gcgccaccat ccagagggat gagaggttcg    152040
ataacctcgt caagttctat cttcctccca ctcaattctc tcgagagaaa ctccttctcg    152100
agaaaagctc cgttttagc aataaacact ttgccctcgg atttaagata gaaggtgtac     152160
ccaactgtct cttttgggta acctatgaag acgcactttt ccgctttggg ttccagtttt    152220
ttaggctg                                                              152228
```

<210> SEQ ID NO 5
<211> LENGTH: 3126
<212> TYPE: DNA
<213> ORGANISM: Hordeum vulgare
<220> FEATURE:
<221> NAME/KEY: CDS
<222> LOCATION: (1)..(3126)

<400> SEQUENCE: 5

```
atg ccg gat cca gtt act att agt gct gct gta gga tgg ggc gta tcc      48
Met Pro Asp Pro Val Thr Ile Ser Ala Ala Val Gly Trp Gly Val Ser
1               5                   10                  15 gca gta ggc tgg ctc gcc tct ccc atc att tca agg gtt gtc aac aaa      96
Ala Val Gly Trp Leu Ala Ser Pro Ile Ile Ser Arg Val Val Asn Lys
            20                  25                  30
```

```
ggt ttc gcc cac ctc gac ttc gat gca gca gag aag ctg aag ata ctt       144
Gly Phe Ala His Leu Asp Phe Asp Ala Ala Glu Lys Leu Lys Ile Leu
         35                  40                  45 gat ata caa gtt cta caa ctg cag cgc gtg ata gaa gta gtc gat gag       192
Asp Ile Gln Val Leu Gln Leu Gln Arg Val Ile Glu Val Val Asp Glu
 50                  55                  60 agc acg tac agg ctt cgc ttg gag cca ctg tta gac aag ctt aga tct       240
Ser Thr Tyr Arg Leu Arg Leu Glu Pro Leu Leu Asp Lys Leu Arg Ser
 65                  70                  75                  80 gct ctt tat gaa gcc gaa gac atc ttg gat gat ttt gat tat cag cgt       288
Ala Leu Tyr Glu Ala Glu Asp Ile Leu Asp Asp Phe Asp Tyr Gln Arg
                 85                  90                  95 ctc gag aag cag atc cat gtt ggg tct agt tcc aca cgt aaa cgc aag       336
Leu Glu Lys Gln Ile His Val Gly Ser Ser Ser Thr Arg Lys Arg Lys
            100                 105                 110 ata gat tcg ctg gag aag aat cat cgg tct gcc atg ccg agt tcc tcc       384
Ile Asp Ser Leu Glu Lys Asn His Arg Ser Ala Met Pro Ser Ser Ser
                115                 120                 125 cta aaa gat aag atg gaa aca ttc ccg agg att tca tcg aag gga aag       432
Leu Lys Asp Lys Met Glu Thr Phe Pro Arg Ile Ser Ser Lys Gly Lys
130                 135                 140 gag act atc aat aat tta ctg agc cag ggg att gga aca tca aaa gtg       480
Glu Thr Ile Asn Asn Leu Leu Ser Gln Gly Ile Gly Thr Ser Lys Val
145                 150                 155                 160 gag ttg aag aaa agc cta gag aaa ata gaa aat acc ata aac gat gca       528
Glu Leu Lys Lys Ser Leu Glu Lys Ile Glu Asn Thr Ile Asn Asp Ala
                165                 170                 175 tgt aaa gtt ttg gaa caa ctg aac ttg ccg agt gta tgt aat gat aat       576
Cys Lys Val Leu Glu Gln Leu Asn Leu Pro Ser Val Cys Asn Asp Asn
                180                 185                 190 ggg aga cga ggt gtt gct acc aat tct cgt agt gca gtc act act gca       624
Gly Arg Arg Gly Val Ala Thr Asn Ser Arg Ser Ala Val Thr Thr Ala
            195                 200                 205 ggt cct cct cta cga gta att ggt cga gat cag gat cgt gac aag atc       672
Gly Pro Pro Leu Arg Val Ile Gly Arg Asp Gln Asp Arg Asp Lys Ile
210                 215                 220 ata gca atg ctt cat gag aag gat gac cgg tgt caa gtc aat ggt aca       720
Ile Ala Met Leu His Glu Lys Asp Asp Arg Cys Gln Val Asn Gly Thr
225                 230                 235                 240 tct tat tct gta att ggc att cat ggc gtc gcc ggg tct ggg aaa tca       768
Ser Tyr Ser Val Ile Gly Ile His Gly Val Ala Gly Ser Gly Lys Ser
                245                 250                 255 aca ctt gca cag tat gtt tat gat cat gag aaa aag tgc aag caa ggt       816
Thr Leu Ala Gln Tyr Val Tyr Asp His Glu Lys Lys Cys Lys Gln Gly
                260                 265                 270 aaa aga gaa ggc tat ttt gat gtt ctc atg tgg att cat gtt tct caa       864
Lys Arg Glu Gly Tyr Phe Asp Val Leu Met Trp Ile His Val Ser Gln
            275                 280                 285 aaa atc ggt ttg gag tcc agt ttc agg gac atg ttt gag ggg gct aca       912
Lys Ile Gly Leu Glu Ser Ser Phe Arg Asp Met Phe Glu Gly Ala Thr
290                 295                 300 ggg aaa gca tgc ccg aat ttt aat agt ctt aac gtc tta aag gaa aag       960
Gly Lys Ala Cys Pro Asn Phe Asn Ser Leu Asn Val Leu Lys Glu Lys
305                 310                 315                 320 ttg gag gag gaa cta cgt gga aaa cgg att ttt ttg gta cta gat gat      1008
Leu Glu Glu Glu Leu Arg Gly Lys Arg Ile Phe Leu Val Leu Asp Asp
                325                 330                 335 gtc tgg tac aac agt aag aat tca gga gac cgt gaa gaa ctg cag aag      1056
Val Trp Tyr Asn Ser Lys Asn Ser Gly Asp Arg Glu Glu Leu Gln Lys
            340                 345                 350
```

|  |  |
|---|---|
| tta att tct ccg ttg aat gtt ggg aag gca gga agc aga atc ttg gtg<br>Leu Ile Ser Pro Leu Asn Val Gly Lys Ala Gly Ser Arg Ile Leu Val<br>      355                        360                  365 | 1104 |
| act agt cga act gaa gct gca tta gta gct ctc cgt gct gca aaa gag<br>Thr Ser Arg Thr Glu Ala Ala Leu Val Ala Leu Arg Ala Ala Lys Glu<br>370                      375                      380 | 1152 |
| gga tgt atc cca ata tct aac ctg gat gat aaa gtt ttc ctt aaa atg<br>Gly Cys Ile Pro Ile Ser Asn Leu Asp Asp Lys Val Phe Leu Lys Met<br>385                      390                      395                  400 | 1200 |
| ttc atg cat tat gca ctt cca cat gca tgg cca gtt ggc aat gat cga<br>Phe Met His Tyr Ala Leu Pro His Ala Trp Pro Val Gly Asn Asp Arg<br>                  405                      410                  415 | 1248 |
| aga aaa ctt gaa atg att gga gag gac att gca aaa aag ctg aag ggt<br>Arg Lys Leu Glu Met Ile Gly Glu Asp Ile Ala Lys Lys Leu Lys Gly<br>                  420                      425                  430 | 1296 |
| tca cct ctg gca gct aga ata gtg ggt tca cgg ctc ggt gat aat cca<br>Ser Pro Leu Ala Ala Arg Ile Val Gly Ser Arg Leu Gly Asp Asn Pro<br>              435                      440                      445 | 1344 |
| aat gtt gaa ttt tgg agg aga gag aaa gac cgg gat ctt atg aac gag<br>Asn Val Glu Phe Trp Arg Arg Glu Lys Asp Arg Asp Leu Met Asn Glu<br>450                      455                      460 | 1392 |
| acg atg gga gca ctt tgg tgg agc tac cag tac ctt gat gag cag gtc<br>Thr Met Gly Ala Leu Trp Trp Ser Tyr Gln Tyr Leu Asp Glu Gln Val<br>465                      470                      475                  480 | 1440 |
| agg cga tgc ttc gct tac atc agc att ttt ccc aga cgt cat cat ttg<br>Arg Arg Cys Phe Ala Tyr Ile Ser Ile Phe Pro Arg Arg His His Leu<br>                      485                      490                      495 | 1488 |
| aaa cgt gat gac tta att aac cta tgg gtg gcc gaa gga ttt ata aag<br>Lys Arg Asp Asp Leu Ile Asn Leu Trp Val Ala Glu Gly Phe Ile Lys<br>              500                      505                  510 | 1536 |
| aca agt aaa gct gaa gag gaa atg gaa gat gtt gcc tcg gaa tac ttt<br>Thr Ser Lys Ala Glu Glu Glu Met Glu Asp Val Ala Ser Glu Tyr Phe<br>        515                      520                      525 | 1584 |
| gat gag ctg ctt tcg ttc cca ttt ctg caa tta gga ggg aaa gat gag<br>Asp Glu Leu Leu Ser Phe Pro Phe Leu Gln Leu Gly Gly Lys Asp Glu<br>530                      535                      540 | 1632 |
| cta ttt gca cgt gag gtc gat tac ttt ata att cat gat ctg ttg tat<br>Leu Phe Ala Arg Glu Val Asp Tyr Phe Ile Ile His Asp Leu Leu Tyr<br>545                      550                      555                  560 | 1680 |
| gat tta gca gag gag gtt gct gga aga gat tgc ttc agg ata gag aaa<br>Asp Leu Ala Glu Glu Val Ala Gly Arg Asp Cys Phe Arg Ile Glu Lys<br>                  565                      570                  575 | 1728 |
| ggt ttc aca gga gaa gtc cct ccg gat gtt cgc tat ctt ttt gtt ggg<br>Gly Phe Thr Gly Glu Val Pro Pro Asp Val Arg Tyr Leu Phe Val Gly<br>                    580                      585                  590 | 1776 |
| act tac gat aaa gag atg ctt act gag aag ata tcc agg ttg caa aat<br>Thr Tyr Asp Lys Glu Met Leu Thr Glu Lys Ile Ser Arg Leu Gln Asn<br>              595                      600                  605 | 1824 |
| tta cgc act ctc ttc gtc gat aag tac ata cag att tta tca ccc aag<br>Leu Arg Thr Leu Phe Val Asp Lys Tyr Ile Gln Ile Leu Ser Pro Lys<br>610                      615                      620 | 1872 |
| tac gat gat ttt gtt agt atg gtg act atg ttg atg ggg ctg cgg aaa<br>Tyr Asp Asp Phe Val Ser Met Val Thr Met Leu Met Gly Leu Arg Lys<br>625                      630                      635                  640 | 1920 |
| ttg agg gta ctg aat tta cat ttc act gga tat ggt att cct aaa ttc<br>Leu Arg Val Leu Asn Leu His Phe Thr Gly Tyr Gly Ile Pro Lys Phe<br>                  645                      650                      655 | 1968 |
| tca ttg ccg gat tct att ctt cag tgg aag cat ctg cgt tac ttt gct<br>Ser Leu Pro Asp Ser Ile Leu Gln Trp Lys His Leu Arg Tyr Phe Ala | 2016 |

-continued

```
          660             665             670
ttt ggg gtg tcc ccg ttt acc aag cta act tta cca tgc gct ttt acc      2064
Phe Gly Val Ser Pro Phe Thr Lys Leu Thr Leu Pro Cys Ala Phe Thr
                675             680             685 aag ctt tac cac ttg cat gtg gta gat ttc ggt gat tgc aat agt ttg      2112
Lys Leu Tyr His Leu His Val Val Asp Phe Gly Asp Cys Asn Ser Leu
            690             695             700 gag ttt tct cgt ggt gaa tac atg atg aac ctg gtc aat ttg cgc cgt      2160
Glu Phe Ser Arg Gly Glu Tyr Met Met Asn Leu Val Asn Leu Arg Arg
705             710             715             720 gta atc tac aag aat tat ctc gac ttt ccg aac att ggc agg ctg aca      2208
Val Ile Tyr Lys Asn Tyr Leu Asp Phe Pro Asn Ile Gly Arg Leu Thr
                725             730             735 tgg ctg caa tcg ttg ccg tgc ttc aga ata agg aag aaa cat ggg tat      2256
Trp Leu Gln Ser Leu Pro Cys Phe Arg Ile Arg Lys Lys His Gly Tyr
            740             745             750 gaa tca cat cag ctg aaa cac cta aac aag ctt caa ggc agg ctg tac      2304
Glu Ser His Gln Leu Lys His Leu Asn Lys Leu Gln Gly Arg Leu Tyr
        755             760             765 att ggt ggt ctt cag aat gtt gag agc aag gag gaa gct ctt aat gtg      2352
Ile Gly Gly Leu Gln Asn Val Glu Ser Lys Glu Glu Ala Leu Asn Val
770             775             780 aac ctt gca gcc aag gaa aaa ctc aca gaa gtg gta ctg cgc tgg agt      2400
Asn Leu Ala Ala Lys Glu Lys Leu Thr Glu Val Val Leu Arg Trp Ser
785             790             795             800 gat aat agc tgc agt cca gaa att caa gca gag gta ctt gag ggc ctt      2448
Asp Asn Ser Cys Ser Pro Glu Ile Gln Ala Glu Val Leu Glu Gly Leu
                805             810             815 tgt cct tca aag tat ctt gaa ata cta gaa atc aag tta tac aat ggc      2496
Cys Pro Ser Lys Tyr Leu Glu Ile Leu Glu Ile Lys Leu Tyr Asn Gly
            820             825             830 atg aag ttt cca aat tgg atg acg agt aag cat aag ggt ggg cca aag      2544
Met Lys Phe Pro Asn Trp Met Thr Ser Lys His Lys Gly Gly Pro Lys
        835             840             845 aac ctg caa gaa ctt aga ttc aga cag agc acc ctg gga tct gct cct      2592
Asn Leu Gln Glu Leu Arg Phe Arg Gln Ser Thr Leu Gly Ser Ala Pro
850             855             860 gat gtt ggg gct ttc att cac ctt cag tcg tta ttt att tat caa tgc      2640
Asp Val Gly Ala Phe Ile His Leu Gln Ser Leu Phe Ile Tyr Gln Cys
865             870             875             880 agc tgg gat acc tta cca ggg aat atg gag cac ctc aca gcg ctc aag      2688
Ser Trp Asp Thr Leu Pro Gly Asn Met Glu His Leu Thr Ala Leu Lys
                885             890             895 aaa ctg gag ata cgg tca tgc aat aat att cgg tcg ctt cca aca ctg      2736
Lys Leu Glu Ile Arg Ser Cys Asn Asn Ile Arg Ser Leu Pro Thr Leu
            900             905             910 ccc aag tcc ctt gag cag ttt gcg atc tgg tcc tgc agc ttg gat gct      2784
Pro Lys Ser Leu Glu Gln Phe Ala Ile Trp Ser Cys Ser Leu Asp Ala
        915             920             925 tta ccg ggc aat atg gag cac ctc aca gca ctc aag aaa ctg gag ata      2832
Leu Pro Gly Asn Met Glu His Leu Thr Ala Leu Lys Lys Leu Glu Ile
930             935             940 cgg tca tgc aat aat att cgg tgg ctt cca aca ctg ccc aag tcc ctt      2880
Arg Ser Cys Asn Asn Ile Arg Trp Leu Pro Thr Leu Pro Lys Ser Leu
945             950             955             960 gag cag ttt gcg atc tcg cgc tgc agc ttg gat gct tta ccg ggc aat      2928
Glu Gln Phe Ala Ile Ser Arg Cys Ser Leu Asp Ala Leu Pro Gly Asn
                965             970             975 atg gag cac ctc aca gcg ctc aag aaa ctg gat ata tgg tca tgc gag      2976
```

```
                Met Glu His Leu Thr Ala Leu Lys Lys Leu Asp Ile Trp Ser Cys Glu
                            980                 985                 990 aat ata cgg tcg ctt cca aca cta ccc aag tct ctt gag gag ttt aca         3024
Asn Ile Arg Ser Leu Pro Thr Leu Pro Lys Ser Leu Glu Glu Phe Thr
        995                 1000                1005 gtc tgg aac tgc act agt gag ttc atg caa tct tgt atg acg act             3069
Val Trp Asn Cys Thr Ser Glu Phe Met Gln Ser Cys Met Thr Thr
1010                1015                1020 gat gat cca aac tgg cag aag att gag cac gtt cca aac aaa aaa             3114
Asp Asp Pro Asn Trp Gln Lys Ile Glu His Val Pro Asn Lys Lys
    1025                1030                1035 att gga ttt cta                                                         3126
Ile Gly Phe Leu
    1040

<210> SEQ ID NO 6
<211> LENGTH: 1042
<212> TYPE: PRT
<213> ORGANISM: Hordeum vulgare

<400> SEQUENCE: 6

Met Pro Asp Pro Val Thr Ile Ser Ala Ala Val Gly Trp Gly Val Ser
1               5                   10                  15

Ala Val Gly Trp Leu Ala Ser Pro Ile Ile Ser Arg Val Val Asn Lys
            20                  25                  30

Gly Phe Ala His Leu Asp Phe Asp Ala Ala Glu Lys Leu Lys Ile Leu
        35                  40                  45

Asp Ile Gln Val Leu Gln Leu Gln Arg Val Ile Glu Val Val Asp Glu
    50                  55                  60

Ser Thr Tyr Arg Leu Arg Leu Glu Pro Leu Leu Asp Lys Leu Arg Ser
65              70                  75                  80

Ala Leu Tyr Glu Ala Glu Asp Ile Leu Asp Asp Phe Asp Tyr Gln Arg
            85                  90                  95

Leu Glu Lys Gln Ile His Val Gly Ser Ser Ser Thr Arg Lys Arg Lys
        100                 105                 110

Ile Asp Ser Leu Glu Lys Asn His Arg Ser Ala Met Pro Ser Ser Ser
    115                 120                 125

Leu Lys Asp Lys Met Glu Thr Phe Pro Arg Ile Ser Ser Lys Gly Lys
130                 135                 140

Glu Thr Ile Asn Asn Leu Leu Ser Gln Gly Ile Gly Thr Ser Lys Val
145                 150                 155                 160

Glu Leu Lys Lys Ser Leu Glu Lys Ile Glu Asn Thr Ile Asn Asp Ala
                165                 170                 175

Cys Lys Val Leu Glu Gln Leu Asn Leu Pro Ser Val Cys Asn Asp Asn
            180                 185                 190

Gly Arg Arg Gly Val Ala Thr Asn Ser Arg Ser Ala Val Thr Thr Ala
        195                 200                 205

Gly Pro Pro Leu Arg Val Ile Gly Arg Asp Gln Asp Arg Asp Lys Ile
    210                 215                 220

Ile Ala Met Leu His Glu Lys Asp Asp Arg Cys Gln Val Asn Gly Thr
225                 230                 235                 240

Ser Tyr Ser Val Ile Gly Ile His Gly Val Ala Gly Ser Gly Lys Ser
                245                 250                 255

Thr Leu Ala Gln Tyr Val Tyr Asp His Glu Lys Lys Cys Lys Gln Gly
            260                 265                 270

Lys Arg Glu Gly Tyr Phe Asp Val Leu Met Trp Ile His Val Ser Gln
```

-continued

```
            275                 280                 285
Lys Ile Gly Leu Glu Ser Ser Phe Arg Asp Met Phe Glu Gly Ala Thr
290                 295                 300
Gly Lys Ala Cys Pro Asn Phe Asn Ser Leu Asn Val Leu Lys Glu Lys
305                 310                 315                 320
Leu Glu Glu Glu Leu Arg Gly Lys Arg Ile Phe Leu Val Leu Asp Asp
                325                 330                 335
Val Trp Tyr Asn Ser Lys Asn Ser Gly Asp Arg Glu Glu Leu Gln Lys
                340                 345                 350
Leu Ile Ser Pro Leu Asn Val Gly Lys Ala Gly Ser Arg Ile Leu Val
                355                 360                 365
Thr Ser Arg Thr Glu Ala Ala Leu Val Ala Leu Arg Ala Ala Lys Glu
370                 375                 380
Gly Cys Ile Pro Ile Ser Asn Leu Asp Asp Lys Val Phe Leu Lys Met
385                 390                 395                 400
Phe Met His Tyr Ala Leu Pro His Ala Trp Pro Val Gly Asn Asp Arg
                405                 410                 415
Arg Lys Leu Glu Met Ile Gly Glu Asp Ile Ala Lys Lys Leu Lys Gly
                420                 425                 430
Ser Pro Leu Ala Ala Arg Ile Val Gly Ser Arg Leu Gly Asp Asn Pro
                435                 440                 445
Asn Val Glu Phe Trp Arg Arg Glu Lys Asp Arg Asp Leu Met Asn Glu
450                 455                 460
Thr Met Gly Ala Leu Trp Trp Ser Tyr Gln Tyr Leu Asp Glu Gln Val
465                 470                 475                 480
Arg Arg Cys Phe Ala Tyr Ile Ser Ile Phe Pro Arg Arg His His Leu
                485                 490                 495
Lys Arg Asp Asp Leu Ile Asn Leu Trp Val Ala Glu Gly Phe Ile Lys
                500                 505                 510
Thr Ser Lys Ala Glu Glu Met Gly Asp Val Ala Ser Glu Tyr Phe
                515                 520                 525
Asp Glu Leu Leu Ser Phe Pro Phe Leu Gln Leu Gly Gly Lys Asp Glu
                530                 535                 540
Leu Phe Ala Arg Glu Val Asp Tyr Phe Ile Ile His Asp Leu Leu Tyr
545                 550                 555                 560
Asp Leu Ala Glu Glu Val Ala Gly Arg Asp Cys Phe Arg Ile Glu Lys
                565                 570                 575
Gly Phe Thr Gly Glu Val Pro Pro Asp Val Arg Tyr Leu Phe Val Gly
                580                 585                 590
Thr Tyr Asp Lys Glu Met Leu Thr Glu Lys Ile Ser Arg Leu Gln Asn
                595                 600                 605
Leu Arg Thr Leu Phe Val Asp Lys Tyr Ile Gln Ile Leu Ser Pro Lys
            610                 615                 620
Tyr Asp Asp Phe Val Ser Met Val Thr Met Leu Met Gly Leu Arg Lys
625                 630                 635                 640
Leu Arg Val Leu Asn Leu His Phe Thr Gly Tyr Gly Ile Pro Lys Phe
                645                 650                 655
Ser Leu Pro Asp Ser Ile Leu Gln Trp Lys His Leu Arg Tyr Phe Ala
                660                 665                 670
Phe Gly Val Ser Pro Phe Thr Lys Leu Thr Leu Pro Cys Ala Phe Thr
            675                 680                 685
Lys Leu Tyr His Leu His Val Val Asp Phe Gly Asp Cys Asn Ser Leu
            690                 695                 700
```

```
Glu Phe Ser Arg Gly Glu Tyr Met Met Asn Leu Val Asn Leu Arg Arg
705                 710                 715                 720

Val Ile Tyr Lys Asn Tyr Leu Asp Phe Pro Asn Ile Gly Arg Leu Thr
            725                 730                 735

Trp Leu Gln Ser Leu Pro Cys Phe Arg Ile Arg Lys Lys His Gly Tyr
        740                 745                 750

Glu Ser His Gln Leu Lys His Leu Asn Lys Leu Gln Gly Arg Leu Tyr
    755                 760                 765

Ile Gly Gly Leu Gln Asn Val Glu Ser Lys Glu Glu Ala Leu Asn Val
770                 775                 780

Asn Leu Ala Ala Lys Glu Lys Leu Thr Glu Val Val Leu Arg Trp Ser
785                 790                 795                 800

Asp Asn Ser Cys Ser Pro Glu Ile Gln Ala Glu Val Leu Glu Gly Leu
                805                 810                 815

Cys Pro Ser Lys Tyr Leu Glu Ile Leu Glu Ile Lys Leu Tyr Asn Gly
            820                 825                 830

Met Lys Phe Pro Asn Trp Met Thr Ser Lys His Lys Gly Gly Pro Lys
        835                 840                 845

Asn Leu Gln Glu Leu Arg Phe Arg Gln Ser Thr Leu Gly Ser Ala Pro
    850                 855                 860

Asp Val Gly Ala Phe Ile His Leu Gln Ser Leu Phe Ile Tyr Gln Cys
865                 870                 875                 880

Ser Trp Asp Thr Leu Pro Gly Asn Met Glu His Leu Thr Ala Leu Lys
                885                 890                 895

Lys Leu Glu Ile Arg Ser Cys Asn Ile Arg Ser Leu Pro Thr Leu
            900                 905                 910

Pro Lys Ser Leu Glu Gln Phe Ala Ile Trp Ser Cys Ser Leu Asp Ala
        915                 920                 925

Leu Pro Gly Asn Met Glu His Leu Thr Ala Leu Lys Lys Leu Glu Ile
930                 935                 940

Arg Ser Cys Asn Asn Ile Arg Trp Leu Pro Thr Leu Pro Lys Ser Leu
945                 950                 955                 960

Glu Gln Phe Ala Ile Ser Arg Cys Ser Leu Asp Ala Leu Pro Gly Asn
                965                 970                 975

Met Glu His Leu Thr Ala Leu Lys Lys Leu Asp Ile Trp Ser Cys Glu
            980                 985                 990

Asn Ile Arg Ser Leu Pro Thr Leu Pro Lys Ser Leu Glu Glu Phe Thr
        995                 1000                 1005

Val Trp Asn Cys Thr Ser Glu Phe Met Gln Ser Cys Met Thr Thr
1010                 1015                 1020

Asp Asp Pro Asn Trp Gln Lys Ile Glu His Val Pro Asn Lys Lys
    1025                 1030                 1035

Ile Gly Phe Leu
     1040

<210> SEQ ID NO 7
<211> LENGTH: 3126
<212> TYPE: DNA
<213> ORGANISM: Hordeum vulgare
<220> FEATURE:
<221> NAME/KEY: CDS
<222> LOCATION: (1)..(3126)

<400> SEQUENCE: 7 atg ccg gat cca gtt act att agt gct gct gta gga tgg ggc gta tcc      48
```

```
Met Pro Asp Pro Val Thr Ile Ser Ala Ala Val Gly Trp Gly Val Ser
1               5                   10                  15 gca gta ggc tgg ctc gcc tct ccc atc att tca agg gtt gtc aac aaa         96
Ala Val Gly Trp Leu Ala Ser Pro Ile Ile Ser Arg Val Val Asn Lys
            20                  25                  30 ggt ttc gcc cac ctc gac ttc gat gca gca gag aag ctg aag ata ctt        144
Gly Phe Ala His Leu Asp Phe Asp Ala Ala Glu Lys Leu Lys Ile Leu
        35                  40                  45 gat ata caa gtt cta caa ctg cag cgc gtg ata gaa gta gtc gat gag        192
Asp Ile Gln Val Leu Gln Leu Gln Arg Val Ile Glu Val Val Asp Glu
    50                  55                  60 agc acg tac agg ctt cgc ttg gag cca ctg tta gac aag ctt aga tct        240
Ser Thr Tyr Arg Leu Arg Leu Glu Pro Leu Leu Asp Lys Leu Arg Ser
65                  70                  75                  80 gct ctc tat gaa gcc gaa gac atc ttg gat gat ttt gat tat gag cgt        288
Ala Leu Tyr Glu Ala Glu Asp Ile Leu Asp Asp Phe Asp Tyr Glu Arg
                85                  90                  95 ctc gag aag cag atc cat gtt ggg tct agt tcc aca cgt aaa cgc aag        336
Leu Glu Lys Gln Ile His Val Gly Ser Ser Ser Thr Arg Lys Arg Lys
            100                 105                 110 ata gat tcg ctg gag aag aat cat cgg tct gcc atg ccg agt tcc tcc        384
Ile Asp Ser Leu Glu Lys Asn His Arg Ser Ala Met Pro Ser Ser Ser
        115                 120                 125 cta aaa gat aag atg gaa aca ttc ccg agg att tca tct aag gga aag        432
Leu Lys Asp Lys Met Glu Thr Phe Pro Arg Ile Ser Ser Lys Gly Lys
    130                 135                 140 gag act atc aag aat tta ctg agc cag ggg att gga aca tca aaa gtg        480
Glu Thr Ile Lys Asn Leu Leu Ser Gln Gly Ile Gly Thr Ser Lys Val
145                 150                 155                 160 gag ttg aag aaa agc cta gag aaa ata gaa aat acc ata aac gat gca        528
Glu Leu Lys Lys Ser Leu Glu Lys Ile Glu Asn Thr Ile Asn Asp Ala
                165                 170                 175 tgt aaa gtt ttg gaa caa ctg aac ttg ccg agt gta tgt aat gat aat        576
Cys Lys Val Leu Glu Gln Leu Asn Leu Pro Ser Val Cys Asn Asp Asn
            180                 185                 190 ggg aga cga ggt gtt gct acc aat tct cgt agt gca gtc act act gca        624
Gly Arg Arg Gly Val Ala Thr Asn Ser Arg Ser Ala Val Thr Thr Ala
        195                 200                 205 ggt cct cct cta cga gta att ggt cga gat cag gat cgt gac aag atc        672
Gly Pro Pro Leu Arg Val Ile Gly Arg Asp Gln Asp Arg Asp Lys Ile
    210                 215                 220 ata gca atg ctt cat gag aag gat gac cgg tgt caa gtc aat ggt aca        720
Ile Ala Met Leu His Glu Lys Asp Asp Arg Cys Gln Val Asn Gly Thr
225                 230                 235                 240 tct tat tct gta att ggc att cat ggc gtc gcc ggg tct ggg aaa tca        768
Ser Tyr Ser Val Ile Gly Ile His Gly Val Ala Gly Ser Gly Lys Ser
                245                 250                 255 aca ctt gca cag tat gtt tat gat cat gag aaa aag tgc aag caa ggt        816
Thr Leu Ala Gln Tyr Val Tyr Asp His Glu Lys Lys Cys Lys Gln Gly
            260                 265                 270 aaa aga gaa ggc tat ttt gat gtt ctc atg tgg att cat gtt tct caa        864
Lys Arg Glu Gly Tyr Phe Asp Val Leu Met Trp Ile His Val Ser Gln
        275                 280                 285 aaa atc ggt ttg gag tcc agt ttc agg gac atg ttt gag ggg gct aca        912
Lys Ile Gly Leu Glu Ser Ser Phe Arg Asp Met Phe Glu Gly Ala Thr
    290                 295                 300 ggg aaa gca tgc ccg aat ttt aat agt ctt aac gtc tta aag gaa aag        960
Gly Lys Ala Cys Pro Asn Phe Asn Ser Leu Asn Val Leu Lys Glu Lys
305                 310                 315                 320
```

```
ttg gag gag gaa cta cgt gga aaa cgg att ttt ttg gta cta gat gat        1008
Leu Glu Glu Glu Leu Arg Gly Lys Arg Ile Phe Leu Val Leu Asp Asp
                325                 330                 335 gtc tgg tac aac agt aag aat tca gga gac cgt gaa gaa ctg cag aag        1056
Val Trp Tyr Asn Ser Lys Asn Ser Gly Asp Arg Glu Glu Leu Gln Lys
                340                 345                 350 tta att tct ccg ttg aat gtt ggg aag gca gga agc aga atc ttg gtg        1104
Leu Ile Ser Pro Leu Asn Val Gly Lys Ala Gly Ser Arg Ile Leu Val
                355                 360                 365 act agt aga act gaa gct gca tta gta gct ctc cgt gct gca aaa gag        1152
Thr Ser Arg Thr Glu Ala Ala Leu Val Ala Leu Arg Ala Ala Lys Glu
    370                 375                 380 gga tgt atc cca ata tct aac ctg gat gat aaa gtt ttc ctt aaa atg        1200
Gly Cys Ile Pro Ile Ser Asn Leu Asp Asp Lys Val Phe Leu Lys Met
385                 390                 395                 400 ttc atg cat tat gca ctt cca cat gca tgg cca gtt ggc aat gat cga        1248
Phe Met His Tyr Ala Leu Pro His Ala Trp Pro Val Gly Asn Asp Arg
                405                 410                 415 aga aaa ctt gaa atg att gga gag gac att gca aaa aag ctg aag ggg        1296
Arg Lys Leu Glu Met Ile Gly Glu Asp Ile Ala Lys Lys Leu Lys Gly
                420                 425                 430 tca cct ctg gca gct aga ata gtg ggt tca cgg ctc ggt gat aat cca        1344
Ser Pro Leu Ala Ala Arg Ile Val Gly Ser Arg Leu Gly Asp Asn Pro
                435                 440                 445 aat gtt gaa ttt tgg agg aga gag aaa gac cgg gat ctt atg aac gag        1392
Asn Val Glu Phe Trp Arg Arg Glu Lys Asp Arg Asp Leu Met Asn Glu
                450                 455                 460 aca atg gga gca ctt tgg tgg agc tat cag tac ctt gat gag cag gtc        1440
Thr Met Gly Ala Leu Trp Trp Ser Tyr Gln Tyr Leu Asp Glu Gln Val
465                 470                 475                 480 agg cga tgc ttc gct tac atc agc att ttt ccc aga cga cat cat ttg        1488
Arg Arg Cys Phe Ala Tyr Ile Ser Ile Phe Pro Arg Arg His His Leu
                485                 490                 495 aaa cgt gat gac tta att aac cta tgg gtg gcg gaa gga ttt ata aag        1536
Lys Arg Asp Asp Leu Ile Asn Leu Trp Val Ala Glu Gly Phe Ile Lys
                500                 505                 510 aca agt aaa gct gaa gaa gaa atg gaa gat gtt gcc tcg gaa tac ttt        1584
Thr Ser Lys Ala Glu Glu Glu Met Glu Asp Val Ala Ser Glu Tyr Phe
        515                 520                 525 gat gag ctg ctt tcg ttc tca ttt ctg caa tca gga ggg aaa gat gag        1632
Asp Glu Leu Leu Ser Phe Ser Phe Leu Gln Ser Gly Gly Lys Asp Glu
        530                 535                 540 cta ttt gca cgt gag gtc gat tac ttt ata att cat gat ctg ttg tat        1680
Leu Phe Ala Arg Glu Val Asp Tyr Phe Ile Ile His Asp Leu Leu Tyr
545                 550                 555                 560 gat tta gca gag gag gtt gcc gga aga gat tgc ttc agg ata gag aaa        1728
Asp Leu Ala Glu Glu Val Ala Gly Arg Asp Cys Phe Arg Ile Glu Lys
                565                 570                 575 ggc ttc aca gga gaa gtt cct ccg gat gtt cgc tat ctt ttt gtt ggg        1776
Gly Phe Thr Gly Glu Val Pro Pro Asp Val Arg Tyr Leu Phe Val Gly
                580                 585                 590 act tac gat aaa gag atg ctt act gag aag ata tcc agg ttg caa aat        1824
Thr Tyr Asp Lys Glu Met Leu Thr Glu Lys Ile Ser Arg Leu Gln Asn
                595                 600                 605 tta cgc act ctc ttc gtc gat aag tac ata cag att tta tca ccc aag        1872
Leu Arg Thr Leu Phe Val Asp Lys Tyr Ile Gln Ile Leu Ser Pro Lys
        610                 615                 620 tac gat gat ttt gtg agt atg gtg act atg ttg atg ggg ctg cgg aaa        1920
Tyr Asp Asp Phe Val Ser Met Val Thr Met Leu Met Gly Leu Arg Lys
625                 630                 635                 640
```

| | | |
|---|---|---|
| ctg agg gta ctg aac tta cat ttc act gga tat ggt att cct aaa ttc<br>Leu Arg Val Leu Asn Leu His Phe Thr Gly Tyr Gly Ile Pro Lys Phe<br>645 650 655 | | 1968 |
| tca ttg ccg gat tct att ctt cag ttg aag cat ctg cgt tac ttt gct<br>Ser Leu Pro Asp Ser Ile Leu Gln Leu Lys His Leu Arg Tyr Phe Ala<br>660 665 670 | | 2016 |
| ttt ggg gtg tcc ccg ttt acc gag cta act tta cca tgc gct ttt acc<br>Phe Gly Val Ser Pro Phe Thr Glu Leu Thr Leu Pro Cys Ala Phe Thr<br>675 680 685 | | 2064 |
| aag ctt tac cac ttg cat gtg gta gac ttc ggt gat tgc aat agt ttg<br>Lys Leu Tyr His Leu His Val Val Asp Phe Gly Asp Cys Asn Ser Leu<br>690 695 700 | | 2112 |
| gag ttt tct cgt ggt gaa tac atg atg aac ctg gtc aat ttg cgc cgt<br>Glu Phe Ser Arg Gly Glu Tyr Met Met Asn Leu Val Asn Leu Arg Arg<br>705 710 715 720 | | 2160 |
| gta atc tac aag aat tat ctc gac ttt ccg aac att ggc agg ctg aca<br>Val Ile Tyr Lys Asn Tyr Leu Asp Phe Pro Asn Ile Gly Arg Leu Thr<br>725 730 735 | | 2208 |
| tgg ctg caa tcg ttg ccg tgc ttc aga ata agg aag aaa cat ggg tat<br>Trp Leu Gln Ser Leu Pro Cys Phe Arg Ile Arg Lys Lys His Gly Tyr<br>740 745 750 | | 2256 |
| gaa tca cat cag ctg aaa cac cta aac aag ctt caa ggc agg ctg tac<br>Glu Ser His Gln Leu Lys His Leu Asn Lys Leu Gln Gly Arg Leu Tyr<br>755 760 765 | | 2304 |
| att ggt ggt ctt cag aat gtt gag agc aag gag gaa gct ctt aat gtg<br>Ile Gly Gly Leu Gln Asn Val Glu Ser Lys Glu Glu Ala Leu Asn Val<br>770 775 780 | | 2352 |
| aac ctt gca gcc aag gaa aaa ctc aca gaa gtg gta ctg cgc tgg agt<br>Asn Leu Ala Ala Lys Glu Lys Leu Thr Glu Val Val Leu Arg Trp Ser<br>785 790 795 800 | | 2400 |
| gat aat agc tgc agt cca gaa att caa gca gag gta ctt gag ggc ctt<br>Asp Asn Ser Cys Ser Pro Glu Ile Gln Ala Glu Val Leu Glu Gly Leu<br>805 810 815 | | 2448 |
| tgt cct tca aag tat ctt gaa ata cta gaa atc aag tta tac aat ggc<br>Cys Pro Ser Lys Tyr Leu Glu Ile Leu Glu Ile Lys Leu Tyr Asn Gly<br>820 825 830 | | 2496 |
| atg aag ttt cca aat tgg atg acg agt aag cat aag ggt ggg cca aag<br>Met Lys Phe Pro Asn Trp Met Thr Ser Lys His Lys Gly Gly Pro Lys<br>835 840 845 | | 2544 |
| aac ctg caa gaa ctt aga ttc aga cag agc acc ctg gga tct gct cct<br>Asn Leu Gln Glu Leu Arg Phe Arg Gln Ser Thr Leu Gly Ser Ala Pro<br>850 855 860 | | 2592 |
| gat gtt ggg gct ttc att cac ctt cag tcg tta ttt att tat caa tgc<br>Asp Val Gly Ala Phe Ile His Leu Gln Ser Leu Phe Ile Tyr Gln Cys<br>865 870 875 880 | | 2640 |
| agc tgg gat acc tta cca ggg aat atg gag cac ctc aca gcg ctc aag<br>Ser Trp Asp Thr Leu Pro Gly Asn Met Glu His Leu Thr Ala Leu Lys<br>885 890 895 | | 2688 |
| aaa ctg gag ata cgg tca tgc aat aat att cgg tcg ctt cca aca ctg<br>Lys Leu Glu Ile Arg Ser Cys Asn Asn Ile Arg Ser Leu Pro Thr Leu<br>900 905 910 | | 2736 |
| ccc aag tcc ctt gag cag ttt gcg atc tgg tcc tgc agc ttg gat gct<br>Pro Lys Ser Leu Glu Gln Phe Ala Ile Trp Ser Cys Ser Leu Asp Ala<br>915 920 925 | | 2784 |
| tta ccg ggc aat atg gag cac ctc aca gca ctc aag aaa ctg gag ata<br>Leu Pro Gly Asn Met Glu His Leu Thr Ala Leu Lys Lys Leu Glu Ile<br>930 935 940 | | 2832 |
| cgg tca tgc aat aat att cgg tgg ctt cca aca ctg ccc aag tcc ctt<br>Arg Ser Cys Asn Asn Ile Arg Trp Leu Pro Thr Leu Pro Lys Ser Leu | | 2880 |

```
                945                  950                  955                  960
gag cag ttt gcg atc tcg cgc tgc agc ttg gat gct tta ccg ggc aat        2928
Glu Gln Phe Ala Ile Ser Arg Cys Ser Leu Asp Ala Leu Pro Gly Asn
            965                  970                  975 atg gag cac ctc aca gcg ctc aag aaa ctg gat ata tgg tca tgc gag        2976
Met Glu His Leu Thr Ala Leu Lys Lys Leu Asp Ile Trp Ser Cys Glu
        980                  985                  990 aat ata cgg tcg ctt cca aca cta ccc aag tct ctt gag gag ttt aca        3024
Asn Ile Arg Ser Leu Pro Thr Leu Pro Lys Ser Leu Glu Glu Phe Thr
        995                 1000                 1005 gtc tgg aac tgc act agt gag ttc atg caa tct tgt atg acg act            3069
Val Trp Asn Cys Thr Ser Glu Phe Met Gln Ser Cys Met Thr Thr
    1010                 1015                 1020 gat gat cca aac tgg cag aag att gag cac gtt cca aac aaa aaa            3114
Asp Asp Pro Asn Trp Gln Lys Ile Glu His Val Pro Asn Lys Lys
    1025                 1030                 1035 att gga ttt cta                                                        3126
Ile Gly Phe Leu
    1040

<210> SEQ ID NO 8
<211> LENGTH: 1042
<212> TYPE: PRT
<213> ORGANISM: Hordeum vulgare

<400> SEQUENCE: 8

Met Pro Asp Pro Val Thr Ile Ser Ala Ala Val Gly Trp Gly Val Ser
1               5                   10                  15

Ala Val Gly Trp Leu Ala Ser Pro Ile Ile Ser Arg Val Val Asn Lys
            20                  25                  30

Gly Phe Ala His Leu Asp Phe Asp Ala Ala Glu Lys Leu Lys Ile Leu
        35                  40                  45

Asp Ile Gln Val Leu Gln Leu Gln Arg Val Ile Glu Val Val Asp Glu
    50                  55                  60

Ser Thr Tyr Arg Leu Arg Leu Glu Pro Leu Leu Asp Lys Leu Arg Ser
65                  70                  75                  80

Ala Leu Tyr Glu Ala Gly Asp Ile Leu Asp Phe Asp Tyr Glu Arg
            85                  90                  95

Leu Glu Lys Gln Ile His Val Gly Ser Ser Thr Arg Lys Arg Lys
        100                 105                 110

Ile Asp Ser Leu Glu Lys Asn His Arg Ser Ala Met Pro Ser Ser Ser
    115                 120                 125

Leu Lys Asp Lys Met Glu Thr Phe Pro Arg Ile Ser Ser Lys Gly Lys
130                 135                 140

Glu Thr Ile Lys Asn Leu Leu Ser Gln Gly Ile Gly Thr Ser Lys Val
145                 150                 155                 160

Glu Leu Lys Lys Ser Leu Glu Lys Ile Glu Asn Thr Ile Asn Asp Ala
            165                 170                 175

Cys Lys Val Leu Glu Gln Leu Asn Leu Pro Ser Val Cys Asn Asp Asn
        180                 185                 190

Gly Arg Arg Gly Val Ala Thr Asn Ser Arg Ser Ala Val Thr Thr Ala
    195                 200                 205

Gly Pro Pro Leu Arg Val Ile Gly Arg Asp Gln Asp Arg Asp Lys Ile
    210                 215                 220

Ile Ala Met Leu His Glu Lys Asp Asp Arg Cys Gln Val Asn Gly Thr
225                 230                 235                 240
```

```
Ser Tyr Ser Val Ile Gly Ile His Gly Val Ala Gly Ser Gly Lys Ser
                245                 250                 255

Thr Leu Ala Gln Tyr Val Tyr Asp His Glu Lys Lys Cys Lys Gln Gly
            260                 265                 270

Lys Arg Glu Gly Tyr Phe Asp Val Leu Met Trp Ile His Val Ser Gln
        275                 280                 285

Lys Ile Gly Leu Glu Ser Ser Phe Arg Asp Met Phe Glu Gly Ala Thr
    290                 295                 300

Gly Lys Ala Cys Pro Asn Phe Asn Ser Leu Asn Val Leu Lys Glu Lys
305                 310                 315                 320

Leu Glu Glu Glu Leu Arg Gly Lys Arg Ile Phe Leu Val Leu Asp Asp
                325                 330                 335

Val Trp Tyr Asn Ser Lys Asn Ser Gly Asp Arg Glu Glu Leu Gln Lys
            340                 345                 350

Leu Ile Ser Pro Leu Asn Val Gly Lys Ala Gly Ser Arg Ile Leu Val
        355                 360                 365

Thr Ser Arg Thr Glu Ala Ala Leu Val Ala Leu Arg Ala Ala Lys Glu
    370                 375                 380

Gly Cys Ile Pro Ile Ser Asn Leu Asp Asp Lys Val Phe Leu Lys Met
385                 390                 395                 400

Phe Met His Tyr Ala Leu Pro His Ala Trp Pro Val Gly Asn Asp Arg
                405                 410                 415

Arg Lys Leu Glu Met Ile Gly Glu Asp Ile Ala Lys Lys Leu Lys Gly
            420                 425                 430

Ser Pro Leu Ala Ala Arg Ile Val Gly Ser Arg Leu Gly Asp Asn Pro
        435                 440                 445

Asn Val Glu Phe Trp Arg Arg Glu Lys Asp Arg Asp Leu Met Asn Glu
    450                 455                 460

Thr Met Gly Ala Leu Trp Trp Ser Tyr Gln Tyr Leu Asp Glu Gln Val
465                 470                 475                 480

Arg Arg Cys Phe Ala Tyr Ile Ser Ile Phe Pro Arg Arg His His Leu
                485                 490                 495

Lys Arg Asp Asp Leu Ile Asn Leu Trp Val Ala Glu Gly Phe Ile Lys
            500                 505                 510

Thr Ser Lys Ala Glu Glu Met Glu Asp Val Ala Ser Glu Tyr Phe
        515                 520                 525

Asp Glu Leu Leu Ser Phe Ser Phe Leu Gln Ser Gly Gly Lys Asp Glu
    530                 535                 540

Leu Phe Ala Arg Glu Val Asp Tyr Phe Ile His Asp Leu Leu Tyr
545                 550                 555                 560

Asp Leu Ala Glu Glu Val Ala Gly Arg Asp Cys Phe Arg Ile Glu Lys
                565                 570                 575

Gly Phe Thr Gly Glu Val Pro Pro Asp Val Arg Tyr Leu Phe Val Gly
            580                 585                 590

Thr Tyr Asp Lys Glu Met Leu Thr Glu Lys Ile Ser Arg Leu Gln Asn
        595                 600                 605

Leu Arg Thr Leu Phe Val Asp Lys Tyr Ile Gln Ile Leu Ser Pro Lys
    610                 615                 620

Tyr Asp Asp Phe Val Ser Met Val Thr Met Leu Met Gly Leu Arg Lys
625                 630                 635                 640

Leu Arg Val Leu Asn Leu His Phe Thr Gly Tyr Gly Ile Pro Lys Phe
                645                 650                 655

Ser Leu Pro Asp Ser Ile Leu Gln Leu Lys His Leu Arg Tyr Phe Ala
```

```
                660              665              670
Phe Gly Val Ser Pro Phe Thr Glu Leu Thr Leu Pro Cys Ala Phe Thr
            675              680              685
Lys Leu Tyr His Leu His Val Asp Phe Gly Asp Cys Asn Ser Leu
        690              695              700
Glu Phe Ser Arg Gly Glu Tyr Met Met Asn Leu Val Asn Leu Arg Arg
705              710              715              720
Val Ile Tyr Lys Asn Tyr Leu Asp Phe Pro Asn Ile Gly Arg Leu Thr
                725              730              735
Trp Leu Gln Ser Leu Pro Cys Phe Arg Ile Arg Lys Lys His Gly Tyr
            740              745              750
Glu Ser His Gln Leu Lys His Leu Asn Lys Leu Gln Gly Arg Leu Tyr
        755              760              765
Ile Gly Gly Leu Gln Asn Val Glu Ser Lys Glu Ala Leu Asn Val
        770              775              780
Asn Leu Ala Ala Lys Glu Lys Leu Thr Glu Val Val Leu Arg Trp Ser
785              790              795              800
Asp Asn Ser Cys Ser Pro Glu Ile Gln Ala Glu Val Leu Glu Gly Leu
            805              810              815
Cys Pro Ser Lys Tyr Leu Glu Ile Leu Glu Ile Lys Leu Tyr Asn Gly
            820              825              830
Met Lys Phe Pro Asn Trp Met Thr Ser Lys His Lys Gly Gly Pro Lys
        835              840              845
Asn Leu Gln Glu Leu Arg Phe Arg Gln Ser Thr Leu Gly Ser Ala Pro
850              855              860
Asp Val Gly Ala Phe Ile His Leu Gln Ser Leu Phe Ile Tyr Gln Cys
865              870              875              880
Ser Trp Asp Thr Leu Pro Gly Asn Met Glu His Leu Thr Ala Leu Lys
                885              890              895
Lys Leu Glu Ile Arg Ser Cys Asn Asn Ile Arg Ser Leu Pro Thr Leu
                900              905              910
Pro Lys Ser Leu Glu Gln Phe Ala Ile Trp Ser Cys Ser Leu Asp Ala
            915              920              925
Leu Pro Gly Asn Met Glu His Leu Thr Ala Leu Lys Lys Leu Glu Ile
        930              935              940
Arg Ser Cys Asn Asn Ile Arg Trp Leu Pro Thr Leu Pro Lys Ser Leu
945              950              955              960
Glu Gln Phe Ala Ile Ser Arg Cys Ser Leu Asp Ala Leu Pro Gly Asn
                965              970              975
Met Glu His Leu Thr Ala Leu Lys Lys Leu Asp Ile Trp Ser Cys Glu
            980              985              990
Asn Ile Arg Ser Leu Pro Thr Leu Pro Lys Ser Leu Glu Glu Phe Thr
        995             1000             1005
Val Trp Asn Cys Thr Ser Glu Phe Met Gln Ser Cys Met Thr Thr
    1010             1015             1020
Asp Asp Pro Asn Trp Gln Lys Ile Glu His Val Pro Asn Lys Lys
    1025             1030             1035
Ile Gly Phe Leu
    1040

<210> SEQ ID NO 9
<211> LENGTH: 3126
<212> TYPE: DNA
<213> ORGANISM: Hordeum vulgare
```

```
<220> FEATURE:
<221> NAME/KEY: CDS
<222> LOCATION: (1)..(3126)

<400> SEQUENCE: 9 atg ccg gat cca gtt act att agt gct gct gta gga tgg ggc gta tcc     48
Met Pro Asp Pro Val Thr Ile Ser Ala Ala Val Gly Trp Gly Val Ser
1               5                  10                  15 gca gta ggc tgg ctc gcc tct ccc atc att tca agg gtt gtc aac aaa     96
Ala Val Gly Trp Leu Ala Ser Pro Ile Ile Ser Arg Val Val Asn Lys
            20                  25                  30 ggt ttc gcc cac ctc gac ttc gat gca gca gag aag ctg aag ata ctt    144
Gly Phe Ala His Leu Asp Phe Asp Ala Ala Glu Lys Leu Lys Ile Leu
        35                  40                  45 gat ata caa gtt cta caa ctg cag cgc gtg ata gaa gta gtc gat gag    192
Asp Ile Gln Val Leu Gln Leu Gln Arg Val Ile Glu Val Val Asp Glu
    50                  55                  60 agc acg tac agg ctt cgc ttg gag cca ctg tta gac aag ctt aga tct    240
Ser Thr Tyr Arg Leu Arg Leu Glu Pro Leu Leu Asp Lys Leu Arg Ser
65                  70                  75                  80 gct ctt tat gaa gcc gaa gac atc ttg gat gat ttt gat tat cag cgt    288
Ala Leu Tyr Glu Ala Glu Asp Ile Leu Asp Asp Phe Asp Tyr Gln Arg
                85                  90                  95 ctc gag aag cag atc cat gtt ggg tct agt tcc aca cgt aaa cgc aag    336
Leu Glu Lys Gln Ile His Val Gly Ser Ser Ser Thr Arg Lys Arg Lys
            100                 105                 110 ata tcg ctg gag aag aat cat cgg tct gcc atg ccg agt tcc tcc        384
Ile Asp Ser Leu Glu Lys Asn His Arg Ser Ala Met Pro Ser Ser Ser
        115                 120                 125 cta aaa gat aag atg gaa aca ttc ccg agg att tca tcg aag gga aag    432
Leu Lys Asp Lys Met Glu Thr Phe Pro Arg Ile Ser Ser Lys Gly Lys
    130                 135                 140 gag act atc aag aat tta ctg agc cag ggg att gga aca tca aaa gtg    480
Glu Thr Ile Lys Asn Leu Leu Ser Gln Gly Ile Gly Thr Ser Lys Val
145                 150                 155                 160 gag ttg aag aaa agc cta gag aaa ata gaa aat acc ata aac gat gca    528
Glu Leu Lys Lys Ser Leu Glu Lys Ile Glu Asn Thr Ile Asn Asp Ala
                165                 170                 175 tgt aaa gtt ttg gaa caa ctg aac ttg ccg agt gta tgt aat gat aat    576
Cys Lys Val Leu Glu Gln Leu Asn Leu Pro Ser Val Cys Asn Asp Asn
            180                 185                 190 ggg aga cga ggt gtt gct acc aat tct cgt agt gca gtc act act gca    624
Gly Arg Arg Gly Val Ala Thr Asn Ser Arg Ser Ala Val Thr Thr Ala
        195                 200                 205 ggt cct cct cta cga gta att ggt cga gat cag gat cgt gac aag atc    672
Gly Pro Pro Leu Arg Val Ile Gly Arg Asp Gln Asp Arg Asp Lys Ile
    210                 215                 220 ata gca atg ctt cat gag aag gat gac cgg tgt caa gtc aat ggt aca    720
Ile Ala Met Leu His Glu Lys Asp Asp Arg Cys Gln Val Asn Gly Thr
225                 230                 235                 240 tct tat tct gta att ggc att cat ggc gtc gcc ggg tct ggg aaa tca    768
Ser Tyr Ser Val Ile Gly Ile His Gly Val Ala Gly Ser Gly Lys Ser
                245                 250                 255 aca ctt gca cag tat gtt tat gat cat gag aaa aag tgc aag caa ggt    816
Thr Leu Ala Gln Tyr Val Tyr Asp His Glu Lys Lys Cys Lys Gln Gly
            260                 265                 270 aaa aga gaa ggc tat ttt gat gtt ctc atg tgg att cat gtt tct caa    864
Lys Arg Glu Gly Tyr Phe Asp Val Leu Met Trp Ile His Val Ser Gln
        275                 280                 285 aaa atc ggt ttg gag tcc agt ttc agg gac atg ttt gag ggg gct aca    912
Lys Ile Gly Leu Glu Ser Ser Phe Arg Asp Met Phe Glu Gly Ala Thr
```

```
                Lys Ile Gly Leu Glu Ser Ser Phe Arg Asp Met Phe Glu Gly Ala Thr
                    290                 295                 300 ggg aaa gca tgc ccg aat ttt aat agt ctt aac gtc tta aag gaa aag          960
Gly Lys Ala Cys Pro Asn Phe Asn Ser Leu Asn Val Leu Lys Glu Lys
305                 310                 315                 320 ttg gag gag gaa cta cgt gga aaa cgg att ttt ttg gta cta gat gat         1008
Leu Glu Glu Glu Leu Arg Gly Lys Arg Ile Phe Leu Val Leu Asp Asp
                    325                 330                 335 gtc tgg tac aac agt aag aat tca gga gac cgt gaa gaa ctg cag aag         1056
Val Trp Tyr Asn Ser Lys Asn Ser Gly Asp Arg Glu Glu Leu Gln Lys
                340                 345                 350 tta att tct ccg ttg aat gtt ggg aag gca gga agc aga atc ttg gtg         1104
Leu Ile Ser Pro Leu Asn Val Gly Lys Ala Gly Ser Arg Ile Leu Val
            355                 360                 365 act agt cga act gaa gct gca tta gta gct ctc cgt gct gca aaa gag         1152
Thr Ser Arg Thr Glu Ala Ala Leu Val Ala Leu Arg Ala Ala Lys Glu
370                 375                 380 gga tgt atc cca ata tct aac ctg gat gat aaa gtt ttc ctt aaa atg         1200
Gly Cys Ile Pro Ile Ser Asn Leu Asp Asp Lys Val Phe Leu Lys Met
385                 390                 395                 400 ttc atg cat tat gca ctt cca cat gca tgg cca gtt ggc aat gat cga         1248
Phe Met His Tyr Ala Leu Pro His Ala Trp Pro Val Gly Asn Asp Arg
                    405                 410                 415 aga aaa ctt gaa atg att gga gag gac att gca aaa aag ctg aag ggt         1296
Arg Lys Leu Glu Met Ile Gly Glu Asp Ile Ala Lys Lys Leu Lys Gly
                420                 425                 430 tca cct ctg gca gct aga ata gtg ggt tca cgg ctc ggt gat aat cca         1344
Ser Pro Leu Ala Ala Arg Ile Val Gly Ser Arg Leu Gly Asp Asn Pro
            435                 440                 445 aat gtt gaa ttt tgg agg aga gag aaa gac cgg gat ctt atg aac gag         1392
Asn Val Glu Phe Trp Arg Arg Glu Lys Asp Arg Asp Leu Met Asn Glu
450                 455                 460 acg atg gga gca ctt tgg tgg agc tac cag tac ctt gat gag cag gtc         1440
Thr Met Gly Ala Leu Trp Trp Ser Tyr Gln Tyr Leu Asp Glu Gln Val
465                 470                 475                 480 agg cga tgc ttc gct tac atc agc att ttt ccc aga cgt cat cat ttg         1488
Arg Arg Cys Phe Ala Tyr Ile Ser Ile Phe Pro Arg Arg His His Leu
                    485                 490                 495 aaa cgt gat gac tta att aac cta tgg gtg gcc gaa gga ttt ata aag         1536
Lys Arg Asp Asp Leu Ile Asn Leu Trp Val Ala Glu Gly Phe Ile Lys
                500                 505                 510 aca agt aaa gct gaa gag gaa atg gaa gat gtt gcc tcg gaa tac ttt         1584
Thr Ser Lys Ala Glu Glu Glu Met Glu Asp Val Ala Ser Glu Tyr Phe
            515                 520                 525 gat gag ctg ctt tcg ttc tca ttt ctg caa tta gga ggg aaa gat gag         1632
Asp Glu Leu Leu Ser Phe Ser Phe Leu Gln Leu Gly Gly Lys Asp Glu
530                 535                 540 cta ttt gca cgt gag gtc gat tac ttt ata att cat gat ctg ttg tat         1680
Leu Phe Ala Arg Glu Val Asp Tyr Phe Ile Ile His Asp Leu Leu Tyr
545                 550                 555                 560 gat tta gca gag gag gtt gct gga aga gat tgc ttc agg ata gag aaa         1728
Asp Leu Ala Glu Glu Val Ala Gly Arg Asp Cys Phe Arg Ile Glu Lys
                    565                 570                 575 ggt ttc aca gga gaa gtc cct ccg gat gtt cgc tat ctt ttt gtt ggg         1776
Gly Phe Thr Gly Glu Val Pro Pro Asp Val Arg Tyr Leu Phe Val Gly
                580                 585                 590 act tac gat aaa gag atg ctt act gag aag ata tcc agg ttg caa aat         1824
Thr Tyr Asp Lys Glu Met Leu Thr Glu Lys Ile Ser Arg Leu Gln Asn
            595                 600                 605
```

|  |  |
|---|---:|
| tta cgc act ctc ttc gtc gat aag tac ata cag att tta tca ccc aag<br>Leu Arg Thr Leu Phe Val Asp Lys Tyr Ile Gln Ile Leu Ser Pro Lys<br>610                615                     620 | 1872 |
| tac gat gat ttt gtt agt atg gtg act atg ttg atg ggg ctg cgg aaa<br>Tyr Asp Asp Phe Val Ser Met Val Thr Met Leu Met Gly Leu Arg Lys<br>625                630                 635              640 | 1920 |
| ttg agg gta ctg aat tta cat ttc act gga tat ggt att cct aaa ttc<br>Leu Arg Val Leu Asn Leu His Phe Thr Gly Tyr Gly Ile Pro Lys Phe<br>                      645                 650                     655 | 1968 |
| tca ttg ccg gat tct att ctt cag tgg aag cat ctg cgt tac ttt gct<br>Ser Leu Pro Asp Ser Ile Leu Gln Trp Lys His Leu Arg Tyr Phe Ala<br>                      660                 665                     670 | 2016 |
| ttt ggg gtg tcc ccg ttt acc aag cta act tta cca tgc gct ttt acc<br>Phe Gly Val Ser Pro Phe Thr Lys Leu Thr Leu Pro Cys Ala Phe Thr<br>                 675                 680                     685 | 2064 |
| aag ctt tac cac ttg cat gtg gta gat ttc ggt gat tgc aat agt ttg<br>Lys Leu Tyr His Leu His Val Val Asp Phe Gly Asp Cys Asn Ser Leu<br>690                695                    700 | 2112 |
| gag ttt tct cgt ggt gaa tac atg atg aac ctg gtc aat ttg cgc cgt<br>Glu Phe Ser Arg Gly Glu Tyr Met Met Asn Leu Val Asn Leu Arg Arg<br>705                710                 715              720 | 2160 |
| gta atc tac aag aat tat ctc gac ttt ccg aac att ggc agg ctg aca<br>Val Ile Tyr Lys Asn Tyr Leu Asp Phe Pro Asn Ile Gly Arg Leu Thr<br>                      725                 730                     735 | 2208 |
| tgg ctg caa tcg ttg ccg tgc ttc aga ata agg aag aaa cat ggg tat<br>Trp Leu Gln Ser Leu Pro Cys Phe Arg Ile Arg Lys Lys His Gly Tyr<br>                      740                 745                     750 | 2256 |
| gaa tca cat cag ctg aaa cac cta aac aag ctt caa ggc agg ctg tac<br>Glu Ser His Gln Leu Lys His Leu Asn Lys Leu Gln Gly Arg Leu Tyr<br>755                760                 765 | 2304 |
| att ggt ggt ctt cag aat gtt gag agc aag gag gaa gct ctt aat gtg<br>Ile Gly Gly Leu Gln Asn Val Glu Ser Lys Glu Glu Ala Leu Asn Val<br>770                775                 780 | 2352 |
| aac ctt gca gcc aag gaa aaa ctc aca gaa gtg gta ctg cgc tgg agt<br>Asn Leu Ala Ala Lys Glu Lys Leu Thr Glu Val Val Leu Arg Trp Ser<br>785                790                 795              800 | 2400 |
| gat aat agc tgc agt cca gaa att caa gca gag gta ctt gag ggc ctt<br>Asp Asn Ser Cys Ser Pro Glu Ile Gln Ala Glu Val Leu Glu Gly Leu<br>                      805                 810                     815 | 2448 |
| tgt cct tca aag tat ctt gaa ata cta gaa atc aag tta tac aat ggc<br>Cys Pro Ser Lys Tyr Leu Glu Ile Leu Glu Ile Lys Leu Tyr Asn Gly<br>                      820                 825                     830 | 2496 |
| atg aag ttt cca aat tgg atg acg agt aag cat aag ggt ggg cca aag<br>Met Lys Phe Pro Asn Trp Met Thr Ser Lys His Lys Gly Gly Pro Lys<br>                 835                 840                     845 | 2544 |
| aac ctg caa gaa ctt aga ttc aga cag agc acc ctg gga tct gct cct<br>Asn Leu Gln Glu Leu Arg Phe Arg Gln Ser Thr Leu Gly Ser Ala Pro<br>850                855                    860 | 2592 |
| gat gtt ggg gct ttc att cac ctt cag tcg tta ttt att tat caa tgc<br>Asp Val Gly Ala Phe Ile His Leu Gln Ser Leu Phe Ile Tyr Gln Cys<br>865                870                 875              880 | 2640 |
| agc tgg gat acc tta cca ggg aat atg gag cac ctc aca gcg ctc aag<br>Ser Trp Asp Thr Leu Pro Gly Asn Met Glu His Leu Thr Ala Leu Lys<br>                      885                 890                     895 | 2688 |
| aaa ctg gag ata cgg tca tgc aat aat att cgg tcg ctt cca aca ctg<br>Lys Leu Glu Ile Arg Ser Cys Asn Asn Ile Arg Ser Leu Pro Thr Leu<br>                      900                 905                     910 | 2736 |
| ccc aag tcc ctt gag cag ttt gcg atc tgg tcc tgc agc ttg gat gct<br>Pro Lys Ser Leu Glu Gln Phe Ala Ile Trp Ser Cys Ser Leu Asp Ala<br>                 915                 920                     925 | 2784 |

```
tta ccg ggc aat atg gag cac ctc aca gca ctc aag aaa ctg gag ata    2832
Leu Pro Gly Asn Met Glu His Leu Thr Ala Leu Lys Lys Leu Glu Ile
        930                 935                 940 cgg tca tgc aat aat att cgg tgg ctt cca aca ctg ccc aag tcc ctt    2880
Arg Ser Cys Asn Asn Ile Arg Trp Leu Pro Thr Leu Pro Lys Ser Leu
945                 950                 955                 960 gag cag ttt gcg atc tcg cgc tgc agc ttg gat gct tta ccg ggc aat    2928
Glu Gln Phe Ala Ile Ser Arg Cys Ser Leu Asp Ala Leu Pro Gly Asn
                965                 970                 975 atg gag cac ctc aca gcg ctc aag aaa ctg gat ata tgg tca tgc gag    2976
Met Glu His Leu Thr Ala Leu Lys Lys Leu Asp Ile Trp Ser Cys Glu
            980                 985                 990 aat ata cgg tcg ctt cca aca cta ccc aag tct ctt gag gag ttt aca    3024
Asn Ile Arg Ser Leu Pro Thr Leu Pro Lys Ser Leu Glu Glu Phe Thr
        995                 1000                1005 gtc tgg aac tgc act agt gag ttc atg caa tct tgt atg acg act         3069
Val Trp Asn Cys Thr Ser Glu Phe Met Gln Ser Cys Met Thr Thr
    1010                1015                1020 gat gat cca aac tgg cag aag att gag cac gtt cca aac aaa aaa         3114
Asp Asp Pro Asn Trp Gln Lys Ile Glu His Val Pro Asn Lys Lys
1025                1030                1035 att gga ttt cta                                                      3126
Ile Gly Phe Leu
1040
```

<210> SEQ ID NO 10
<211> LENGTH: 1042
<212> TYPE: PRT
<213> ORGANISM: Hordeum vulgare

<400> SEQUENCE: 10

```
Met Pro Asp Pro Val Thr Ile Ser Ala Ala Val Gly Trp Gly Val Ser
1               5                   10                  15

Ala Val Gly Trp Leu Ala Ser Pro Ile Ile Ser Arg Val Val Asn Lys
            20                  25                  30

Gly Phe Ala His Leu Asp Phe Asp Ala Ala Glu Lys Leu Lys Ile Leu
        35                  40                  45

Asp Ile Gln Val Leu Gln Leu Gln Arg Val Ile Glu Val Val Asp Glu
    50                  55                  60

Ser Thr Tyr Arg Leu Arg Leu Glu Pro Leu Leu Asp Lys Leu Arg Ser
65                  70                  75                  80

Ala Leu Tyr Glu Ala Glu Asp Ile Leu Asp Asp Phe Asp Tyr Gln Arg
                85                  90                  95

Leu Glu Lys Gln Ile His Val Gly Ser Ser Ser Thr Arg Lys Arg Lys
            100                 105                 110

Ile Asp Ser Leu Glu Lys Asn His Arg Ser Ala Met Pro Ser Ser Ser
        115                 120                 125

Leu Lys Asp Lys Met Glu Thr Phe Pro Arg Ile Ser Ser Lys Gly Lys
    130                 135                 140

Glu Thr Ile Lys Asn Leu Leu Ser Gln Gly Ile Gly Thr Ser Lys Val
145                 150                 155                 160

Glu Leu Lys Lys Ser Leu Glu Ile Glu Asn Thr Ile Asn Asp Ala
                165                 170                 175

Cys Lys Val Leu Glu Gln Leu Asn Leu Pro Ser Val Cys Asn Asp Asn
            180                 185                 190

Gly Arg Arg Gly Val Ala Thr Asn Ser Arg Ser Ala Val Thr Thr Ala
        195                 200                 205
```

```
Gly Pro Pro Leu Arg Val Ile Gly Arg Asp Gln Asp Arg Asp Lys Ile
    210                 215                 220

Ile Ala Met Leu His Glu Lys Asp Asp Arg Cys Gln Val Asn Gly Thr
225                 230                 235                 240

Ser Tyr Ser Val Ile Gly Ile His Gly Val Ala Gly Ser Gly Lys Ser
                245                 250                 255

Thr Leu Ala Gln Tyr Val Tyr Asp His Glu Lys Lys Cys Lys Gln Gly
            260                 265                 270

Lys Arg Glu Gly Tyr Phe Asp Val Leu Met Trp Ile His Val Ser Gln
        275                 280                 285

Lys Ile Gly Leu Glu Ser Ser Phe Arg Asp Met Phe Glu Gly Ala Thr
    290                 295                 300

Gly Lys Ala Cys Pro Asn Phe Asn Ser Leu Asn Val Leu Lys Glu Lys
305                 310                 315                 320

Leu Glu Glu Glu Leu Arg Gly Lys Arg Ile Phe Leu Val Leu Asp Asp
                325                 330                 335

Val Trp Tyr Asn Ser Lys Asn Ser Gly Asp Arg Glu Leu Gln Lys
            340                 345                 350

Leu Ile Ser Pro Leu Asn Val Gly Lys Ala Gly Ser Arg Ile Leu Val
        355                 360                 365

Thr Ser Arg Thr Glu Ala Ala Leu Val Ala Leu Arg Ala Ala Lys Glu
370                 375                 380

Gly Cys Ile Pro Ile Ser Asn Leu Asp Asp Lys Val Phe Leu Lys Met
385                 390                 395                 400

Phe Met His Tyr Ala Leu Pro His Ala Trp Pro Val Gly Asn Asp Arg
                405                 410                 415

Arg Lys Leu Glu Met Ile Gly Glu Asp Ile Ala Lys Lys Leu Lys Gly
            420                 425                 430

Ser Pro Leu Ala Ala Arg Ile Val Gly Ser Arg Leu Gly Asp Asn Pro
        435                 440                 445

Asn Val Glu Phe Trp Arg Arg Glu Lys Asp Arg Asp Leu Met Asn Glu
    450                 455                 460

Thr Met Gly Ala Leu Trp Trp Ser Tyr Gln Tyr Leu Asp Glu Gln Val
465                 470                 475                 480

Arg Arg Cys Phe Ala Tyr Ile Ser Ile Phe Pro Arg Arg His His Leu
                485                 490                 495

Lys Arg Asp Asp Leu Ile Asn Leu Trp Val Ala Glu Gly Phe Ile Lys
            500                 505                 510

Thr Ser Lys Ala Glu Glu Glu Met Glu Asp Val Ala Ser Glu Tyr Phe
    515                 520                 525

Asp Glu Leu Leu Ser Phe Ser Phe Leu Gln Leu Gly Gly Lys Asp Glu
530                 535                 540

Leu Phe Ala Arg Glu Val Asp Tyr Phe Ile Ile His Asp Leu Leu Tyr
545                 550                 555                 560

Asp Leu Ala Glu Glu Val Ala Gly Arg Asp Cys Phe Arg Ile Glu Lys
                565                 570                 575

Gly Phe Thr Gly Glu Val Pro Pro Asp Val Arg Tyr Leu Phe Val Gly
            580                 585                 590

Thr Tyr Asp Lys Glu Met Leu Thr Glu Lys Ile Ser Arg Leu Gln Asn
        595                 600                 605

Leu Arg Thr Leu Phe Val Asp Lys Tyr Ile Gln Ile Leu Ser Pro Lys
    610                 615                 620
```

Tyr Asp Asp Phe Val Ser Met Val Thr Met Leu Met Gly Leu Arg Lys
625                 630                 635                 640

Leu Arg Val Leu Asn Leu His Phe Thr Gly Tyr Gly Ile Pro Lys Phe
            645                 650                 655

Ser Leu Pro Asp Ser Ile Leu Gln Trp Lys His Leu Arg Tyr Phe Ala
            660                 665                 670

Phe Gly Val Ser Pro Phe Thr Lys Leu Thr Leu Pro Cys Ala Phe Thr
        675                 680                 685

Lys Leu Tyr His Leu His Val Val Asp Phe Gly Asp Cys Asn Ser Leu
        690                 695                 700

Glu Phe Ser Arg Gly Glu Tyr Met Met Asn Leu Val Asn Leu Arg Arg
705                 710                 715                 720

Val Ile Tyr Lys Asn Tyr Leu Asp Phe Pro Asn Ile Gly Arg Leu Thr
            725                 730                 735

Trp Leu Gln Ser Leu Pro Cys Phe Arg Ile Arg Lys Lys His Gly Tyr
            740                 745                 750

Glu Ser His Gln Leu Lys His Leu Asn Lys Leu Gln Gly Arg Leu Tyr
            755                 760                 765

Ile Gly Gly Leu Gln Asn Val Glu Ser Lys Glu Glu Ala Leu Asn Val
770                 775                 780

Asn Leu Ala Ala Lys Glu Lys Leu Thr Glu Val Val Leu Arg Trp Ser
785                 790                 795                 800

Asp Asn Ser Cys Ser Pro Glu Ile Gln Ala Glu Val Leu Glu Gly Leu
            805                 810                 815

Cys Pro Ser Lys Tyr Leu Glu Ile Leu Glu Ile Lys Leu Tyr Asn Gly
            820                 825                 830

Met Lys Phe Pro Asn Trp Met Thr Ser Lys His Lys Gly Gly Pro Lys
            835                 840                 845

Asn Leu Gln Glu Leu Arg Phe Arg Gln Ser Thr Leu Gly Ser Ala Pro
850                 855                 860

Asp Val Gly Ala Phe Ile His Leu Gln Ser Leu Phe Ile Tyr Gln Cys
865                 870                 875                 880

Ser Trp Asp Thr Leu Pro Gly Asn Met Glu His Leu Thr Ala Leu Lys
            885                 890                 895

Lys Leu Glu Ile Arg Ser Cys Asn Asn Ile Arg Ser Leu Pro Thr Leu
            900                 905                 910

Pro Lys Ser Leu Glu Gln Phe Ala Ile Trp Ser Cys Ser Leu Asp Ala
        915                 920                 925

Leu Pro Gly Asn Met Glu His Leu Thr Ala Leu Lys Lys Leu Glu Ile
    930                 935                 940

Arg Ser Cys Asn Asn Ile Arg Trp Leu Pro Thr Leu Pro Lys Ser Leu
945                 950                 955                 960

Glu Gln Phe Ala Ile Ser Arg Cys Ser Leu Asp Ala Leu Pro Gly Asn
            965                 970                 975

Met Glu His Leu Thr Ala Leu Lys Lys Leu Asp Ile Trp Ser Cys Glu
        980                 985                 990

Asn Ile Arg Ser Leu Pro Thr Leu  Pro Lys Ser Leu Glu  Glu Phe Thr
        995                 1000                 1005

Val Trp  Asn Cys Thr Ser Glu  Phe Met Gln Ser Cys  Met Thr Thr
        1010                1015                1020

Asp Asp  Pro Asn Trp Gln Lys  Ile Glu His Val Pro  Asn Lys Lys
        1025                1030                1035

Ile Gly  Phe Leu

<210> SEQ ID NO 11
<211> LENGTH: 3126
<212> TYPE: DNA
<213> ORGANISM: Hordeum vulgare
<220> FEATURE:
<221> NAME/KEY: CDS
<222> LOCATION: (1)..(3126)

<400> SEQUENCE: 11

| | | | | | | | | | | | | | | | | |
|---|---|---|---|---|---|---|---|---|---|---|---|---|---|---|---|---|
| atg | ccg | gat | cca | gtt | act | att | agt | gct | gct | gta | gga | tgg | ggc | gta | tcc | 48 |
| Met | Pro | Asp | Pro | Val | Thr | Ile | Ser | Ala | Ala | Val | Gly | Trp | Gly | Val | Ser | |
| 1 | | | | 5 | | | | | 10 | | | | | 15 | | |
| gca | gta | ggc | tgg | ctc | gcc | tct | ccc | atc | att | tca | agg | gtt | gtc | aac | aaa | 96 |
| Ala | Val | Gly | Trp | Leu | Ala | Ser | Pro | Ile | Ile | Ser | Arg | Val | Val | Asn | Lys | |
| | | 20 | | | | | 25 | | | | | 30 | | | | |
| ggt | ttc | gcc | cac | ctc | gac | ttc | gat | gca | gca | gag | aag | ctg | aag | ata | ctt | 144 |
| Gly | Phe | Ala | His | Leu | Asp | Phe | Asp | Ala | Ala | Glu | Lys | Leu | Lys | Ile | Leu | |
| | | | 35 | | | | | 40 | | | | | 45 | | | |
| gat | ata | caa | gtt | cta | caa | ctg | cag | cgc | gtg | ata | gaa | gta | gtc | gat | gag | 192 |
| Asp | Ile | Gln | Val | Leu | Gln | Leu | Gln | Arg | Val | Ile | Glu | Val | Val | Asp | Glu | |
| | 50 | | | | | 55 | | | | | 60 | | | | | |
| agc | acg | tac | agg | ctt | cgc | ttg | gag | cca | ctg | tta | gac | aag | ctt | aga | tct | 240 |
| Ser | Thr | Tyr | Arg | Leu | Arg | Leu | Glu | Pro | Leu | Leu | Asp | Lys | Leu | Arg | Ser | |
| 65 | | | | | 70 | | | | | 75 | | | | | 80 | |
| gct | ctc | tat | gaa | gcc | gaa | gac | atc | ttg | gat | gat | ttt | gat | tat | gag | cgt | 288 |
| Ala | Leu | Tyr | Glu | Ala | Glu | Asp | Ile | Leu | Asp | Asp | Phe | Asp | Tyr | Glu | Arg | |
| | | | | 85 | | | | | 90 | | | | | 95 | | |
| ctc | gag | aag | cag | atc | cat | gtt | ggg | tct | agt | tcc | aca | cgt | aaa | cgc | aag | 336 |
| Leu | Glu | Lys | Gln | Ile | His | Val | Gly | Ser | Ser | Ser | Thr | Arg | Lys | Arg | Lys | |
| | | | 100 | | | | | 105 | | | | | 110 | | | |
| ata | gat | tcg | ctg | gag | aag | aat | cat | cgg | tct | gcc | atg | ccg | agt | tcc | tcc | 384 |
| Ile | Asp | Ser | Leu | Glu | Lys | Asn | His | Arg | Ser | Ala | Met | Pro | Ser | Ser | Ser | |
| | | 115 | | | | | 120 | | | | | 125 | | | | |
| cta | aaa | gat | aag | atg | gaa | aca | ttc | ccg | agg | att | tca | tcg | aag | gga | aag | 432 |
| Leu | Lys | Asp | Lys | Met | Glu | Thr | Phe | Pro | Arg | Ile | Ser | Ser | Lys | Gly | Lys | |
| | 130 | | | | | 135 | | | | | 140 | | | | | |
| gag | act | atc | aag | aat | tta | ctg | agc | cag | ggg | att | gga | aca | tca | aaa | gtg | 480 |
| Glu | Thr | Ile | Lys | Asn | Leu | Leu | Ser | Gln | Gly | Ile | Gly | Thr | Ser | Lys | Val | |
| 145 | | | | | 150 | | | | | 155 | | | | | 160 | |
| gag | ttg | aag | aaa | agc | cta | gag | aaa | ata | gaa | aat | acc | ata | aac | gat | gca | 528 |
| Glu | Leu | Lys | Lys | Ser | Leu | Glu | Lys | Ile | Glu | Asn | Thr | Ile | Asn | Asp | Ala | |
| | | | | 165 | | | | | 170 | | | | | 175 | | |
| tgt | aaa | gtt | ttg | gaa | caa | ctg | aac | ttg | ccg | agt | gta | tgt | aat | gat | aat | 576 |
| Cys | Lys | Val | Leu | Glu | Gln | Leu | Asn | Leu | Pro | Ser | Val | Cys | Asn | Asp | Asn | |
| | | | 180 | | | | | 185 | | | | | 190 | | | |
| ggg | aga | cga | ggt | gtt | gct | acc | aat | tct | cgt | agt | gca | gtc | act | act | gca | 624 |
| Gly | Arg | Arg | Gly | Val | Ala | Thr | Asn | Ser | Arg | Ser | Ala | Val | Thr | Thr | Ala | |
| | | 195 | | | | | 200 | | | | | 205 | | | | |
| ggt | cct | cct | cta | cga | gta | att | ggt | cga | gat | cag | gat | cgt | gac | aag | atc | 672 |
| Gly | Pro | Pro | Leu | Arg | Val | Ile | Gly | Arg | Asp | Gln | Asp | Arg | Asp | Lys | Ile | |
| | 210 | | | | | 215 | | | | | 220 | | | | | |
| ata | gca | atg | ctt | cat | gag | aag | gat | gac | cgg | tgt | caa | gtc | aat | ggt | aca | 720 |
| Ile | Ala | Met | Leu | His | Glu | Lys | Asp | Asp | Arg | Cys | Gln | Val | Asn | Gly | Thr | |
| 225 | | | | | 230 | | | | | 235 | | | | | 240 | |
| tct | tat | tct | gta | att | ggc | att | cat | ggc | gtc | gcc | ggg | tct | ggg | aaa | tca | 768 |
| Ser | Tyr | Ser | Val | Ile | Gly | Ile | His | Gly | Val | Ala | Gly | Ser | Gly | Lys | Ser | |
| | | | | 245 | | | | | 250 | | | | | 255 | | |
| aca | ctt | gca | cag | tat | gtt | tat | gat | cat | gag | aaa | aag | tgc | aag | caa | ggt | 816 |
| Thr | Leu | Ala | Gln | Tyr | Val | Tyr | Asp | His | Glu | Lys | Lys | Cys | Lys | Gln | Gly | |

```
              260                 265                 270
aaa aga gaa ggc tat ttt gat gtt ctc atg tgg att cat gtt tct caa    864
Lys Arg Glu Gly Tyr Phe Asp Val Leu Met Trp Ile His Val Ser Gln
        275                 280                 285 aaa atc ggt ttg gag tcc agt ttc agg gac atg ttt gag ggg gct aca    912
Lys Ile Gly Leu Glu Ser Ser Phe Arg Asp Met Phe Glu Gly Ala Thr
290                 295                 300 ggg aaa gca tgc ccg aat ttt aat agt ctt aac gtc tta aag gaa aag    960
Gly Lys Ala Cys Pro Asn Phe Asn Ser Leu Asn Val Leu Lys Glu Lys
305                 310                 315                 320 ttg gag gag gaa cta cgt gga aaa cgg att ttt ttg gta cta gat gat   1008
Leu Glu Glu Glu Leu Arg Gly Lys Arg Ile Phe Leu Val Leu Asp Asp
                325                 330                 335 gtc tgg tac aac agt aag aat tca gga gac cgt gaa gaa ctg cag aag   1056
Val Trp Tyr Asn Ser Lys Asn Ser Gly Asp Arg Glu Glu Leu Gln Lys
                340                 345                 350 tta att tct ccg ttg aat gtt ggg aag gca gga agc aga atc ttg gtg   1104
Leu Ile Ser Pro Leu Asn Val Gly Lys Ala Gly Ser Arg Ile Leu Val
                355                 360                 365 act agt cga act gaa gct gca tta gta gct ctc cgt gct gca aaa gag   1152
Thr Ser Arg Thr Glu Ala Ala Leu Val Ala Leu Arg Ala Ala Lys Glu
370                 375                 380 gga tgt atc cca ata tct aac ctg gat gat aaa gtt ttc ctt aaa atg   1200
Gly Cys Ile Pro Ile Ser Asn Leu Asp Asp Lys Val Phe Leu Lys Met
385                 390                 395                 400 ttc atg cat tat gca ctt cca cat gca tgg cca gtt ggc aat gat cga   1248
Phe Met His Tyr Ala Leu Pro His Ala Trp Pro Val Gly Asn Asp Arg
                405                 410                 415 aga aaa ctt gaa atg att gga gag gac att gca aaa aag ctg aag ggt   1296
Arg Lys Leu Glu Met Ile Gly Glu Asp Ile Ala Lys Lys Leu Lys Gly
                420                 425                 430 tca cct ctg gca gct aga ata gtg ggt tca cgg ctc ggt gat aat cca   1344
Ser Pro Leu Ala Ala Arg Ile Val Gly Ser Arg Leu Gly Asp Asn Pro
                435                 440                 445 aat gtt gaa ttt tgg agg aga gag aaa gac cgg gat ctt atg aac gag   1392
Asn Val Glu Phe Trp Arg Arg Glu Lys Asp Arg Asp Leu Met Asn Glu
        450                 455                 460 acg atg gga gca ctt tgg tgg agc tac cag tac ctt gat gag cag gtc   1440
Thr Met Gly Ala Leu Trp Trp Ser Tyr Gln Tyr Leu Asp Glu Gln Val
465                 470                 475                 480 agg cga tgc ttc gct tac atc agc att ttt ccc aga cgt cat cat ttg   1488
Arg Arg Cys Phe Ala Tyr Ile Ser Ile Phe Pro Arg Arg His His Leu
                485                 490                 495 aaa cgt gat gac tta att aac cta tgg gtg gcc gaa gga ttt ata aag   1536
Lys Arg Asp Asp Leu Ile Asn Leu Trp Val Ala Glu Gly Phe Ile Lys
                500                 505                 510 aca agt aaa gct gaa gag gaa atg gaa gat gtt gcc tcg gaa tac ttt   1584
Thr Ser Lys Ala Glu Glu Glu Met Glu Asp Val Ala Ser Glu Tyr Phe
        515                 520                 525 gat gag ctg ctt tcg ttc tca ttt ctg caa tta gga ggg aaa gat gag   1632
Asp Glu Leu Leu Ser Phe Ser Phe Leu Gln Leu Gly Gly Lys Asp Glu
530                 535                 540 cta ttt gca cgt gag gtc gat tac ttt ata att cat gat ctg ttg tat   1680
Leu Phe Ala Arg Glu Val Asp Tyr Phe Ile Ile His Asp Leu Leu Tyr
545                 550                 555                 560 gat tta gca gag gag gtt gct gga aga gat tgc ttc agg ata gag aaa   1728
Asp Leu Ala Glu Glu Val Ala Gly Arg Asp Cys Phe Arg Ile Glu Lys
                565                 570                 575 ggt ttc aca gga gaa gtc cct ccg gat gtt cgc tat ctt ttt gtt ggg   1776
```

```
Gly Phe Thr Gly Glu Val Pro Pro Asp Val Arg Tyr Leu Phe Val Gly
                580                 585                 590 act tac gat aaa gag atg ctt act gag aag ata tcc agg ttg caa aat       1824
Thr Tyr Asp Lys Glu Met Leu Thr Glu Lys Ile Ser Arg Leu Gln Asn
            595                 600                 605 tta cgc act ctc ttc gtc gat aag tac ata cag att tta tca ccc aag       1872
Leu Arg Thr Leu Phe Val Asp Lys Tyr Ile Gln Ile Leu Ser Pro Lys
        610                 615                 620 tac gat gat ttt gtt agt atg gtg act atg ttg atg ggg ctg cgg aaa       1920
Tyr Asp Asp Phe Val Ser Met Val Thr Met Leu Met Gly Leu Arg Lys
625                 630                 635                 640 ttg agg gta ctg aat tta cat ttc act gga tat ggt att cct aaa ttc       1968
Leu Arg Val Leu Asn Leu His Phe Thr Gly Tyr Gly Ile Pro Lys Phe
                645                 650                 655 tca ttg ccg gat tct att ctt cag tgg aag cat ctg cgt tac ttt gct       2016
Ser Leu Pro Asp Ser Ile Leu Gln Trp Lys His Leu Arg Tyr Phe Ala
            660                 665                 670 ttt ggg gtg tcc ccg ttt acc aag cta act tta cca tgc gct ttt acc       2064
Phe Gly Val Ser Pro Phe Thr Lys Leu Thr Leu Pro Cys Ala Phe Thr
        675                 680                 685 aag ctt tac cac ttg cat gtg gta gat ttc ggt gat tgc aat agt ttg       2112
Lys Leu Tyr His Leu His Val Val Asp Phe Gly Asp Cys Asn Ser Leu
690                 695                 700 gag ttt tct cgt ggt gaa tac atg atg aac ctg gtc aat ttg cgc cgt       2160
Glu Phe Ser Arg Gly Glu Tyr Met Met Asn Leu Val Asn Leu Arg Arg
705                 710                 715                 720 gta atc tac aag aat tat ctc gac ttt ccg aac att ggc agg ctg aca       2208
Val Ile Tyr Lys Asn Tyr Leu Asp Phe Pro Asn Ile Gly Arg Leu Thr
                725                 730                 735 tgg ctg caa tcg ttg ccg tgc ttc aga ata agg aag aaa cat ggg tat       2256
Trp Leu Gln Ser Leu Pro Cys Phe Arg Ile Arg Lys Lys His Gly Tyr
            740                 745                 750 gaa tca cat cag ctg aaa cac cta aac aag ctt caa ggc agg ctg tac       2304
Glu Ser His Gln Leu Lys His Leu Asn Lys Leu Gln Gly Arg Leu Tyr
        755                 760                 765 att ggt ggt ctt cag aat gtt gag agc aag gag gaa gct ctt aat gtg       2352
Ile Gly Gly Leu Gln Asn Val Glu Ser Lys Glu Glu Ala Leu Asn Val
770                 775                 780 aac ctt gca gcc aag gaa aaa ctc aca gaa gtg gta ctg cgc tgg agt       2400
Asn Leu Ala Ala Lys Glu Lys Leu Thr Glu Val Val Leu Arg Trp Ser
785                 790                 795                 800 gat aat agc tgc agt cca gaa att caa gca gag gta ctt gag ggc ctt       2448
Asp Asn Ser Cys Ser Pro Glu Ile Gln Ala Glu Val Leu Glu Gly Leu
                805                 810                 815 tgt cct tca aag tat ctt gaa ata cta gaa atc aag tta tac aat ggc       2496
Cys Pro Ser Lys Tyr Leu Glu Ile Leu Glu Ile Lys Leu Tyr Asn Gly
            820                 825                 830 atg aag ttt cca aat tgg atg acg agt aag cat aag ggt ggg cca aag       2544
Met Lys Phe Pro Asn Trp Met Thr Ser Lys His Lys Gly Gly Pro Lys
        835                 840                 845 aac ctg caa gaa ctt aga ttc aga cag agc acc ctg gga tct gct cct       2592
Asn Leu Gln Glu Leu Arg Phe Arg Gln Ser Thr Leu Gly Ser Ala Pro
850                 855                 860 gat gtt ggg gct ttc att cac ctt cag tcg tta ttt att tat caa tgc       2640
Asp Val Gly Ala Phe Ile His Leu Gln Ser Leu Phe Ile Tyr Gln Cys
865                 870                 875                 880 agc tgg gat acc tta cca ggg aat atg gag cac ctc aca gcg ctc aag       2688
Ser Trp Asp Thr Leu Pro Gly Asn Met Glu His Leu Thr Ala Leu Lys
                885                 890                 895
```

-continued

```
aaa ctg gag ata cgg tca tgc aat aat att cgg tcg ctt cca aca ctg    2736
Lys Leu Glu Ile Arg Ser Cys Asn Asn Ile Arg Ser Leu Pro Thr Leu
            900                 905                 910 ccc aag tcc ctt gag cag ttt gtg atc tgg tcc tgc agc ttg gat gct    2784
Pro Lys Ser Leu Glu Gln Phe Val Ile Trp Ser Cys Ser Leu Asp Ala
        915                 920                 925 tta ccg ggc aat atg gag cac ctc aca gca ctc aag aaa ctg gag ata    2832
Leu Pro Gly Asn Met Glu His Leu Thr Ala Leu Lys Lys Leu Glu Ile
    930                 935                 940 cgg tca tgc aat aat att cgg tgg ctt cca aca ctg ccc aag tcc ctt    2880
Arg Ser Cys Asn Asn Ile Arg Trp Leu Pro Thr Leu Pro Lys Ser Leu
945                 950                 955                 960 gag cag ttt gcg atc tcg cgc tgc agc ttg gat gct tta ccg ggc aat    2928
Glu Gln Phe Ala Ile Ser Arg Cys Ser Leu Asp Ala Leu Pro Gly Asn
                965                 970                 975 atg gag cac ctc aca gcg ctc aag aaa ctg gat ata tgg tca tgc gag    2976
Met Glu His Leu Thr Ala Leu Lys Lys Leu Asp Ile Trp Ser Cys Glu
            980                 985                 990 aat ata cgg tcg ctt cca aca cta  ccc aag tct ctt gag  gag ttt aca   3024
Asn Ile Arg Ser Leu Pro Thr Leu  Pro Lys Ser Leu Glu  Glu Phe Thr
        995                 1000                1005 gtc tgg aac tgc act agt gag ttc atg caa tct tgt  atg acg act        3069
Val Trp Asn Cys Thr Ser Glu Phe Met Gln Ser Cys  Met Thr Thr
1010                1015                 1020 gat gat cca aac tgg cag aag att gag cac gtt cca  aac aaa aaa        3114
Asp Asp Pro Asn Trp Gln Lys Ile Glu His Val Pro  Asn Lys Lys
1025                1030                1035 att gga ttt cta                                                     3126
Ile Gly Phe Leu
    1040
```

<210> SEQ ID NO 12
<211> LENGTH: 1042
<212> TYPE: PRT
<213> ORGANISM: Hordeum vulgare

<400> SEQUENCE: 12

```
Met Pro Asp Pro Val Thr Ile Ser Ala Ala Val Gly Trp Gly Val Ser
1               5                   10                  15

Ala Val Gly Trp Leu Ala Ser Pro Ile Ile Ser Arg Val Val Asn Lys
            20                  25                  30

Gly Phe Ala His Leu Asp Phe Asp Ala Ala Glu Lys Leu Lys Ile Leu
        35                  40                  45

Asp Ile Gln Val Leu Gln Leu Gln Arg Val Ile Glu Val Val Asp Glu
    50                  55                  60

Ser Thr Tyr Arg Leu Arg Leu Glu Pro Leu Leu Asp Lys Leu Arg Ser
65                  70                  75                  80

Ala Leu Tyr Glu Ala Glu Asp Ile Leu Asp Asp Phe Asp Tyr Glu Arg
                85                  90                  95

Leu Glu Lys Gln Ile His Val Gly Ser Ser Thr Arg Lys Arg Lys
            100                 105                 110

Ile Asp Ser Leu Glu Lys Asn His Arg Ser Ala Met Pro Ser Ser Ser
        115                 120                 125

Leu Lys Asp Lys Met Glu Thr Phe Pro Arg Ile Ser Lys Gly Lys
    130                 135                 140

Glu Thr Ile Lys Asn Leu Leu Ser Gln Gly Ile Gly Thr Ser Lys Val
145                 150                 155                 160

Glu Leu Lys Lys Ser Leu Glu Lys Ile Glu Asn Thr Ile Asn Asp Ala
```

```
                    165                 170                 175
Cys Lys Val Leu Glu Gln Leu Asn Leu Pro Ser Val Cys Asn Asp Asn
                180                 185                 190

Gly Arg Arg Gly Val Ala Thr Asn Ser Arg Ser Ala Val Thr Thr Ala
            195                 200                 205

Gly Pro Pro Leu Arg Val Ile Gly Arg Asp Gln Asp Arg Asp Lys Ile
210                 215                 220

Ile Ala Met Leu His Glu Lys Asp Asp Arg Cys Gln Val Asn Gly Thr
225                 230                 235                 240

Ser Tyr Ser Val Ile Gly Ile His Gly Val Ala Gly Ser Gly Lys Ser
                245                 250                 255

Thr Leu Ala Gln Tyr Val Tyr Asp His Glu Lys Lys Cys Lys Gln Gly
                260                 265                 270

Lys Arg Glu Gly Tyr Phe Asp Val Leu Met Trp Ile His Val Ser Gln
            275                 280                 285

Lys Ile Gly Leu Glu Ser Ser Phe Arg Asp Met Phe Glu Gly Ala Thr
        290                 295                 300

Gly Lys Ala Cys Pro Asn Phe Asn Ser Leu Asn Val Leu Lys Glu Lys
305                 310                 315                 320

Leu Glu Glu Glu Leu Arg Gly Lys Arg Ile Phe Leu Val Leu Asp Asp
                325                 330                 335

Val Trp Tyr Asn Ser Lys Asn Ser Gly Asp Arg Glu Glu Leu Gln Lys
                340                 345                 350

Leu Ile Ser Pro Leu Asn Val Gly Lys Ala Gly Ser Arg Ile Leu Val
            355                 360                 365

Thr Ser Arg Thr Glu Ala Ala Leu Val Ala Leu Arg Ala Ala Lys Glu
        370                 375                 380

Gly Cys Ile Pro Ile Ser Asn Leu Asp Asp Lys Val Phe Leu Lys Met
385                 390                 395                 400

Phe Met His Tyr Ala Leu Pro His Ala Trp Pro Val Gly Asn Asp Arg
                405                 410                 415

Arg Lys Leu Glu Met Ile Gly Glu Asp Ile Ala Lys Lys Leu Lys Gly
                420                 425                 430

Ser Pro Leu Ala Ala Arg Ile Val Gly Ser Arg Leu Gly Asp Asn Pro
            435                 440                 445

Asn Val Glu Phe Trp Arg Arg Glu Lys Asp Arg Asp Leu Met Asn Glu
        450                 455                 460

Thr Met Gly Ala Leu Trp Trp Ser Tyr Gln Tyr Leu Asp Glu Gln Val
465                 470                 475                 480

Arg Arg Cys Phe Ala Tyr Ile Ser Ile Phe Pro Arg Arg His His Leu
                485                 490                 495

Lys Arg Asp Asp Leu Ile Asn Leu Trp Val Ala Glu Gly Phe Ile Lys
            500                 505                 510

Thr Ser Lys Ala Glu Glu Glu Met Glu Asp Val Ala Ser Glu Tyr Phe
        515                 520                 525

Asp Glu Leu Leu Ser Phe Ser Phe Leu Gln Leu Gly Gly Lys Asp Glu
            530                 535                 540

Leu Phe Ala Arg Glu Val Asp Tyr Phe Ile Ile His Asp Leu Leu Tyr
545                 550                 555                 560

Asp Leu Ala Glu Glu Val Ala Gly Arg Asp Cys Phe Arg Ile Glu Lys
                565                 570                 575

Gly Phe Thr Gly Glu Val Pro Pro Asp Val Arg Tyr Leu Phe Val Gly
            580                 585                 590
```

-continued

```
Thr Tyr Asp Lys Glu Met Leu Thr Glu Lys Ile Ser Arg Leu Gln Asn
        595                 600                 605
Leu Arg Thr Leu Phe Val Asp Lys Tyr Ile Gln Ile Leu Ser Pro Lys
        610                 615                 620
Tyr Asp Asp Phe Val Ser Met Val Thr Met Leu Met Gly Leu Arg Lys
625                 630                 635                 640
Leu Arg Val Leu Asn Leu His Phe Thr Gly Tyr Gly Ile Pro Lys Phe
                645                 650                 655
Ser Leu Pro Asp Ser Ile Leu Gln Trp Lys His Leu Arg Tyr Phe Ala
            660                 665                 670
Phe Gly Val Ser Pro Phe Thr Lys Leu Thr Leu Pro Cys Ala Phe Thr
        675                 680                 685
Lys Leu Tyr His Leu His Val Val Asp Phe Gly Asp Cys Asn Ser Leu
        690                 695                 700
Glu Phe Ser Arg Gly Glu Tyr Met Met Asn Leu Val Asn Leu Arg Arg
705                 710                 715                 720
Val Ile Tyr Lys Asn Tyr Leu Asp Phe Pro Asn Ile Gly Arg Leu Thr
                725                 730                 735
Trp Leu Gln Ser Leu Pro Cys Phe Arg Ile Arg Lys Lys His Gly Tyr
            740                 745                 750
Glu Ser His Gln Leu Lys His Leu Asn Lys Leu Gln Gly Arg Leu Tyr
        755                 760                 765
Ile Gly Gly Leu Gln Asn Val Glu Ser Lys Glu Ala Leu Asn Val
        770                 775                 780
Asn Leu Ala Ala Lys Glu Lys Leu Thr Glu Val Leu Arg Trp Ser
785                 790                 795                 800
Asp Asn Ser Cys Ser Pro Glu Ile Gln Ala Glu Val Leu Glu Gly Leu
                805                 810                 815
Cys Pro Ser Lys Tyr Leu Glu Ile Leu Glu Ile Lys Leu Tyr Asn Gly
            820                 825                 830
Met Lys Phe Pro Asn Trp Met Thr Ser Lys His Lys Gly Gly Pro Lys
        835                 840                 845
Asn Leu Gln Glu Leu Arg Phe Arg Gln Ser Thr Leu Gly Ser Ala Pro
        850                 855                 860
Asp Val Gly Ala Phe Ile His Leu Gln Ser Leu Phe Ile Tyr Gln Cys
865                 870                 875                 880
Ser Trp Asp Thr Leu Pro Gly Asn Met Glu His Leu Thr Ala Leu Lys
                885                 890                 895
Lys Leu Glu Ile Arg Ser Cys Asn Asn Ile Arg Ser Leu Pro Thr Leu
            900                 905                 910
Pro Lys Ser Leu Glu Gln Phe Val Ile Trp Ser Cys Ser Leu Asp Ala
        915                 920                 925
Leu Pro Gly Asn Met Glu His Leu Thr Ala Leu Lys Lys Leu Glu Ile
        930                 935                 940
Arg Ser Cys Asn Asn Ile Arg Trp Leu Pro Thr Leu Pro Lys Ser Leu
945                 950                 955                 960
Glu Gln Phe Ala Ile Ser Arg Cys Ser Leu Asp Ala Leu Pro Gly Asn
                965                 970                 975
Met Glu His Leu Thr Ala Leu Lys Lys Leu Asp Ile Trp Ser Cys Glu
            980                 985                 990
Asn Ile Arg Ser Leu Pro Thr Leu  Pro Lys Ser Leu Glu  Glu Phe Thr
        995                 1000                1005
```

```
Val Trp Asn Cys Thr Ser Glu Phe Met Gln Ser Cys Met Thr Thr
    1010                1015                1020

Asp Asp Pro Asn Trp Gln Lys Ile Glu His Val Pro Asn Lys Lys
    1025                1030                1035

Ile Gly Phe Leu
    1040

<210> SEQ ID NO 13
<211> LENGTH: 3126
<212> TYPE: DNA
<213> ORGANISM: Hordeum vulgare
<220> FEATURE:
<221> NAME/KEY: CDS
<222> LOCATION: (1)..(3126)

<400> SEQUENCE: 13 atg ccg gat cca gtt act att agt gct gct gta gga tgg ggc gta tcc    48
Met Pro Asp Pro Val Thr Ile Ser Ala Ala Val Gly Trp Gly Val Ser
1               5                   10                  15 gca gta ggc tgg ctc gcc tct ccc atc att tca agg gtt gtc aac aaa    96
Ala Val Gly Trp Leu Ala Ser Pro Ile Ile Ser Arg Val Val Asn Lys
                20                  25                  30 ggt ttc gcc cac ctc gac ttc gat gca gca gag aag ctg aag ata ctt   144
Gly Phe Ala His Leu Asp Phe Asp Ala Ala Glu Lys Leu Lys Ile Leu
            35                  40                  45 gat ata caa gtt cta caa ctg cag cgc gtg ata gaa gta gtc gat gag   192
Asp Ile Gln Val Leu Gln Leu Gln Arg Val Ile Glu Val Val Asp Glu
        50                  55                  60 agc acg tac agg ctt cgc ttg gag cca ctg tta gac aag ctt aga tct   240
Ser Thr Tyr Arg Leu Arg Leu Glu Pro Leu Leu Asp Lys Leu Arg Ser
65                  70                  75                  80 gct ctc tat gaa gcc gaa gac atc ttg gat gat ttt gat tat gag cgt   288
Ala Leu Tyr Glu Ala Glu Asp Ile Leu Asp Asp Phe Asp Tyr Glu Arg
                85                  90                  95 ctc gag aag cag atc cat gtt ggg tct agt tcc aca cgt aaa cgc aag   336
Leu Glu Lys Gln Ile His Val Gly Ser Ser Ser Thr Arg Lys Arg Lys
            100                 105                 110 ata gat tcg ctg gag aag aat cat cgg tct gcc atg ccg agt tcc tcc   384
Ile Asp Ser Leu Glu Lys Asn His Arg Ser Ala Met Pro Ser Ser Ser
        115                 120                 125 cta aaa gat aag atg gaa aca ttc ccg agg att tca tcg aag gga aag   432
Leu Lys Asp Lys Met Glu Thr Phe Pro Arg Ile Ser Ser Lys Gly Lys
    130                 135                 140 gag act atc aag aat tta ctg agc cag ggg att gga aca tca aaa gtg   480
Glu Thr Ile Lys Asn Leu Leu Ser Gln Gly Ile Gly Thr Ser Lys Val
145                 150                 155                 160 gag ttg aag aaa agc cta gag aaa ata gaa aat acc ata aac gat gca   528
Glu Leu Lys Lys Ser Leu Glu Lys Ile Glu Asn Thr Ile Asn Asp Ala
                165                 170                 175 tgt aaa gtt ttg gaa caa ctg aac ttg ccg agt gta tgt aat gat aat   576
Cys Lys Val Leu Glu Gln Leu Asn Leu Pro Ser Val Cys Asn Asp Asn
            180                 185                 190 ggg aga cga ggt gtt gct acc aat tct cgt agt gca gtc act act gca   624
Gly Arg Arg Gly Val Ala Thr Asn Ser Arg Ser Ala Val Thr Thr Ala
        195                 200                 205 ggt cct cct cta cga gta att ggt cga gat cag gat cgt gac aag atc   672
Gly Pro Pro Leu Arg Val Ile Gly Arg Asp Gln Asp Arg Asp Lys Ile
    210                 215                 220 ata gca atg ctt cat gag aag gat gac cgg tgt caa gtc aat ggt aca   720
Ile Ala Met Leu His Glu Lys Asp Asp Arg Cys Gln Val Asn Gly Thr
225                 230                 235                 240
```

| | | | | | | | | | | | | | | | | |
|---|---|---|---|---|---|---|---|---|---|---|---|---|---|---|---|---|
| tct | tat | tct | gta | att | ggc | att | cat | ggc | gtc | gcc | ggg | tct | ggg | aaa | tca | 768 |
| Ser | Tyr | Ser | Val | Ile | Gly | Ile | His | Gly | Val | Ala | Gly | Ser | Gly | Lys | Ser | |
| | | | 245 | | | | | 250 | | | | | 255 | | | |
| aca | ctt | gca | cag | tat | gtt | tat | gat | cat | gag | aaa | aag | tgc | aag | caa | ggt | 816 |
| Thr | Leu | Ala | Gln | Tyr | Val | Tyr | Asp | His | Glu | Lys | Lys | Cys | Lys | Gln | Gly | |
| | | | 260 | | | | | 265 | | | | | 270 | | | |
| aaa | aga | gaa | ggc | tat | ttt | gat | gtt | ctc | atg | tgg | att | cat | gtt | tct | caa | 864 |
| Lys | Arg | Glu | Gly | Tyr | Phe | Asp | Val | Leu | Met | Trp | Ile | His | Val | Ser | Gln | |
| | | 275 | | | | | 280 | | | | | 285 | | | | |
| aaa | atc | ggt | ttg | gag | tcc | agt | ttc | agg | gac | atg | ttt | gag | ggg | gct | aca | 912 |
| Lys | Ile | Gly | Leu | Glu | Ser | Ser | Phe | Arg | Asp | Met | Phe | Glu | Gly | Ala | Thr | |
| | 290 | | | | | 295 | | | | | 300 | | | | | |
| ggg | aaa | gca | tgc | ccg | aat | ttt | aat | agt | ctt | aac | gtc | tta | aag | gaa | aag | 960 |
| Gly | Lys | Ala | Cys | Pro | Asn | Phe | Asn | Ser | Leu | Asn | Val | Leu | Lys | Glu | Lys | |
| 305 | | | | 310 | | | | | 315 | | | | | 320 | | |
| ttg | gag | gag | gaa | cta | cgt | gga | aaa | cgg | att | ttt | ttg | gta | cta | gat | gat | 1008 |
| Leu | Glu | Glu | Glu | Leu | Arg | Gly | Lys | Arg | Ile | Phe | Leu | Val | Leu | Asp | Asp | |
| | | | 325 | | | | | 330 | | | | | 335 | | | |
| gtc | tgg | tac | aac | agt | aag | aat | tca | gga | gac | cgt | gaa | gaa | ctg | cag | aag | 1056 |
| Val | Trp | Tyr | Asn | Ser | Lys | Asn | Ser | Gly | Asp | Arg | Glu | Glu | Leu | Gln | Lys | |
| | | | 340 | | | | | 345 | | | | | 350 | | | |
| tta | att | tct | ccg | ttg | aat | gtt | ggg | aag | gca | gga | agc | aga | atc | ttg | gtg | 1104 |
| Leu | Ile | Ser | Pro | Leu | Asn | Val | Gly | Lys | Ala | Gly | Ser | Arg | Ile | Leu | Val | |
| | | 355 | | | | | 360 | | | | | 365 | | | | |
| act | agt | cga | act | gaa | gct | gca | tta | gta | gct | ctc | cgt | gct | gca | aaa | gag | 1152 |
| Thr | Ser | Arg | Thr | Glu | Ala | Ala | Leu | Val | Ala | Leu | Arg | Ala | Ala | Lys | Glu | |
| | 370 | | | | | 375 | | | | | 380 | | | | | |
| gga | tgt | atc | cca | ata | tct | aac | ctg | gat | gat | aaa | gtt | ttc | ctt | aaa | atg | 1200 |
| Gly | Cys | Ile | Pro | Ile | Ser | Asn | Leu | Asp | Asp | Lys | Val | Phe | Leu | Lys | Met | |
| 385 | | | | 390 | | | | | 395 | | | | | 400 | | |
| ttc | atg | cat | tat | gca | ctt | cca | cat | gca | tgg | cca | gtt | ggc | aat | gat | cga | 1248 |
| Phe | Met | His | Tyr | Ala | Leu | Pro | His | Ala | Trp | Pro | Val | Gly | Asn | Asp | Arg | |
| | | | 405 | | | | | 410 | | | | | 415 | | | |
| aga | aaa | ctt | gaa | atg | att | gga | gag | gac | att | gca | aaa | aag | ctg | aag | ggt | 1296 |
| Arg | Lys | Leu | Glu | Met | Ile | Gly | Glu | Asp | Ile | Ala | Lys | Lys | Leu | Lys | Gly | |
| | | | 420 | | | | | 425 | | | | | 430 | | | |
| tca | cct | ctg | gca | gct | aga | ata | gtg | ggt | tca | cgg | ctc | ggt | gat | aat | cca | 1344 |
| Ser | Pro | Leu | Ala | Ala | Arg | Ile | Val | Gly | Ser | Arg | Leu | Gly | Asp | Asn | Pro | |
| | | | 435 | | | | | 440 | | | | | 445 | | | |
| aat | gtt | gaa | ttt | tgg | agg | aga | gag | aaa | gac | cgg | gat | ctt | atg | aac | gag | 1392 |
| Asn | Val | Glu | Phe | Trp | Arg | Arg | Glu | Lys | Asp | Arg | Asp | Leu | Met | Asn | Glu | |
| | | | 450 | | | | | 455 | | | | | 460 | | | |
| acg | atg | gga | gca | ctt | tgg | tgg | agc | tac | cag | tac | ctt | gat | gag | cag | gtc | 1440 |
| Thr | Met | Gly | Ala | Leu | Trp | Trp | Ser | Tyr | Gln | Tyr | Leu | Asp | Glu | Gln | Val | |
| 465 | | | | 470 | | | | | 475 | | | | | 480 | | |
| agg | cga | tgc | ttc | gct | tac | atc | agc | att | ttt | ccc | aga | cgt | cat | cat | ttg | 1488 |
| Arg | Arg | Cys | Phe | Ala | Tyr | Ile | Ser | Ile | Phe | Pro | Arg | Arg | His | His | Leu | |
| | | | | 485 | | | | | 490 | | | | | 495 | | |
| aaa | cgt | gat | gac | tta | att | aac | cta | tgg | gtg | gcc | gaa | gga | ttt | ata | aag | 1536 |
| Lys | Arg | Asp | Asp | Leu | Ile | Asn | Leu | Trp | Val | Ala | Glu | Gly | Phe | Ile | Lys | |
| | | | 500 | | | | | 505 | | | | | 510 | | | |
| aca | agt | aaa | gct | gaa | gag | gaa | atg | gaa | gat | gtt | gcc | tcg | gaa | tac | ttt | 1584 |
| Thr | Ser | Lys | Ala | Glu | Glu | Glu | Met | Glu | Asp | Val | Ala | Ser | Glu | Tyr | Phe | |
| | | 515 | | | | | 520 | | | | | 525 | | | | |
| gat | gag | ctg | ctt | tcg | ttc | tca | ttt | ctg | caa | tta | gga | ggg | aaa | gat | gag | 1632 |
| Asp | Glu | Leu | Leu | Ser | Phe | Ser | Phe | Leu | Gln | Leu | Gly | Gly | Lys | Asp | Glu | |
| | 530 | | | | | 535 | | | | | 540 | | | | | |
| cta | ttt | gca | cgt | gag | gtc | gat | tac | ttt | ata | att | cat | gat | ctg | ttg | tat | 1680 |
| Leu | Phe | Ala | Arg | Glu | Val | Asp | Tyr | Phe | Ile | Ile | His | Asp | Leu | Leu | Tyr | |

```
                  545                 550                 555                 560
gat tta gca gag gag gtt gct gga aga gat tgc ttc agg ata gag aaa      1728
Asp Leu Ala Glu Glu Val Ala Gly Arg Asp Cys Phe Arg Ile Glu Lys
                565                 570                 575 ggt ttc aca gga gaa gtc cct ccg gat gtt cgc tat ctt ttt gtt ggg      1776
Gly Phe Thr Gly Glu Val Pro Pro Asp Val Arg Tyr Leu Phe Val Gly
            580                 585                 590 act tac gat aaa gag atg ctt act gag aag ata tcc agg ttg caa aat      1824
Thr Tyr Asp Lys Glu Met Leu Thr Glu Lys Ile Ser Arg Leu Gln Asn
        595                 600                 605 tta cgc act ctc ttc gtc gat aag tac ata cag att tta tca ccc aag      1872
Leu Arg Thr Leu Phe Val Asp Lys Tyr Ile Gln Ile Leu Ser Pro Lys
    610                 615                 620 tac gat gat ttt gtt agt atg gtg act atg ttg atg ggg ctg cgg aaa      1920
Tyr Asp Asp Phe Val Ser Met Val Thr Met Leu Met Gly Leu Arg Lys
625                 630                 635                 640 ttg agg gta ctg aat tta cat ttc act gga tat ggt att cct aaa ttc      1968
Leu Arg Val Leu Asn Leu His Phe Thr Gly Tyr Gly Ile Pro Lys Phe
                645                 650                 655 tca ttg ccg gat tct att ctt cag tgg aag cat ctg cgt tac ttt gct      2016
Ser Leu Pro Asp Ser Ile Leu Gln Trp Lys His Leu Arg Tyr Phe Ala
            660                 665                 670 ttt ggg gtg tcc ccg ttt acc aag cta act tta cca tgc gct ttt acc      2064
Phe Gly Val Ser Pro Phe Thr Lys Leu Thr Leu Pro Cys Ala Phe Thr
        675                 680                 685 aag ctt tac cac ttg cat gtg gta gat ttc ggt gat tgc aat agt ttg      2112
Lys Leu Tyr His Leu His Val Val Asp Phe Gly Asp Cys Asn Ser Leu
    690                 695                 700 gag ttt tct cgt ggt gaa tac atg atg aac ctg gtc aat ttg cgc cgt      2160
Glu Phe Ser Arg Gly Glu Tyr Met Met Asn Leu Val Asn Leu Arg Arg
705                 710                 715                 720 gta atc tac aag aat tat ctc gac ttt ccg aac att ggc agg ctg aca      2208
Val Ile Tyr Lys Asn Tyr Leu Asp Phe Pro Asn Ile Gly Arg Leu Thr
                725                 730                 735 tgg ctg caa tcg ttg ccg tgc ttc aga ata agg aag aaa cat ggg tat      2256
Trp Leu Gln Ser Leu Pro Cys Phe Arg Ile Arg Lys Lys His Gly Tyr
            740                 745                 750 gaa tca cat cag ctg aaa cac cta aac aag ctt caa ggc agg ctg tac      2304
Glu Ser His Gln Leu Lys His Leu Asn Lys Leu Gln Gly Arg Leu Tyr
        755                 760                 765 att ggt ggt ctt cag aat gtt gag agc aag gag gaa gct ctt aat gtg      2352
Ile Gly Gly Leu Gln Asn Val Glu Ser Lys Glu Glu Ala Leu Asn Val
    770                 775                 780 aac ctt gca gcc aag gaa aaa ctc aca gaa gtg gta ctg cgc tgg agt      2400
Asn Leu Ala Ala Lys Glu Lys Leu Thr Glu Val Val Leu Arg Trp Ser
785                 790                 795                 800 gat aat agc tgc agt cca gaa att caa gca gag gta ctt gag ggc ctt      2448
Asp Asn Ser Cys Ser Pro Glu Ile Gln Ala Glu Val Leu Glu Gly Leu
                805                 810                 815 tgt cct tca aag tat ctt gaa ata cta gaa atc aag tta tac aat ggc      2496
Cys Pro Ser Lys Tyr Leu Glu Ile Leu Glu Ile Lys Leu Tyr Asn Gly
            820                 825                 830 atg aag ttt cca aat tgg atg acg agt aag cat aag ggt ggg cca aag      2544
Met Lys Phe Pro Asn Trp Met Thr Ser Lys His Lys Gly Gly Pro Lys
        835                 840                 845 aac ctg caa gaa ctt aga ttc aga cag agc acc ctg gga tct gct cct      2592
Asn Leu Gln Glu Leu Arg Phe Arg Gln Ser Thr Leu Gly Ser Ala Pro
    850                 855                 860 gat gtt ggg gct ttc att cac ctt cag tcg tta ttt att tat caa tgc      2640
Asp Val Gly Ala Phe Ile His Leu Gln Ser Leu Phe Ile Tyr Gln Cys
```

```
Asp Val Gly Ala Phe Ile His Leu Gln Ser Leu Phe Ile Tyr Gln Cys
865                 870                 875                 880 agc tgg gat acc tta cca ggg aat atg gag cac ctc aca gcg ctc aag        2688
Ser Trp Asp Thr Leu Pro Gly Asn Met Glu His Leu Thr Ala Leu Lys
                    885                 890                 895 aaa ctg gag ata cgg tca tgc aat aat att cgg tcg ctt cca aca ctg        2736
Lys Leu Glu Ile Arg Ser Cys Asn Asn Ile Arg Ser Leu Pro Thr Leu
                900                 905                 910 ccc aag tcc ctt gag cag ttt gtg atc tgg tcc tgc agc ttg gat gct        2784
Pro Lys Ser Leu Glu Gln Phe Val Ile Trp Ser Cys Ser Leu Asp Ala
            915                 920                 925 tta ccg ggc aat atg gag cac ctc aca gca ctc aag aaa ctg gag ata        2832
Leu Pro Gly Asn Met Glu His Leu Thr Ala Leu Lys Lys Leu Glu Ile
        930                 935                 940 cgg tca tgc aat aat att cgg tgg ctt cca aca ctg ccc aag tcc ctt        2880
Arg Ser Cys Asn Asn Ile Arg Trp Leu Pro Thr Leu Pro Lys Ser Leu
945                 950                 955                 960 gag cag ttt gcg atc tcg cgc tgc agc ttg gat gct tta ccg ggc aat        2928
Glu Gln Phe Ala Ile Ser Arg Cys Ser Leu Asp Ala Leu Pro Gly Asn
                    965                 970                 975 atg gag cac ctc aca gcg ctc aag aaa ctg gat ata tgg tca tgc gag        2976
Met Glu His Leu Thr Ala Leu Lys Lys Leu Asp Ile Trp Ser Cys Glu
                980                 985                 990 aat ata cgg tcg ctt cca aca cta ccc aag tct ctt gag gag ttt aca        3024
Asn Ile Arg Ser Leu Pro Thr Leu Pro Lys Ser Leu Glu Glu Phe Thr
            995                 1000                1005 gtc tgg aac tgc act agt gag ttc atg caa tct tgt atg acg act            3069
Val Trp Asn Cys Thr Ser Glu Phe Met Gln Ser Cys Met Thr Thr
1010                1015                1020 gat gat cca aac tgg cag aag att gag cac gtt cca aac aaa aaa            3114
Asp Asp Pro Asn Trp Gln Lys Ile Glu His Val Pro Asn Lys Lys
    1025                1030                1035 att gga ttt cta                                                        3126
Ile Gly Phe Leu
    1040
```

<210> SEQ ID NO 14
<211> LENGTH: 1042
<212> TYPE: PRT
<213> ORGANISM: Hordeum vulgare

<400> SEQUENCE: 14

```
Met Pro Asp Pro Val Thr Ile Ser Ala Ala Val Gly Trp Gly Val Ser
1               5                   10                  15

Ala Val Gly Trp Leu Ala Ser Pro Ile Ile Ser Arg Val Val Asn Lys
            20                  25                  30

Gly Phe Ala His Leu Asp Phe Asp Ala Ala Glu Lys Leu Lys Ile Leu
        35                  40                  45

Asp Ile Gln Val Leu Gln Leu Gln Arg Val Ile Glu Val Val Asp Glu
    50                  55                  60

Ser Thr Tyr Arg Leu Arg Leu Glu Pro Leu Leu Asp Lys Leu Arg Ser
65                  70                  75                  80

Ala Leu Tyr Glu Ala Glu Asp Ile Leu Asp Asp Phe Asp Tyr Glu Arg
                85                  90                  95

Leu Glu Lys Gln Ile His Val Gly Ser Ser Thr Arg Lys Arg Lys
            100                 105                 110

Ile Asp Ser Leu Glu Lys Asn His Arg Ser Ala Met Pro Ser Ser Ser
        115                 120                 125
```

Leu Lys Asp Lys Met Glu Thr Phe Pro Arg Ile Ser Lys Gly Lys
130                 135                 140

Glu Thr Ile Lys Asn Leu Leu Ser Gln Gly Ile Gly Thr Ser Lys Val
145                 150                 155                 160

Glu Leu Lys Lys Ser Leu Glu Lys Ile Glu Asn Thr Ile Asn Asp Ala
                165                 170                 175

Cys Lys Val Leu Glu Gln Leu Asn Leu Pro Ser Val Cys Asn Asp Asn
                180                 185                 190

Gly Arg Arg Gly Val Ala Thr Asn Ser Arg Ser Ala Val Thr Thr Ala
        195                 200                 205

Gly Pro Pro Leu Arg Val Ile Gly Arg Asp Gln Asp Arg Asp Lys Ile
210                 215                 220

Ile Ala Met Leu His Glu Lys Asp Asp Arg Cys Gln Val Asn Gly Thr
225                 230                 235                 240

Ser Tyr Ser Val Ile Gly Ile His Gly Val Ala Gly Ser Gly Lys Ser
                245                 250                 255

Thr Leu Ala Gln Tyr Val Tyr Asp His Glu Lys Lys Cys Lys Gln Gly
        260                 265                 270

Lys Arg Glu Gly Tyr Phe Asp Val Leu Met Trp Ile His Val Ser Gln
        275                 280                 285

Lys Ile Gly Leu Glu Ser Ser Phe Arg Asp Met Phe Glu Gly Ala Thr
290                 295                 300

Gly Lys Ala Cys Pro Asn Phe Asn Ser Leu Asn Val Leu Lys Glu Lys
305                 310                 315                 320

Leu Glu Glu Glu Leu Arg Gly Lys Arg Ile Phe Leu Val Leu Asp Asp
                325                 330                 335

Val Trp Tyr Asn Ser Lys Asn Ser Gly Asp Arg Glu Glu Leu Gln Lys
        340                 345                 350

Leu Ile Ser Pro Leu Asn Val Gly Lys Ala Gly Ser Arg Ile Leu Val
        355                 360                 365

Thr Ser Arg Thr Glu Ala Ala Leu Val Ala Leu Arg Ala Ala Lys Glu
370                 375                 380

Gly Cys Ile Pro Ile Ser Asn Leu Asp Asp Lys Val Phe Leu Lys Met
385                 390                 395                 400

Phe Met His Tyr Ala Leu Pro His Ala Trp Pro Val Gly Asn Asp Arg
                405                 410                 415

Arg Lys Leu Glu Met Ile Gly Glu Asp Ile Ala Lys Lys Leu Lys Gly
        420                 425                 430

Ser Pro Leu Ala Ala Arg Ile Val Gly Ser Arg Leu Gly Asp Asn Pro
        435                 440                 445

Asn Val Glu Phe Trp Arg Arg Glu Lys Asp Arg Asp Leu Met Asn Glu
450                 455                 460

Thr Met Gly Ala Leu Trp Trp Ser Tyr Gln Tyr Leu Asp Glu Gln Val
465                 470                 475                 480

Arg Arg Cys Phe Ala Tyr Ile Ser Ile Phe Pro Arg Arg His His Leu
                485                 490                 495

Lys Arg Asp Asp Leu Ile Asn Leu Trp Val Ala Glu Gly Phe Ile Lys
        500                 505                 510

Thr Ser Lys Ala Glu Glu Met Glu Asp Val Ala Ser Glu Tyr Phe
        515                 520                 525

Asp Glu Leu Leu Ser Phe Ser Phe Leu Gln Leu Gly Gly Lys Asp Glu
530                 535                 540

Leu Phe Ala Arg Glu Val Asp Tyr Phe Ile Ile His Asp Leu Leu Tyr

```
545                 550                 555                 560
Asp Leu Ala Glu Glu Val Ala Gly Arg Asp Cys Phe Arg Ile Glu Lys
                565                 570                 575

Gly Phe Thr Gly Glu Val Pro Pro Asp Val Arg Tyr Leu Phe Val Gly
                580                 585                 590

Thr Tyr Asp Lys Glu Met Leu Thr Glu Lys Ile Ser Arg Leu Gln Asn
                595                 600                 605

Leu Arg Thr Leu Phe Val Asp Lys Tyr Ile Gln Ile Leu Ser Pro Lys
            610                 615                 620

Tyr Asp Asp Phe Val Ser Met Val Thr Met Leu Met Gly Leu Arg Lys
625                 630                 635                 640

Leu Arg Val Leu Asn Leu His Phe Thr Gly Tyr Gly Ile Pro Lys Phe
                645                 650                 655

Ser Leu Pro Asp Ser Ile Leu Gln Trp Lys His Leu Arg Tyr Phe Ala
                660                 665                 670

Phe Gly Val Ser Pro Phe Thr Lys Leu Thr Leu Pro Cys Ala Phe Thr
                675                 680                 685

Lys Leu Tyr His Leu His Val Val Asp Phe Gly Asp Cys Asn Ser Leu
            690                 695                 700

Glu Phe Ser Arg Gly Glu Tyr Met Met Asn Leu Val Asn Leu Arg Arg
705                 710                 715                 720

Val Ile Tyr Lys Asn Tyr Leu Asp Phe Pro Asn Ile Gly Arg Leu Thr
                725                 730                 735

Trp Leu Gln Ser Leu Pro Cys Phe Arg Ile Arg Lys Lys His Gly Tyr
                740                 745                 750

Glu Ser His Gln Leu Lys His Leu Asn Lys Leu Gln Gly Arg Leu Tyr
            755                 760                 765

Ile Gly Gly Leu Gln Asn Val Glu Ser Lys Glu Ala Leu Asn Val
            770                 775                 780

Asn Leu Ala Ala Lys Glu Lys Leu Thr Glu Val Val Leu Arg Trp Ser
785                 790                 795                 800

Asp Asn Ser Cys Ser Pro Glu Ile Gln Ala Glu Val Leu Glu Gly Leu
                805                 810                 815

Cys Pro Ser Lys Tyr Leu Glu Ile Leu Glu Ile Lys Leu Tyr Asn Gly
                820                 825                 830

Met Lys Phe Pro Asn Trp Met Thr Ser Lys His Lys Gly Gly Pro Lys
            835                 840                 845

Asn Leu Gln Glu Leu Arg Phe Arg Gln Ser Thr Leu Gly Ser Ala Pro
850                 855                 860

Asp Val Gly Ala Phe Ile His Leu Gln Ser Leu Phe Ile Tyr Gln Cys
865                 870                 875                 880

Ser Trp Asp Thr Leu Pro Gly Asn Met Glu His Leu Thr Ala Leu Lys
                885                 890                 895

Lys Leu Glu Ile Arg Ser Cys Asn Asn Ile Arg Ser Leu Pro Thr Leu
                900                 905                 910

Pro Lys Ser Leu Glu Gln Phe Val Ile Trp Ser Cys Ser Leu Asp Ala
            915                 920                 925

Leu Pro Gly Asn Met Glu His Leu Thr Ala Leu Lys Lys Leu Glu Ile
            930                 935                 940

Arg Ser Cys Asn Asn Ile Arg Trp Leu Pro Thr Leu Pro Lys Ser Leu
945                 950                 955                 960

Glu Gln Phe Ala Ile Ser Arg Cys Ser Leu Asp Ala Leu Pro Gly Asn
                965                 970                 975
```

```
Met Glu His Leu Thr Ala Leu Lys Lys Leu Asp Ile Trp Ser Cys Glu
            980                 985                 990

Asn Ile Arg Ser Leu Pro Thr Leu Pro Lys Ser Leu Glu Glu Phe Thr
            995                 1000                1005

Val Trp Asn Cys Thr Ser Glu Phe Met Gln Ser Cys Met Thr Thr
    1010                1015                1020

Asp Asp Pro Asn Trp Gln Lys Ile Glu His Val Pro Asn Lys Lys
    1025                1030                1035

Ile Gly Phe Leu
    1040

<210> SEQ ID NO 15
<211> LENGTH: 13276
<212> TYPE: DNA
<213> ORGANISM: Artificial Sequence
<220> FEATURE:
<223> OTHER INFORMATION: Artificial DNA construct

<400> SEQUENCE: 15
tttttatccc cggaagcctg tggatagagg gtagttatcc acgtgaaacc gctaatgccc      60
cgcaaagcct tgattcacgg ggcttttccgg cccgctccaa aaactatcca cgtgaaatcg     120
ctaatcaggg tacgtgaaat cgctaatcgg agtacgtgaa atcgctaata aggtcacgtg     180
aaatcgctaa tcaaaaaggc acgtgagaac gctaatagcc ctttcagatc aacagcttgc     240
aaacacccct cgctccggca agtagttaca gcaagtagta tgttcaatta gcttttcaat     300
tatgaatata tatatcaatt attggtcgcc cttggcttgt ggacaatgcg ctacgcgcac     360
cggctccgcc cgtggacaac cgcaagcggt tgcccaccgt cgagcgccag cgcctttgcc     420
cacaacccgg cggccggccg caacagatcg ttttataaat ttttttttt gaaaagaaa      480
aagcccgaaa ggcggcaacc tctcgggctt ctggatttcc gatccccgga attagatctt     540
ggcaggatat attgtggtgt aacgtatcac aagtttgtac aaaaaagcag gctccgcggc     600
cgccccttc acctagactc gacgcgtcct agagatccgt caacatggtg gagcacgaca     660
ctctcgtcta ctccaagaat atcaaagata cagtctcaga agaccaaagg gctattgaga     720
cttttcaaca agggtaata tcgggaaacc tcctcggatt ccattgccca gctatctgtc     780
acttcatcaa aaggacagta gaaaggaag gtggcaccta caaatgccat cattgcgata     840
aaggaaaggc tatcgttcaa gatgcctctg ccgacagtgg tcccaaagat ggaccccac     900
ccacgaggag catcgtggaa aagaagacg ttccaaccac gtcttcaaag caagtggatt     960
gatgtgatat ctccactgac gtaagggatg acgcacaatc ccactatcct tcgcaagacc    1020
cttcctctat ataaggaagt tcatttcatt tggagaggac gacccgata tgaaaaagcc    1080
tgaactcacc gcgacgtctg tcgagaagtt tctgatcgaa aagttcgaca gcgtctccga    1140
cctgatgcag ctctcggagg gcgaagaatc tcgtgctttc agcttcgatg taggagggcg    1200
tggatatgtc ctgcgggtaa atagctgcgc cgatggtttc tacaaagatc gttatgttta    1260
tcggcacttt gcatcggccg cgctcccgat tccggaagtg cttgacattg ggaattcag    1320
cgagagcctg acctattgca tctcccgccg tgcacaggt gtcacgttgc aagacctgcc    1380
tgaaaccgaa ctgcccgctg ttctgcaggt aaatttctag ttttttctcct tcatttcttt    1440
ggttaggacc cttttctctt tttatttttt tgagctttga tctttcttta aactgatcta    1500
ttttttaatt gattggttat ggtgtaaata ttacatagct ttaactgata atctgattac    1560
tttatttcgt gtgtctatga tgatgatgat aactgcagcc ggtcgcggag gccatggatg    1620
```

-continued

```
cgatcgctgc ggccgatctt agccagacga gcgggttcgg cccattcgga ccgcaaggaa    1680
tcggtcaata cactacatgg cgtgatttca tatgcgcgat tgctgatccc catgtgtatc    1740
actggcaaac tgtgatggac gacaccgtca gtgcgtccgt cgcgcaggct ctcgatgagc    1800
tgatgctttg ggccgaggac tgccccgaag tccggcacct cgtgcacgcg gatttcggct    1860
ccaacaatgt cctgacggac aatggccgca taacagcggt cattgactgg agcgaggcga    1920
tgttcgggga ttcccaatac gaggtcgcca acatcttctt ctggaggccg tggttggctt    1980
gtatggagca gcagacgcgc tacttcgagc ggaggcatcc ggagcttgca ggatcgccgc    2040
ggctccgggc gtatatgctc cgcattggtc ttgaccaact ctatcagagc ttggttgacg    2100
gcaatttcga tgatgcagct tgggcgcagg tcgatgcga cgcaatcgtc cgatccggag    2160
ccgggactgt cgggcgtaca caaatcgccc gcagaagcgc ggccgtctgg accgatggct    2220
gtgtagaagt actcgccgat agtggaaacc gacgcccag cactcgtccg agggcaaagg    2280
aatagagtag atgccgaccg ggatccggag agctcgaatt ccccgatcg ttcaaacatt    2340 tggcaataaa gtttcttaag attgaatcct gttgccggtc ttgcgatgat tatcatataa    2400
tttctgttga attacgttaa gcatgtaata attaacatgt aatgcatgac gttatttatg    2460
agatgggttt ttatgattag agtcccgcaa ttatacattt aatacgcgat agaaaacaaa    2520
atatagcgcg caaactagga taaattatcg cgcgcggtgt catctatgtt actagatcgg    2580
gaattcatcg atgatatcag atcaagggtg ggcgcgccga accagctttc ttgtacaaag    2640
tggtgatccc cctcgaggtc gacggtatcg ataagcttga tatcgaattc ccgtgcctca    2700
tgcaatagaa aataaaacat aaaacatgtt ttttttttca ttctgaaagg cacgggtcat    2760
gcctcttgcg aaggcaaaac cgtgcctctc gcggaaaaaa agagagcaga aaacgtgttt    2820 ttccccttt cagaagaggc acggacgtgt ctctcgcgaa ggcaaaaccg agactttcgc    2880
ggaagcaaaa gtgtgtctct cgcaaaagaa aaacacgttt tttcccttc gggagaaaac    2940 cgtgcctctc gcagaaaaac aaacaaacag aaaacgcatt ttttttcatt caggagaggc    3000
ctctcgcaaa ggtaaaactg tgcctttcgc aaaaggaaaa ccgtgcctct cgcagaaaaa    3060
taaacaaaca gaaaacgcgt ttttctttct ttccgaagag gcacggtcgt gcctctcgcg    3120
aaggtaaaat catgccttc gcggaagcaa aaccgtgcct ctcgcaaaaa aacaaaaaac    3180
acgttttttt ttcctttcag agaggcacga ccgtgcctct cgtgatagca aaaccgtgtc    3240
tcgcaaaaaa aaagtttttt cacgtacaaa taaagaaaa tgtgtttttt caccaaaata    3300
aagtacgaat ttcttttcgt tcaaaagtta cgaaagatcg gtgaaaaacc ataacacaat    3360
tttttcgaaa aaatcactca aaaaggaga aaacgcgtgc gaaaatatt taaaaaaaaa    3420 tttaaggaa acgttcagaa cacgacacgt ggcgacggct ggaaacgcgt caactggcga    3480
cgcgcgggag caatcgctgg gaggctcccg aaaaagcact cgctaactag ttgcttcttt    3540
ttcctccagc ataatccaca acggttcgct gaaaagaaaa gtttaatcaa caccagaggc    3600
aatgtgaggc caccgacgtc tctgatgctg cttgtcgggg gcatcaatcc ggcggacggg    3660
ggcgacaacc cgtcagaaac tcgagccatc catggtgaag acgtcgacac aggtctccgg    3720
ccgggaggtc tacgccaacc agcgacttct tcattcgtaa aacaaacaaa caaacaaaca    3780
aacagctgtt ggatcagaga ccggaaaaac acaggcgacc acaaaggctg tgaacgaatg    3840
gaacacgagc acagagacaa ccatattttg cgaggcccaa ctgccgtcct cttttcttgt    3900
tttttttttc ttttattcta ttaacgtaac aaacaaagag attacaaagc atgtgtaaca    3960
```

```
gccggacgac tgggccgact ccaacgccac gatccgtcca tatcgtgcca tcccacgatt    4020
gacttggtga tcatgactaa caaactactt ctacttacat gcagcgactc gaagtgcatg    4080
tacacaccca tcatatctgt atagcgtacg tactaaatac atgcaactag cacatgcacc    4140
accaggatgt gatcctgtct aacaacctaa cctagctgct aaaaacaact gaatatgcat    4200
gacacagacc ttgtaacaag attagcacca acaacagcga gctctaggac tcgaaccatt    4260
ctgagagaaa tttcatcgga ggagagatat gcataccaac cggctccttt ttatctcgga    4320
aattccatcc aatattcatg tcttgttctt gtactgaata gtttaggagc aatttctgtc    4380 tagcttttc attagttaga acagggcaga ggatagatac atagtgggac aaatgataag    4440
atgagatact gacctgtgct gtgtaagaaa agaacctgcc taagctactc gagtcgtcca    4500
ttccgaaatt ggaccgactc ttcattcagc atttgacctt caaaggcagc aggcagcagg    4560
ccagagagtg gtaccgacgc gaggatgtga agagaagaaa tacaatacga cattttcgct    4620
ccaagcaaag aaaacaaata cggtatatat gtcgaaaatg agtggatgaa agctcgttcg    4680
gaatagtatt cgccgtcgac atctagtctt gagtagacaa ggatgagaaa aggccgatcg    4740
atgtgcagca tccagttacc attgacctgc atgtagtacg tcaatgattc cttaggttca    4800
cacctctagt gcatgggaaa agcctagata ttataaccta caaattcaag gaggcaaatt    4860
tatgggcttt tgtctaattt taacatttac tggtaggtgt cgatccatcg gaaattccct    4920
tgaagcatcc atgccaattc gtcaagtctt gaattaatag atagcgactt gagaggatgt    4980
ggaaagaaaa gaaatacaga cattatcgtt ctaagcaaag aaaagaaata tatatgatat    5040
agctgtaaaa tgagtggagg aaaatgtgtg tggaatagta ttcgtcgtca tcatctagtc    5100
ttgagtggat aaaggtgcga gaggatgtgc accatacatg atatatacat gtaaattcat    5160
gctgttaata ctgcataaat tgtgtgtttg tgtgagagaa actgagagag ggagtatcag    5220
ttccattttc tctcttcacc agtgcttgtt catgtatcca agctaccagg tcaccaggtg    5280
tattagcaga gtctatatat atacatactg caggctaact agctagcctt cttccccct    5340 tttaactaag gcttgcaaat gccggatcca gttactatta gtgctgctgt aggatggggc    5400
gtatccgcag taggctggct cgcctctccc atcatttcaa gggttgtcaa caaaggtttc    5460
gcccacctcg acttcgatgc agcagagaag ctgaagatac ttgatataca agttctacaa    5520
ctgcagcgcg tgatagaagt agtcgatgag agcacgtaca ggcttcgctt ggagccactg    5580
ttagacaagc ttagatctgc tctttatgaa gccgaagaca tcttggatga ttttgattat    5640
cagcgtctcg agaagcagat ccatgttggg tctagttcca cacgtaaacg caagatagat    5700
tcgctggaga agaatcatcg gtctgccatg ccgagttcct ccctaaaaga taagatggaa    5760
acattcccga ggatttcatc gaagggaaag gagactatca ataatttact gagccagggg    5820
attggaacat caaaagtgga gttgaagaaa agcctagaga aaatagaaaa taccataaac    5880
gatgcatgta agttttgga acaactgaac ttgccgagtg tatgtaatga taatgggaga    5940
cgaggtgttg ctaccaattc tcgtagtgca gtcactactg caggtcctcc tctacgagta    6000
attggtcgag atcaggatcg tgacaagatc atagcaatgc ttcatgagaa ggatgaccgg    6060
tgtcaagtca atggtacatc ttattctgta attggcattc atggcgtcgc cgggtctggg    6120
aaatcaacac ttgcacagta tgtttatgat catgagaaaa agtgcaagca aggtaaaaga    6180
gaaggctatt ttgatgttct catgtggatt catgtttctc aaaaaatcgg tttggagtcc    6240
agtttcaggg acatgtttga gggggctaca gggaaagcat gcccgaattt taatagtctt    6300
aacgtcttaa aggaaaagtt ggaggaggaa ctacgtggaa aacggatttt tttggtacta    6360
```

```
gatgatgtct ggtacaacag taagaattca ggagaccgtg aagaactgca gaagttaatt    6420
tctccgttga atgttgggaa ggcaggaagc agaatcttgg tgactagtcg aactgaagct    6480
gcattagtag ctctccgtgc tgcaaaagag ggatgtatcc caatatctaa cctggatgat    6540
aaagttttcc ttaaaatgtt catgcattat gcacttccac atgcatggcc agttggcaat    6600
gatcgaagaa aacttgaaat gattggagag gacattgcaa aaaagctgaa gggttcacct    6660
ctggcagcta gaatagtggg ttcacggctc ggtgataatc caaatgttga attttggagg    6720
agagagaaag accgggatct tatgaacgag acgatgggag cactttggtg gagctaccag    6780
taccttgatg agcaggtcag gcgatgcttc gcttacatca gcattttttcc cagacgtcat    6840 catttgaaac gtgatgactt aattaaccta tgggtggccg aaggatttat aaagacaagt    6900
aaagctgaag aggaaatgga agatgttgcc tcggaatact ttgatgagct gctttcgttc    6960
tcatttctgc aattaggagg gaaagatgag ctatttgcac gtgaggtcga ttactttata    7020
attcatgatc tgttgtatga tttagcagag gaggttgctg aagagattg cttcaggata    7080 gagaaaggtt tcacaggaga agtccctccg gatgttcgct atcttttgt tgggacttac    7140 gataaagaga tgcttactga gaagatatcc aggttgcaaa atttacgcac tctcttcgtc    7200
gataagtaca tacagatttt atcacccaag tacgatgatt ttgttagtat ggtgactatg    7260
ttgatggggc tgcggaaatt gagggtactg aatttacatt tcactggata tggtattcct    7320
aaattctcat tgccggattc tattcttcag tggaagcatc tgcgttactt tgcttttggg    7380
gtgtccccgt ttaccaagct aactttacca tgcgcttttta ccaagcttta ccacttgcat    7440
gtggtagatt tcggtgattg caatagtttg gagttttctc gtggtgaata catgatgaac    7500
ctggtcaatt tgcgccgtgt aatctacaag aattatctcg actttccgaa cattggcagg    7560
ctgacatggc tgcaatcgtt gccgtgcttc agaataagga agaaacatgg gtatgaatca    7620
catcagctga aacacctaaa caagcttcaa ggcaggctgt acattggtgg tcttcagaat    7680
gttgagagca aggaggaagc tcttaatgtg aaccttgcag ccaaggaaaa actcacagaa    7740
gtggtactgc gctggagtga taatagctgc agtccagaaa ttcaagcaga ggtacttgag    7800
ggcctttgtc cttcaaagta tcttgaaata ctagaaatca agttatacaa tggcatgaag    7860
tttccaaatt ggatgacgag taagcataag ggtgggccaa agaacctgca agaacttaga    7920
ttcagacaga gcaccctggg atctgctcct gatgttgggg cttttcattca ccttcagtcg    7980 ttatttattt atcaatgcag ctgggatacc ttaccaggga atatggagca cctcacagcg    8040
ctcaagaaac tggagatacg gtcatgcaat aatattcggt cgcttccaac actgcccaag    8100
tcccttgagc agtttgcgat ctggtcctgc agcttggatg ctttaccggg caatatggag    8160
cacctcacag cactcaagaa actggagata cggtcatgca ataatattcg gtggcttcca    8220
acactgccca gtcccttga gcagtttgcg atctcgcgct gcagcttgga tgctttaccg    8280
ggcaatatgg agcacctcac agcgctcaag aaactggata tatggtcatg cgagaatata    8340
cggtcgcttc caacactacc caagtctctt gaggagttta cagtctggaa ctgcactagt    8400
gagttcatgc aatcttgtat gacgactgat gatccaaact ggcagaagat tgagcacgtt    8460
ccaaacaaaa aaattggatt tctatgaaaa cgatacataa agaaggtacg tatttaaatt    8520 ccttttgacgt cttcgttttc catttttgcg tgcagtaaat gttactgcaa caattagccg    8580
ttaaggttcc tggtattttt ctgattcagt tgctaactat taggcgcgtg ccccttttggtt    8640 gaggacggga gatgaagtcg aagccgaagc cgtcagaatc ttgctaaatt tacggtctct    8700
```

```
cttactggat agcctcttgg ttgggttatg cctactttgg ttggttgagt cttgcatgtt    8760
tacacctaaa gtggtgcaaa atgccatctc tccatgcagt cacaactcac aaacagtgga    8820
tttatgaatt gtttacaata tatggattta tggatgcaat aacgtgtaat aatgaacagc    8880
tgattgattt gccttcatat atatatatat atgatttgta acactgccgt gtggatgatg    8940
aacctggccc aaactgtttg attcctagct atatatgatt tgtaacactt tggaatgatt    9000
atcactgaat tcgttccttt cctgtcgttg tttgtatcat ggttcaaaaa aaagtatccg    9060
atttgattgc gaggaattgg gggctacata agcatggtat ggtatgaggt taccagattg    9120
ggcgaagcta acccgaggaa ctgctcctga cattgaggct tccattcatt ttcagtaata    9180
gaatgctaaa aggctttagt ggttgcaatc aacgtgcatt gtaattagtg attgcatttt    9240
tttttctact ggttgcccat tcagggaaag tgctctcaca cggtggcatg ttctctgttc    9300
tgcacacgct ctcgttttgg gcagacgcaa gctttgatgt gtccgcttgg gccttcaaac    9360
acgatgcaac atattctgca aacactattg agtattttct ttctcaattt ttgctcatct    9420
taggagctgt tcggtaacca tccagatcca tgaaatctga gaatctgcgg agtacctctt    9480
gtccagctct gcaatttta cctgctgctc ctccaactcc gggagtgaag atgcggagtg    9540
gaggacatcc gaacaggcct ttaatcaatg aaagcatcgc tagctgctac ctttcgttca    9600
caaaaatgtt ttaaagaagg atgcgacctg tagcatgaaa acaagaacga catagacttc    9660
tgaccactgc caagtgaaat tctgtagatc atcagaacac gctatattgt cagaaagatg    9720
atcacatctg tgacaagtcc acgcgctcga acaacaacc actttgaact ctgaaagctg    9780
atctcatgac gactccacca aattgggtcc aacttgtaca catattcgag accttatgat    9840
cgagccagta tgaaacgaac aaattccagg cgctcatgta gtatctcatt ggtaatgcta    9900
ccacacaggt tggactacat agccagaggc acgccaacat aaggaaaccg agtcgtgaaa    9960
aactcgagat tcgcggaatt ggtacgttga tgttctagga gtcaatatac tacctgacca    10020
cgtggcagta taacaaacaa acttgaactg aagaaaaaac agggaaagaa actgggtggt    10080
tgggatacac agcaagacag aggcacatga acataaagga attcggtcaa gaaaaactcg    10140
tacggaattg gttttgcagg agttcatta ctgcctaggc acattctatc agtataacaa    10200
actacaaagg aaaagaacca aactgggggt gttggtagtg aggaaaaaca gcacaatcgc    10260
ccgaaacttt acgttcagt ccgtcatctc aatcaatatg atttgcattg agattcagag    10320
cacaactatg atactgagat tcaaagagtg gtggagacat tgactgcaat aaagagcaat    10380
ttcagttgcc cgtgctgata agcactcact tcgatctcat gaggttgatt cacataaaac    10440
aacatacgtg ggataacatt tcagtttcct gtgagcacaa gttatgcagg tttatctcga    10500
aacagcaacg taagataaaa ttatacatct gaagatgaag acaagagaac ttctctgctt    10560
ccttacatct atcataagga ctgtacaaaa tgaacaatct ttgacttgaa cgaattttct    10620
tgaggtgaaa caatccaagg taaacagga tataaagttg tattccttct acatttatct    10680
tgaccatcag aactactact caataataat aataataata ataagctggt gtttctagtg    10740
attccatcag gaattcagga ctcatgcata agctactcat agcgtacaag atcattcccc    10800
ttactaaccg cattctctta agatccacta gttctagagc ggccgccacc gcggtggagc    10860
tccagctttt gttcccttta gtgagggtta attccgagct tggcgtaatc atggtcatag    10920
ctgtttcctg tgtgaaattg ttatccgctc acaattccac acaacatacg agccggaagh    10980
cataaagtgt aaagcctggg gtgcctaatg agtgagctaa ctcacattaa ttgcgttgcg    11040
ctcactgccc gctttccagt cgggaaacct gtcgtgccag ctgcattaat gaatcggcca    11100
```

```
acgcgcgggg agaggcggtt tgcgtattgg gcgctcttcc gcttcctcgc tcactgactc   11160
gctgcgctcg gtcgttcggc tgcggcgagc ggtatcagct cactcaaagg cggtaatacg   11220
gttatccaca gaatcagggg ataacgcagg aaagaacatg aaggccttga caggatatat   11280
tggcgggtaa actaagtcgc tgtatgtgtt tgtttgagat ctcatgtgag caaaaggcca   11340
gcaaaaggcc aggaaccgta aaaaggccgc gttgctggcg ttttttccata ggctccgccc   11400 ccctgacgag catcacaaaa atcgacgctc aagtcagagg tggcgaaacc cgacaggact   11460
ataaagatac caggcgtttc ccctggaag ctccctcgtg cgctctcctg ttccgaccct   11520
gccgcttacc ggatacctgt ccgcctttct cccttcggga agcgtggcgc tttctcatag   11580
ctcacgctgt aggtatctca gttcggtgta ggtcgttcgc tccaagctgg gctgtgtgca   11640 cgaaccccc gttcagcccg accgctgcgc cttatccggt aactatcgtc ttgagtccaa   11700
cccggtaaga cacgacttat cgccactggc agcagccact ggtaacagga ttagcagagc   11760
gaggtatgta ggcggtgcta cagagttctt gaagtggtgg cctaactacg gctacactag   11820
aagaacagta tttggtatct gcgctctgct gaagccagtt accttcggaa gaagagttgg   11880
tagctcttga tccggcaaac aaaccaccgc tggtagcggt ggttttttg tttgcaagca   11940 gcagattacg cgcagaaaaa aaggatctca agaagatcct ttgatctttt ctacggggtc   12000
tgacgctcag tggaacgaaa actcacgtta agggattttg gtcatgagat tatcaaaaag   12060
gatcttcacc tagatccttt taaattaaaa atgaagtttt aaatcaatct aaagtatata   12120
tgtgtaacat tggtctagtg attagaaaaa ctcatcgagc atcaaatgaa actgcaattt   12180
attcatatca ggattatcaa taccatattt ttgaaaaagc cgtttctgta atgaaggaga   12240
aaactcaccg aggcagttcc ataggatggc aagatcctgg tatcggtctg cgattccgac   12300
tcgtccaaca tcaatacaac ctattaattt ccctcgtca aaataaggt tatcaagtga   12360 gaaatcacca tgagtgacga ctgaatccgg tgagaatggc aaaagtttat gcatttcttt   12420
ccagacttgt tcaacaggcc agccattacg ctcgtcatca aaatcactcg catcaaccaa   12480
accgttattc attcgtgatt gcgcctgagc gagacgaaat acgcgatcgc tgttaaaagg   12540
acaattacaa acaggaatcg aatgcaaccg gcgcaggaac actgccagcg catcaacaat   12600
attttcacct gaatcaggat attcttctaa tacctggaat gctgttttcc ctgggatcgc   12660
agtggtgagt aaccatgcat catcaggagt acggataaaa tgcttgatgg tcggaagagg   12720
cataaattcc gtcagccagt ttagtctgac catctcatct gtaacaacat tggcaacgct   12780
acctttgcca tgtttcagaa acaactctgg cgcatcgggc ttcccataca atcggtagat   12840
tgtcgcacct gattgcccga cattatcgcg agcccattta tacccatata aatcagcatc   12900
catgttggaa tttaatcgcg gccttgagca agacgtttcc cgttgaatat ggctcataac   12960
accccttgta ttactgttta tgtaagcaga cagttttatt gttcatgatg atatatttt   13020 atcttgtgca atgtaaatc agagattttg agacacaacg tggctttgtt gaataaatcg   13080 aactttgct gagttgaagg atcagatcac gcatcttccc gacaacgcag accgttccgt   13140
ggcaaagcaa aagttcaaaa tcaccaactg gtccacctac aacaaagctc tcatcaaccg   13200
tggctccctc actttctggc tggatgatgg ggcgattcag gcgatcccca tccaacagcc   13260
cgccgtcgag cgggct                                                   13276
```

<210> SEQ ID NO 16
<211> LENGTH: 10753
<212> TYPE: DNA

<213> ORGANISM: Artificial Sequence
<220> FEATURE:
<223> OTHER INFORMATION: Artificial DNA construct

<400> SEQUENCE: 16

```
tggcaggata tattgtggtg taacgtatca caagtttgta caaaaaagca ggctccgcgg    60
ccgccccctt cacctagact cgacgcgtcc tagagatccg tcaacatggt ggagcacgac   120
actctcgtct actccaagaa tatcaaagat acagtctcag aagaccaaag ggctattgag   180
acttttcaac aaagggtaat atcgggaaac ctcctcggat tccattgccc agctatctgt   240
cacttcatca aaaggacagt agaaaaggaa ggtggcacct acaaatgcca tcattgcgat   300
aaaggaaagg ctatcgttca agatgcctct gccgacagtg gtcccaaaga tggaccccca   360
cccacgagga gcatcgtgga aaagaagac gttccaacca cgtcttcaaa gcaagtggat   420
tgatgtgata tctccactga cgtaagggat gacgcacaat cccactatcc ttcgcaagac   480
ccttcctcta tataaggaag ttcatttcat ttggagagga cgaccccgat atgaaaaagc   540
ctgaactcac cgcgacgtct gtcgagaagt ttctgatcga aaagttcgac agcgtctccg   600
acctgatgca gctctcggag ggcgaagaat ctcgtgcttt cagcttcgat gtaggagggc   660
gtggatatgt cctgcgggta aatagctgcg ccgatggttt ctacaaagat cgttatgttt   720
atcggcactt tgcatcggcc gcgctcccga ttccggaagt gcttgacatt ggggaattca   780
gcgagagcct gacctattgc atctcccgcc gtgcacaggg tgtcacgttg caagacctgc   840
ctgaaaccga actgcccgct gttctgcagg taaatttcta gttttttctcc ttcatttct   900
tggttaggac ccttttctct ttttattttt ttgagctttg atctttcttt aaactgatct   960
attttttaat tgattggtta tggtgtaaat attacatagc tttaactgat aatctgatta  1020
ctttatttcg tgtgtctatg atgatgatga taactgcagc cggtcgcgga ggccatggat  1080
gcgatcgctg cggccgatct tagccagacg agcgggttcg gcccattcgg accgcaagga  1140
atcggtcaat acactacatg gcgtgatttc atatgcgcga ttgctgatcc ccatgtgtat  1200
cactggcaaa ctgtgatgga cgacaccgtc agtgcgtccg tcgcgcaggc tctcgatgag  1260
ctgatgcttt gggccgagga ctgccccgaa gtccggcacc tcgtgcacgc ggatttcggc  1320
tccaacaatg tcctgacgga caatggccgc ataacagcgg tcattgactg agcgaggcg  1380
atgttcgggg attcccaata cgaggtcgcc aacatcttct tctggaggcc gtggttggct  1440
tgtatggagc agcagacgcg ctacttcgag cggaggcatc cggagcttgc aggatcgccg  1500
cggctccggg cgtatatgct ccgcattggt cttgaccaac tctatcagag cttggttgac  1560
ggcaatttcg atgatgcagc ttgggcgcag gtcgatgcg acgcaatcgt ccgatccgga  1620
gccgggactg tcgggcgtac acaaatcgcc cgcagaagcg cggccgtctg gaccgatggc  1680
tgtgtagaag tactcgccga tagtggaaac cgacgcccca gcactcgtcc gagggcaaag  1740
gaatagagta gatgccgacc gggatccgga gagctcgaat tccccgatc gttcaaacat  1800
ttggcaataa agtttcttaa gattgaatcc tgttgccggt cttgcgatga ttatcatata  1860
atttctgttg aattacgtta agcatgtaat aattaacatg taatgcatga cgttatttat  1920
gagatgggtt tttatgatta gagtcccgca attatacatt taatacgcga tagaaaacaa  1980
aatatagcgc gcaaactagg ataaattatc gcgcgcggtg tcatctatgt tactagatcg  2040
ggaattcatc gatgatatca gatcaagggt gggcgcgccg aaccagcttt cttgtacaaa  2100
gtggtgatcc ccctcgaggt cgacggtatc gataagcttg atatcgaatt cccgtgcctc  2160
atgcaataga aaataaaaca taaaacatgt tttttttttc attctgaaag gcacgggtca  2220
```

```
tgcctcttgc gaaggcaaaa ccgtgcctct cgcggaaaaa aagagagcag aaaacgtgtt    2280
tttccccttt tcagaagagg cacgacgtg tctctcgcga aggcaaaacc gagactttcg     2340
cggaagcaaa agtgtgtctc tcgcaaaaga aaaacacgtt ttttcccttt cgggagaaaa    2400
ccgtgcctct cgcagaaaaa caaacaaaca gaaaacgcat ttttttttcat tcaggagagg   2460 cctctcgcaa aggtaaaact gtgcctttcg caaaaggaaa accgtgcctc tcgcagaaaa    2520
ataaacaaac agaaaacgcg ttttctttc tttccgaaga ggcacggtcg tgcctctcgc    2580
gaaggtaaaa tcatgccttt cgcggaagca aaaccgtgcc tctcgcaaaa aacaaaaaa    2640 cacgtttttt tttcctttca gagaggcacg accgtgcctc tcgtgatagc aaaaccgtgt   2700
ctcgcaaaaa aaagttttt tcacgtacaa ataaagaaa atgtgttttt tcaccaaaat    2760
aaagtacgaa tttcttttcg ttcaaaagtt acgaagatc ggtgaaaaac cataacacaa    2820 tttttcgaa aaatcactc aaaaaggag aaaacgcgtg cgaaaaatat ttaaaaaaaa      2880
atttaaagga aacgttcaga acacgacacg tggcgacggc tggaaacgcg tcaactggcg   2940
acgcgcggga gcaatcgctg ggaggctccc gaaaaagcac tcgctaacta gttgcttctt   3000
tttcctccag cataatccac aacggttcgc tgaaagaaa agtttaatca acaccagagg    3060
caatgtgagg ccaccgacgt ctctgatgct gcttgtcggg ggcatcaatc cggcggacgg    3120
gggcgacaac ccgtcagaaa ctcgagccat ccatggtgaa gacgtcgaca caggtctccg   3180
gccgggaggt ctacgccaac cagcgacttc ttcattcgta aaacaaacaa acaaacaaac   3240
aaacagctgt tggatcagag accggaaaaa cacaggcgac cacaaaggct gtgaacgaat   3300
ggaacacgag cacagagaca accatatttt gcgaggccca actgccgtcc tcttttcttg   3360
tttttttttt cttttattct attaacgtaa caaacaaaga gattacaaag catgtgtaac   3420
agccggacga ctgggccgac tccaacgcca cgatccgtcc atatcgtgcc atcccacgat   3480
tgacttggtg atcatgacta acaaactact tctacttaca tgcagcgact cgaagtgcat   3540
gtacacaccc atcatatctg tatagcgtac gtactaaata catgcaacta gcacatgcac   3600
caccaggatg tgatcctgtc taacaaccta acctagctgc taaaaacaac tgaatatgca   3660
tgacacagac cttgtaacaa gattagcacc aacaacagcg agctctagga ctcgaaccat   3720
tctgagagaa atttcatcgg aggagagata tgcataccaa ccggctcctt tttatctcgg   3780
aaattccatc caatattcat gtcttgttct tgtactgaat agtttaggag caatttctgt   3840
ctagcttttt cattagttag aacagggcag aggatagata catagtggga caaatgataa   3900
gatgagatac tgacctgtgc tgtgtaagaa agaacctgc ctaagctact cgagtcgtcc    3960
attccgaaat tggaccgact cttcattcag catttgacct tcaaaggcag caggcagcag   4020
gccagagagt ggtaccgacg cgaggatgtg aagagaagaa atacaatacg acattttcgc   4080
tccaagcaaa gaaaacaaat acggtatata tgtcgaaaat gagtggatga agctcgttc    4140 ggaatagtat tcgccgtcga catctagtct tgagtagaca aggatgagaa aaggccgatc   4200
gatgtgcagc atccagttac cattgacctg catgtagtac gtcaatgatt ccttaggttc   4260
acacctctag tgcatgggaa aagcctagat attataacct acaaattcaa ggaggcaaat   4320
ttatgggctt ttgtctaatt ttaacattta ctggtaggtg tcgatccatc ggaaattccc   4380
ttgaagcatc catgccaatt cgtcaagtct tgaattaata gatagcgact tgagaggatg   4440
tggaaagaaa agaaatacag acattatcgt tctaagcaaa gaaagaaat atatatgata    4500 tagctgtaaa atgagtggag gaaaatgtgt gtggaatagt attcgtcgtc atcatctagt   4560
```

```
cttgagtgga taaaggtgcg agaggatgtg caccatacat gatatataca tgtaaattca    4620
tgctgttaat actgcataaa ttgtgtgttt gtgtgagaga aactgagaga gggagtatca    4680
gttccatttt ctctcttcac cagtgcttgt tcatgtatcc aagctaccag gtcaccaggt    4740
gtattagcag agtctatata tatacatact gcaggctaac tagctagcct tcttccccccc  4800 ttttaactaa ggcttgcaaa tgccggatcc agttactatt agtgctgctg taggatgggg   4860
cgtatccgca gtaggctggc tcgcctctcc catcatttca agggttgtca acaaaggttt    4920
cgcccacctc gacttcgatg cagcagagaa gctgaagata cttgatatac aagttctaca   4980
actgcagcgc gtgatagaag tagtcgatga gagcacgtac aggcttcgct tggagccact    5040
gttagacaag cttagatctg ctctttatga agccgaagac atcttggatg attttgatta   5100
tcagcgtctc gagaagcaga tccatgttgg gtctagttcc acacgtaaac gcaagataga   5160
ttcgctggag aagaatcatc ggtctgccat gccgagttcc tccctaaaag ataagatgga   5220
aacattcccg aggatttcat cgaagggaaa ggagactatc aataatttac tgagccaggg   5280
gattggaaca tcaaaagtgg agttgaagaa aagcctagag aaaatagaaa ataccataaa   5340
cgatgcatgt aaagttttgg aacaactgaa cttgccgagt gtatgtaatg ataatgggag   5400
acgaggtgtt gctaccaatt ctcgtagtgc agtcactact gcaggtcctc ctctacgagt   5460
aattggtcga gatcaggatc gtgacaagat catagcaatg cttcatgaga aggatgaccg   5520
gtgtcaagtc aatggtacat cttattctgt aattggcatt catggcgtcg ccgggtctgg   5580
gaaatcaaca cttgcacagt atgtttatga tcatgagaaa aagtgcaagc aaggtaaaag   5640
agaaggctat tttgatgttc tcatgtggat tcatgtttct caaaaaatcg gtttggagtc   5700
cagtttcagg gacatgtttg aggggctac agggaaagca tgcccgaatt ttaatagtct   5760
taacgtctta aaggaaaagt tggaggagga actacgtgga aaacggattt ttttggtact   5820
agatgatgtc tggtacaaca gtaagaattc aggagaccgt gaagaactgc agaagttaat   5880
ttctccgttg aatgttggga aggcaggaag cagaatcttg gtgactagtc gaactgaagc   5940
tgcattagta gctctccgtg ctgcaaaaga gggatgtatc ccaatatcta acctggatga   6000
taaagttttc cttaaaatgt tcatgcatta tgcacttcca catgcatggc cagttggcaa   6060
tgatcgaaga aaacttgaaa tgattggaga ggacattgca aaaaagctga agggttcacc   6120
tctggcagct agaatagtgg gttcacggct cggtgataat ccaaatgttg aattttggag   6180
gagagagaaa gaccgggatc ttatgaacga gacgatggga gcactttggt ggagctacca   6240
gtaccttgat gagcaggtca ggcgatgctt cgcttacatc agcatttttc ccagacgtca   6300
tcatttgaaa cgtgatgact aattaacct atgggtggcc gaaggattta taaagacaag   6360
taaagctgaa gaggaaatgg aagatgttgc ctcggaatac tttgatgagc tgcttcgtt    6420 ctcatttctg caattaggag ggaaagatga gctatttgca cgtgaggtcg attactttat   6480
aattcatgat ctgttgtatg atttagcaga ggaggttgct ggaagagatt gcttcaggat   6540
agagaaaggt ttcacaggag aagtccctcc ggatgttcgc tatcttttg ttgggactta    6600 cgataaagag atgcttactg agaagatatc caggttgcaa aatttacgca ctctcttcgt   6660
cgataagtac atacagattt tatcacccaa gtacgatgat tttgttagta tggtgactat   6720
gttgatgggg ctgcggaaat tgagggtact gaatttacat ttcactggat atggtattcc   6780
taaattctca ttgccggatt ctattcttca gtggaagcat ctgcgttact ttgcttttgg   6840
ggtgtccccg tttaccaagc taactttacc atgcgctttt accaagcttt accacttgca   6900
tgtggtagat ttcggtgatt gcaatagttt ggagttttct cgtggtgaat acatgatgaa   6960
```

```
cctggtcaat tgcgccgtg taatctacaa gaattatctc gactttccga acattggcag   7020
gctgacatgg ctgcaatcgt tgccgtgctt cagaataagg aagaaacatg ggtatgaatc   7080
acatcagctg aaacacctaa acaagcttca aggcaggctg tacattggtg gtcttcagaa   7140
tgttgagagc aaggaggaag ctcttaatgt gaaccttgca gccaaggaaa aactcacaga   7200
agtggtactg cgctggagtg ataatagctg cagtccagaa attcaagcag aggtacttga   7260
gggcctttgt ccttcaaagt atcttgaaat actagaaatc aagttataca atggcatgaa   7320
gtttccaaat tggatgacga gtaagcataa gggtgggcca agaacctgc aagaacttag    7380 attcagacag agcaccctgg gatctgctcc tgatgttggg gctttcattc accttcagtc   7440
gttatttatt tatcaatgca gctgggatac cttaccaggg aatatggagc acctcacagc   7500
gctcaagaaa ctggagatac ggtcatgcaa taatattcgg tcgcttccaa cactgcccaa   7560
gtcccttgag cagtttgcga tctggtcctg cagcttggat gctttaccgg caatatgga    7620 gcacctcaca gcactcaaga aactggagat acggtcatgc aataatattc ggtggcttcc   7680
aacactgccc aagtcccttg agcagtttgc gatctcgcgc tgcagcttgg atgctttacc   7740
gggcaatatg gagcacctca cagcgctcaa gaaactggat atatggtcat gcagaaatat   7800
acggtcgctt ccaacactac ccaagtctct tgaggagttt acagtctgga actgcactag   7860
tgagttcatg caatcttgta tgacgactga tgatccaaac tggcagaaga ttgagcacgt   7920
tccaaacaaa aaaattggat ttctatgaaa acgatacata agaaggtac gtatttaaat    7980 tcctttgacg tcttcgtttt ccattttgc gtgcagtaaa tgttactgca acaattagcc    8040
gttaaggttc ctggtatttt tctgattcag ttgctaacta ttaggcgcgt gccctttggt   8100
tgaggacggg agatgaagtc gaagccgaag ccgtcagaat cttgctaaat ttacggtctc   8160
tcttactgga tagcctcttg gttgggttat gcctactttg gttggttgag tcttgcatgt   8220
ttacacctaa agtggtgcaa aatgccatct ctccatgcag tcacaactca caaacagtgg   8280
atttatgaat tgtttacaat atatggattt atggatgcaa taacgtgtaa taatgaacag   8340
ctgattgatt tgccttcata tatatatata tatgatttgt aacactgccg tgtggatgat   8400
gaacctggcc caaactgttt gattcctagc tatatatgat ttgtaacact ttggaatgat   8460
tatcactgaa ttcgttcctt tcctgtcgtt gtttgtatca tggttcaaaa aaaagtatcc   8520
gatttgattg cgaggaattg ggggctacat aagcatggta tggtatgagg ttaccagatt   8580
gggcgaagct aacccgagga actgctcctg acattgaggc ttccattcat tttcagtaat   8640
agaatgctaa aaggctttag tggttgcaat caacgtgcat tgtaattagt gattgcattt   8700 tttttctac tggttgccca ttcagggaaa gtgctctcac acggtggcat gttctctgtt    8760
ctgcacacgc tctcgttttg ggcagacgca agctttgatg tgtccgcttg ggccttcaaa   8820
cacgatgcaa catattctgc aaacactatt gagtattttc tttctcaatt tttgctcatc   8880
ttaggagctg ttcggtaacc atccagatcc atgaaatctg agaatctgcg gagtacctct   8940
tgtccagctc tgcaattttt acctgctgct cctccaactc cgggagtgaa gatgcggagt   9000
ggaggacatc cgaacaggcc tttaatcaat gaaagcatcg ctagctgcta cctttcgttc   9060
acaaaaatgt tttaaagaag gatgcgacct gtagcatgaa aacaagaacg acatagactt   9120
ctgaccactg ccaagtgaaa ttctgtagat catcagaaca cgctatattg tcagaaagat   9180
gatcacatct gtgacaagtc cacgcgctcg aacaacaac cactttgaac tctgaaagct    9240
gatctcatga cgactccacc aaattgggtc caacttgtac acatattcga gaccttatga   9300
```

```
tcgagccagt atgaaacgaa caaattccag gcgctcatgt agtatctcat tggtaatgct   9360
accacacagg ttggactaca tagccagagg cacgccaaca taaggaaacc gagtcgtgaa   9420
aaactcgaga ttcgcggaat tggtacgttg atgttctagg agtcaatata ctacctgacc   9480
acgtggcagt ataacaaaca aacttgaact gaagaaaaaa cagggaaaga aactgggtgg   9540
ttgggataca cagcaagaca gaggcacatg aacataaagg aattcggtca agaaaaactc   9600
gtacggaatt ggttttgcag gagttcattt actgcctagg cacattctat cagtataaca   9660
aactacaaag gaaaagaacc aaactgggggg tgttggtagt gaggaaaaac agcacaatcg   9720
cccgaaactt tacgtttcag tccgtcatct caatcaatat gatttgcatt gagattcaga   9780
gcacaactat gatactgaga ttcaaagagt ggtggagaca ttgactgcaa taagagcaa    9840
tttcagttgc ccgtgctgat aagcactcac ttcgatctca tgaggttgat tcacataaaa   9900
caacatacgt gggataacat ttcagtttcc tgtgagcaca agttatgcag gtttatctcg   9960
aaacagcaac gtaagataaa attatacatc tgaagatgaa gacaagagaa cttctctgct  10020
tccttacatc tatcataagg actgtacaaa atgaacaatc tttgacttga acgaattttc  10080
ttgaggtgaa acaatccaag gtaaaacagg atataaagtt gtattccttc tacatttatc  10140
ttgaccatca gaactactac tcaataataa taataataat aataagctgg tgtttctagt  10200
gattccatca ggaattcagg actcatgcat aagctactca tagcgtacaa gatcattccc  10260
cttactaacc gcattctctt aagatccact agttctagag cggccgccac cgcggtggag  10320
ctccagcttt tgttcccttt agtgagggtt aattccgagc ttggcgtaat catggtcata  10380
gctgtttcct gtgtgaaatt gttatccgct cacaattcca cacaacatac gagccggaag  10440
hcataaagtg taaagcctgg ggtgcctaat gagtgagcta actcacatta attgcgttgc  10500
gctcactgcc cgctttccag tcgggaaacc tgtcgtgcca gctgcattaa tgaatcggcc  10560
aacgcgcggg gagaggcggt ttgcgtattg ggcgctcttc cgcttcctcg ctcactgact  10620
cgctgcgctc ggtcgttcgg ctgcggcgag cggtatcagc tcactcaaag gcggtaatac  10680
ggttatccac agaatcaggg gataacgcag gaaagaacat gaaggccttg acaggatata  10740
ttggcgggta aac                                                     10753
```

<210> SEQ ID NO 17
<211> LENGTH: 8130
<212> TYPE: DNA
<213> ORGANISM: Artificial Sequence
<220> FEATURE:
<223> OTHER INFORMATION: Artificial DNA construct

<400> SEQUENCE: 17

```
cgtgcctcat gcaatagaaa ataaaacata aacatgtttt ttttttttcat tctgaaaggc     60
acgggtcatg cctcttgcga aggcaaaacc gtgcctctcg cggaaaaaaa gagagcagaa    120
aacgtgtttt tcccctttc agaagaggca cggacgtgtc tctcgcgaag gcaaaaccga    180
gactttcgcg gaagcaaaag tgtgtctctc gcaaaagaaa acacgttttt tccctttcg    240
ggagaaaacc gtgcctctcg cagaaaaaca aacaacaga aaacgcattt ttttcattc     300
aggagaggcc tctcgcaaag gtaaaactgt gcctttcgca aaggaaaaac cgtgcctctc    360
gcagaaaaat aaacaaacag aaaacgcgtt tttctttctt tccgaagagg cacggtcgtg    420
cctctcgcga aggtaaaatc atgccttcg cggaagcaaa accgtgcctc tcgcaaaaaa    480
acaaaaaaca cgttttttt tccttcaga gaggcacgac cgtgcctctc gtgatagcaa    540
aaccgtgtct cgcaaaaaaa aagtttttc acgtacaaat aaagaaaat gtgttttttc      600
```

```
accaaaataa agtacgaatt tcttttcgtt caaaagttac gaaagatcgg tgaaaaacca    660
taacacaatt ttttcgaaaa aatcactcaa aaaaggagaa aacgcgtgcg aaaaatattt    720
aaaaaaaaat ttaaaggaaa cgttcagaac acgacacgtg gcgacggctg gaaacgcgtc    780
aactggcgac gcgcgggagc aatcgctggg aggctcccga aaaagcactc gctaactagt    840
tgcttctttt tcctccagca taatccacaa cggttcgctg aaaagaaaag tttaatcaac    900
accagaggca atgtgaggcc accgacgtct ctgatgctgc ttgtcggggg catcaatccg    960
gcggacgggg gcgacaaccc gtcagaaact cgagccatcc atggtgaaga cgtcgacaca   1020
ggtctccggc cgggaggtct acgccaacca gcgacttctt cattcgtaaa acaaacaaac   1080
aaacaaacaa acagctgttg gatcagagac cggaaaaaca caggcgacca caaaggctgt   1140
gaacgaatgg aacacgagca cagagacaac catattttgc gaggcccaac tgccgtcctc   1200
ttttcttgtt ttttttttct tttattctat taacgtaaca aacaaagaga ttacaaagca   1260
tgtgtaacag ccggacgact gggccgactc caacgccacg atccgtccat atcgtgccat   1320
cccacgattg acttggtgat catgactaac aaactacttc tacttacatg cagcgactcg   1380
aagtgcatgt acacacccat catatctgta tagcgtacgt actaaataca tgcaactagc   1440
acatgcacca ccaggatgtg atcctgtcta acaacctaac ctagctgcta aaaacaactg   1500
aatatgcatg acacagacct tgtaacaaga ttagcaccaa caacagcgag ctctaggact   1560
cgaaccattc tgagagaaat ttcatcggag gagagatatg cataccaacc ggctcctttt   1620
tatctcggaa attccatcca atattcatgt cttgttcttg tactgaatag tttaggagca   1680
atttctgtct agcttttttca ttagttagaa cagggcagag gatagataca tagtgggaca   1740
aatgataaga tgagatactg acctgtgctg tgtaagaaaa gaacctgcct aagctactcg   1800
agtcgtccat tccgaaattg gaccgactct tcattcagca tttgaccttc aaaggcagca   1860
ggcagcaggc cagagagtgg taccgacgcg aggatgtgaa gagaagaaat acaatacgac   1920
attttcgctc caagcaaaga aaacaaatac ggtatatatg tcgaaaatga gtggatgaaa   1980
gctcgttcgg aatagtattc gccgtcgaca tctagtcttg agtagacaag gatgagaaaa   2040
ggccgatcga tgtgcagcat ccagttacca ttgacctgca tgtagtacgt caatgattcc   2100
ttaggttcac acctctagtg catgggaaaa gcctagatat tataacctac aaattcaagg   2160
aggcaaattt atgggctttt gtctaatttt aacatttact ggtaggtgtc gatccatcgg   2220
aaattccctt gaagcatcca tgccaattcg tcaagtcttg aattaataga tagcgacttg   2280
agaggatgtg gaaagaaaag aaatacagac attatcgttc taagcaaaga aaagaaatat   2340
atatgatata gctgtaaaat gagtggagga aaatgtgtgt ggaatagtat tcgtcgtcat   2400
catctagtct tgagtggata aaggtgcgag aggatgtgca ccatacatga tatatacatg   2460
taaattcatg ctgttaatac tgcataaatt gtgtgtttgt gtgagagaaa ctgagagagg   2520
gagtatcagt tccattttct ctcttcacca gtgcttgttc atgtatccaa gctaccaggt   2580
caccaggtgt attagcagag tctatatata tacatactgc aggctaacta gctagccttc   2640 ttccccccctt ttaactaagg cttgcaaatg ccggatccag ttactattag tgctgctgta   2700
ggatggggcg tatccgcagt aggctggctc gcctctccca tcatttcaag ggttgtcaac   2760
aaaggtttcg cccacctcga cttcgatgca gcagagaagc tgaagatact tgatatacaa   2820
gttctacaac tgcagcgcgt gatagaagta gtcgatgaga gcacgtacag gcttcgcttg   2880
gagccactgt tagacaagct tagatctgct ctttatgaag ccgaagacat cttggatgat   2940
```

```
tttgattatc agcgtctcga gaagcagatc catgttgggt ctagttccac acgtaaacgc    3000
aagatagatt cgctggagaa gaatcatcgg tctgccatgc cgagttcctc cctaaaagat    3060
aagatggaaa cattcccgag gatttcatcg aagggaaagg agactatcaa taatttactg    3120
agccagggga ttggaacatc aaaagtggag ttgaagaaaa gcctagagaa aatagaaaat    3180
accataaacg atgcatgtaa agttttggaa caactgaact tgccgagtgt atgtaatgat    3240
aatgggagac gaggtgttgc taccaattct cgtagtgcag tcactactgc aggtcctcct    3300
ctacgagtaa ttggtcgaga tcaggatcgt gacaagatca tagcaatgct tcatgagaag    3360
gatgaccggt gtcaagtcaa tggtacatct tattctgtaa ttggcattca tggcgtcgcc    3420
gggtctggga aatcaacact tgcacagtat gtttatgatc atgagaaaaa gtgcaagcaa    3480
ggtaaaagag aaggctattt tgatgttctc atgtggattc atgtttctca aaaaatcggt    3540
ttggagtcca gtttcaggga catgtttgag ggggctacag ggaaagcatg cccgaatttt    3600
aatagtctta acgtcttaaa ggaaaagttg gaggaggaac tacgtggaaa acggattttt    3660
ttggtactag atgatgtctg gtacaacagt aagaattcag agaccgtgaa agaactgcag    3720
aagttaattt ctccgttgaa tgttgggaag gcaggaagca gaatcttggt gactagtcga    3780
actgaagctg cattagtagc tctccgtgct gcaaagagg gatgtatccc aatatctaac    3840
ctggatgata agttttcct taaaatgttc atgcattatg cacttccaca tgcatggcca    3900
gttggcaatg atcgaagaaa acttgaaatg attggagagg acattgcaaa aaagctgaag    3960
ggttcacctc tggcagctag aatagtgggt tcacggctcg gtgataatcc aaatgttgaa    4020
ttttggagga gagagaaaga ccgggatctt atgaacgaga cgatgggagc actttggtgg    4080
agctaccagt accttgatga gcaggtcagg cgatgcttcg cttacatcag catttttccc    4140
agacgtcatc atttgaaacg tgatgactta attaacctat gggtggccga aggatttata    4200
aagacaagta agctgaaga ggaaatggaa gatgttgcct cggaatactt tgatgagctg    4260
ctttcgttct catttctgca attaggaggg aaagatgagc tatttgcacg tgaggtcgat    4320
tactttataa ttcatgatct gttgtatgat ttagcagagg aggttgctgg aagagattgc    4380
ttcaggatag agaaaggttt cacaggagaa gtccctccgg atgttcgcta tcttttttgtt    4440
gggacttacg ataaagagat gcttactgag aagatatcca ggttgcaaaa tttacgcact    4500
ctcttcgtcg ataagtacat acagatttta tcacccaagt acgatgattt tgttagtatg    4560
gtgactatgt tgatggggct gcggaaattg agggtactga atttacattt cactggatat    4620
ggtattccta aattctcatt gccggattct attcttcagt ggaagcatct gcgttacttt    4680
gcttttgggg tgtccccgtt taccaagcta actttaccat gcgcttttac caagctttac    4740
cacttgcatg tggtagattt cggtgattgc aatagtttgg agttttctcg tggtgaatac    4800
atgatgaacc tggtcaattt gcgccgtgta atctacaaga attatctcga ctttccgaac    4860
attggcaggc tgacatggct gcaatcgttg ccgtgcttca gaataaggaa gaaacatggg    4920
tatgaatcac atcagctgaa acacctaaac aagcttcaag gcaggctgta cattggtggt    4980
cttcagaatg ttgagagcaa ggaggaagct cttaatgtga accttgcagc caaggaaaaa    5040
ctcacagaag tggtactgcg ctggagtgat aatagctgca gtccagaaat tcaagcagag    5100
gtacttgagg gcctttgtcc ttcaaagtat cttgaaatac tagaaatcaa gttatacaat    5160
ggcatgaagt ttccaaattg gatgacgagt aagcataagg gtgggccaaa gaacctgcaa    5220
gaacttagat tcagacagag caccctggga tctgctcctg atgttggggc tttcattcac    5280
cttcagtcgt tatttatta tcaatgcagc tgggatacct taccagggaa tatggagcac    5340
```

```
ctcacagcgc tcaagaaact ggagatacgg tcatgcaata atattcggtc gcttccaaca    5400
ctgcccaagt cccttgagca gtttgcgatc tggtcctgca gcttggatgc tttaccgggc    5460
aatatggagc acctcacagc actcaagaaa ctggagatac ggtcatgcaa taatattcgg    5520
tggcttccaa cactgcccaa gtcccttgag cagtttgcga tctcgcgctg cagcttggat    5580
gctttaccgg gcaatatgga gcacctcaca gcgctcaaga aactggatat atggtcatgc    5640
gagaatatac ggtcgcttcc aacactaccc aagtctcttg aggagtttac agtctggaac    5700
tgcactagtg agttcatgca atcttgtatg acgactgatg atccaaactg cagaagatt    5760 gagcacgttc caaacaaaaa aattggattt ctatgaaaac gatacataaa gaaggtacgt    5820
atttaaattc ctttgacgtc ttcgttttcc attttttgcgt gcagtaaatg ttactgcaac    5880
aattagccgt taaggttcct ggtatttttc tgattcagtt gctaactatt aggcgcgtgc    5940
cctttggttg aggacgggag atgaagtcga agccgaagcc gtcagaatct tgctaaattt    6000
acggtctctc ttactggata gcctcttggt tgggttatgc ctactttggt tggttgagtc    6060
ttgcatgttt acacctaaag tggtgcaaaa tgccatctct ccatgcagtc acaactcaca    6120
aacagtggat ttatgaattg tttacaatat atggatttat ggatgcaata acgtgtaata    6180
atgaacagct gattgatttg ccttcatata tatatatata tgatttgtaa cactgccgtg    6240
tggatgatga acctggccca aactgtttga ttcctagcta tatgatttt gtaacacttt    6300 ggaatgatta tcactgaatt cgttccttc ctgtcgttgt ttgtatcatg gttcaaaaaa    6360
aagtatccga tttgattgcg aggaattggg ggctacataa gcatggtatg gtatgaggtt    6420
accagattgg gcgaagctaa cccgaggaac tgctcctgac attgaggctt ccattcattt    6480
tcagtaatag aatgctaaaa ggctttagtg gttgcaatca acgtgcattg taattagtga    6540
ttgcattttt ttttctactg gttgcccatt cagggaaagt gctctcacac ggtggcatgt    6600
tctctgttct gcacacgctc tcgtttgggg cagacgcaag cttttgatgtg tccgcttggg    6660 ccttcaaaca cgatgcaaca tattctgcaa acactattga gtattttctt tctcaattt    6720 tgctcatctt aggagctgtt cggtaaccat ccagatccat gaaatctgag aatctgcgga    6780
gtacctcttg tccagctctg caatttttac ctgctgctcc tccaactccg ggagtgaaga    6840
tgcggagtgg aggacatccg aacaggcctt taatcaatga aagcatcgct agctgctacc    6900
tttcgttcac aaaaatgttt taagaagga tgcgacctgt agcatgaaaa caagaacgac    6960
atagacttct gaccactgcc aagtgaaatt ctgtagatca tcagaacacg ctatattgtc    7020
agaaagatga tcacatctgt gacaagtcca cgcgctcgaa acaacaacca ctttgaactc    7080
tgaaagctga tctcatgacg actccaccaa attgggtcca acttgtacac atattcgaga    7140
ccttatgatc gagccagtat gaaacgaaca aattccaggc gctcatgtag tatctcattg    7200
gtaatgctac cacacaggtt ggactacata gccagaggca cgccaacata aggaaaccga    7260
gtcgtgaaaa actcgagatt cgcggaattg gtacgttgat gttctaggag tcaatatact    7320
acctgaccac gtggcagtat aacaaacaaa cttgaactga agaaaaaaca gggaaagaaa    7380
ctgggtggtt gggatacaca gcaagacaga ggcacatgaa cataaaggaa ttcggtcaag    7440
aaaaactcgt acggaattgg ttttgcagga gttcatttac tgcctaggca cattctatca    7500
gtataacaaa ctacaaagga aaagaaccaa actgggggtg ttggtagtga ggaaaaacag    7560
cacaatcgcc cgaaacttta cgtttcagtc cgtcatctca atcaatatga tttgcattga    7620
gattcagagc acaactatga tactgagatt caaagagtgg tggagacatt gactgcaata    7680
```

-continued

```
aagagcaatt tcagttgccc gtgctgataa gcactcactt cgatctcatg aggttgattc     7740
acataaaaca acatacgtgg gataacattt cagtttcctg tgagcacaag ttatgcaggt     7800
ttatctcgaa acagcaacgt aagataaaat tatacatctg aagatgaaga caagagaact     7860
tctctgcttc cttacatcta tcataaggac tgtacaaaat gaacaatctt tgacttgaac     7920
gaattttctt gaggtgaaac aatccaaggt aaaacaggat ataaagttgt attccttcta     7980
catttatctt gaccatcaga actactactc aataataata ataataataa taagctggtg     8040
tttctagtga ttccatcagg aattcaggac tcatgcataa gctactcata gcgtacaaga     8100
tcattcccct tactaaccgc attctcttaa                                     8130
```

<210> SEQ ID NO 18
<211> LENGTH: 18
<212> TYPE: DNA
<213> ORGANISM: Artificial Sequence
<220> FEATURE:
<223> OTHER INFORMATION: PCR Primer

<400> SEQUENCE: 18
aggccgatcg atgtgcag                                                    18

<210> SEQ ID NO 19
<211> LENGTH: 19
<212> TYPE: DNA
<213> ORGANISM: Artificial Sequence
<220> FEATURE:
<223> OTHER INFORMATION: PCR Primer

<400> SEQUENCE: 19
acctggtgac ctggtagct                                                   19

<210> SEQ ID NO 20
<211> LENGTH: 19
<212> TYPE: DNA
<213> ORGANISM: Artificial Sequence
<220> FEATURE:
<223> OTHER INFORMATION: PCR Primer

<400> SEQUENCE: 20
agctaccagg tcaccaggt                                                   19

<210> SEQ ID NO 21
<211> LENGTH: 18
<212> TYPE: DNA
<213> ORGANISM: Artificial Sequence
<220> FEATURE:
<223> OTHER INFORMATION: PCR Primer

<400> SEQUENCE: 21
tgcccgtgac aaagcaga                                                    18

<210> SEQ ID NO 22
<211> LENGTH: 18
<212> TYPE: DNA
<213> ORGANISM: Artificial Sequence
<220> FEATURE:
<223> OTHER INFORMATION: PCR Primer

<400> SEQUENCE: 22
ggtctgccat gccgagtt                                                    18

<210> SEQ ID NO 23
<211> LENGTH: 21

```
<212> TYPE: DNA
<213> ORGANISM: Artificial Sequence
<220> FEATURE:
<223> OTHER INFORMATION: PCR Primer

<400> SEQUENCE: 23
accatggttg tgcttgatcc t                                          21

<210> SEQ ID NO 24
<211> LENGTH: 18
<212> TYPE: DNA
<213> ORGANISM: Artificial Sequence
<220> FEATURE:
<223> OTHER INFORMATION: PCR Primer

<400> SEQUENCE: 24
ggtctgccat gccgagtt                                              18

<210> SEQ ID NO 25
<211> LENGTH: 19
<212> TYPE: DNA
<213> ORGANISM: Artificial Sequence
<220> FEATURE:
<223> OTHER INFORMATION: PCR Primer

<400> SEQUENCE: 25
ccctttccca tcacctccg                                             19

<210> SEQ ID NO 26
<211> LENGTH: 18
<212> TYPE: DNA
<213> ORGANISM: Artificial Sequence
<220> FEATURE:
<223> OTHER INFORMATION: PCR Primer

<400> SEQUENCE: 26
cggcgtcatg caaaaggg                                              18

<210> SEQ ID NO 27
<211> LENGTH: 18
<212> TYPE: DNA
<213> ORGANISM: Artificial Sequence
<220> FEATURE:
<223> OTHER INFORMATION: PCR Primer

<400> SEQUENCE: 27
gatttcccag acccggcg                                              18

<210> SEQ ID NO 28
<211> LENGTH: 18
<212> TYPE: DNA
<213> ORGANISM: Artificial Sequence
<220> FEATURE:
<223> OTHER INFORMATION: PCR Primer

<400> SEQUENCE: 28
cagggaaagc atgcccga                                              18

<210> SEQ ID NO 29
<211> LENGTH: 18
<212> TYPE: DNA
<213> ORGANISM: Artificial Sequence
<220> FEATURE:
<223> OTHER INFORMATION: PCR Primer

<400> SEQUENCE: 29
```
cgaagcatcg cctgacct                                                  18

<210> SEQ ID NO 30
<211> LENGTH: 18
<212> TYPE: DNA
<213> ORGANISM: Artificial Sequence
<220> FEATURE:
<223> OTHER INFORMATION: PCR Primer

<400> SEQUENCE: 30
ggttcacggc tcggtgat                                                  18

<210> SEQ ID NO 31
<211> LENGTH: 18
<212> TYPE: DNA
<213> ORGANISM: Artificial Sequence
<220> FEATURE:
<223> OTHER INFORMATION: PCR Primer

<400> SEQUENCE: 31
ttccgcagcc ccatcaac                                                  18

<210> SEQ ID NO 32
<211> LENGTH: 18
<212> TYPE: DNA
<213> ORGANISM: Artificial Sequence
<220> FEATURE:
<223> OTHER INFORMATION: PCR Primer

<400> SEQUENCE: 32
gttgatgggg ctgcggaa                                                  18

<210> SEQ ID NO 33
<211> LENGTH: 18
<212> TYPE: DNA
<213> ORGANISM: Artificial Sequence
<220> FEATURE:
<223> OTHER INFORMATION: PCR Primer

<400> SEQUENCE: 33
cactccagcg cagtacca                                                  18

<210> SEQ ID NO 34
<211> LENGTH: 22234
<212> TYPE: DNA
<213> ORGANISM: Artificial Sequence
<220> FEATURE:
<223> OTHER INFORMATION: Artificial DNA construct
<220> FEATURE:
<221> NAME/KEY: misc_feature
<222> LOCATION: (2773)..(2776)
<223> OTHER INFORMATION: n is a, c, g, or t
<220> FEATURE:
<221> NAME/KEY: misc_feature
<222> LOCATION: (3158)..(3158)
<223> OTHER INFORMATION: n is a, c, g, or t
<220> FEATURE:
<221> NAME/KEY: misc_feature
<222> LOCATION: (18402)..(18402)
<223> OTHER INFORMATION: n is a, c, g, or t

<400> SEQUENCE: 34
tttttatccc cggaagcctg tggatagagg gtagttatcc acgtgaaacc gctaatgccc    60
cgcaaagcct tgattcacgg ggctttccgg cccgctccaa aaactatcca cgtgaaatcg   120
ctaatcaggg tacgtgaaat cgctaatcgg agtacgtgaa atcgctaata aggtcacgtg   180
aaatcgctaa tcaaaaaggc acgtgagaac gctaatagcc ctttcagatc aacagcttgc   240

-continued

```
aaacacccct cgctccggca agtagttaca gcaagtagta tgttcaatta gcttttcaat      300
tatgaatata tatatcaatt attggtcgcc cttggcttgt ggacaatgcg ctacgcgcac      360
cggctccgcc cgtggacaac cgcaagcggt tgcccaccgt cgagcgccag cgcctttgcc      420
cacaacccgg cggccggccg caacagatcg ttttataaat tttttttttt gaaaagaaa      480 aagcccgaaa ggcggcaacc tctcgggctt ctggatttcc gatccccgga attagatctt      540
ggcaggatat attgtggtgt aacgtatcac aagtttgtac aaaaaagcag gctccgcggc      600
cgcccccttc acctagactc gacgcgtcct agagatccgt caacatggtg gagcacgaca      660
ctctcgtcta ctccaagaat atcaaagata cagtctcaga agaccaaagg gctattgaga      720
cttttcaaca aagggtaata tcgggaaacc tcctcggatt ccattgccca gctatctgtc      780
acttcatcaa aaggacagta gaaaaggaag gtggcaccta caaatgccat cattgcgata      840
aaggaaaggc tatcgttcaa gatgcctctg ccgacagtgg tcccaaagat ggaccccac      900 ccacgaggag catcgtggaa aaagaagacg ttccaaccac gtcttcaaag caagtggatt      960
gatgtgatat ctccactgac gtaagggatg acgcacaatc ccactatcct tcgcaagacc     1020
cttcctctat ataaggaagt tcatttcatt tggagaggac gacccgata tgaaaagcc      1080 tgaactcacc gcgacgtctg tcgagaagtt tctgatcgaa aagttcgaca gcgtctccga     1140
cctgatgcag ctctcggagg gcgaagaatc tcgtgctttc agcttcgatg taggagggcg     1200
tggatatgtc ctgcgggtaa atagctgcgc cgatggtttc tacaaagatc gttatgttta     1260 tcggcactttt gcatcggccg cgctcccgat tccggaagtg cttgacattg ggaattcag     1320 cgagagcctg acctattgca tctcccgccg tgcacagggt gtcacgttgc aagacctgcc     1380
tgaaaccgaa ctgcccgctg ttctgcaggt aaatttctag tttttctcct tcattttctt     1440
ggttaggacc cttttctctt tttatttttt tgagctttga tctttcttta aactgatcta     1500
ttttttaatt gattggttat ggtgtaaata ttacatagct ttaactgata atctgattac     1560
tttatttcgt gtgtctatga tgatgatgat aactgcagcc ggtcgcggag gccatggatg     1620
cgatcgctgc ggccgatctt agccagacga gcgggttcgg cccattcgga ccgcaaggaa     1680
tcggtcaata cactacatgg cgtgatttca tatgcgcgat tgctgatccc catgtgtatc     1740
actggcaaac tgtgatggac gacaccgtca gtgcgtccgt cgcgcaggct ctcgatgagc     1800
tgatgctttg gccgaggac tgccccgaag tccggcacct cgtgcacgcg gatttcggct     1860
ccaacaatgt cctgacggac aatggccgca taacagcggt cattgactgg agcgaggcga     1920
tgttcgggga ttcccaatac gaggtcgcca acatcttctt ctggaggccg tggttggctt     1980
gtatggagca gcagacgcgc tacttcgagc ggaggcatcc ggagcttgca ggatcgccgc     2040
ggctccgggc gtatatgctc cgcattggtc ttgaccaact ctatcagagc ttggttgacg     2100
gcaatttcga tgatgcagct tgggcgcagg gtcgatgcga cgcaatcgtc cgatccggag     2160
ccgggactgt cgggcgtaca caaatcgccc gcagaagcgc ggccgtctgg accgatggct     2220
gtgtagaagt actcgccgat agtggaaacc gacgcccag cactcgtccg agggcaaagg     2280
aatagagtag atgccgaccg ggatccggag agctcgaatt ccccgatcg ttcaaacatt     2340 tggcaataaa gtttcttaag attgaatcct gttgccggtc ttgcgatgat tatcatataa     2400
tttctgttga attacgttaa gcatgtaata attaacatgt aatgcatgac gttatttatg     2460
agatgggttt ttatgattag agtcccgcaa ttatacattt aatacgcgat agaaaacaaa     2520
atatagcgcg caaactagga taaattatcg cgcgcggtgt catctatgtt actagatcgg     2580
```

```
gaattcatcg atgatatcag atcaagggtg ggcgcgccga accagctttc ttgtacaaag    2640
tggtgatccc cctcgaggtc gacggtatcg ataagcttga tatcgaattc ccgtgcctca    2700
tgcaatagaa aataaaacat aaaacatgtt ttttttttca ttctgaaagg cacgggtcat    2760
gcctcttgcg aannnnaaac cgtgcctctc gcggaaaaaa agagagcaga aaacgtgttt    2820 ttccccttttt cagaagaggc acggacgtgt ctctcgcgaa ggcaaaaccg agactttcgc    2880
ggaagcaaaa gtgtgtctct cgcaaaagaa aaacacgttt tttccctttc gggagaaaac    2940
cgtgcctctc gcagaaaaac aaacaaacag aaaacgcatt ttttttcatt caggagaggc    3000
ctctcgcaaa ggtaaaactg tgcctttcgc aaaaggaaaa ccgtgcctct cgcagaaaaa    3060
taaacaaaca gaaaacgcgt ttttctttct ttccgaagag gcacggtcgt gcctctcgcg    3120
aaggtaaaat catgcctttc gcggaagcaa accgtgncct ctcgcaaaaa acaaaaaaac    3180 acgtttttttt ttccttttcag agaggcacga ccgtgcctct cgtgatagca aaaccgtgtc    3240
tcgcaaaaaa aaagtttttt cacgtacaaa taaagaaaaa tgtgtttttt caccaaaata    3300
aagtacgaat ttcttttcgt tcaaaagtta cgaaagatcg gtgaaaaacc ataacacaat    3360
tttttcgaaa aaatcactca aaaaaggaga aaacgcgtgc gaaaaatatt taaaaaaaaa    3420
tttaaaggaa acgttcagaa cacgacacgt ggcgacggct ggaaacgcgt caactggcga    3480
cgcgcgggag caatcgctgg gaggctcccg aaaaagcact cgctaactag ttgcttcttt    3540
ttcctccagc ataatccaca acggttcgct gaaaagaaaa gtttaatcaa caccagaggc    3600
aatgtgaggc caccgacgtc tctgatgctg cttgtcgggg gcatcaatcc ggcggacggg    3660
ggcgacaacc cgtcagaaac tcgagccatc catggtgaag acgtcgacac aggtctccgg    3720
ccgggaggtc tacgccaacc agcgacttct tcattcgtaa acaaacaaa caaacaaaca    3780 aacagctgtt ggatcagaga ccggaaaaac acaggcgacc acaaaggctg tgaacgaatg    3840
gaacacgagc acagagacaa ccatattttg cgaggcccaa ctgccgtcct cttttcttgt    3900 ttttttttc ttttattcta ttaacgtaac aaacaaagag attacaaagc atgtgtaaca    3960
gccggacgac tgggccgact ccaacgccac gatccgtcca tatcgtgcca tcccacgatt    4020
gacttggtga tcatgactaa caaactactt ctacttacat gcagcgactc gaagtgcatg    4080
tacacaccca tcatatctgt atagcgtacg tactaaatac atgcaactag cacatgcacc    4140
accaggatgt gatcctgtct aacaacctaa cctagctgct aaaaacaact gaatatgcat    4200
gacacagacc ttgtaacaag attagcacca acaacagcga gctctaggac tcgaaccatt    4260
ctgagagaaa tttcatcgga ggagagatat gcataccaac cggctccttt ttatctcgga    4320
aattccatcc aatattcatg tcttgttctt gtactgaata gtttaggagc aatttctgtc    4380
tagcttttcc attagttaga acagggcaga ggatagatac atagtgggac aaatgataag    4440
atgagatact gacctgtgct gtgtaagaaa agaacctgcc taagctactc gagtcgtcca    4500
ttccgaaatt ggaccgactc ttcattcagc atttgacctt caaaggcagc aggcagcagg    4560
ccagagagtg gtaccgacgc gaggatgtga agagaagaaa tacaatacga cattttcgct    4620
ccaagcaaag aaaacaaata cggtatatat gtcgaaaatg agtggatgaa agctcgttcg    4680
gaatagtatt cgccgtcgac atctagtctt gagtagacaa ggatgagaaa aggccgatcg    4740
atgtgcagca tccagttacc attgacctgc atgtagtacg tcaatgattc cttaggttca    4800
cacctctagt gcatgggaaa agcctagata ttataaccta caaattcaag gaggcaaatt    4860
tatgggcttt tgtctaattt taacatttac tggtaggtgt cgatccatcg gaaattccct    4920
tgaagcatcc atgccaattc gtcaagtctt gaattaatag atagcgactt gagaggatgt    4980
```

```
ggaaagaaaa gaaatacaga cattatcgtt ctaagcaaag aaaagaaata tatatgatat    5040
agctgtaaaa tgagtggagg aaaatgtgtg tggaatagta ttcgtcgtca tcatctagtc    5100
ttgagtggat aaaggtgcga gaggatgtgc accatacatg atatatacat gtaaattcat    5160
gctgttaata ctgcataaat tgtgtgtttg tgtgagagaa actgagagag ggagtatcag    5220 ttccatttc tctcttcacc agtgcttgtt catgtatcca agctaccagg tcaccaggtg    5280
tattagcaga gtctatatat atacatactg caggctaact agctagcctt cttcccccct    5340
tttaactaag gcttgcaaat gccggatcca gttactatta gtgctgctgt aggatggggc    5400
gtatccgcag taggctggct cgcctctccc atcatttcaa gggttgtcaa caaaggtttc    5460
gcccacctcg acttcgatgc agcagagaag ctgaagatac ttgatataca agttctacaa    5520
ctgcagcgcg tgatagaagt agtcgatgag agcacgtaca ggcttcgctt ggagccactg    5580
ttagacaagc ttagatctgc tctttatgaa gccgaagaca tcttggatga ttttgattat    5640
cagcgtctcg agaagcagat ccatgttggg tctagttcca cacgtaaacg caagatagat    5700
tcgctggaga agaatcatcg gtctgccatg ccgagttcct ccctaaaaga taaggtattt    5760
ccttgctctc atacttgatt ttcttttct gctttgtcac gggcaccata tttctttcca    5820
tgtatatata tgtaataaaa actaggaact gtattcaact ttattgttta ttcttttcc    5880 catgattaga tggaaacatt cccgaggatt tcatcgaagg gaaggagac tatcaataat    5940 ttactgagcc aggtatataa gcatccactc tgatcatgct gaaatcatac ttgcattatt    6000
catatttttc tttagtttaa tgtgcattat taatatttaa gaaaaaaaat gttatttaat    6060
ggtagaaatt agctatgcac atatactctt cctccatctc gaaggaatga atgtatctag    6120
atgcattcta gttctagata cattcatttc tatccatctt tgtaacaagt aattccggac    6180
ggaggaagta tatttcaatt taatatatca tacattcata ggatcaagca caaccatggt    6240
ttgatcatcg agtatgacct taagaagat ttaattcaga accacttctc ggaggtgatg    6300
ggaaagggga atcgacgaga cttagacctt aactaggatg agttggacct tgtgccacat    6360
gacctcttgg tcttcgaggg ccaaattatg gagcatgagg tgttggaagc aatcactgat    6420
atgcctactg acaaggcccc caggcctggt ggcttcgccg gcctcttta aaagaaatat    6480 tggggtaaaa tgaggcataa cattgtgagg gtgattgggc tctttgaatg cgtgcatgag    6540
gccaacatcc attggctcaa gagcatctac agccggaccc cttaaatgac ccctcataca    6600
tccgtggatg cattcggtta gtgacgggag aggggagaga aggaaaaaag tgacccaatc    6660 ggaccctca tatcgtccct gtatgcctgg gctgtccatg aaccctcata tccatctcaa    6720
ataaggggag gatatgaggc ctcgcgaacg ctctcggtcc accgcatagg acgcgaccct    6780
acctcggacc acctttatct tttcttttatt cattcttttc tttctctctc ttcctctcca    6840
ccaatcacat acaagtgacc gggcctatga gaaagaaaat aaggaatctg gttgcgtgga    6900
cggacaaata ggaaacacgc ccggtcactg atcgcgcgcg tccgcgagta tttgagggac    6960
cggatttgca agttctggct atagatgatt ttaatcccgt gaatactatg cttttaccaa    7020
agacggatag tttggagggc attaatgact ataggcccat tagctttata tattcatgtg    7080
attgccaagc tcactgcgat gatcttcgtc acttgtacac gcctgcacat ggacactctc    7140
atatccaact cacaaagtgc tttcataaag aagagaagca ttcatgaaac cttcacatat    7200
gtgaggaatc ttgctcagca gtttcacaaa gacaagacct cttctctcct cttcaaactt    7260
gatgtacgta aggccttcaa cttggtcaag tgggagtaca ttattgatct tattcaaaga    7320
```

```
tgaggcttcc caagcaagtt cgcggattgg attaccatgc tcctctctat ctcctcctct   7380
cggatacttc tcaatgtggg ggccggaccg cctatcaagc atgatcatgg gctacggcaa   7440
agggattcag tcttgcttct cctttggtc attgccattg acccactcca aaaaaacctt    7500
catgttgcca ccaccaaaat tttgctacac aagattctag gtcgacatgc catagtgtag   7560
atgtccttat atacggatga tgtggtggta tccatgaaac ccataaagcg ggagagcgac   7620
aacctctcta ccatactcaa atgttttggc caggtcatgt cgccaagggc cttgatacaa   7680
acttccagag gcggattcag gccctaggca gccaaggcct cggcctgggg cgtggtgact   7740
gtagcaaaaa tatccaatgt agcacattgt attatactat agccatacag cctgcctgcg   7800
aattgatctg attctagctc cgattatcca cataattaag atgccgtgaa atacaacttg   7860
gccccttctt caacacttgc tgacaagaaa acaacctttc ctatgagata tttggggaag   7920
ccgcttttgg tctggcaact caagagggtg aacttccaat tcttaaagga caaggtgggt   7980
tccaagattc caccctggga cggaaaaaac atcagcacca ttggttgtac agttcttgtc   8040
aaattcgtgt tatcctccga agcggtctac ctcatcactc ccctcattgc aacacccagc   8100
atcctatgca acacaaacaa gctcaagtgt gcctttcttt ggtaaggttc aaacaagatt   8160
aacggtgcaa attgcaaagt gcaaagttaa caaggatttc gtatgctggc aatgttatga   8220
tctctacaca ttttgcatag aacttgaatt attccacaat atgcaagaac aagcatgtag   8280
tcatgtaact ttcagatagc cgtattatgt gcaaacatat tgcatagaac ttgcatggtt   8340
ccacaatatt caagaacaag cataagtagt gtaactttga dacaacaata tgattttcac   8400
acagatagca ttgaacttgc atttatacat ccatgctgtg cacagtgttg aaacaacata   8460
acaaaaacat tggcgatcaa tcatttcttg acatgtcgaa gatgaattgc atcccacgtt   8520
ggtgttgcct ccccaattta tgtcttgctc tttctctcat agaaacgagt gtgcattccc   8580
gcacacacac gcacatacac aacaaacaga catagcaaag tacgcaaata cacaagaaa   8640 aaacagctaa cacaagaaaa atctaaacac aaagaacttt tccaaaatca atgaactttt   8700
ttttaatcca tccattattt tccgaaagtc catgaatgtt ttctcaattc atggtatttt   8760
tcaatttgtg aacattttc ctacgaatga acttttccaa aaagatgaac catttgtcaa    8820
aaacaacagt cagatgtcaa acatgtcagt ggtcaactta tcgcccaggt taccatgaag   8880
aagttttttt gttgaaccgt gaagaagcga tcaggtgtat gatgttgcgt gttgagcgac   8940
agctgatcac tggtgtagtg gagtgttgca tccgctacaa aaagaactag acaagtgctg   9000
cctaggaggt cccgttgtac atggaaaggc atcacacaaa ccaaagcgca caagcctaca   9060
tcctgcacct ggccttttt ttttgttctt tttttacct tcaaaaaatc agtgcatgaa     9120
gtaggatttg aacctggac ctcttggatt agttccatcc gtaatgaact ggaacatctc    9180
acttgttacg tctaattact ttatttattt cttttattgt gaatcttctc agtctggttt   9240
tcttctcgtg ttgcttttgt tttgctttt tctttagtt ttttttttca tttctctata     9300
tttcttcttc tttctctctt ttcttttttc ctttctctaa atttatgaac attttcttaa   9360
atttgtgaaa aaaaattcaa tttcaagacc ttatttttg aatccatgtt tatttctcaa    9420
ataatgaatg tttttcaagtt tgcaaacttt tgtcaattca atggacttta ttttgtcaac  9480
tctgtgaatg ttcctaaaat tgatgaactt tttaaaaatg tgtgaaactt tttgtcaaat   9540
tctataactt ctttgagaaa ttagtgactt cttttaaagc cgattacata ttttaatttc   9600
atggattatt ttcaaatcgc tgtttttaa acaacattt gaacttttct ttaatctaag     9660
ggttgcgtta taaaccgaaa acttgatttt taccattcga tttattctaa attttggttg   9720
```

-continued

```
gcaaaactat aaactggaat gaatatgggg aagcaaataa ccataattc ggttcaacgg      9780 cttattcggt ttgatgttca gttttacacc gagcaaactc gtcaaatgtg ttgctttcta      9840
ttaggacact ctgtcacatt atatagcaaa ttttgtccc ctatttagt agctcagccg      9900 gatttgacta aattggacgc tatgcgcaac ttgggtgtac gatgtcaccg aaaggctcgt      9960
gcgggtttgt gccttcgttg tactaaaatt tgcatggagt actagaatgg gaacaccaat     10020
ggcaaaattt aggtaaattt tactaatatc cacaagtaca tcatgtacaa cggaggggtt     10080
ttggtttagg cggaagagtt cgtcccctag cacggttttt agcatacatc aaatactcct     10140
aaaaaaacac cctagaatta tcatggcatg gacccatgcc aacttccatc gaattttgac     10200
tttttttgta tttcctatgg ggtttccggt caaaaaacct caagtactga ccgaacggga     10260
tgcagcgtgc attcgttctt cgaattcgtt caaattttgc gtcgagtact agaatggcat     10320
gctcagctgc ctgcaaaagt tggataaatt taatgaatgt ccacagatac atcatgtaca     10380
accgagcggt tcggttata gcacttttc acatagatct aacagacgca aatgtgttat     10440
gttcatttga cgcatgtcga gtcacaacat gctctcaaac ataggctatt tctttcggaa     10500
aaaaattcga tctattcatt ctcaatcatg gtaatacaac gaataccaga ataataaaa      10560 attacatcta gatccgtaga gcacctagcg acgattacaa ttactgaagc gagccgaagg     10620
cagaaaaaat ttcgatctat tcattctcaa tcatggtaat acaacgaata ccagaaataa     10680
taaaaattac atctagatcc gtagaccacc tagcgacaat tacaattact gaagcgagcc     10740
gaaggcacgc ctgttggaaa taaccacgac atgtgtggtc tgtgtccggt tcgtacacac     10800
gacaatcatc gtatagtggt aggattagga ttcatagccg tgtaggttat cttatctaat     10860
gtcctgacta ttatatatag gtagctatcc ccttgtaagc tgcaaccgtg agatcgtgag     10920
atcaaaagat caaaagcaat aaaagtgcaa ggcttggccc agacccgacg tcgacgttgt     10980
tgccgtgtac tttccggcaa tacatacgta cgatactagc tcgagtgctt tccgagctat     11040
ccgtcggaga ggtaaacgta gacgtagaca gcaatcgtgc acgtatacac gaaggctgct     11100
ggatggttcc tcctgtgcta gctagcacgt actactgcac gagatctttg gctgatcgat     11160
ctatgcggcg agaacacagg aaacactcgg cgagttggcc aaaaggagcc ttgcacttt      11220 attgcttttg atcttttgat ctcacgatct cacggttgca gcttacaagg ggatagctac     11280 ctatataaa tagtcaggac attagataag ataacctaca cggctacgaa tcctaatcct     11340
accactatat gatgattgtc ctgtgtaaga accggacaca gaccacacat gtcgtggtta     11400
tttccaacaa cgccgccgtc attgctcctc catcaccgga gtcgagcaca atttgttgta     11460
gtagacagtc gggaagtcgt cgtgctaagg ccccgtagca ccggtgcacc agaacagcaa     11520
ccaccgcaga tgaagaataa catagatcaa aaggatccaa tccgaagaca cacgaacata     11580
gacgaacaac gatgagatcc gagcaaatcc accaaagata aatctgtcgg agacacaact     11640
ccacacgctc accaacggtg ctaggcacac cgccgtaatg ggggctagga agggagacct     11700
ttattccatc ttcacgcagc cgccgccgtc tcgtcttcct gagcaggaca caaaccctag     11760
caaaactgaa agtaacgact aaaaacggag ccctcccgcc ggcgcttgct gagatccacc     11820
gcgctcccat ggccctaggg gcaccggagt ggaggcgacc tgcggcggcg ccggcaggac     11880
gcagaaaccc taactttttt ttttgtgaag gaggaggagg cggacttttg tgtcaaacat     11940
aggcttatgg cccaccaggc cacccttatat tgaacatggt gcttctttgg acattttaa     12000 aatgacacta agttttttag taggtgggta tgcccataat ttaaacaaaa atttaaaact     12060
```

```
gttatgttga gttttaacg taaaaatat atagaaaaag gagaaaaaat aaaacagcca    12120
atgtttgct aaagctaata catatttgaa aaaatgaata taatgtttga cagttactta    12180
aaactgttat tttgatattc caaaaatat ttcaatttcg cgaacaagct tcaaaaataa    12240
aaataaacct ttaaaaggag aaaaatgaat taacggaaaa tgagaaaata gaaagaaaat    12300
aagcttaggc cttcgcggaa ctagaacacg acatcgctct tgtcgggcgg ctgttaggcc    12360
gaggcaagtg ctcgggattt caataagctc aacgattcaa aaaatgtccc tattttcaaa    12420
attcgtttat aaataaaaaa atgttccctt tttcaagctt gtacataaac tgaaattcct    12480
ttgcgggagt ttctaataat gttcgtactt tcaaatgatt ttcctaactt caaaaatatt    12540
cctgttttca aaagcaatat acacaaataa aatgatgata ggggaaattc acaaaaataa    12600
tgttcgctct tctagaaaaa tgtttctgtt ttgtgacttt taggaactta aagcaacaa    12660
tattttgaag taataactat aaaatgtgta aaaaagtttg tgaggtctat taaaatgttt    12720
gtcgttgaaa gtgatcattt ttgctctttt aaaatgattg aaatgtctat ttcaaaattt    12780
ctatacaatt tttataatgt gaatattttt agtttcgtaa ttatacattt ttataaattt    12840
tgaaaaaaca aatacttggg tctggcgatg tcgatttgag gacctaatag tcagcgcttt    12900
aagcgccagt taggaagcta gcgctcgagc ccagtattgc gcaagcttgc ttgcttcacc    12960
cgatggcttt gacaaaaatt catgaatttc aaaacgttaa taagtttgaa gtatagtttg    13020
tggatttgaa aattgttcac gagtaaaatg taaaaagctc atgatcgtga aaaggttcac    13080
aaatttgaaa acaagtttct gaatattaaa attgttgcac gttcaaattt caaaattatc    13140
atgattttaa aaacatttat gaatttgaaa actgttcacg agatatattt tataaatttt    13200
ataaaaaaaa catgagttta gacaatgttc acaaatttgg aagtagttgg cgggtttgaa    13260
acaaattta tgaattttt taaccttgat aaacataaat ggaaattcat gaaaaaaagt    13320
ggaaagggta aaataaatat aaaacgaaat tggcaaaaag aaagagaaaa aaccgagaga    13380
aaaccatgca taaaaacga aaaggaaaat tgtccagaaa aactatgcat agccagaacc    13440
ggaaatgtag agaacaagaa gaaaagaag tggaactatg cagaacatgt tatctatccg    13500
aggtggtaat tttgaatccg gacgcagagt ttctgctccc aagctcattt gagctcgatg    13560
aaaacatttg gcatgaaata acattcctac aaagtttggc aaaaacaaaa tcgatgctgt    13620
gaaaagcgga ttttcagagt gtccattttt tttgctacga attgtaggaa tgttatttca    13680
taccaatttg tttttacact taaaactttg tcattgctgg tcacaaaaaa aaaatcagaa    13740
ttatttgaac gtttcttgat tttttttga ttttttactgt tcaccgagct caaatgagct    13800
cggggggcaga agggcacttt caaatcccaa gtggcacaat agccaacatc aaataggagc    13860
ttcgctacta tacaacaccg tatacataca aacatggata taatttgtca aaggtttata    13920
ttgcccttta tacgtttca ttcttttata atgcaacatg taagtggaca atccagtggt    13980
ccggctcagc tttgtgcgaa acatgctagc acggtgactg tcaccgaaag ctggcttacg    14040
aaaactccta gcttcctgat tagcagcctt caagctgact gctcagcaaa cgcctttgtt    14100
tgaataaagc ttaaaattcc atgcaaaaaa gttattgccc tttatatgtt ttctgagagg    14160
ggagggggag ggggtatcaa agcgggacta gagatataag cccgctaacc tggtcggggc    14220
atttggaatt gcaagaaaaa caggcacggg tttttagatc ttcggtttga caaacgaaac    14280
atgtgcaata aggcagcaaa agtatatatt caagttgatt cgattactaa tctaatgata    14340
tctatttttt actggcatat ctcacatgtt ctgttagtca aattgaagac ctaagaactc    14400
atgcgctcct ttgaaattga acaaaactag ttcatttcta aaacttcaac acaaaatgac    14460
```

```
ctcgatccga aaatacttca caaattggct ccttttttgca tgacgcccga ggatagggct   14520
ccatgctatt tagcatgacg ccctaggcca aggctgtatc taccatgaca ccctggcccc   14580
ggccggcgtc atgcaaaagg gccagtttgt gaaatatttt gagatggagg ccattttgtt   14640
ttgaagtttc agaaaagggc tagtttcgtc aattttttact acactcctta ccaacccgga   14700
tagaggagta aatatatatt cctcaaatag agcagttatt gatagtttca acttacctgt   14760
tattcggttt tataggggat tggaacatca aaagtggagt tgaagaaaag cctagagaaa   14820
atagaaaata ccataaacga tgcatgtaaa gttttggaac aactgaactt gccgagtgta   14880
tgtaatgata atgggagacg aggtgttgct accaattctc gtagtgcagt cactactgca   14940
ggtcctcctc tacgagtaat tggtcgagat caggatcgtg acaagatcat agcaatgctt   15000
catgagaagg atgaccggtg tcaagtcaat ggtacatctt attctgtaat tggcattcat   15060
ggcgtcgccg ggtctgggaa atcaacactt gcacagtatg tttatgatca tgagaaaaag   15120
tgcaagcaag gtaaaagaga aggctatttt gatgttctca tgtggattca tgtttctcaa   15180
aaaatcggtt tggagtccag tttcagggac atgtttgagg gggctacagg gaaagcatgc   15240 ccgaattttta atagtcttaa cgtcttaaag gaaaagttgg aggaggaact acgtggaaaa   15300
cggatttttt tggtactaga tgatgtctgg tacaacagta agaattcagg agaccgtgaa   15360
gaactgcaga agttaatttc tccgttgaat gttgggaagg caggaagcag aatcttggtg   15420
actagtcgaa ctgaagctgc attagtagct ctccgtgctg caaaagaggg atgtatccca   15480
atatctaacc tggatgataa agttttcctt aaaatgttca tgcattatgc acttccacat   15540
gcatggccag ttggcaatga tcgaagaaaa cttgaaatga ttggagagga cattgcaaaa   15600
aagctgaagg gttcacctct ggcagctaga atagtgggtt cacggctcgg tgataatcca   15660
aatgttgaat tttggaggag agagaaagac cgggatctta tgaacgagac gatgggagca   15720
ctttggtgga gctaccagta ccttgatgag caggtcaggc gatgcttcgc ttacatcagc   15780 attttttccca gacgtcatca tttgaaacgt gatgacttaa ttaacctatg ggtggccgaa   15840
ggatttataa agacaagtaa agctgaagag gaaatggaag atgttgcctc ggaatacttt   15900
gatgagctgc tttcgttctc atttctgcaa ttaggaggga aagatgagct atttgcacgt   15960
gaggtcgatt actttataat tcatgatctg ttgtatgatt tagcagagga ggttgctgga   16020
agagattgct tcaggataga gaaaggtttc acaggagaag tccctccgga tgttcgctat   16080 cttttttgttg ggacttacga taaagagatg cttactgaga agatatccag gttgcaaaat   16140
ttacgcactc tcttcgtcga taagtacata cagattttat cacccaagta cgatgatttt   16200
gttagtatgg tgactatgtt gatggggctg cggaaattga gggtactgaa tttacatttc   16260
actggatatg gtattcctaa attctcattg ccggattcta ttcttcagtg gaagcatctg   16320
cgttactttg cttttggggt gtccccgttt accaagctaa ctttaccatg cgcttttacc   16380
aagctttacc acttgcatgt ggtagatttc ggtgattgca atagtttgga gttttctcgt   16440
ggtgaataca tgatgaacct ggtcaatttg cgccgtgtaa tctacaagaa ttatctcgac   16500
tttccgaaca ttggcaggct gacatggctg caatcgttgc cgtgcttcag aataaggaag   16560
aaacatgggt atgaatcaca tcagctgaaa cacctaaaca agcttcaagg caggctgtac   16620
attggtggtc ttcagaatgt tgagagcaag gaggaagctc ttaatgtgaa ccttgcagcc   16680
aaggaaaaac tcacagaagt ggtactgcgc tggagtgata atagctgcag tccagaaatt   16740
caagcagagg tacttgaggg cctttgtcct tcaaagtatc ttgaaatact agaaatcaag   16800
```

```
ttatacaatg gcatgaagtt tccaaattgg atgacgagta agcataaggg tgggccaaag    16860
aacctgcaag aacttagatt cagacagagc accctgggat ctgctcctga tgttggggct    16920
ttcattcacc ttcagtcgtt atttatttat caatgcagct gggataccct accagggaat    16980
atggagcacc tcacagcgct caagaaactg gagatacggt catgcaataa tattcggtcg    17040
cttccaacac tgcccaagtc ccttgagcag tttgcgatct ggtcctgcag cttggatgct    17100
ttaccgggca atatggagca cctcacagca ctcaagaaac tggagatacg gtcatgcaat    17160
aatattcggt ggcttccaac actgcccaag tcccttgagc agtttgcgat ctcgcgctgc    17220
agcttggatg ctttaccggg caatatggag cacctcacag cgctcaagaa actggatata    17280
tggtcatgcg agaatatacg gtcgcttcca acactaccca agtctcttga ggagtttaca    17340
gtctggaact gcactagtga gttcatgcaa tcttgtatga cgactgatga tccaaactgg    17400
cagaagattg agcacgttcc aaacaaaaaa attggatttc tatgaaaacg atacataaag    17460
aaggtacgta tttaaattcc tttgacgtct tcgttttcca tttttgcgtg cagtaaatgt    17520
tactgcaaca attagccgtt aaggttcctg gtattttttct gattcagttg ctaactatta    17580
ggcgcgtgcc ctttggttga ggacgggaga tgaagtcgaa gccgaagccg tcagaatctt    17640
gctaaattta cggtctctct tactggatag cctcttggtt gggttatgcc tactttggtt    17700
ggttgagtct tgcatgttta cacctaaagt ggtgcaaaat gccatctctc catgcagtca    17760
caactcacaa acagtggatt tatgaattgt ttacaatata tggatttatg gatgcaataa    17820
cgtgtaataa tgaacagctg attgatttgc cttcatatat atatatatat gatttgtaac    17880
actgccgtgt ggatgatgaa cctggcccaa actgtttgat tcctagctat atatgatttg    17940
taacactttg gaatgattat cactgaattc gttcctttcc tgtcgttgtt tgtatcatgg    18000
ttcaaaaaaa agtatccgat ttgattgcga ggaattgggg gctacataag catggtatgg    18060
tatgaggtta ccagattggg cgaagctaac ccgaggaact gctcctgaca ttgaggcttc    18120
cattcatttt cagtaataga atgctaaaag gctttagtgg ttgcaatcaa cgtgcattgt    18180
aattagtgat tgcattttt tttctactgg ttgcccattc agggaaagtg ctctcacacg    18240
gtggcatgtt ctctgttctg cacacgctct cgttttgggc agacgcaagc tttgatgtgt    18300
ccgcttgggc cttcaaacac gatgcaacat attctgcaaa cactattgag tattttcttt    18360
ctcaattttt gctcatctta ggagctgttc ggtaaccatc cngctccatg aaatctgaga    18420
atctgcggag tacctcttgt ccagctctgc aattttttacc tgctgctcct ccaactccgg    18480
gagtgaagat gcggagtgga ggacatccga acaggccttt aatcaatgaa agcatcgcta    18540
gctgctacct ttcgttcaca aaaatgtttt aaagaaggat gcgacctgta gcatgaaaac    18600
aagaacgaca tagacttctg accactgcca agtgaaattc tgtagatcat cagaacacgc    18660
tatattgtca gaaagatgat cacatctgtg acaagtccac gcgctcgaaa caacaaccac    18720
tttgaactct gaaagctgat ctcatgacga ctccaccaaa ttgggtccaa cttgtacaca    18780
tattcgagac cttatgatcg agccagtatg aaacgaacaa attccaggcg ctcatgtagt    18840
atctcattgg taatgctacc acacaggttg gactacatag ccagaggcac gccaacataa    18900
ggaaaccgag tcgtgaaaaa ctcgagattc gcggaattgg tacgttgatg ttctaggagt    18960
caatatacta cctgaccacg tggcagtata acaaacaaac ttgaactgaa gaaaaaacag    19020
ggaaagaaac tgggtggttg ggatacacag caagacagag gcacatgaac ataaaggaat    19080
tcggtcaaga aaaactcgta cggaattggt tttgcaggag ttcatttact gcctaggcac    19140
attctatcag tataacaaac tacaaaggaa aagaaccaaa ctgggggtgt tggtagtgag    19200
```

```
gaaaaacagc acaatcgccc gaaactttac gtttcagtcc gtcatctcaa tcaatatgat   19260
ttgcattgag attcagagca caactatgat actgagattc aaagagtggt ggagacattg   19320
actgcaataa agagcaattt cagttgcccg tgctgataag cactcacttc gatctcatga   19380
ggttgattca cataaaacaa catacgtggg ataacatttc agtttcctgt gagcacaagt   19440
tatgcaggtt tatctcgaaa cagcaacgta agataaaatt atacatctga agatgaagac   19500
aagagaactt ctctgcttcc ttacatctat cataaggact gtacaaaatg aacaatctttt  19560 gacttgaacg aattttcttg aggtgaaaca atccaaggta aaacaggata taaagttgta   19620
ttccttctac atttatcttg accatcagaa ctactactca ataataataa taataataat   19680
aagctggtgt ttctagtgat tccatcagga attcaggact catgcataag ctactcatag   19740
cgtacaagat cattcccctt actaaccgca ttctcttaag atccactagt tctagagcgg   19800
ccgccaccgc ggtggagctc cagcttttgt tccctttagt gagggttaat tccgagcttg   19860
gcgtaatcat ggtcatagct gtttcctgtg tgaaattgtt atccgctcac aattccacac   19920
aacatacgag ccggaaghca taaagtgtaa agcctggggt gcctaatgag tgagctaact   19980
cacattaatt gcgttgcgct cactgcccgc tttccagtcg gaaacctgt cgtgccagct    20040 gcattaatga atcggccaac gcgcggggag aggcggtttg cgtattgggc gctcttccgc   20100
ttcctcgctc actgactcgc tgcgctcggt cgttcggctg cggcgagcgg tatcagctca   20160
ctcaaaggcg gtaatacggt tatccacaga atcaggggat aacgcaggaa agaacatgaa   20220
ggccttgaca ggatatattg gcgggtaaac taagtcgctg tatgtgtttg tttgagatct   20280
catgtgagca aaaggccagc aaaaggccag gaaccgtaaa aaggccgcgt tgctggcgtt   20340
tttccatagg ctccgccccc ctgacgagca tcacaaaaat cgacgctcaa gtcagaggtg   20400
gcgaaacccg acaggactat aaagatacca ggcgtttccc cctggaagct ccctcgtgcg   20460
ctctcctgtt ccgaccctgc cgcttaccgg atacctgtcc gcctttctcc cttcgggaag   20520
cgtggcgctt tctcatagct cacgctgtag gtatctcagt tcggtgtagg tcgttcgctc   20580
caagctgggc tgtgtgcacg aaccccccgt tcagcccgac cgctgcgcct tatccggtaa   20640
ctatcgtctt gagtccaacc cggtaagaca cgacttatcg ccactggcag cagccactgg   20700
taacaggatt agcagagcga ggtatgtagg cggtgctaca gagttcttga agtggtggcc   20760
taactacggc tacactagaa gaacagtatt tggtatctgc gctctgctga gccagttac   20820 cttcggaaga gagttggta gctcttgatc cggcaaacaa accaccgctg gtagcggtgg    20880
tttttttgtt tgcaagcagc agattacgcg cagaaaaaaa ggatctcaag aagatccttt   20940
gatcttttct acggggtctg acgctcagtg gaacgaaaac tcacgttaag ggattttggt   21000
catgagatta tcaaaaagga tcttcaccta gatcctttta aattaaaaat gaagttttaa   21060
atcaatctaa agtatatatg tgtaacattg gtctagtgat tagaaaaact catcgagcat   21120
caaatgaaac tgcaatttat tcatatcagg attatcaata ccatatttt gaaaagccg     21180 tttctgtaat gaaggagaaa actcaccgag gcagttccat aggatggcaa gatcctggta   21240
tcggtctgcg attccgactc gtccaacatc aatacaacct attaatttcc cctcgtcaaa   21300
aataaggtta tcaagtgaga aatcaccatg agtgacgact gaatccggtg agaatggcaa   21360
aagtttatgc atttctttcc agacttgttc aacaggccag ccattacgct cgtcatcaaa   21420
atcactcgca tcaaccaaac cgttattcat tcgtgattgc gcctgagcga gacgaaatac   21480
gcgatcgctg ttaaaaggac aattacaaac aggaatcgaa tgcaaccggc gcaggaacac   21540
```

| | |
|---|---:|
| tgccagcgca tcaacaatat tttcacctga atcaggatat tcttctaata cctggaatgc | 21600 |
| tgttttccct gggatcgcag tggtgagtaa ccatgcatca tcaggagtac ggataaaatg | 21660 |
| cttgatggtc ggaagaggca taaattccgt cagccagttt agtctgacca tctcatctgt | 21720 |
| aacaacattg gcaacgctac cttttgccatg tttcagaaac aactctggcg catcgggctt | 21780 |
| cccatacaat cggtagattg tcgcacctga ttgcccgaca ttatcgcgag cccatttata | 21840 |
| cccatataaa tcagcatcca tgttggaatt taatcgcggc cttgagcaag acgtttcccg | 21900 |
| ttgaatatgg ctcataacac cccttgtatt actgtttatg taagcagaca gttttattgt | 21960 |
| tcatgatgat atatttttat cttgtgcaat gtaacatcag attttgag acacaacgtg | 22020 |
| gctttgttga ataaatcgaa cttttgctga gttgaaggat cagatcacgc atcttcccga | 22080 |
| caacgcagac cgttccgtgg caaagcaaaa gttcaaaatc accaactggt ccacctacaa | 22140 |
| caaagctctc atcaaccgtg gctccctcac tttctggctg gatgatgggg cgattcaggc | 22200 |
| gatccccatc aacagcccg ccgtcgagcg ggct | 22234 |

```
<210> SEQ ID NO 35
<211> LENGTH: 20522
<212> TYPE: DNA
<213> ORGANISM: Artificial Sequence
<220> FEATURE:
<223> OTHER INFORMATION: Artificial DNA construct

<400> SEQUENCE: 35
```

| | |
|---|---:|
| tttttatccc cggaagcctg tggatagagg gtagttatcc acgtgaaacc gctaatgccc | 60 |
| cgcaaagcct tgattcacgg ggctttccgg cccgctccaa aaactatcca cgtgaaatcg | 120 |
| ctaatcaggg tacgtgaaat cgctaatcgg agtacgtgaa atcgctaata aggtcacgtg | 180 |
| aaatcgctaa tcaaaaaggc acgtgagaac gctaatagcc ctttcagatc aacagcttgc | 240 |
| aaacacccct cgctccggca agtagttaca gcaagtagta tgttcaatta gcttttcaat | 300 |
| tatgaatata tatatcaatt attggtcgcc cttggcttgt ggacaatgcg ctacgcgcac | 360 |
| cggctccgcc cgtggacaac cgcaagcggt tgcccaccgt cgagcgcctt gcccacaac | 420 |
| ccggcggccg ccgcaacag atcgtttat aaattttttt ttttgaaaaa gaaaaagccc | 480 |
| gaaaggcggc aacctctcgg gcttctggat ttccgatccc cggaattaga tcttggcagg | 540 |
| atatattgtg gtgtaacgta tcacaagttt gtacaaaaaa gcaggctccg cggccgcccc | 600 |
| cttcacctag actcgacgcg tcctagagat ccgtcaacat ggtggagcac gacactctcg | 660 |
| tctactccaa gaatatcaaa gatacagtct cagaagacca aagggctatt gagacttttc | 720 |
| aacaaagggt aatatcggga aacctcctcg gattccattg cccagctatc tgtcacttca | 780 |
| tcaaaaggac agtagaaaag gaaggtggca cctacaaatg ccatcattgc gataaaggaa | 840 |
| aggctatcgt tcaagatgcc tctgccgaca gtggtcccaa agatggaccc ccacccacga | 900 |
| ggagcatcgt ggaaaaagaa gacgttccaa ccacgtcttc aaagcaagtg gattgatgtg | 960 |
| atatctccac tgacgtaagg gatgacgcac aatcccacta tccttcgcaa gacccttcct | 1020 |
| ctatataagg aagttcattt catttggaga ggacgacccc gatatgaaaa agcctgaact | 1080 |
| caccgcgacg tctgtcgaga agtttctgat cgaaaagttc gacagcgtct ccgacctgat | 1140 |
| gcagctctcg gagggcgaag aatctcgtgc tttcagcttc gatgtaggag ggcgtggata | 1200 |
| tgtcctgcgg gtaaatagct gcgccgatgg tttctacaaa gatcgttatg tttatcggca | 1260 |
| ctttgcatcg gccgcgctcc cgattccgga agtgcttgac attggggaat tcagcgagag | 1320 |
| cctgacctat tgcatctccc gccgtgcaca gggtgtcacg ttgcaagacc tgcctgaaac | 1380 |

```
cgaactgccc gctgttctgc aggtaaattt ctagtttttc tccttcattt tcttggttag   1440
gaccctttc  tcttttatt  tttttgagct ttgatctttc tttaaactga tctatttttt   1500
aattgattgg ttatggtgta aatattacat agctttaact gataatctga ttactttatt   1560
tcgtgtgtct atgatgatga tgataactgc agccggtcgc ggaggccatg gatgcgatcg   1620
ctgcggccga tcttagccag acgagcgggt tcggcccatt cggaccgcaa ggaatcggtc   1680
aatacactac atggcgtgat ttcatatgcg cgattgctga tccccatgtg tatcactggc   1740
aaactgtgat ggacgacacc gtcagtgcgt ccgtcgcgca ggctctcgat gagctgatgc   1800
tttgggccga ggactgcccc gaagtccggc acctcgtgca cgcggatttc ggctccaaca   1860
atgtcctgac ggacaatggc cgcataacag cggtcattga ctggagcgag gcgatgttcg   1920
gggattccca atacgaggtc gccaacatct tcttctggag gccgtggttg gcttgtatgg   1980
agcagcagac gcgctacttc gagcggaggc atccggagct tgcaggatcg ccgcggctcc   2040
gggcgtatat gctccgcatt ggtcttgacc aactctatca gagcttggtt gacggcaatt   2100
tcgatgatgc agcttgggcg cagggtcgat gcgacgcaat cgtccgatcc ggagccggga   2160
ctgtcgggcg tacacaaatc gcccgcagaa gcgcggccgt ctggaccgat ggctgtgtag   2220
aagtactcgc cgatagtgga aaccgacgcc ccagcactcg tccgagggca aggaatagaa   2280
gtagatgccg accgggatcc ggagagctcg aatttcccg  atcgttcaaa catttggcaa   2340
taaagtttct taagattgaa tcctgttgcc ggtcttgcga tgattatcat ataatttctg   2400
ttgaattacg ttaagcatgt aataattaac atgtaatgca tgacgttatt tatgagatgg   2460
gtttttatga ttagagtccc gcaattatac atttaatacg cgatagaaaa caaaatatag   2520
cgcgcaaact aggataaatt atcgcgcgcg gtgtcatcta tgttactaga tcgggaattc   2580
atcgatgata tcagatcaag ggtgggcgcg ccgacccagc tttcttgtac aaagtggtga   2640
tcccctcga  ggtcgacggt atcgataagc ttgatatcga attccttcag gtgcactgga   2700
acatgagact cattgggtat ttccggtgtt gatttgagga gtaatttacc acctggcaaa   2760
tgactgcata  acagaggag taatgcatga tgtggactga ccaaccaact gaggagattc   2820
agagaaatga gaggagagta aatgcagtga atgatggctg gtggacggac catatacagt   2880
gtatgtaatt attttgctct gaatccctgt ctctctgtga cccactgaat aaacacatca   2940
gccaaaagca gtactgttcg gacttcggag ggatcgtgga gtagtagtaa tttcctctct   3000
tgactgttgt tcctctgagt cctgtgctcc ccgcctccac tgactgctac ctccatctcg   3060
tctcagtcct ctccttcatt tcaagctgtg aaccgaaaac atgcacccag tccggccttg   3120
atgtaatgca ggcaaccaat cgacatggag atgtcgattt ttagcgtata tatgcttagc   3180
cagacccaac tagatcaaat atgcaaggta cctgaaaacg atgccggtaa ccccaaatcg   3240
cgtcgtgaac cggagtaatg ctagacttac gtaaagattt acatatgttt acgggccggg   3300
ctgatttggc tatgtttgat tggattaggt ggaggattag gcccacccat cctgaaaatc   3360
aggaaggggt cagtattatt agtttaatga aaagggagaa ttagtacgta agattttgta   3420
gacttttacg taagtctagc cattattgtt aaccaccaca gtccacgtct ctgcgtccgc   3480
tcatatcacc ttgctcgatc gtctcctcca caaactttc  tttccggccg tgtgtggatg   3540
atagtgtgta ctctctagca gttgattgaa ggattggact gagtctagtc gacgctagtg   3600
acctaagggg acgaagatgc gaggaaggcc ggtcctgtac tctctcgtcc atgcatgtcg   3660
cgagctgcgt cgtccccatc accgccacca ccaccgccat ggtaggtctc caccttggtc   3720
```

```
gacctcctcc acagactttt cgcaccaatt aattccggcc agtcggcgac gaccacttcc    3780
cgtggtgctg gtgaatgaat ttatgcgtgt gtgtgctatg cttgtcattc cagagatatg    3840
ccagttgcgt tctcacggct gagtcattgg cacctcacct tctgtctctc tcgttaaatt    3900
tgtatcgata tataagtgct tttgagtact tgcatatata agtgcttttg gatctaaaaa    3960
gttattagtt ttcatgctta agtatctgat caatttgcgg tggtagtggc atctttcttg    4020
ctattctgct ctaatgaaat ctttcacgtc cacacgttct tgttatagat ctgctgattt    4080
gcttagatta aagttcttc ttattcttcc agatcgattg gagcgaccct cacgcctctg     4140
gtgcgccgtc gctgtgttct gctccgccgt gaagaatcaa ggtgggcttg gtccagatct    4200
agctaagctt taatttcgca gcttgttcaa ggcttcacac aatttggatt gcgttacagc    4260
tccctttatt catcaattta caggcttcca gctgattgat acggagatct cgtcctcctg    4320
ctctcatgcc ggatccagtt actattagtg ctgctgtagg atgggcgta tccgcagtag     4380
gctggctcgc ctctcccatc atttcaaggg ttgtcaacaa aggtttcgcc cacctcgact    4440
tcgatgcagc agagaagctg aagatacttg atatacaagt tctacaactg cagcgcgtga    4500
tagaagtagt cgatgagagc acgtacaggc ttcgcttgga gccactgtta gacaagctta    4560
gatctgctct ttatgaagcc gaagacatct tggatgattt tgattatcag cgtctcgaga    4620
agcagatcca tgttgggtct agttccacac gtaaacgcaa gatagattcg ctggagaaga    4680
atcatcggtc tgccatgccg agttcctccc taaaagataa ggtatttcct tgctctcata    4740
cttgattttc tttttctgct ttgtcacggg caccatattt ctttccatgt atatatatgt    4800
aataaaaact aggaactgta ttcaacttta ttgtttattc tttttcccat gattagatgg    4860
aaacattccc gaggatttca tcgaagggaa aggagactat caataattta ctgagccagg    4920
tatataagca tccactctga tcatgctgaa atcatacttg cattattcat atttttcttt    4980
agtttaatgt gcattattaa tatttaagaa aaaaaatgtt atttaatggt agaaattagc    5040
tatgcacata tactcttcct ccatctcgaa ggaatgaatg tatctagatg cattctagtt    5100
ctagatacat tcatttctat ccatctttgt aacaagtaat tccggacgga ggaagtatat    5160
ttcaatttaa tatatcatac attcatagga tcaagcacaa ccatggtttg atcatcgagt    5220
atgaccttaa agaagattta attcagaacc acttctcgga ggtgatggga aaggggaatc    5280
gacgagactt agaccttaac taggatgagt tggaccttgt gccacatgac ctcttggtct    5340
tcgagggcca aattatggag catgaggtgt tggaagcaat cactgatatg cctactgaca    5400
aggcccccag gcctggtggc ttcgccggcc tcttttaaaa gaaatattgg ggtaaaatga    5460
ggcataacat tgtgagggtg attgggctct ttgaatgcgt gcatgaggcc aacatccatt    5520
ggctcaagag catctacagc cggacccctt aaatgacccc tcatacatcc gtggatgcat    5580
tcggttagtg acgggagagg ggagagaagg aaaaaagtga cccaatcgga cccctcatat    5640
cgtccctgta tgcctgggct gtccatgaac cctcatatcc atctcaaata aggggaggat    5700
atgaggcctc gcgaacgctc tcggtccacc gcataggacg cgaccctacc tcggaccacc    5760
tttatctttt ctttattcat tcttttcttt ctctctcttc ctctccacca atcacataca    5820
agtgaccggg cctatgagaa agaaaataag gaatctggtt gcgtggacgg acaaatagga    5880
aacacgcccg gtcactgatc gcgcgcgtcc gcgagtattt gagggaccgg atttgcaagt    5940
tctggctata gatgatttta atcccgtgaa tactatgctt ttaccaaaga cggatagttt    6000
ggagggcatt aatgactata ggcccattag ctttatatat tcatgtgatt gccaagctca    6060
ctgcgatgat cttcgtcact tgtacacgcc tgcacatgga cactctcata tccaactcac    6120
```

```
aaagtgcttt cataaagaag agaagcattc atgaaacctt cacatatgtg aggaatcttg     6180
ctcagcagtt tcacaaagac aagacctctt ctctcctctt caaacttgat gtacgtaagg    6240
ccttcaactt ggtcaagtgg gagtacatta ttgatcttat tcaaagatga ggcttcccaa    6300
gcaagttcgc ggattggatt accatgctcc tctctatctc ctcctctcgg atacttctca    6360
atgtggggc cggaccgcct atcaagcatg atcatgggct acggcaaagg gattcagtct     6420
tgcttctcct tttggtcatt gccattgacc cactccaaaa aaaccttcat gttgccacca    6480
ccaaaatttt gctacacaag attctaggtc gacatgccat agtgtagatg tccttatata    6540
cggatgatgt ggtggtatcc atgaaaccca taaagcggga gagcgacaac ctctctacca    6600
tactcaaatg ttttggccag gtcatgtcgc caagggcctt gatacaaact tccagaggcg    6660
gattcaggcc ctaggcagcc aaggcctcgg cctggggcgt ggtgactgta gcaaaaatat    6720
ccaatgtagc acattgtatt atactatagc catacagcct gcctgcgaat tgatctgatt    6780
ctagctccga ttatccacat aattaagatg ccgtgaaata caacttggcc ccttcttcaa    6840
cacttgctga caagaaaaca acctttccta tgagatattt ggggaagccg cttttggtct    6900
ggcaactcaa gagggtgaac ttccaattct taaaggacaa ggtgggttcc aagattccac    6960
cctgggacgg aaaaaacatc agcaccattg gttgtacagt tcttgtcaaa ttcgtgttat    7020
cctccgaagc ggtctacctc atcactcccc tcattgcaac acccagcatc ctatgcaaca    7080
caaacaagct caagtgtgcc tttctttggt aaggttcaaa caagattaac ggtgcaaatt    7140
gcaaagtgca aagttaacaa ggatttcgta tgctggcaat gttatgatct ctacacattt    7200
tgcatagaac ttgaattatt ccacaatatg caagaacaag catgtagtca tgtaactttc    7260
agatagccgt attatgtgca aacatattgc atagaacttg catggttcca caatattcaa    7320
gaacaagcat aagtagtgta actttgagac aacaatatga ttttcacaca gatagcattg    7380
aacttgcatt tatacatcca tgctgtgcac agtgttgaaa caacataaca aaaacattgg    7440
cgatcaatca tttcttgaca tgtcgaagat gaattgcatc ccacgttggt gttgcctccc    7500
caatttatgt cttgctcttt ctctcataga aacgagtgtg cattcccgca cacacacgca    7560
catacacaac aaacagacat agcaaagtac gcaaatacac aaagaaaaaa cagctaacac    7620
aagaaaaatc taaacacaaa gaacttttcc aaaatcaatg aactttttt taatccatcc     7680
attattttcc gaaagtccat gaatgttttc tcaattcatg gtatttttca atttgtgaac    7740
atttttccta cgaatgaact tttccaaaaa gatgaaccat ttgtcaaaaa caacagtcag    7800
atgtcaaaca tgtcagtggt caacttatcg cccaggttac catgaagaag ttttttttgtt   7860
gaaccgtgaa gaagcgatca ggtgtatgat gttgcgtgtt gagcgacagc tgatcactgg    7920
tgtagtggag tgttgcatcc gctacaaaaa gaactagaca agtgctgcct aggaggtccc    7980
gttgtacatg gaaaggcatc acacaaacca agcgcacaa gcctacatcc tgcacctggc     8040
cttttttttt tgttctttt tttaccttca aaaatcagt gcatgaagta ggatttgaac       8100
catggacctc ttggattagt tccatccgta atgaactgga acatctcact tgttacgtct    8160
aattactta tttatttctt ttattgtgaa tcttctcagt ctggttttct tctcgtgttg      8220
cttttgtttt gctttttttc tttagttttt ttttcatttt ctctatattt cttcttcttt    8280
ctctcttttc tttttttcctt tctctaaatt tatgaacatt tcttaaatt tgtgaaaaaa    8340
aattcaattt caagacccta ttttttgaat ccatgtttat ttctcaaata atgaatgttt    8400
tcaagtttgc aaacttttgt caattcatg gactttattt tgtcaactct gtgaatgttc     8460
```

```
ctaaaattga tgaactttt aaaaatgtgt gaaactttt gtcaaattct ataacttctt    8520
tgagaaatta gtgacttctt ttaaagccga ttacatattt taatttcatg gattattttc    8580
aaatcgctgt tttttaaaac aacatttgaa cttttcttta atctaagggt tgcgttataa    8640
accgaaaact tgattttac cattcgattt attctaaatt ttggttggca aaactataaa    8700
ctggaatgaa tatggggaag caaataacca ataattcggt tcaacggctt attcggtttg    8760
atgttcagtt ttacaccgag caaactcgtc aaatgtgttg ctttctatta ggacactctg    8820
tcacattata tagcaaattt tgtcccta ttttagtagc tcagccggat ttgactaaat    8880
tggacgctat gcgcaacttg ggtgtacgat gtcaccgaaa ggctcgtgcg ggttgtgcc    8940
ttcgttgtac taaaatttgc atggagtact agaatgggaa caccaatggc aaaatttagg    9000
taaatttac taatatccac aagtacatca tgtacaacgg aggggtttg gtttaggcgg    9060
aagagttcgt ccctagcac ggtttttagc atacatcaaa tactcctaaa aaacacct    9120
agaattatca tggcatggac ccatgccaac ttccatcgaa ttttgacttt ttttgtattt    9180
cctatggggt ttccggtcaa aaaacctcaa gtactgaccg aacgggatgc agcgtgcatt    9240
cgttcttcga attcgttcaa attttgcgtc gagtactaga atggcatgct cagctgcctg    9300
caaaagttgg ataaatttaa tgaatgtcca cagatacatc atgtacaacc gagcggtttc    9360
ggttatagca ctttttcaca tagatctaac agacgcaaat gtgttatgtt catttgacgc    9420
atgtcgagtc acaacatgct ctcaaacata ggctatttct ttcggaaaaa aattcgatct    9480
attcattctc aatcatggta atacaacgaa taccagaaat aataaaaatt acatctagat    9540
ccgtagagca cctagcgacg attacaatta ctgaagcgag ccgaaggcag aaaaaattc    9600
gatctattca ttctcaatca tggtaataca acgaatacca gaataataa aaattacatc    9660
tagatccgta gaccacctag cgacaattac aattactgaa gcgagccgaa ggcacgcctg    9720
ttggaaataa ccacgacatg tgtggtctgt gtccggttcg tacacacgac aatcatcgta    9780
tagtggtagg attaggattc atagccgtgt aggttatctt atctaatgtc ctgactatta    9840
tatataggta gctatcccct tgtaagctgc aaccgtgaga tcgtgagatc aaaagatcaa    9900
aagcaataaa agtgcaaggc ttggcccaga cccgacgtcg acgttgttgc cgtgtacttt    9960
ccggcaatac atacgtacga tactagctcg agtgctttcc gagctatccg tcggagaggt   10020
aaacgtagac gtagacagca atcgtgcacg tatacgaa ggctgctgga tggttcctcc   10080
tgtgctagct agcacgtact actgcacgag atctttggct gatcgatcta tgcggcgaga   10140
acacaggaaa cactcggcga gttggccaaa aggagccttg cacttttatt gcttttgatc   10200
ttttgatctc acgatctcac ggttgcagct tacaagggga tagctaccta tatataatag   10260
tcaggacatt agataagata acctacacgg ctacgaatcc taatcctacc actatatgat   10320
gattgtcctg tgtaagaacc ggacacagac cacacatgtc gtggttattt ccaacaacgc   10380
cgccgtcatt gctcctccat caccggagtc gagcacaatt tgttgtagta gacagtcggg   10440
aagtcgtcgt gctaaggccc cgtagcaccg gtgcaccaga acagcaacca ccgcagatga   10500
agaataacat agatcaaaag gatccaatcc gaagacacac gaacatagac gaacaacgat   10560
gagatccgag caaatccacc aaagataaat ctgtcggaga cacaactcca cacgctcacc   10620
aacggtgcta ggcacaccgc cgtaatgggg gctaggaagg gagacctta ttccatcttc   10680
acgcagccgc cgccgtctcg tcttcctgag caggacacaa accctagcaa aactgaaagt   10740
aacgactaaa aacggagccc tcccgccggc gcttgctgag atccaccgcg ctcccatggc   10800
cctaggggca ccggagtgga ggcggacctg cggcggcgcc ggcaggacgc agaaaaccct   10860
```

```
actttttttt ttgtgaagga ggaggaggcg gacttttgtg tcaaacatag gcttatggcc    10920
caccaggcca ccttatattg aacatggtgc ttctttggac attttttaaaa tgacactaag    10980 ttttttagta ggtgggtatg cccataattt aaacaaaaat ttaaaactgt tatgttgagt    11040
ttttaacgta aaaatatat agaaaaagga gaaaaaataa aacagccaat gttttgctaa    11100
agctaataca tatttgaaaa aatgaatata atgtttgaca gttacttaaa actgttattt    11160
tgatattcca aaaaatattt caatttcgcg aacaagcttc aaaataaaa ataaacctttt    11220 aaaaggagaa aaatgaatta acggaaaatg agaaaataga agaaaaataa gcttaggcct    11280
tcgcggaact agaacacgac atcgctcttg tcgggcggct gttaggccga ggcaagtgct    11340
cgggatttca ataagctcaa cgattcaaaa aatgtcccta ttttcaaaat tcgtttataa    11400
ataaaaaaat gttccctttt tcaagcttgt acataaactg aaattccttt gcgggagttt    11460
ctaataatgt tcgtactttc aaatgatttt cctaacttca aaaatattcc tgttttcaaa    11520
agcaatatac acaaataaaa tgatgatagg ggaaattcac aaaaataatg ttcgctcttc    11580
tagaaaaatg tttctgtttt gtgacttta ggaacttaaa gacaacaata ttttgaagta    11640
ataactataa aatgtgtaaa aaagtttgtg aggtctatta aaatgtttgt cgttgaaagt    11700
gatcattttt gctcttttaa aatgattgaa atgtctattt caaaatttct atacaatttt    11760
tataatgtga atatttttag tttcgtaatt atacattttt ataaattttg aaaaaacaaa    11820
tacttgggtc tggcgatgtc gatttgagga cctaatagtc agcgctttaa gcgccagtta    11880
ggaagctagc gctcgagccc agtattgcgc aagcttgctt gcttcacccg atggctttga    11940
caaaaattca tgaatttcaa aacgttaata agtttgaagt atagtttgtg gatttgaaaa    12000
ttgttcacga gtaaaatgta aaagctcat gatcgtgaaa aggttcacaa atttgaaaac    12060
aagtttctga atattaaaat tgttcacgt tcaaatttca aaattatcat gattttaaaa    12120
acatttatga atttgaaaac tgttcacgag atatatttta taaattttat aaaaaaaaca    12180
tgagtttaga caatgttcac aaatttggaa gtagttggcg ggtttgaaac aaattttatg    12240
aattttttta accttgataa acataaatgg aaattcatga aaaaagtgg aaagggtaaa    12300 ataaatataa acgaaattg gcaaaaagaa agagaaaaaa ccgagagaaa accatgcata    12360
aaaaacgaaa aggaaaattg tccagaaaaa ctatgcatag ccagaaccgg aaatgtagag    12420
aacaagaaga aaaagaagtg gaactatgca gaacatgtta tctatccgag gtggtaattt    12480
tgaatccgga cgcagagttt ctgctcccaa gctcatttga gctcgatgaa acatttggc    12540 atgaaataac attcctacaa agtttggcaa aaacaaaatc gatgctgtga aaagcggatt    12600
ttcagagtgt ccattttttt tgctacgaat tgtaggaatg ttatttcata ccaatttgtt    12660
tttacactta aaactttgtc attgctggtc acaaaaaaaa aatcagaatt atttgaacgt    12720 ttcttgatt tttttttgatt tttactgttc accgagctca aatgagctcg ggggcagaag    12780 ggcacttca aatcccaagt ggcacaatag ccaacatcaa ataggagctt cgctactata    12840
caacaccgta tacatacaaa catggatata atttgtcaaa ggtttatatt gcccttata    12900 cgttttcatt ctttttataat gcaacatgta agtggacaat ccagtggtcc ggctcagctt    12960
tgtgcgaaac atgctagcac ggtgactgtc accgaaagct ggcttacgaa aactcctagc    13020
ttcctgatta gcagccttca agctgactgc tcagcaaacg ccttttgttg aataaagctt    13080
aaaattccat gcaaaaagt tattgccctt tatatgtttt ctgagagggg aggggagg    13140 ggtatcaaag cgggactaga gatataagcc cgctaacctg gtcggggcat ttggaattgc    13200
```

```
aagaaaaaca ggcacgggtt tttagatctt cggtttgaca aacgaaacat gtgcaataag    13260
gcagcaaaag tatatattca agttgattcg attactaatc taatgatatc tatttttac    13320 tggcatatct cacatgttct gttagtcaaa ttgaagacct aagaactcat gcgctccttt    13380
gaaattgaac aaaactagtt catttctaaa acttcaacac aaaatgacct cgatccgaaa    13440
atacttcaca aattggctcc tttttgcatg acgcccgagg atagggctcc atgctattta    13500
gcatgacgcc ctaggccaag gctgtatcta ccatgacacc ctggcccggg ccggcgtcat    13560
gcaaaagggc cagtttgtga aatattttga gatggaggcc attttgtttt gaagtttcag    13620
aaaagggcta gtttcgtcaa tttttactac actccttacc aacccggata gaggagtaaa    13680
tatatattcc tcaaatagag cagttattga tagtttcaac ttacctgtta ttcggtttta    13740
taggggattg gaacatcaaa agtggagttg aagaaaagcc tagagaaaat agaaaatacc    13800
ataaacgatg catgtaaagt tttggaacaa ctgaacttgc cgagtgtatg taatgataat    13860
gggagacgag gtgttgctac caattctcgt agtgcagtca ctactgcagg tcctcctcta    13920
cgagtaattg gtcgagatca ggatcgtgac aagatcatag caatgcttca tgagaaggat    13980
gaccggtgtc aagtcaatgg tacatcttat tctgtaattg gcattcatgg cgtcgccggg    14040
tctgggaaat caacacttgc acagtatgtt tatgatcatg agaaaaagtg caagcaaggt    14100
aaaagagaag gctattttga tgttctcatg tggattcatg tttctcaaaa aatcggtttg    14160
gagtccagtt tcagggacat gtttgagggg gctacaggga aagcatgccc gaatttaat    14220 agtcttaacg tcttaaagga aaagttggag gaggaactac gtggaaaacg gatttttttg    14280
gtactagatg atgtctggta caacagtaag aattcaggag accgtgaaga actgcagaag    14340
ttaatttctc cgttgaatgt tgggaaggca ggaagcagaa tcttggtgac tagtcgaact    14400
gaagctgcat tagtagctct ccgtgctgca aagagggat gtatcccaat atctaacctg    14460
gatgataaag tttccttaa aatgttcatg cattatgcac ttccacatgc atggccagtt    14520
ggcaatgatc gaagaaaact tgaaatgatt ggagaggaca ttgcaaaaaa gctgaagggt    14580
tcacctctgg cagctagaat agtgggttca cggctcggtg ataatccaaa tgttgaattt    14640
tggaggagag agaaagaccg ggatcttatg aacgagacga tgggagcact ttggtggagc    14700
taccagtacc ttgatgagca ggtcaggcga tgcttcgctt acatcagcat ttttcccaga    14760
cgtcatcatt tgaaacgtga tgacttaatt aacctatggg tggccgaagg atttataaag    14820
acaagtaaag ctgaagagga aatggaagat gttgcctcgg aatactttga tgagctgctt    14880
tcgttctcat ttctgcaatt aggagggaaa gatgagctat ttgcacgtga ggtcgattac    14940
tttataattc atgatctgtt gtatgattta gcagaggagg ttgctggaag agattgcttc    15000
aggatagaga aaggtttcac aggagaagtc cctccggatg ttcgctatct ttttgttggg    15060
acttacgata aagagatgct tactgagaag atatccaggt tgcaaaattt acgcactctc    15120
ttcgtcgata agtacataca gatttttatca cccaagtacg atgattttgt tagtatggtg    15180
actatgttga tggggctgcg gaaattgagg gtactgaatt tacatttcac tggatatggt    15240
attcctaaat tctcattgcc ggattctatt cttcagtgga agcatctgcg ttactttgct    15300
tttggggtgt ccccgtttac caagctaact ttaccatgcg cttttaccaa gctttaccac    15360
ttgcatgtgg tagatttcgg tgattgcaat agtttggagt tttctcgtgg tgaatacatg    15420
atgaacctgg tcaatttgcg ccgtgtaatc tacaagaatt atctcgactt tccgaacatt    15480
ggcaggctga catggctgca atcgttgccg tgcttcagaa taaggaagaa acatgggtat    15540
gaatcacatc agctgaaaca cctaaacaag cttcaaggca ggctgtacat tggtggtctt    15600
```

```
cagaatgttg agagcaagga ggaagctctt aatgtgaacc ttgcagccaa ggaaaaactc    15660
acagaagtgg tactgcgctg gagtgataat agctgcagtc cagaaattca agcagaggta    15720
cttgagggcc tttgtccttc aaagtatctt gaaatactag aaatcaagtt atacaatggc    15780
atgaagtttc caaattggat gacgagtaag cataagggtg ggccaaagaa cctgcaagaa    15840
cttagattca gacagagcac cctgggatct gctcctgatg ttggggcttt cattcacctt    15900
cagtcgttat ttatttatca atgcagctgg gataccttac cagggaatat ggagcacctc    15960
acagcgctca agaaactgga gatacggtca tgcaataata ttcggtcgct ccaacactg     16020 cccaagtccc ttgagcagtt tgcgatctgg tcctgcagct tggatgcttt accgggcaat    16080
atggagcacc tcacagcact caagaaactg agatacggt catgcaataa tattcggtgg     16140
cttccaacac tgcccaagtc ccttgagcag tttgcgatct cgcgctgcag cttggatgct    16200
ttaccgggca atatggagca cctcacagcg ctcaagaaac tggatatatg gtcatgcgag    16260
aatatacggt cgcttccaac actacccaag tctcttgagg agtttacagt ctggaactgc    16320
actagtgagt tcatgcaatc ttgtatgacg actgatgatc caaactggca gaagattgag    16380
cacgttccaa acaaaaaaat tggatttcta tgatttctga tccagagcga ctcacattgc    16440
atcagatgtg ctctcgaggt atgtagcaga taagaaacag attaaggtat ttacaaaaat    16500
tgcttagaca taagtatctg atcagaaaag tggacttggc agtgtagtgt gaaacttgcc    16560
tagtcacttt tttggcaagg ggtgatgaaa gataagaatt attttatgca aattgataga    16620
aggatagtca gtaatgggga attggggata tgactagatt ttcagaagtt atatgtacaa    16680
ggagtgttgt tttaccgaaa aggctttcat cccggtttat atataaagca aaccaccaga    16740
tcaagagtac aagcataaga ccaaaccaga cacgcataca catacccaag atagaacgac    16800
gtcaaatacg ggggttctgc tgagggcaca gctcaacaag ccctaaaaaa caaaataagg    16860
cggagggacc gcaatagaag caactaatct ggctctggag gtggtggcgg aaccaagcgg    16920
aaggccatca tccgcagatc tgcgatgatg gagtcgatgg cgtcctgatc cgggaggggt    16980
gctgttttag gtgacaagta ccccaggtta tacagtttat ctgtagctag agtgctacac    17040
gctaatttca ctgctctaaa atgtagaggg gatctgtatg gtgaaactgc tgagctacga    17100
catcgattgc ttgctgatcg tgaaggcttt ggtcttgagg aatgagcaag attcatgtag    17160
atgacgccgc aaaataaata tatacgtaat ggctttcaaa gaataatggg gtattttctg    17220
tgcatcctat atttatagct ttgaatgctc aacaagtgaa atgaccataa agaaaatttt    17280
ggcatgtaaa aggtccactt acgatcatag tttttttata ttagcattca gaaatagtat    17340
cggcagagtt aatctgaatc gtcgaggaat ggtaattgct tgaaaaatgt tttcgctgag    17400
gatatttgat gttttattgg tctgtctaac aaagaataga aatgcacgat atgtaggtag    17460
cagcggcgcg gggcgttgga gttacagctg gtggcatcag agatgcttgt ttcacaaaca    17520
gttcgggcgg cgcgctgacca tgcaaatgtt tcgaactttg ctggaacttg tgtgatgagc    17580
ttcttttaaa tggcactcag cttgcagaaa gaaacatggt tttgttttgt aatgaataag    17640
caagggtgtt ggggtgaatt gatccttaca aggatagctt tgcttttctt tagttgaggg    17700
ccaccgttgc tgctctgttt tgcatgttgt tgttacatgg gaggacatgc tagtgtattt    17760
tgtttttaag ctgagccgaa caaacctgag tatgtattat cagttccgtg ttgaatgaaa    17820
tctgagctca ttaattcaat aaaaactgtg gtttactgtt ggacttgtta cttaaaagct    17880
acccacttcg tccggaatta ttagcattta gagacatcca tttgaacctc aggtagttct    17940
```

```
ggacggaggt agtactattt actagttcta ctaacatgtt tgtgtttaca tacaaatgaa    18000
aagtgtgatt cgaactaaca agtacgtacg atttctaagg tgtgcttcca actaacaagc    18060
atgtgtacga tccactagtt ctagagcggc cgccaccgcg gtggagctcc agcttttgtt    18120 cccttttagtg agggttaatt gcgcgcttgg cgtaatcatg gtcatagctg tttcctgtgt    18180
gaaattgtta tccgctcaca attccacaca acatacgagc cggaagcata agtgtaaag     18240 cctggggtgc ctaatgagtg agctaactca cattaattgc gttgcgctca ctgcccgctt    18300
tccagtcggg aaacctgtcg tgccagctgc attaatgaat cggccaacgc gcggggagag    18360
gcggtttgcg tattgggcgc tcttccgctt cctcgctcac tgactcgctg cgctcggtcg    18420
ttcggctgcg gcgagcggta tcagctcact caaaggcggt aatacggtta ccacagaat    18480 caggggataa gcaggaaag aacatgaagg ccttgacagg atatattggc gggtaaaacta   18540 agtcgctgta tgtgtttgtt tgagatctca tgtgagcaaa aggccagcaa aaggccagga    18600
accgtaaaaa ggccgcgttg ctggcgtttt tccataggct ccgcccccct gacgagcatc    18660
acaaaaatcg acgctcaagt cagaggtggc gaaacccgac aggactataa agataccagg    18720
cgtttccccc tggaagctcc ctcgtgcgct ctcctgttcc gaccctgccg cttaccggat    18780
acctgtccgc ctttctccct tcgggaagcg tggcgctttc tcatagctca cgctgtaggt    18840
atctcagttc ggtgtaggtc gttcgctcca agctgggctg tgtgcacgaa ccccccgttc    18900
agcccgaccg ctgcgcctta tccggtaact atcgtcttga gtccaacccg gtaagacacg    18960
acttatcgcc actggcagca gccactggta acaggattag cagagcgagg tatgtaggcg    19020
gtgctacaga gttcttgaag tggtggccta actacggcta cactagaaga acagtatttg    19080
gtatctgcgc tctgctgaag ccagttacct tcggaagaag agttggtagc tcttgatccg    19140
gcaaacaaac caccgctggt agcggtggtt tttttgtttg caagcagcag attacgcgca    19200
gaaaaaaagg atctcaagaa gatcctttga tcttttctac ggggtctgac gctcagtgga    19260
acgaaaactc acgttaaggg attttggtca tgagattatc aaaaaggatc ttcacctaga    19320
tccttttaaa ttaaaaatga agttttaaat caatctaaag tatatatgtg taacattggt    19380
ctagtgatta gaaaaactca tcgagcatca aatgaaactg caatttattc atatcaggat    19440
tatcaatacc atatttttga aaaagccgtt tctgtaatga aggagaaaac tcaccgaggc    19500
agttccatag gatggcaaga tcctggtatc ggtctgcgat tccgactcgt ccaacatcaa    19560
tacaacctat taatttcccc tcgtcaaaaa taaggttatc aagtgagaaa tcaccatgag    19620
tgacgactga atccggtgag aatggcaaaa gtttatgcat ttctttccag acttgttcaa    19680
caggccagcc attacgctcg tcatcaaaat cactcgcatc aaccaaaccg ttattcattc    19740
gtgattgcgc ctgagcgaga cgaaatacgc gatcgctgtt aaaaggacaa ttacaaacag    19800
gaatcgaatg caaccggcgc aggaacactg ccagcgcatc aacaatattt tcacctgaat    19860
caggatattc ttctaatacc tggaatgctg tttttccctgg gatcgcagtg gtgagtaacc    19920
atgcatcatc aggagtacgg ataaaatgct tgatggtcgg aagaggcata aattccgtca    19980
gccagtttag tctgaccatc tcatctgtaa catcattggc aacgctacct ttgccatgtt    20040
tcagaaacaa ctctggcgca tcgggcttcc catacaatcg gtagattgtc gcacctgatt    20100
gcccgacatt atcgcgagcc catttatacc catataaatc agcatccatg ttggaattta    20160
atcgcggcct tgagcaagac gtttcccgtt gaatatggct cataacaccc cttgtattac    20220
tgtttatgta agcagacagt tttattgttc atgatgatat ttttatct tgtgcaatgt     20280 aacatcagag attttgagac acaacgtggc tttgttgaat aaatcgaact tttgctgagt    20340
```

```
tgaaggatca gatcacgcat cttcccgaca acgcagaccg ttccgtggca aagcaaaagt  20400
tcaaaatcac caactggtcc acctacaaca aagctctcat caaccgtggc tccctcactt  20460
tctggctgga tgatggggcg attcaggcga tccccatcca acagcccgcc gtcgagcggg  20520
ct                                                                20522
```